US012435341B2

(12) United States Patent
Shan et al.

(10) Patent No.: US 12,435,341 B2
(45) Date of Patent: Oct. 7, 2025

(54) GENETIC LOCI ASSOCIATED WITH RUST RESISTANCE IN SOYBEANS

(71) Applicants: OIL CROPS RESEARCH INSTITUTE, CHINESE ACADEMY OF AGRICULTRAL SCIENCES, Wuhan (CN); SYNGENTA CROP PROTECTION AG, Basel (CH)

(72) Inventors: Zhihui Shan, Wuhan (CN); Qingnan Hao, Wuhan (CN); Haifeng Chen, Wuhan (CN); Yanyan Yang, Wuhan (CN); Chanjuan Zhang, Wuhan (CN); Limiao Chen, Wuhan (CN); Songli Yuan, Wuhan (CN); Dong Cao, Wuhan (CN); Wei Guo, Wuhan (CN); Xiaojuan Zhang, Wuhan (CN); Shuilian Chen, Wuhan (CN); Zhonglu Yang, Wuhan (CN); Dezhen Qiu, Wuhan (CN); Xinan Zhou, Wuhan (CN); Qingli Liu, Durham, NC (US); Becky Welsh Breitinger, Durham, NC (US); Shujie Dong, Durham, NC (US)

(73) Assignees: OIL CROPS RESEARCH INSTITUTE, CHINESE ACADEMY OF AGRICULTURAL SCIENCES, Hubei (CN); SYNGENTA CROP PROTECTION AG, Basel (CH)

( * ) Notice: Subject to any disclaimer, the term of this patent is extended or adjusted under 35 U.S.C. 154(b) by 371 days.

(21) Appl. No.: 17/624,173

(22) PCT Filed: Jul. 1, 2020

(86) PCT No.: PCT/CN2020/099619

§ 371 (c)(1),
(2) Date: Dec. 30, 2021

(87) PCT Pub. No.: WO2021/000878

PCT Pub. Date: Jan. 7, 2021

(65) Prior Publication Data

US 2022/0380796 A1 Dec. 1, 2022

(30) Foreign Application Priority Data

Jul. 1, 2019 (CN) ........................ 201910584420.1

(51) Int. Cl.

| | |
|---|---|
| ***C12N 15/82*** | (2006.01) |
| ***C07K 14/41*** | (2006.01) |
| ***C07K 14/415*** | (2006.01) |
| ***C12Q 1/68*** | (2018.01) |
| ***C12Q 1/6895*** | (2018.01) |

(52) U.S. Cl.
CPC ........ *C12N 15/8282* (2013.01); *C07K 14/415* (2013.01); *C12N 15/8205* (2013.01); *C12Q 1/6895* (2013.01); *C07K 2319/00* (2013.01); *C12Q 2600/13* (2013.01); *C12Q 2600/156* (2013.01)

(58) Field of Classification Search
CPC .......................... C12N 15/8282; C07K 14/415
See application file for complete search history.

(56) References Cited

U.S. PATENT DOCUMENTS

2018/0103600 A1* 4/2018 Rairdan ............. C12N 15/8282

FOREIGN PATENT DOCUMENTS

| | | | |
|---|---|---|---|
| CN | 104164502 | B | 10/2015 |
| CN | 104293922 | B | 3/2016 |
| CN | 104164501 | B | 5/2016 |
| CN | 104232775 | B | 8/2016 |
| WO | 2009132089 | A2 | 10/2009 |
| WO | 2014165066 | A2 | 10/2014 |
| WO | 2016183130 | A1 | 11/2016 |

OTHER PUBLICATIONS

Chen et al., 2015, Genetic analysis and molecular mapping of resistance gene to Phakopsora pachyrhizi in soybean germplasm SX6907, Theoretical and Applied Genetics, 128, 733-743 (Year: 2015).*
Chen et al., 2015, Genetic analysis and molecular mapping of resistance gene to Phakopsora pachyrhizi in soybean germplasm SX6907, Theoretical and Applied Genetics, 128, 733-743 (previously cited). (Year: 2015).*
Goellner et al., 2010, Phakopsora pachyrhizi, the causal agent of Asian soybean rust. Molecular plant pathology, 11(2), 169-177. (Year: 2010).*
Pedley et al., 2019, Rpp1 encodes a ULP1-NBS-LRR protein that controls immunity to Phakopsora pachyrhizi in soybean. Molecular plant-microbe interactions, 32(1), 120-133. (Year: 2019).*
Guo et al., 2004, Protein tolerance to random amino acid change. Proceedings of the National Academy of Sciences, 101(25), 9205-9210. (Year: 2004).*
NCBI Reference Sequence: XM_028359655.1, 2019, Predicted_ Glycine soja putative disease resistance RPP13-like protein—Nucleotide—NCBI Gen Bank. (Year: 2019).*
Bettgenhaeuser et al., 2014, Nonhost resistance to rust pathogens—a continuation of continua. Frontiers in plant science, 5, 120596. (Year: 2014).*
Hao et al., 2024, An pair of an atypical NLR encoding genes confer Asian soybean rust resistance in soybean. Nature Communications, 15(1), 3310. (Year: 2024).*
Soybean locus in SX6907, PP508376, NCBI Nucleotide GenBank, Accessed Jan. 21, 2024 at https://blast.ncbi.nlm.nih.gov/Blast.cgi (Year: 2024).*

(Continued)

*Primary Examiner* — David H Kruse
*Assistant Examiner* — Santosh Sharma
(74) *Attorney, Agent, or Firm* — Womble Bond Dickinson (US) LLP

(57) ABSTRACT

The present invention provides methods and compositions for identifying, selecting, and/or producing a soybean plant or germplasm resistant to Asian soybean rust using markers, genes and chromosomal intervals derived from *Glycine max* strain SX6907. Asian soybean rust resistant soybean seeds, plants, and germplasms are also provided.

38 Claims, 6 Drawing Sheets

Specification includes a Sequence Listing.

(56) References Cited

OTHER PUBLICATIONS

Alignment results of SEQ ID No. 2 to NCBI nucleotide database, Accessed Jan. 21, 2024 at https://blast.ncbi.nlm.nih.gov/Blast.cgi. (Year: 2024).*

Haifeng Chen, et al., "Genetic Analysis and Molecular Mapping of Resistance Gene to Phakopsora Pachyrhizi in Soybean Germplasm SX6907", Theoretical and Applied Genetics, Feb. 12, 2015, pp. 733-743, vol. 128.

Chen et al. "Genetic analysis and molecular mapping of resistance gene to Phakopsora pachyrhizi in soybean germplasm SX6907." Theoretical and Applied Genetics 128 (2015): 733-743.

Written Opinion of the International Searching Authority and International Search Report for PCT/CN2020/099619.

Liu, M., et al., "Identification of a soybean rust resistance gene in PI 567104B," *Theor Appl Genet*, 2016, vol. 129, pp. 863-877.

Kato, Masayasu, "Effectiveness of Resistance Genes to the Soybean Rust Pathogen *Phakopsora pachyrhizi,* " *JARQ*, 2017, vol. 51(3), pp. 199-207.

Mchale, L., et al., "Plant NBS-LRR proteins: adaptable guards," *Genome Biology*, 2006, vol. 7(4), pp. 212.1-212.11.

Van Der Biezen, E., et al., "The NB-ARC domain: a novel signalling motif shared by plant resistance gene products and regulators of cell death in animals," *Current Biology*, 1998, vol. 8(7), pp. R226-R227.

Keskin, O., et al., "A new, structurally nonredundant, diverse data set of protein-protein interfaces and its implications," *Protein Science*, 2004, vol. 13, pp. 1043-1055.

Pakula, A., et al., "Genetic analysis of protein stability and function," *Annu. Rev. Genet, 1989*, vol. 23, pp. 289-310.

* cited by examiner

SX6907 L2 L3 Tialong No. 1

GENETIC LOCI ASSOCIATED WITH RUST RESISTANCE IN SOYBEANS

CROSS REFERENCE TO RELATED APPLICATIONS

This application is a 371 National Stage application of International Application No. PCT/CN2020/099619 filed Jul. 1, 2020, which claims the priority to Chinese Patent Application No. 201910584420.1, filed Jul. 1, 2019, the disclosure of which is incorporated herein in its entirety.

SEQUENCE LISTING

The instant application contains a Sequence Listing, which has been filed electronically in ASCII format and is hereby incorporated by reference in its entirety. Said ASCII copy, created Jun. 22, 2020, is named 115479.000346 Sequence Listing_22June2020_ST25.txt and is 167,289 bytes in size.

TECHNICAL FIELD

The invention relates to the field of plant genetic engineering, in particular to a protein related to rust resistance in soybeans, a coding gene and use thereof.

BACKGROUND

Soybean (*Glycine max*) is one of the four major oil-bearing crops around the world and one of the most important crops for producing proteins. Rust is a major disease in soybean production around the world and the main method to control the disease is the application of foliar fungicides.

At present, there are no commercial varieties with complete resistance against rust. The pathogen of rust is *Phakopsora pachyrhizi*, and the hosts of the pathogen of rust include a wide range of leguminous plants (at least 31 species in 17 genera; Slaminko et al., (2008) *Plant Dis.,* 92: 797-771; and at least 42 species in 19 genera; Frederick et al., (2002) *Mycology,* 92: 217-227, respectively). In addition, another 152 species have been recognized as potential hosts of *Phakopsora pachyrhizi* (Bonde et al., (2008) *Plant Dis.,* 92: 30-38; Goellner et al., (2010) *Molecular Plant Pathology,* 11: 169-177; Ono et al., (1992) *Mycol. Res.,* 96 (10): 825-850; and Slaminko et al., (2008) *Plant Dis.,* 92: 797-771). The application of fungicides is currently the only available method to mitigate rust.

There are few soybean resources that are resistant to *Phakopsora pachyrhizi*. The resistance of soybean resources to *Phakopsora pachyrhizi* is specific for individual physiological races, therefore, when using resistant resources for breeding, if such resistance specificity is ignored, the resistance in the resistant resources may be lost due to the incompatibility between host resistance and the physiological races, which is not conducive to the persistent utilization of the resistant resources.

Cultivating rust-resistant varieties is the most economical and effective way to prevent rust damage. By exploring new resistance genes for diseases in soybean germplasm and other leguminous plants and transferring them as a single gene, multiple genes or in the form of multiple gene cassettes to soybean, these resistance genes may be able to provide resistance to *Phakopsora pachyrhizi* through homologous or heterologous expression. Accordingly, what is needed are novel resistance genes to rust that can be introduced into commercial soybean plants to control rust resistance.

SUMMARY OF THE INVENTION

This summary lists several embodiments of the presently disclosed subject matter, and in many cases lists variations and permutations of these embodiments.

Thus, it is an object of the presently disclosed subject matter to provide methods for conveying rust resistance into non-resistant soybean germplasm or plant lines. Further the presently disclosed subject matter provides novel *Glycine max* lines comprising in its genome a chromosome interval, loci, and/or gene that is derived from *Glycine max* strains SX6907 and further confers Asian soybean rust resistance (herein, "ASR") in said novel *Glycine max* line.

The present invention provides for chromosomal intervals derived from *Glycine max* strain SX6907 that when introduced into a plant (e.g. a soybean such as *Glycine max* strain Williams 82) are sufficient to confer increased rust resistance, such as e.g. Asian soybean rust ("ASR") resistance, as compared to a control plant not comprising said chromosomal interval. The invention also provides for proteins and nucleic acids derived from *Glycine max* strain SX6907 that confer rust resistance.

Compositions and methods for identifying, selecting, and producing Glycine plants (including wild *Glycines* (e.g. *Glycine tomentella* and *Glycine max* lines)) with enhanced rust resistance are also provided. Rust resistant soybean plants and germplasms are also provided.

In some embodiments, methods of identifying a rust resistant soybean plant or germplasm are provided. Such methods may comprise detecting, in the soybean plant or germplasm, a genetic loci or molecular marker (e.g. SNP or a Quantitative Trait Loci (QTL)) associated with enhanced disease resistance, in particular ASR resistance. In some embodiments the genetic loci or molecular marker associates with the presence of a chromosomal interval comprising the nucleotide sequence or a portion thereof of SEQ ID NOs 11, 12, or 13, or a portion thereof wherein the portion thereof associates with ASR resistance. In another embodiment, the genetic loci or molecular marker associates with the presence of nucleotide of SEQ ID NO: 2 or a portion thereof associated with ASR resistance. In yet another embodiment, the genetic loci or molecular marker associates with the presence of nucleotide encoding the amino acid sequence of SEQ ID NO: 1 or a portion thereof associated with ASR resistance.

In some embodiments, methods of producing ASR resistant soybean plants are provided. Such methods may comprise detecting, in a soybean plant or germplasm, the presence of a genetic loci and/or a genetic marker associated with enhanced pathogen resistance (e.g. ASR) and producing a progeny plant from said soybean germplasm. In some embodiments, the methods are used to generate novel ASR resistant *Glycine max* strains.

Other embodiments include methods of selecting a disease resistant soybean plant or germplasm. Such methods may include crossing a first soybean plant or germplasm with a second soybean plant or germplasm, wherein the first soybean plant or germplasm comprises a genetic loci derived from *Glycine max* strains SX6907 or a progeny plant thereof comprising any one of SEQ ID NOs 2, 11, 12, or 13, or a portion thereof associated with enhanced disease and/or ASR resistance, and/or tolerance, and selecting a progeny plant or germplasm that possesses the genetic loci.

In some embodiments, methods of introgressing a genetic loci derived from soybean strains SX6907 associated with enhanced rust resistance into a soybean plant or germplasm are provided. Such methods may comprise crossing a first soybean plant or germplasm comprising a chromosomal interval (e.g. SEQ ID Nos 11, 12, or 13, or a portion thereof) derived from soybean strains SX6907 associated with enhanced rust (ASR) resistance with a second soybean plant or germplasm that lacks said genetic loci and optionally repeatedly backcrossing progeny plants comprising said genetic allele with the second soybean plant or germplasm to produce an soybean plant (e.g. *Glycine max*) or germplasm with enhanced pathogen resistance comprising the chromosomal interval derived from soybean strains SX6907 and/or ZRYCR1 associated with enhanced ASR resistance. In one embodiment, the chromosome interval comprises SEQ ID NO: 2. In another embodiment, the chromosome interval comprises SEQ ID NO: 1.

Progeny comprising the chromosomal interval associated with enhanced pathogen resistance may be identified by detecting, in their genomes, the presence of a marker associated with or genetically linked to said chromosomal interval derived from soybean accession number strains SX6907 and/or ZRYCR1 wherein said chromosomal interval comprises SEQ ID NOs 11, 12, or 13, or a portion thereof and the marker can be any of the favorable alleles as described in Table 1.

Soybean plants and/or germplasms identified, produced or selected by the methods of this invention are also provided, as are any progeny and/or seeds derived from a soybean plant or germplasm identified, produced or selected by these methods. In one embodiment molecular markers associating with the presence of a chromosomal intervals depicted in any one of SEQ ID NOs 11, 12, or 13 may be used to identify or select for plant lines resistant to ASR. Further said molecular markers may be located within 20 cM, 10 cM, 5 cM, 4 cM, 3 cM, 2 cM, and 1 cM of said chromosomal interval or from any respective favorable allele associated with ASR resistance as depicted in Table 1. In another embodiment, said molecular marker may be located within 20 cM, 10 cM, 5 cM, 4 cM, 3 cM, 2 cM, 1 cM of any SNP markers associated with ASR as described in Table 1.

Non-naturally occurring soybean seeds, plants and/or germplasms comprising one or genetic loci derived from strains SX6907 and/or ZRYCR1 associated with enhanced rust resistance are also provided. In specific embodiments said genetic loci comprises any one of SEQ ID NO: 11, 12, or 13, or a portion thereof and/or any favorable alleles as depicted in Table 1. In other embodiments, the genetic loci comprises the nucleic acid sequence of SEQ ID NO: 2 or a nucleic acid encoding the protein of SEQ ID NO: 1.

A marker associated with enhanced rust (ASR) resistance may comprise, consist essentially of or consist of a single allele or a combination of alleles at one or more genetic loci derived from strains SX6907 and/or ZRYCR1 that associate with enhanced pathogen (ASR) resistance. In one embodiment, the marker is within a chromosomal interval as described by SEQ ID NO: 11, 12, or 13. In another embodiment, the marker is within SEQ ID NO: 2. In another embodiment, the marker is any one of the favorable alleles as depicted in Table 1.

Additional compositions and methods for producing Glycine plants having enhanced disease resistance are also provided. In one aspect of the invention, there is provided a DNA construct that comprises a promoter that functions in plant cells operably linked to a DNA molecule encoding a protein having at least 80%100% homology to SEQ ID NO: 1. The current disclosure is also directed to DNA molecules. Exemplary DNA molecules include (B1) a DNA molecule shown in SEQ ID NO: 2; (B2) a DNA molecule hybridizing to the DNA molecule defined in (B1) under a stringent condition and encoding the protein; (B3) a DNA molecule having more than 99%, more than 95%, more than 90%, more than 85%, or more than 80% homology with the DNA sequences defined in (B1) and (B2) and encoding the protein.

In another aspect of the invention is directed to an expression cassette, a recombinant vector, a recombinant bacterium, or a transgenic cell line comprising the nucleic acid molecule. The invention is also directed to a method of preparing a fertile transgenic plant comprising providing a plant expression cassette comprising at least one of an RG21 gene and an RG22 gene and contacting recipient plant cells with the plant expression cassette under conditions permitting the uptake of the plant expression cassette by the recipient cells; selecting the recipient plant cells that contain the plant expression cassette; regenerating plants from the selected recipient plant cells; and identifying a fertile transgenic plant that is resistant to soybean pathogens, particularly ASR.

In another aspect of the invention there is provided a fertile transgenic plant that comprises a plant expression cassette as described above wherein the plant is resistant to soybean pathogens, particularly ASR.

In another aspect of the invention there is provided a method of controlling ASR in a field comprising the step of planting the seed from a plant comprising an expression cassette as described herein.

As a further aspect are seeds that produce the transgenic plants of the invention and seeds produced by the transgenic plants of the invention.

Also provided are harvested products derived from the transgenic plants of the invention, wherein the harvested product optionally comprises a nucleotide sequence, expression cassette, vector and/or at least one of a protein or DNA molecule of the invention. Further provided are processed products derived from the harvested products of the invention, wherein the harvested product optionally comprises a nucleotide sequence, expression cassette, vector and/or at least one of a protein or DNA molecule of the invention.

Still further, the disclosure provides as an additional aspect a method of producing a transgenic plant with increased resistance to a soybean pathogen. In embodiments, the method may comprise increasing the expression level and/or activity of a protein having at least 80%-100% homology to SEQ ID NO: 1. In another, the disclosure is directed to methods for breeding a plant variety with improved resistance against rust, comprising the step of increasing the expression level and/or activity of a protein having at least 80%-100% homology to SEQ ID NO: 1 in a recipient plant.

Compositions of the invention also include probes and primer pairs for detecting the novel resistance genes disclosed herein.

The foregoing and other objects and aspects of the present invention are explained in detail in the drawings and specification set forth below.

Figure 3:
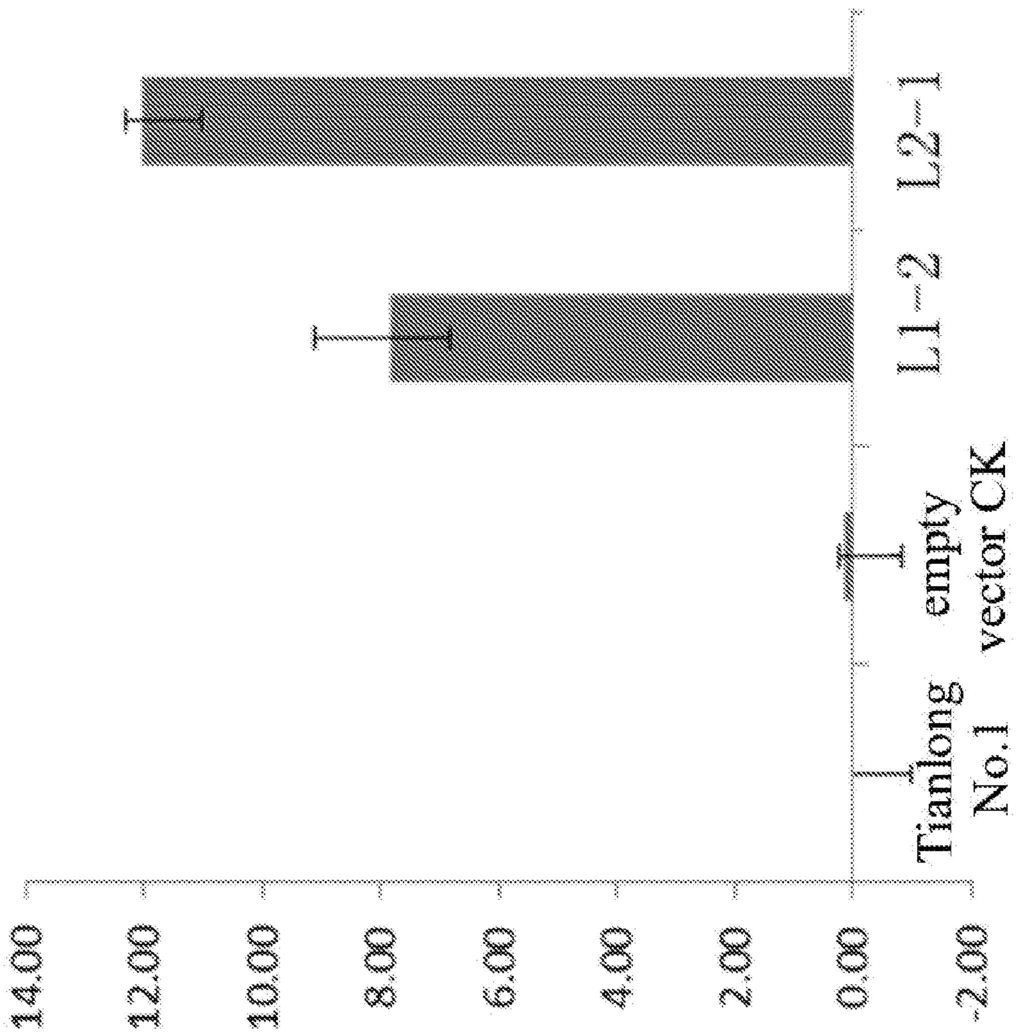

FIG. 3 shows the RT-PCR identification of the expression of RppRC1 gene in T1 generation of transgenic plants. L1-2 is an individual plant of the T1 plants of transformation event L1, and L2-1 is an individual plant of the T1 plants of transformation event L2.

Figure 4:
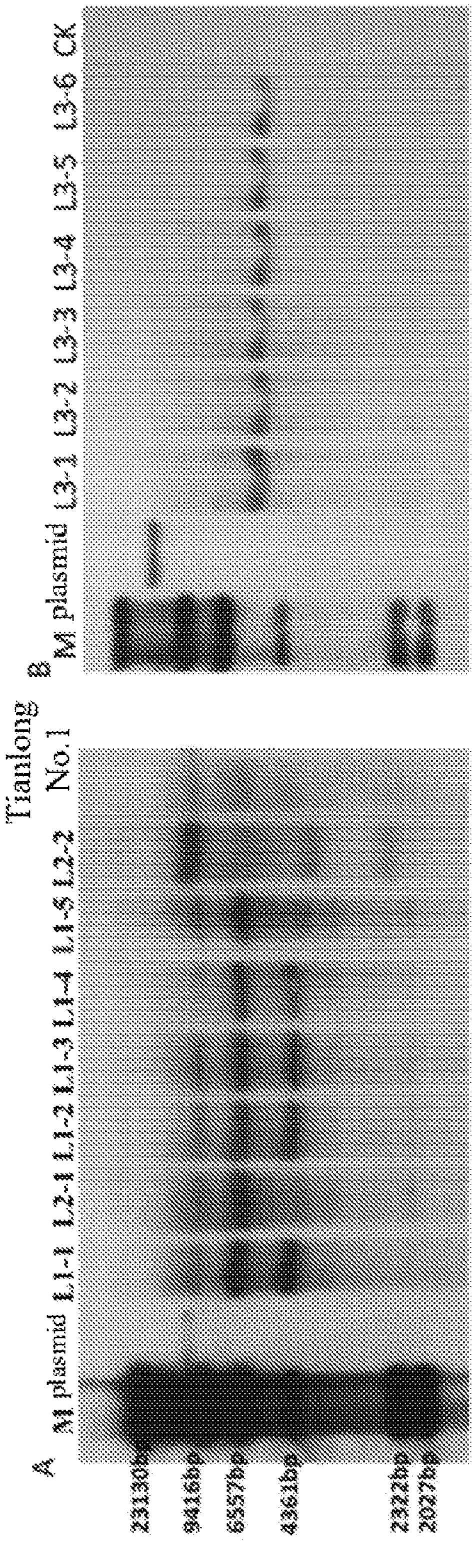

FIGS. 4A and 4B show the southern analysis of transgenic plants. FIG. 4A shows southern analysis of RppRC1 transgenic plants. L1-1, L1-2, L1-3, L1-4 and L1-5 are partial individual plants of the T1 plants of transformation event L1, respectively. L2-1 and L2-2 are partial individual plants of the T1 plants of transformation event L2, while Tianlong No. 1 is the negative control. FIG. 4B shows southern analysis of transgenic plants with empty vector. L3-1, L3-2, L3-3, L3-4, L3-5 and L3-6 were partial individual plants of the T1 plants of empty vector transformation event L3. CK is Tianlong No. 1.

Figure 5:
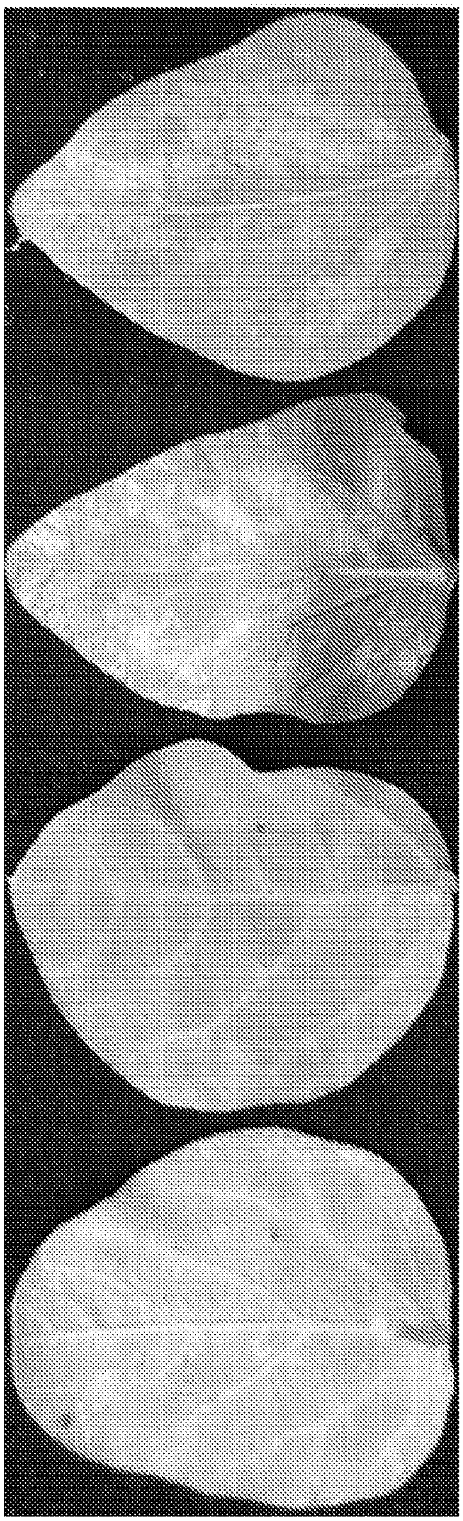

FIG. 5 shows the phenotype for resistance identification of T0 transgenic plants 12 days after inoculation. SX6907 is a resistance control and shows immunity; RppRC1 transformation event L2 shows immunity; empty vector transformation event L3 shows susceptibility; non-transgenic Tianlong No. 1 shows susceptibility.

Figure 6:
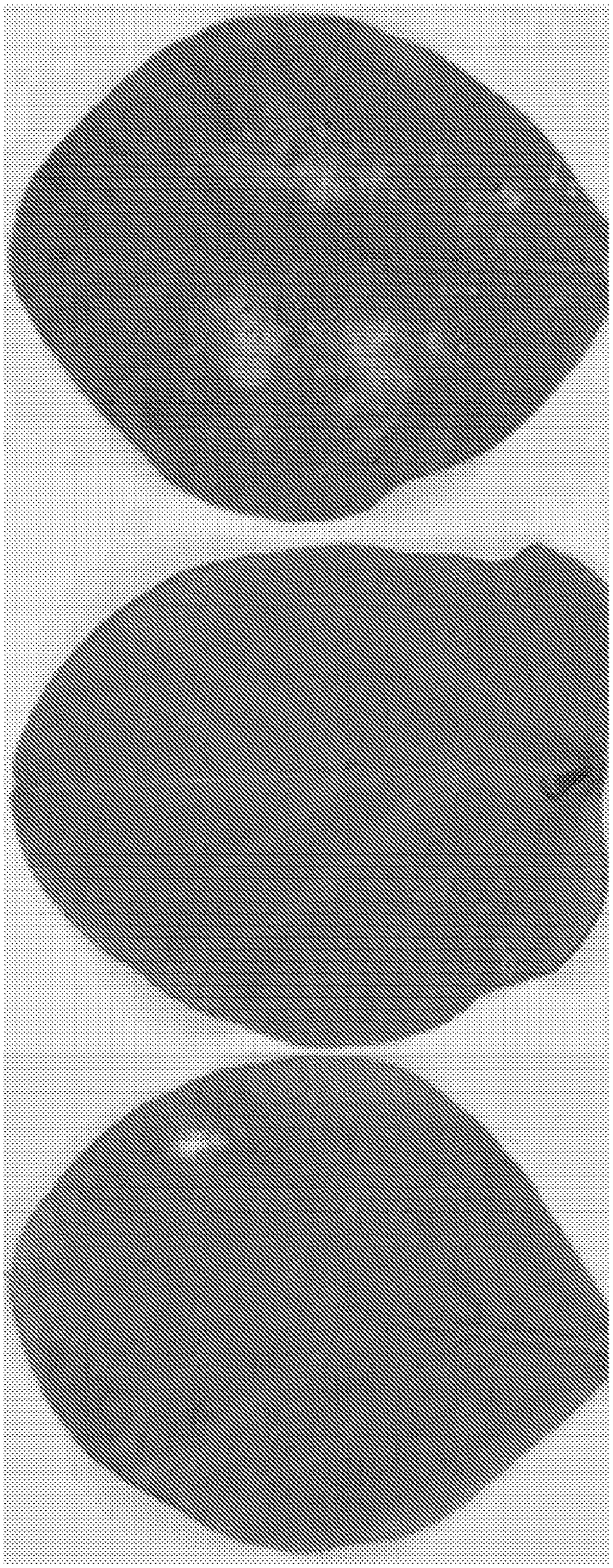

FIG. 6 shows the phenotype for resistance identification of T1 transgenic plants 12 days after inoculation. SX6907 is a resistance control and shows immunity; the individual plant L2-1 of the T1 plants of RppRC1 transformation event L2 shows immunity; the negative control Tianlong No. 1 shows susceptibility.

With reference to FIG. 1-6, the same transformation event is marked with the same label and the same individual plant is marked with the same label.

DETAILED DESCRIPTION OF ILLUSTRATIVE EMBODIMENTS

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

All patents, published patent applications, and publications cited herein are incorporated by reference as if set forth fully herein.

Unless defined otherwise, all technical and scientific terms used herein have the same meaning commonly understood to one of ordinary skill in the art to which this invention pertains. Otherwise, certain terms used herein have the meanings as set forth in the specification.

The instant application is directed to new genes encoding proteins for rust resistance and their use to provide rust resistance in plants, in particular in soybeans. In one embodiment of the invention, the gene is derived from soybean (*Glycine max*) SX6907.

Accordingly, in one aspect, the instant application provides proteins related to rust resistance in a plant, a coding gene and use thereof. In the invention, the resistance against rust of transgenic soybean obtained by transforming RppRC1 gene into soybean variety Tianlong No. 1 is significantly higher than that of wild-type soybean, indicating that RppRC1 and the coding gene thereof can regulate and control the resistance of leguminous plants against rust, and improve the rust resistance of plants after overexpression. RppRC1 and the coding gene thereof can be used to improve the disease resistance of leguminous crops and are of great significance for breeding new varieties with disease resistance.

Other aspects of the invention include methods for conveying rust resistance into non-resistant soybean germplasm or plant lines. Further the presently disclosed subject matter provides novel *Glycine max* lines comprising in its genome a chromosome interval, loci, and/or gene that is derived from *Glycine max* SX6907 and further confers soybean rust resistance in said novel *Glycine max* line.

Definitions

Unless defined otherwise, all technical and scientific terms used herein have the same meaning as commonly understood to one of ordinary skill in the art to which the presently disclosed subject matter belongs.

Although the following terms are believed to be well understood by one of ordinary skill in the art, the following definitions are set forth to facilitate understanding of the presently disclosed subject matter.

Unless explicitly stated otherwise in the context, the singular forms "a," "an," and "the" as used herein include multiple references. Thus, for example, references to "a cell" include a plurality of such cells, and references to "the protein" include references to one or more proteins and their equivalents known to those skilled in the art, and so on. Unless explicitly stated otherwise, all technical and scientific terms used herein have the same meanings generally understood by those of ordinary skill in the art to which the present invention belongs.

As used in the specification and claims, the term "comprise" and grammatical variations thereof may include aspects of "consist of" and "substantially consist of". "Comprise" and grammatical variations thereof may also mean "comprise, but not limited to".

As used herein, the word "or" refers to any member of a particular list and also comprises any combination of members of the list.

As used herein, the term "and/or" refers to and encompasses any and all possible combinations of one or more of the associated listed items, as well as the lack of combinations when interpreted in the alternative ("or").

The range may be expressed in the present invention as being from "about" one specific value and/or to "about" another specific value. When expressing such ranges, other aspects include from one specific value and/or to other specific values. Similarly, when the value is expressed as an approximation, it should be understood that by using the antecedent "about", the specific value forms another aspect. It should also be understood that the endpoints of each of the ranges are both significantly related to and independent of the other endpoint. It should also be understood that there are multiple values disclosed in the present invention and, in addition to the value itself, each value is also disclosed herein in the form of "about" the specific value. For example, if the value "10" is disclosed, "about 10" is also disclosed. It should also be understood that each unit between two specific units is also disclosed. For example, if 10 and 15 are disclosed, 11, 12, 13 and 14 are also disclosed.

The term "consists essentially of" (and grammatical variants thereof), as applied to a polynucleotide sequence of this invention, means a polynucleotide sequence that consists of both the recited sequence (e.g., SEQ ID NO) and a total of ten or less (e.g., 1, 2, 3, 4, 5, 6, 7, 8, 9, or 10) additional nucleotides on the 5' and/or 3' ends of the recited sequence such that the function of the polynucleotide is not materially altered. The total of ten or less additional nucleotides includes the total number of additional nucleotides on both ends added together. The term "materially altered," as applied to polynucleotides of the invention, refers to an increase or decrease in ability to express the polynucleotide sequence of at least about 50% or more as compared to the expression level of a polynucleotide sequence consisting of the recited sequence.

The term "introduced" as used herein, in connection to a plant, means accomplished by any manner including but not limited to; introgression, transgenic, Clustered Regularly Interspaced Short Palindromic Repeats modification (CRISPR), Transcription activator-like effector nucleases (TALENs) (Feng et al. 2013, Joung & Sander 2013), meganucleases, or zinc finger nucleases (ZFNs).

As used herein, the term "soybean" refers to soybean and any plant variety bred or cultured using soybean including "wild glycine" plants.

As used herein, the term "wild glycine" refers to a perennial Glycine plant, for example any one of *G. canescens, G. argyrea, G. clandestine, G. latrobeana, G. albicans, G. aphyonota, G. arenaria, G. curvata, G. cyrtoloba, G. dolichocarpa, G. falcate, G. gracei, G. hirticaulis, G. lactovirens, G. latifolia, G. microphylla, G. montis-douglas, G. peratosa, G. pescadrensis, G. pindanica, G. pullenii, G. rubiginosa, G. stenophita, G. syndetika*, or *G. tomentella.*

In the present invention, "nucleic acid" refers to a deoxyribonucleotide or ribonucleotide polymer in single-stranded or double-stranded form and, unless otherwise limited, encompasses known analogues (e.g., peptide nucleic acids) that have the basic properties of natural nucleotides in the following aspects: it hybridizes to single-stranded nucleic acids in a manner similar to that of naturally occurring nucleotides.

The term "a variant" and grammatical variations thereof refer to a substantially similar sequence. For nucleic acid molecules, variants comprise deletion and/or addition of one or more nucleotides at one or more sites in the native nucleic acid molecule, and/or substitution of one or more nucleotides at one or more sites in the native nucleic acid molecule.

The term "protein" refers to a polymer of amino acid residues. The term applies to amino acid polymers in which one or more amino acid residues are artificial chemical analogues of corresponding natural amino acids, and to natural amino acid polymers.

As used herein, a "native" nucleic acid molecule or protein comprises a naturally occurring nucleotide sequence or an amino acid sequence, respectively.

As used herein, the term "coding" or "encoding" and grammatical variations thereof are used to mean that a nucleic acid comprises the desired information, which is specified by the use of codons to direct the translation of nucleotide sequences (for example, leguminous sequences) into specific proteins. A nucleic acid coding a protein may comprise an untranslated sequence (e.g., an intron) within the translation region of the nucleic acid or may lack such an intermediate untranslated sequence (e.g., as in cDNA).

As used herein, the term "allele" refers to one of two or more different nucleotides or nucleotide sequences that occur at a specific locus.

A marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced pathogen resistance" refers to a marker whose presence or absence can be used to predict whether and/or to what extent a plant will display a pathogen resistant phenotype (e.g. any favorable SNP allele as described herein are "associated with" ASR (rust) resistance in a soybean plant).

As used herein, the terms "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example, in* Techniques et Utilisations des Marqueurs Moleculaires Les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-53 (1994). The initial cross gives rise to the F1 generation. The term "BC1" refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval defined by and including," used in reference to particular loci and/or alleles, refers to a chromosomal interval delimited by and encompassing the stated loci/alleles.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "desired allele", "favorable allele" and "allele of interest" are used interchangeably to refer to an allele associated with a desired trait (e.g. ASR resistance).

As used herein, the terms "inhibit," "reduce," etc., and grammatical variations thereof refer to any reduction in the expression or function of a target gene product, including any relative reduction in the expression or function up to and including complete elimination of the expression or function of the target gene product.

The term "enhance" and grammatical variations thereof refer to improvement, increase, amplification, reproduction, rise and/or elevation to reduce one or more disease symptoms.

As used herein, the terms "increase", "enhance" etc., and grammatical variations thereof are used to refer to any promotion or gain or increase in the expression, function or activity of a product of a target gene (for example, a resistance gene) as compared to a susceptible plant, thereby providing increased resistance to one or more pathogens (for example, *Phakopsora*) or diseases (for example, rust). Additionally, as used herein, the term "cause" or "increase" and grammatical variations thereof may refer to a higher expression of a target gene product such that the level is increased by 10% or more, 50% or more, or 100%, relative to a cell or plant lacking the target gene or protein disclosed herein.

The term "immunity" or "immune" is used in the present invention to refer to the absence of any macroscopically visible disease symptoms. The term "partial resistance" is used in the present invention to refer to the presence of macroscopically visible lesions without or with limited spore formation and/or a reduction in the scope or degree of any disease symptoms and/or a delay in the progression of any disease symptoms, and may, for example, manifest a reduction in the number of lesions or lesions with reduced spore formation. As used herein, the term "susceptibility" or the phrase "lack of resistance" in terms of rust refers to the occurrence of a lesion in the case where the spore formation level is equal to or higher than the spore formation level observed in a reference standard, such as, for example, the variety Williams or Peking.

The term "resistance" is used herein to refer to the absence or reduction of one or more disease symptoms caused by plant pathogens in plants. Resistance may mean that disease symptoms, such as the number of diseased plants, defoliation, and associated yield loss, are reduced, minimized or decreased when compared to plants susceptible to the diseases or plants that do not comprise effective resistance genes that reduce one or more disease symptoms. In addition, resistance may include prevention or delay of pathogen proliferation. Generally speaking, the term "resistance" includes immunity and partial resistance as defined above.

As used herein, the terms "enhanced pathogen resistance", "enhanced plant pathogen resistance", or "enhanced disease resistance" refers to an improvement, enhancement, or increase in a plant's ability to endure and/or thrive despite being infected with a disease (e.g. Asian soybean rust) as compared to one or more control plants (e.g., one or both of the parents, or a plant lacking a marker associated with enhanced pathogen resistance to respective pathogen/disease). Enhanced disease resistance includes any mechanism (other than whole-plant immunity or resistance) that reduces the expression of symptoms indicative of infection for a respective disease such as Asian soybean rust, soybean cyst nematode, *Phytophthora*, etc.

"A plant pathogen" and grammatical variations thereof can be used herein to refer to, for example, a fungal pathogen of the genus *Phakopsora* of the class Basidiomycetes (including *Phakopsora pachyrhizi* and *Phakopsora meibomiae*). The plant diseases or the diseases of leguminous crops may be, for example, rust.

The term "disease resistance gene" or "resistance gene" is used in the present invention to refer to a gene encoding a protein capable of enhancing or improving the defense or immune system response in plants.

The term "orthologue" and grammatical variations thereof refer to genes derived from common ancestral genes and present in different species due to speciation.

An "elite line" or "elite strain" is an agronomically superior line that has resulted from many cycles of breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean.

An "elite" plant is any plant from an elite line, such that an elite plant is a representative plant from an elite variety. Non-limiting examples of elite soybean varieties that are commercially available to farmers or soybean breeders include: AG00802, A0868, AG0902, A1923, AG2403, A2824, A3704, A4324, A5404, AG5903, AG6202 AG0934; AG1435; AG2031; AG2035; AG2433; AG2733; AG2933; AG3334; AG3832; AG4135; AG4632; AG4934; AG5831; AG6534; and AG7231 (Asgrow Seeds, Des Moines, Iowa, USA); BPR0144RR, BPR 4077NRR and BPR 4390NRR (Bio Plant Research, Camp Point, Ill., USA); DKB17-51 and DKB37-51 (DeKalb Genetics, DeKalb, Ill., USA); DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS 13-K2 (NK Division of Syngenta Seeds, Golden Valley, Minnesota, USA); 90M01, 91M30, 92M33, 93M11, 94M30, 95M30, 97B52, P008T22R2; P16T17R2; P22T69R; P25T51R; P34T07R2; P35T58R; P39T67R; P47T36R; P46T21R; and P56T03R2 (Pioneer Hi-Bred International, Johnston, Iowa, USA); SG4771NRR and SG5161NRR/STS (Soygenetics, LLC, Lafayette, Ind., USA); S00-K5, S11-L2, S28-Y2, S43-B1, S53-A1, S76-L9, S78-G6, 50009-M2; S007-Y4; S04-D3; S14-A6; S20-T6; S21-M7; S26-P3; S28-N6; S30-V6; S35-C3; S36-Y6; S39-C4; S47-K5; S48-D9; S52-Y2; S58-Z4; S67-R6; S73-S8; and S78-G6 (Syngenta Seeds, Henderson, Ky., USA); Richer (Northstar Seed Ltd. Alberta, CA); 14RD62 (Stine Seed Co. Ia., USA); or Armor 4744 (Armor Seed, LLC, Ar., USA).

The terms "agronomically elite" as used herein, means a genotype that has a culmination of many distinguishable traits such as emergence, vigor, vegetative vigor, disease resistance, seed set, standability, yield and threshability which allows a producer to harvest a product of commercial significance.

As used herein, the term "commercially significant yield" or "agronomically acceptable yield" refers to a grain yield of at least 100% of a commercial check variety such as AG2703 or DKB23-51.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

The term "germplasm" is used in the present invention to refer to genetic material derived from an individual (e.g., a plant), a group of individuals (e.g., a plant germline, variety, or family), or a clone derived from a strain, variety, species, or culture. Germplasm can be part of an organism or a cell, or can be isolated from an organism or a cell. Germplasm provides genetic material having a specific molecular composition that provides the physical basis for some or all of the genetic properties of an organism or cell culture A "genetic map" is a description of genetic linkage relationships among loci on one or more chromosomes within a given species, generally depicted in a diagrammatic or tabular form. For each genetic map, distances between loci are measured by the recombination frequencies between them. Recombinations between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety, or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm may refer to seeds, cells (including protoplasts and calli) or tissues from which new plants may be grown, as well as plant parts that can be cultured into a whole plant (e.g., stems, buds, roots, leaves, etc.).

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" refers to a seed and/or plant produced when at least two genetically dissimilar parents are crossed.

As used herein, the term "inbred" refers to a substantially homozygous plant or variety. The term may refer to a plant or variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be repeatedly backcrossed to a line having a desired genetic background and selected for the desired allele, with the result being that the desired allele becomes fixed in the desired genetic background. For example, a marker associated with enhanced ASR tolerance may be introgressed from a donor into a recurrent parent that is not disease resistant. The resulting offspring could then be repeatedly backcrossed and selected until the progeny possess the ASR tolerance allele(s) in the recurrent parent background.

As used herein, the term "linkage" refers to the degree with which one marker locus is associated with another marker locus or some other locus (for example, an ASR tolerance locus). The linkage relationship between a molecular marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM). For example, embodiments of the invention herein, provide for marker loci closely linked to ASR resistant chromosomal intervals comprising a nucleotide sequence of any one of SEQ ID NOs 2, 11, 12, or 13.

In some aspects of the present invention, it is advantageous to define a bracketed range of linkage, for example, from about 10 cM and about 20 cM, from about 10 cM and about 30 cM, or from about 10 cM and about 40 cM. The more closely a marker is linked to a second locus, the better an indicator for the second locus that marker becomes. Thus, "closely linked loci" such as a marker locus and a second locus display an inter-locus recombination frequency of about 10%, 9%, 8%, 7%, 6%, 5%, 4%, 3%, or 2% or less. In some embodiments, the relevant loci display a recombination frequency of about 1% or less, e.g., about 0.75%, 0.5%, 0.25% or less. Two loci that are localized to the same chromosome, and at such a distance that recombination between the two loci occurs at a frequency of less than about 10% (e.g., about 9%, 8%, 7%, 6%, 5%, 4%, 3%, 2%, 1%, 0.75%, 0.5%, or 0.25%, or less) may also be said to be "proximal to" each other. Since one cM is the distance between two markers that show a 1% recombination frequency, any marker is closely linked (genetically and physically) to any other marker that is in close proximity, e.g., at or less than about 10 cM distant. Two closely linked markers on the same chromosome may be positioned about 9, 8, 7, 6, 5, 4, 3, 2, 1, 0.75, 0.5 or 0.25 cM or less from each other.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., Asian Soybean Rust. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a gene or marker or allele is located. In some embodiments, a locus may encompass one or more nucleotides.

As used herein, the terms "marker" and "genetic marker" are used interchangeably to refer to a nucleotide and/or a nucleotide sequence that has been associated with a phenotype, trait, or trait form. In some embodiments, a marker may be associated with an allele or alleles of interest and may be indicative of the presence or absence of the allele or alleles of interest in a cell or organism. A marker may be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234:177 (1993)), a sequence-characterized amplified region (SCAR) (Paran and Michelmore, *Theor. Appl. Genet.* 85:985 (1993)), a sequence-tagged site (STS) (Onozaki et at, *Euphytica* 138: 255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), a chromosome interval, or an RNA cleavage product (such as a Lynx tag). A marker may be present in genomic or expressed nucleic acids (e.g., ESTs). The term marker may also refer to nucleic acids used as probes or primers (e.g., primer pairs) for use in amplifying, hybridizing to and/or detecting nucleic acid molecules according to methods well known in the art. A large number of soybean molecular markers are known in the art, and are published or available from various sources, such as the SoyBase internet resource.

Markers corresponding to genetic polymorphisms between members of a population can be detected by methods well-established in the art. These include, e.g., nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. In some embodiments, marker genotypes are used to identify plants that will be selected for a breeding program or for planting. In some embodiments, marker genotypes are used to identify plants that will not be selected for a breeding program or for planting (i.e., counter-selected plants), allowing them to be removed from the breeding/planting population.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus.

As used herein, the terms "molecular marker" or "genetic marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein are also referred to as hybridization markers when located on an indel region. This is because the insertion region is, by definition, a polymorphism vis-ã-vis a plant without the insertion. Thus, the marker need only indicate whether the indel region is present or absent. Any suitable marker detection technology may be used to identify such a hybridization marker, e.g., SNP technology is used in the examples provided herein.

A "non-naturally occurring variety of soybean" is any variety of soybean that does not naturally exist in nature. A "non-naturally occurring variety of soybean" may be produced by any method known in the art, including, but not limited to, transforming a soybean plant or germplasm, transfecting a soybean plant or germplasm and crossing a naturally occurring variety of soybean with a non-naturally occurring variety of soybean. In some embodiments, a "non-naturally occurring variety of soybean" may comprise one of more heterologous nucleotide sequences. In some embodiments, a "non-naturally occurring variety of soybean" may comprise one or more non-naturally occurring copies of a naturally occurring nucleotide sequence (i.e., extraneous copies of a gene that naturally occurs in soybean). In some embodiments, a "non-naturally occurring variety of soybean" may comprise a non-natural combination of two or more naturally occurring nucleotide sequences (i.e., two or more naturally occurring genes that do not naturally occur in the same soybean, for instance genes not found in *Glycine max* lines).

The term "transformation" and grammatical variations thereof are used in the present invention to refer to, for example, the transfer of nucleic acid fragments into the genome of a host organism, thus obtaining genetically stable heredity. The host organism comprising the transformed nucleic acid fragments is called a "transgenic" organism. The term "host cell" and grammatical variations thereof refer to a cell in which transformation of a recombinant DNA construct takes place and may include yeast cells, bacterial cells and/or plant cells.

As used herein, the term "transgenic" and grammatical variations thereof refer to a plant, including any part derived from the plant, such as a cell, tissue or organ, in which an exogenous nucleic acid (for example, a recombinant construct, vector or expression cassette comprising one or more nucleic acids) is integrated into the genome by a genetic engineering method, such as *Agrobacterium* transformation. Through gene technology, the exogenous nucleic acid is stably integrated into chromosomes, so that the next generation can also be transgenic. As used herein, "transgenic" and grammatical variations thereof also encompass biological treatments, which include plant hybridization and/or natural recombination.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing. Primers can be prepared by any suitable method known in the art. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066. Primers can be labeled, if desired, by incorporating detectable moieties by for instance spectroscopic, fluorescence, photochemical, biochemical, immunochemical, or chemical moieties. Primers diagnostic (i.e. able to identify or select based on presence of ASR resistant alleles) for ASR resistance can be created to any favorable SNP as described in Table 1. The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). Molecular Cloning: A Laboratory Manual, Third Edition, Cold Spring Harbor Laboratory Press, Cold Spring Harbor, New York, United States of America. Generally, lower salt concentration and higher temperature hybridization and/or washes increase the stringency of hybridization conditions.

As used herein, the terms "phenotype," "phenotypic trait" or "trait" refer to one or more traits and/or manifestations of an organism. The phenotype can be a manifestation that is observable to the naked eye, or by any other means of evaluation known in the art, e.g., microscopy, biochemical analysis, or an electromechanical assay. In some cases, a phenotype or trait is directly controlled by a single gene or genetic locus, i.e., a "single gene trait." In other cases, a phenotype or trait is the result of several genes. It is noted that, as used herein, the term "disease resistant phenotype" takes into account environmental conditions that might affect the respective disease such that the effect is real and reproducible.

As used herein, the term "plant" and grammatical variations thereof may refer to a whole plant, any part thereof, or a cell or tissue culture derived from a plant. Thus, the term "plant" can refer to any of: whole plants, plant components or organs (e.g., roots, stems, leaves, buds, flowers, pods, etc.), plant tissues, seeds and/or plant cells. Plant cells are cells of plants, which are obtained directly from seeds or plants, or derived from cell cultures obtained from plants. Progenies, variants, and mutants of regenerated plants are within the scope of the present invention, provided that these parts comprise the introduced resistance genes. Thus, the term "soybean plant" may refer to a whole soybean plant, one or more parts of a soybean plant (e.g., roots, root tips, stems, leaves, buds, flowers, pods, seeds, cotyledons, etc.), soybean plant cells, soybean plant protoplasts and/or soybean plant calli.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue culture from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "polymorphism" refers to a variation in the nucleotide sequence at a locus, where said variation is too common to be due merely to a spontaneous mutation. A polymorphism can be a single nucleotide polymorphism (SNP) or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the terms "closely linked" refers to linked markers displaying a cross over frequency with a given marker of about 10% or less (e.g. the given marker is within about 10 cM of a closely linked ASR marker). Put another way, closely linked loci co-segregate at least about 90% of the time. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less.

As used herein, the term "population" refers to a genetically heterogeneous collection of plants sharing a common genetic derivation.

As used herein, the terms "progeny" and "progeny plant" refer to a plant generated from a vegetative or sexual reproduction from one or more parent plants. A progeny plant may be obtained by cloning or selfing a single parent plant, or by crossing two parental plants.

As used herein, the term "reference sequence" refers to a defined nucleotide sequence used as a basis for nucleotide sequence comparison. The reference sequence for a marker, for example, is obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

As used herein, the terms "disease tolerance" and "disease resistant" refer to a plant's ability to endure and/or thrive despite being infected with a respective disease. When used in reference to germplasm, the terms refer to the ability of a plant that arises from that germplasm to endure and/or thrive despite being infected with a respective disease. In some embodiments, infected Disease resistant soybean plants may yield as well (or nearly as well) as uninfected soybean plants. In general, a plant or germplasm is labeled as "Disease resistant" if it displays "enhanced pathogen resistance."

An "unfavorable allele" of a marker is a marker allele that segregates with the unfavorable plant phenotype, therefore providing the benefit of identifying plants that can be removed from a breeding program or planting. For instance, one could eliminate from a plant breeding program plant lines carrying unfavorable alleles for ASR resistance.

Plant Rust

The present invention pertains to proteins related to rust resistance in plants, nucleic acid sequence encoding such proteins, and uses thereof. The protein and the coding gene thereof and method disclosed in the invention can be used to protect plants from rust pathogens. In certain embodiments, the rust is leguminous plant rust.

In other embodiments, the leguminous plant rust is soybean rust. The pathogen of soybean rust may be *Phakopsora pachyrhizi* or *Phakopsora meibomiae*. As used below and in the claims each reference to soybean rust includes Asian soybean rust.

In a specific embodiment of the present invention, the pathogen of soybean rust is specifically the physiological race SS4 of *Phakopsora pachyrhizi.*

In preferred embodiments, the present invention pertains to proteins related to rust resistance in a leguminous plant.

The leguminous plant can be Glycine plants, *Cicer* plants, *Cajanus* plants, *Lablab* plants, *Medicago* plants, *Phaseolus* plants, *Pisum* plants, *Pueraria* plants, *Trifolium* plants or *Vigna* plants.

The Glycine plants can be *Glycine arenaria, Glycine argyrea, Glycine cyrtoloba, Glycine canescens, Glycine clandestine, Glycine curvata, Glycine falcata, Glycine latifolia, Glycine microphylla, Glycine pescadrensis, Glycine stenophita, Glycine syndetica, Glycine soja Seib.* et *Zucc.*, *Glycine max* (L.) Merrill., *Glycine tabacina* or *Glycine tomentella.*

The *Cicer* plants can be *Cicerarietinum, Cicer echinospermum, Cicer reticulatum* or *Cicer pinnatifidum.*

The Lablab plants can be *Lablab purpureus.*

The *Medicago* plants can be *Medicago truncatula* or *Medicago sativa.*

The *Phaseolus* plants can be *Phaseolus vulgaris, Phaseolus lunatus, Phaseolus acutifolius*, or *Phaseolus coccineus.*

The *Pisum* plants can be *Pisum abyssinicum, Pisum sativum, Pisum elatius, Pisum fulvum, Pisum transcaucasium*, or *Pisumhumile.*

The *Pueraria* plants can be *Pueraria lobata.*

The *Trifolium* plants can be *Trifolium aureum* or *Trifolium occidentale.*

The *Vigna* plants can be *Vigna unguiculata, Vigna dalzelliana, Vigna oblongifolia, Vigna parkeri, Vignafilicaulis, Vigna kirkii, Vigna luteola, Vigna radiata, Vigna trilobata, Vigna luteola*, or *Vigna mungo.*

Furthermore, the leguminous plant can be any of the following: soybean, alfalfa, clover, pea, common bean, lentil, lupin, ghaf tree, carob bean, soybean, peanut, or tamarind.

In a specific embodiment of the present invention, the plant is specifically soybean variety Tianlong No. 1 (天隆一号)

The protein and the coding gene thereof and method disclosed in the invention can be used to protect plants from rust pathogens. The interaction between hosts and pathogens can be described as a continuum of "immunity" to "partial resistance" to "susceptibility".

The method disclosed in the invention can increase, enhance, or improve the resistance of soybean to an obligatory biotrophic parasitic fungus *Phakopsora pachyrhizi* (the main pathogen of rust) or to *Phakopsora meibomiae*. For example, increased or enhanced resistance against rust pathogens can be compared with the impact of pathogens on susceptible plants. The manifestations of increased or enhanced resistance may be at different levels, but are related to the disease symptoms (such as the color of the disease spots) and the morbidity observed on plants or plant tissues (for example, leaves). The values of immunity, resistance and susceptibility can be given. For example, the value of resistance indicates the degree of resistance of plants to plant diseases (for example, rust). The values can also be used to compare the degree of resistance between, for example, plants of interest (e.g., transgenic leguminous plants) and susceptible plants (e.g., Tianlong No. 1 (天隆一号) or Williams) or reference standards.

The protein and the encoding gene thereof and the methods disclosed in the present invention relate to the isolation of a resistance gene from leguminous species and subsequent transfer of the resistance gene to a recipient plant, such as soybean, to provide or enhance resistance to *Phakopsora pachyrhizi*. One embodiment of the application includes transferring the resistance gene to sexually compatible or incompatible species to produce disease resistance. The resistance gene of the present invention can be used alone or in superposition with other resistance genes or together with non-resistance genes to provide or enhance the resistance of the recipient species against rust.

Therefore, the transgenic method disclosed in the present invention can be used alone or in combination with other strategies to produce or confer rust resistance in plants. Other available strategies include, but are not limited to, blocking the functional activity of effectors, inhibiting the uptake of pathogens or pathogen factors (e.g., fungi) into host cells (e.g., plant cells) and/or conventional resistance breeding.

The method disclosed in the present invention can provide or enhance the rust resistance of plants, so that the pathogen of rust cannot reproduce or the reproduction coefficient of the pathogen of rust is significantly reduced. Therefore, the method of the present invention can alleviate one or more symptoms (i.e. disease symptoms) of leguminous plant rust when compared with plants susceptible or tolerant to the genus *Phakopsora*. The plants referred to in the present invention also include transgenic leguminous plants (e.g., soybean) into which disease resistance genes or proteins are introduced by genetic engineering methods so as to enhance their resistance to diseases when exposed to leguminous plant rust.

The plants, plant parts or plant cells of the present invention are derived from plants that include, but are not limited to soybean, alfalfa, clover, pea, common bean, lentil, lupin, ghaf tree, carob, peanut, and tamarind.

The plants of the invention belong to Leguminosae. Examples of Leguminosae include, but are not limited to, *Phaseolus* (for example, French bean, string bean, *Phaseolus vulgaris, Phaseolus lunatus, Phaseolus acutifolius*, and *Phaseolus coccineus*); Glycine (for example, *Glycine soja*, and *Glycine max* (L.)); *Pisum* (for example, de-podded pea (sometimes referred to as smooth pea or round pea, *Pisum sativum* (菜豌豆)), *Pisum sativum* (皱粒豌豆), *Pisum sativum* (糖荚豌豆) which is also known as snow pea, edible-podded pea or *Pisum granda*); peanut (*Arachis hypogaea*), clover (*Trifolium* spp.), alfalfa (*Medicago*), kudzu (*Pueraria lobata*), common alfalfa, alfalfa (*Medicago sativa*), chickpea (*Cicer*), lentil (*Lens culinaris*), and lupin (*Lupinus*); vetch (*Vicia*), broad bean (*Vicia faba*), vetchling (*Lathyrus*) (for example, *Lathyrus sativus*, and *Lathyrus tuberosus*); *Vigna* (for example, *Vigna aconitifolia, Vigna angularis, Vigna mungo, Vigna radiata, Vigna subterrane, Vigna umbellata, Vigna vexillata*, and *Vigna unguiculata* (also known as long cowpea or cowpea)); *Cajanus cajan, Macrotyloma* (for example, *Macrotyloma geocarpum*, and *Macrotyloma uniflorum*); *Psophocarpus tetragonolobus, Sphenostyhs stenocarpa*, Egyptian black beans, *Lablab purpureus, Pachyrhizus erosus*, and *Cyamopsis tetragonolobus*; and/or *Canavalia* (for example, *Canavalia ensiformis*, and *Canavalia gladiata*).

Chromosomal Intervals

One embodiment of the invention is directed to chromosomal intervals derived from *Glycine max* strain SX6907. These chromosomal intervals when introduced into a plant (e.g. a soybean such a *Glycine max* strain Williams 82) are sufficient to confer increased rust resistance, such as e.g. Asian soybean rust (ASR) resistance, as compared to a control plant not comprising said chromosomal interval.

SEQ ID NOs 11, 12, or 13 are chromosomal interval derived from *Glycine max* strain SX6907. Genetic mapping studies indicate that *Glycine max* strain SX6907 contains chromosomal intervals associated with ASR resistance (e.g. corresponding to S SEQ ID NOs 11, 12, or 13). These chromosomal intervals or portions thereof may be introduced (i.e. introgressed through use of marker assisted breeding (MAB), or through use of GM or GE introduction) into *Glycine max* lines to create *Glycine max* lines resistant to various diseases such as ASR. For example, these chromosomal intervals may be introduced into *Glycine max* line Williams 82.

Table 1 indicates single nucleotide polymorphisms (SNP) within SEQ ID NOs 11, 12, or 13 that are associated with ASR resistance.

TABLE 1

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56601565 | A | AC |
| Gm18 | 56601634 | T | C |
| Gm18 | 56602295 | G | T |
| Gm18 | 56602866 | G | GA |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56602929 | T | A |
| Gm18 | 56604482 | G | GATATATAT |
| Gm18 | 56604846 | C | T |
| Gm18 | 56605172 | GTATATTTATATATATA TATATATA (SEQ ID NO: 14) | G |
| Gm18 | 56605243 | G | T |
| Gm18 | 56605859 | A | AATATGCTTT (SEQ ID NO: 15) |
| Gm18 | 56605869 | ATATG | A |
| Gm18 | 56605893 | A | G |
| Gm18 | 56605895 | A | G |
| Gm18 | 56605897 | A | G |
| Gm18 | 56605899 | A | G |
| Gm18 | 56605901 | A | G |
| Gm18 | 56606593 | TA | T |
| Gm18 | 56606764 | C | T |
| Gm18 | 56607175 | T | C |
| Gm18 | 56608059 | T | C |
| Gm18 | 56609308 | C | T |
| Gm18 | 56609424 | A | G |
| Gm18 | 56609508 | A | T |
| Gm18 | 56609511 | C | G |
| Gm18 | 56609554 | T | G |
| Gm18 | 56610268 | T | C |
| Gm18 | 56610625 | T | TAAG |
| Gm18 | 56611386 | T | A |
| Gm18 | 56612772 | C | CTATATA |
| Gm18 | 56613273 | C | T |
| Gm18 | 56613352 | A | G |
| Gm18 | 56613400 | C | T |
| Gm18 | 56613421 | C | T |
| Gm18 | 56613787 | TA | T |
| Gm18 | 56614286 | T | A |
| Gm18 | 56614344 | G | GA |
| Gm18 | 56614630 | A | G |
| Gm18 | 56614906 | G | GT |
| Gm18 | 56615544 | CT | C |
| Gm18 | 56615626 | A | ATG |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56615677 | T | A |
| Gm18 | 56616069 | C | A |
| Gm18 | 56616107 | T | A |
| Gm18 | 56616637 | T | C |
| Gm18 | 56616692 | A | T |
| Gm18 | 56616778 | T | A |
| Gm18 | 56616824 | C | T |
| Gm18 | 56616825 | T | G |
| Gm18 | 56616833 | A | G |
| Gm18 | 56616839 | C | T |
| Gm18 | 56616844 | T | C |
| Gm18 | 56616894 | A | G |
| Gm18 | 56616903 | TGGGTCAACCTGAATG AGTCAGGGTTGACCCA AA(SEQ ID NO: 16) | T |
| Gm18 | 56616938 | CGA | C |
| Gm18 | 56616943 | AT | A |
| Gm18 | 56616965 | ATT | A |
| Gm18 | 56616973 | TAAAAA | T |
| Gm18 | 56616996 | T | TAA |
| Gm18 | 56616997 | T | A |
| Gm18 | 56617058 | A | G |
| Gm18 | 56617072 | AC | A |
| Gm18 | 56617119 | C | A |
| Gm18 | 56617143 | CTTTCTTTAATT (SEQ ID NO: 17) | C |
| Gm18 | 56617792 | A | C |
| Gm18 | 56618125 | C | G |
| Gm18 | 56618647 | TA | T |
| Gm18 | 56621101 | T | C |
| Gm18 | 56621162 | C | A |
| Gm18 | 56621217 | A | C |
| Gm18 | 56621385 | G | A |
| Gm18 | 56621559 | C | G |
| Gm18 | 56621731 | G | A |
| Gm18 | 56621822 | A | G |
| Gm18 | 56621836 | T | C |
| Gm18 | 56621857 | C | T |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56621899 | T | C |
| Gm18 | 56621936 | T | A |
| Gm18 | 56621937 | G | GAA |
| Gm18 | 56621943 | G | A |
| Gm18 | 56622058 | A | AT |
| Gm18 | 56622285 | T | C |
| Gm18 | 56622585 | A | ATGG |
| Gm18 | 56622602 | A | T |
| Gm18 | 56622637 | A | G |
| Gm18 | 56622642 | T | G |
| Gm18 | 56622853 | T | A |
| Gm18 | 56622862 | A | G |
| Gm18 | 56622906 | G | T |
| Gm18 | 56622925 | C | T |
| Gm18 | 56623192 | TC | T |
| Gm18 | 56623667 | A | G |
| Gm18 | 56623903 | C | T |
| Gm18 | 56624060 | C | T |
| Gm18 | 56624065 | T | G |
| Gm18 | 56624185 | AT | A |
| Gm18 | 56624351 | AC | A |
| Gm18 | 56624404 | A | AAAGT |
| Gm18 | 56624427 | T | C |
| Gm18 | 56624464 | A | G |
| Gm18 | 56624551 | G | T |
| Gm18 | 56624606 | C | A |
| Gm18 | 56624609 | TTAA | T |
| Gm18 | 56624664 | G | A |
| Gm18 | 56624955 | C | T |
| Gm18 | 56625057 | C | A |
| Gm18 | 56625513 | A | G |
| Gm18 | 56625553 | A | AATAT |
| Gm18 | 56625571 | A | C |
| Gm18 | 56625591 | C | G |
| Gm18 | 56625648 | C | T |
| Gm18 | 56625668 | AGAT | A |
| Gm18 | 56625720 | C | T |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56625722 | T | A |
| Gm18 | 56625799 | A | G |
| Gm18 | 56625966 | A | G |
| Gm18 | 56626008 | G | A |
| Gm18 | 56626041 | G | T |
| Gm18 | 56626052 | C | T |
| Gm18 | 56626063 | T | G |
| Gm18 | 56626080 | T | G |
| Gm18 | 56626449 | T | G |
| Gm18 | 56626566 | G | A |
| Gm18 | 56626575 | A | G |
| Gm18 | 56626903 | T | C |
| Gm18 | 56626915 | C | G |
| Gm18 | 56626974 | ACATAC | A |
| Gm18 | 56627161 | A | AATAT |
| Gm18 | 56627238 | C | T |
| Gm18 | 56627264 | A | C |
| Gm18 | 56627287 | GT | G |
| Gm18 | 56627317 | A | G |
| Gm18 | 56627338 | G | A |
| Gm18 | 56627360 | T | TA |
| Gm18 | 56627382 | C | A |
| Gm18 | 56627386 | C | T |
| Gm18 | 56627412 | C | G |
| Gm18 | 56627575 | A | T |
| Gm18 | 56627577 | T | C |
| Gm18 | 56627857 | T | G |
| Gm18 | 56627967 | A | G |
| Gm18 | 56628395 | A | G |
| Gm18 | 56628450 | C | G |
| Gm18 | 56629061 | CTG | C |
| Gm18 | 56629276 | G | A |
| Gm18 | 56629622 | T | C |
| Gm18 | 56629688 | C | T |
| Gm18 | 56629764 | T | A |
| Gm18 | 56630232 | T | A |
| Gm18 | 56630293 | AT | A |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56630337 | C | T |
| Gm18 | 56630348 | C | T |
| Gm18 | 56630383 | C | G |
| Gm18 | 56630411 | T | C |
| Gm18 | 56630490 | G | A |
| Gm18 | 56630497 | A | ATTCAAAAATATTTTTTT AATAATT (SEQ ID NO: 18) |
| Gm18 | 56630555 | C | T |
| Gm18 | 56630572 | A | G |
| Gm18 | 56630585 | A | C |
| Gm18 | 56630748 | T | C |
| Gm18 | 56630769 | C | T |
| Gm18 | 56630804 | T | A |
| Gm18 | 56630811 | A | G |
| Gm18 | 56630892 | T | C |
| Gm18 | 56630893 | G | A |
| Gm18 | 56630923 | C | T |
| Gm18 | 56630934 | A | T |
| Gm18 | 56630961 | T | C |
| Gm18 | 56630985 | C | T |
| Gm18 | 56631041 | T | C |
| Gm18 | 56631056 | T | C |
| Gm18 | 56631116 | T | C |
| Gm18 | 56631151 | A | T |
| Gm18 | 56631166 | C | T |
| Gm18 | 56631200 | A | T |
| Gm18 | 56631266 | C | CAT |
| Gm18 | 56631376 | A | G |
| Gm18 | 56631609 | T | G |
| Gm18 | 56631641 | G | T |
| Gm18 | 56631665 | A | T |
| Gm18 | 56632093 | C | T |
| Gm18 | 56632157 | G | A |
| Gm18 | 56632282 | C | A |
| Gm18 | 56632296 | G | C |
| Gm18 | 56633543 | C | T |
| Gm18 | 56634232 | G | A |
| Gm18 | 56635842 | A | T |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56635932 | A | G |
| Gm18 | 56636250 | C | CA |
| Gm18 | 56636303 | T | C |
| Gm18 | 56637522 | G | C |
| Gm18 | 56637889 | A | AT |
| Gm18 | 56639048 | T | C |
| Gm18 | 56639540 | G | C |
| Gm18 | 56640035 | A | C |
| Gm18 | 56640169 | C | T |
| Gm18 | 56640187 | A | T |
| Gm18 | 56640293 | C | G |
| Gm18 | 56640394 | AGGGG | A |
| Gm18 | 56640465 | T | TA |
| Gm18 | 56640696 | CAAA | C |
| Gm18 | 56640962 | A | G |
| Gm18 | 56641591 | C | A |
| Gm18 | 56641739 | G | A |
| Gm18 | 56641791 | T | C |
| Gm18 | 56641865 | G | T |
| Gm18 | 56644131 | CAA | C |
| Gm18 | 56644396 | G | A |
| Gm18 | 56645035 | A | C |
| Gm18 | 56645098 | A | ATAC |
| Gm18 | 56645223 | ATTAAATTTAAATTGATTGTTAAT (SEQ ID NO: 19) | A |
| Gm18 | 56645355 | T | C |
| Gm18 | 56645442 | G | T |
| Gm18 | 56645465 | A | C |
| Gm18 | 56645519 | T | G |
| Gm18 | 56645639 | G | A |
| Gm18 | 56645668 | C | G |
| Gm18 | 56645752 | T | G |
| Gm18 | 56645780 | T | A |
| Gm18 | 56645880 | G | T |
| Gm18 | 56645901 | TTA | T |
| Gm18 | 56645929 | G | T |
| Gm18 | 56645937 | C | CAA |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56645953 | A | T |
| Gm18 | 56645958 | TAAA | T |
| Gm18 | 56645984 | T | C |
| Gm18 | 56646008 | G | A |
| Gm18 | 56646045 | C | A |
| Gm18 | 56646087 | A | AT |
| Gm18 | 56646107 | T | C |
| Gm18 | 56646143 | G | A |
| Gm18 | 56646148 | A | AT |
| Gm18 | 56646159 | C | G |
| Gm18 | 56646193 | G | A |
| Gm18 | 56646220 | T | TTA |
| Gm18 | 56646239 | C | CTATTATACACCGA (SEQ ID NO: 20) |
| Gm18 | 56646257 | G | T |
| Gm18 | 56646309 | T | C |
| Gm18 | 56646347 | C | T |
| Gm18 | 56646350 | T | TGA |
| Gm18 | 56646354 | AT | A |
| Gm18 | 56646357 | CA | C |
| Gm18 | 56646360 | T | G |
| Gm18 | 56646361 | A | G |
| Gm18 | 56646362 | T | TG |
| Gm18 | 56646364 | T | A |
| Gm18 | 56646369 | T | C |
| Gm18 | 56646371 | T | C |
| Gm18 | 56646372 | AAGTG | A |
| Gm18 | 56646382 | G | GT |
| Gm18 | 56646383 | AGG | A |
| Gm18 | 56646387 | G | T |
| Gm18 | 56646389 | C | T |
| Gm18 | 56646390 | A | T |
| Gm18 | 56646392 | A | T |
| Gm18 | 56646394 | ACAC | A |
| Gm18 | 56646398 | C | G |
| Gm18 | 56646400 | A | G |
| Gm18 | 56646401 | C | A |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56646415 | C | T |
| Gm18 | 56646471 | A | G |
| Gm18 | 56646489 | G | A |
| Gm18 | 56646513 | C | T |
| Gm18 | 56646524 | C | T |
| Gm18 | 56646536 | T | C |
| Gm18 | 56646578 | T | C |
| Gm18 | 56646638 | G | A |
| Gm18 | 56646658 | C | T |
| Gm18 | 56646659 | G | T |
| Gm18 | 56646720 | TCTAAA | T |
| Gm18 | 56646727 | CATTAAGGCCT (SEQ ID NO: 21) | C |
| Gm18 | 56646741 | AGATG | A |
| Gm18 | 56646799 | T | A |
| Gm18 | 56646810 | G | A |
| Gm18 | 56646825 | ACG | A |
| Gm18 | 56646842 | G | T |
| Gm18 | 56646855 | G | T |
| Gm18 | 56646871 | TAAGTTC | T |
| Gm18 | 56646931 | C | T |
| Gm18 | 56646932 | G | A |
| Gm18 | 56647024 | T | C |
| Gm18 | 56647026 | A | G |
| Gm18 | 56647039 | C | T |
| Gm18 | 56647040 | C | T |
| Gm18 | 56647041 | T | C |
| Gm18 | 56647053 | C | T |
| Gm18 | 56647057 | T | G |
| Gm18 | 56647059 | G | A |
| Gm18 | 56647065 | T | G |
| Gm18 | 56647068 | C | T |
| Gm18 | 56647069 | T | C |
| Gm18 | 56647104 | C | T |
| Gm18 | 56647112 | C | T |
| Gm18 | 56647127 | A | G |
| Gm18 | 56647145 | T | TATTA |
| Gm18 | 56647174 | A | AG |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56647186 | G | A |
| Gm18 | 56647187 | A | G |
| Gm18 | 56647196 | C | A |
| Gm18 | 56647200 | A | G |
| Gm18 | 56647209 | C | G |
| Gm18 | 56647211 | A | G |
| Gm18 | 56647214 | A | G |
| Gm18 | 56647221 | G | A |
| Gm18 | 56647239 | c | T |
| Gm18 | 56647248 | A | G |
| Gm18 | 56647294 | G | A |
| Gm18 | 56647477 | T | C |
| Gm18 | 56647482 | C | T |
| Gm18 | 56647487 | T | G |
| Gm18 | 56647498 | G | A |
| Gm18 | 56647512 | T | A |
| Gm18 | 56647543 | TTAAGTATATG (SEQ ID NO: 22) | T |
| Gm18 | 56647567 | G | A |
| Gm18 | 56647605 | A | G |
| Gm18 | 56647659 | G | T |
| Gm18 | 56647792 | C | T |
| Gm18 | 56647797 | A | T |
| Gm18 | 56647842 | G | A |
| Gm18 | 56647893 | T | C |
| Gm18 | 56647916 | A | G |
| Gm18 | 56647955 | C | T |
| Gm18 | 56647957 | T | G |
| Gm18 | 56648064 | T | G |
| Gm18 | 56648082 | T | A |
| Gm18 | 56648111 | A | G |
| Gm18 | 56648129 | T | C |
| Gm18 | 56648240 | C | A |
| Gm18 | 56648316 | C | T |
| Gm18 | 56648404 | T | C |
| Gm18 | 56648436 | T | C |
| Gm18 | 56648528 | G | GT |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56648611 | A | AG |
| Gm18 | 56648613 | T | A |
| Gm18 | 56648624 | C | T |
| Gm18 | 56648718 | G | GC |
| Gm18 | 56648732 | TA | T |
| Gm18 | 56648734 | A | T |
| Gm18 | 56648765 | A | ATACATAC |
| Gm18 | 56648914 | A | T |
| Gm18 | 56649033 | C | T |
| Gm18 | 56649889 | G | C |
| Gm18 | 56650186 | G | GT |
| Gm18 | 56650603 | C | G |
| Gm18 | 56650733 | C | A |
| Gm18 | 56651552 | C | T |
| Gm18 | 56651585 | T | C |
| Gm18 | 56651696 | C | A |
| Gm18 | 56651711 | T | C |
| Gm18 | 56651853 | A | AT |
| Gm18 | 56651998 | G | GA |
| Gm18 | 56652522 | T | C |
| Gm18 | 56652542 | C | CCTAA |
| Gm18 | 56652838 | AT | A |
| Gm18 | 56653055 | C | T |
| Gm18 | 56653492 | G | A |
| Gm18 | 56653844 | G | T |
| Gm18 | 56653850 | TGGGGCG | T |
| Gm18 | 56653858 | G | T |
| Gm18 | 56653860 | G | T |
| Gm18 | 56653874 | TGGG | T |
| Gm18 | 56654008 | A | C |
| Gm18 | 56654425 | A | ATATGATAG |
| Gm18 | 56654689 | G | C |
| Gm18 | 56656609 | ATTTCTTCTTTAATTGTT TTTTTTTTTTTTTTGCTC AGCAAAATTAAATATA TTATAGATGAGTACCA GAGGTACTAAAATATA CAGATTTAGAGCCATAT TACAAGTAGTTTTGGAC AGACAATGATACAGTA GCTGAAATATCCCAAA AACTACTCAAATAAGA | A |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| | | CTTGGAGCTATACTCTA<br>AACCTATGATGCTGTCC<br>TAAGAAAAGCATCTTT<br>GAGATTTGAAGACCAT<br>TGATTGAAATGTAGAG<br>AGAAATCTTTTTCAAAA<br>CATCTGAGCCATGTCCA<br>TAAAATAAACACTGCA<br>TCATCCATTAATTTATG<br>AGTGTCAAAATTAGCA<br>TTGGAGAAAATGATGC<br>TGTTCCTATGCTTCCAA<br>ATCGAGTAAGTGAGAG<br>CGAACCACCACCACTG<br>CCATCTTTTTTCCCTGC<br>AACCCTACGGAAGCTC<br>CAAAGATATGCTGACT<br>AAAATGCTGATCCGGC<br>TGATAAGGGAAAACAC<br>CCATCATATTTACCCAA<br>GACTGTGACTCCCACCA<br>TAGAGGACTAACTTTAC<br>TGCAGTGGAAAAATAA<br>GTGACTTGCAGTCTCTT<br>CCACAGATCTGCATAA<br>GGGGCACAAGTACTCT<br>TGTAACTCAACCCGCTT<br>CTTTCTCAAATTGGCTT<br>TAGTTGGCAGTTTGTCT<br>TGAATCAACCTCCACGC<br>GAAGATAGCCACTTTC<br>AATGGGACCCTAAGCT<br>TCCATAATTCCTTGAAC<br>TTTCCATCCTGCTCTTC<br>TCCCACTGTGACATGAT<br>GTATTGCCTTATATGCA<br>CTCTTAGTCGAATAACA<br>GCCACTAGGCTCTGCTG<br>CCCACTTCCATTGGTCA<br>CTTAATTCCGGCCTGAT<br>TGTGAACCCTTCCAGCT<br>GTTGGAGGAAAGCTAC<br>CGCCATATCTATCTCGC<br>TATCAAACAAAGGTCT<br>CCTCCACTTAAGACTCC<br>ATTCCCACCCACCTTCT<br>TTCGCAGCACCTATTTG<br>ATGAATGAAATGATGT<br>TTTTGAGCTGATATGGT<br>ATACAATCTAGGATATT<br>TATCAGCTAAGCAGTTG<br>TCTCCGCCTATCCACCT<br>ATCCTCCCAAAACTTAA<br>ACTTGTCCCCACATCCG<br>ACCCTCCACAATATCAA<br>CCTATTCAGCTGTTGAC<br>CTTGATTCATGCTTTGA<br>TTTACTATCTTTAGATC<br>CCTCCACCATGATGATT<br>CAGTACTAGCCCTCGA<br>AGCTCCATCAAGACTCC<br>TCCATCCTCCATACTTT<br>GATTCAAGGACTCTAG<br>CCCAAGTCTCCTCCTGA<br>TTCTGAAACATCTCCCA<br>TTTCCATTTTCCTAATA<br>ATGATGTGTTGAACGA<br>GATGATATCCTTGACTC<br>CCAACCCACCTTGTTCC<br>TTTGGCAAACACACCTT<br>TTCCCACTTGATCCAAG<br>GGATCTTATTTTGATCA<br>GCTGCACCACCCCATA<br>AGAAGTTCCTTTGTAAT | |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| | | CTGGTTATCTTGCTAAT<br>CACCTGCCTAGGGACC<br>CTGAAAAAAGATAGAA<br>AATAAATTGGAATAGA<br>TGTTAGCACTGAATTTA<br>TGAGAATCACTCTCCCC<br>CCAAAAGACAAGTGTC<br>TCTGTTTCCATCCTGCC<br>AGTTTTCTCTCACACTT<br>ATTGATTAAAGGTTCCC<br>ACGTCTGACATCTTCTA<br>GGATTAGCACCAATAG<br>GTATGCCAAGATATGT<br>GAAAGGAAAAGACATC<br>AATCCACAGTTGAGAT<br>AACTGGATGCACCATA<br>AGTCCACTGCTCAGGC<br>ACCCCAAAGGCCCCAC<br>AACTACTCTTGGCGAA<br>ATTTATCTTTAACCCCG<br>ATGACATCTCAAAAGC<br>ACGAAGTATTGCATTG<br>ATTGTTCTTACATTCGC<br>TAATGTTGCCTCTCCCA<br>AAAATAGTGTCATCTGC<br>ATACTGAAGCAGGCTA<br>ATCTCCACCTTCTTTGA<br>GCCCACTAAAAATCCCT<br>TATAGAATCCTCCCTCA<br>ATTGCTTTGGTCATTAG<br>ACCGCTCAAACCTTCTG<br>CAACAATATTAAACAA<br>AAGGGGTGATAATGGA<br>TCCCCCTGTCTAAGACC<br>TTTCTGTGGATAGAACT<br>CCTTCGTAGGGCTTCCA<br>TTTACCAAGACTGAGAT<br>GGAAGCTGATTTTAAA<br>CATCTCTGTATCCACTG<br>AATCCACTTCGGTCCAA<br>AACCCAATCTCCTCATC<br>ATGTATATCAAAAAAT<br>CCCAAGACACTAAGTC<br>ATACGCCTTCTCATAGT<br>CCACCTTGAAAACCAT<br>GCATGGTTTTTGACATC<br>TTTTGGCCTCTTCAACT<br>ACCTCATTTGCAATCAC<br>CACACTATGAAGCATG<br>TGCCTACCTTGTATGAA<br>TGCTGACTGACGATCAC<br>TAATTATGAGGGGCAT<br>AACTCTCTTCAGTCTAT<br>TAGGCAACACTTTAGC<br>GAGGATTTTATAGGTAC<br>ATCCGATGAGTGAAAT<br>AGGTCTATATTCATTCA<br>ACCCTTGAGGGTCCGCC<br>ACCTTCGGGATTAAAG<br>CTATGAATGATGCGTTC<br>AAGCCCCTCGGGAAGA<br>CTCCGTTGACATAGAAC<br>TCGTCAAAGAATCTAA<br>GAAAATCTGGTTTGATG<br>ACCTCCCAAAATTGCTT<br>GATGAATTTGAAATTG<br>AACCCGTCTGGGCCCG<br>GACTTTTATCACTTCCA<br>CAACTCCAAACAGCCC<br>TCCTTATCTCCTCTTCCT<br>GAAAGTGCTCGACTAA<br>CATGGCATTCTGATGGG<br>AATCAATGGTATTGAA<br>GCTGATCCCATTCAGAG | |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| | | TTGGCCTATCAAAATCT GTTTCCTGGAACCTCTG TGAAAAAAATCTCCTA ACTTCCTCTTTGACTTC AGCCGGCTCCTCCTTCC ACATCCCATCAACCATC AGTCCATTTAGGCTATT GGATCGCCTCCTGGAAT TTATCAGCAAATGTTAA TACCTCGAATTACAATC ACCCTCCTTAATCCACC TGGATCTTGCCTTCTGA CGTAACAGCGACTCAT GAGTTTGGGCTGCCTCC CAAACCTTCTGCTGCAA CTTCTTTTTGAGTATCC GCTCATTATCATCCAGT GGTCTGTCTGCTGATTC CTCTTCTAGTTTGTTCA ACTCTTCCTCTATCCTC TTGAAACGGCTTAAAG TGTCTCCAAAGTGATCT TTATTCCACGCCTTTAT CTTCTGTTTGAGGGCCT TGAATTTGTTTTTTAAA ACATGACCCCCCCATCC ACTCTGAGTATTGGATG ACCAGGTTTCGGACAC CAACTTCTTAAAAGATA CATCAGATAACCAACA ATCCAATAGTCTGAAA GGTTTTGGGCCCCAATC AATGGTTTTAGATCTAA GCAATATGGGACAATG GTCCGAAAAATTCCTG GCTAGCGGTGTTTGGAC CGATCCGGGCCATTTGG AAAGCCACTCTGGGGA AACGAAGGCTCTATCC AACTTGCTTTTAGCTGT ACCGTTCGGTCTAAACC ATGTAAATCTCTTTCCC ACCCAAGGCGCTTCTTC TAATTCCAACTCCTCAA TCCAGCTATTAAAATCC CGTATGCTTCCATCCAC CATCCCCCTCTGCGAAG ACCCCACTCTTTCTCCA CTTATCCTGATGTTGTT AAAGTCCCCTATAATAC ACCAATAACCATTTGG ATTCTGGATTTTCAGCT GAGTGACTTTATCCCAT AACACCCTTTTGTCCTG CAGGTTACATGGGGAG TATATATTTACAACATG CACTGCTATGGATTCTT GACCCCACTTTCCTGAC AGTAGTATGAAGCCCG ATCCAGCTGATTTGCTC TCCACCTTCAGAGACTT TTGATTCCAAATACAGA GAATACCACCAGCTGT ATTTACGGCTGGAACCT CCTCCCAGCAGAAATC AGAATTCCCCCATAGA GCCCTGCACATACTCTT ATTGACCGTTTCCTTCT TTGTTTCTTGTAAGCAT AAAAGGTCAATATGAT ACTCTTTGACCATACGT CTAATTGCTGGCCATTT AACCCCCCTCCCCAACC CCCTTACATTATAAGAG | |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| | | ATGATATTCATGAGTCC | |
| | | CTTCCCCTTCCTCCCAA | |
| | | GCTATCTGCCTCTTTTC | |
| | | CATCTCTATCTTCCATT | |
| | | TCTGTCAACTGTTGAAC | |
| | | ATAATCTCTTTGAGTTT | |
| | | TTCCTGTTGTCAGTCCC | |
| | | AACTCCTTGATCATTCT | |
| | | CCATAGACTTTCTTCGT | |
| | | GCGAGTCAAAAGTTTC | |
| | | CTCCTGGAGCTGATTTT | |
| | | CCTGCCTATTGTGAGTT | |
| | | GATGATGTTTCTGTTTG | |
| | | TATTTGGGGGTTGGCTG | |
| | | ATCCACGTCCCTCGTTA | |
| | | TCTCGCTGGAATAGTCC | |
| | | ATTTTGAACATGCTCTG | |
| | | GGCTTGAAAGCACTTG | |
| | | GTTCGAAACAACCTCA | |
| | | CCTATTTGGGCTTTAAC | |
| | | TCTCTTCATTTTCCCTTT | |
| | | ACGGGAATACGTTAAC | |
| | | AAAGGGGTTAGGAGAG | |
| | | GTGTTGTTTTTAAAACT | |
| | | GGGCCATTTTTGGGAG | |
| | | AAGGACATAATTTAGG | |
| | | TGGGGTGTTAATAGCTT | |
| | | GGCCCAAATCCAGCAG | |
| | | CCCCATCATCTCCTTGT | |
| | | CACGTGACTTGGGTGA | |
| | | GGGGGATTCAAAATTA | |
| | | TGTTTGTCTTCCTCGTA | |
| | | CACCATGCCTCCAACGT | |
| | | TTCTTGTCTGCCTCCTC | |
| | | ATACTATTTTCATACAA | |
| | | ATTGCCCAAACCGTCA | |
| | | GGGCCGACATCCCCCC | |
| | | CGAGGTTATCTTCTTCC | |
| | | CCTAAATCGGTCTTCCC | |
| | | TTCTTCCTGCGACACTG | |
| | | GTAGCTCACGGTCCCTG | |
| | | GTCTGCACGCATTTATC | |
| | | ACCTGTCAGTGCATTAT | |
| | | CTGCTTGCTTCACGACC | |
| | | CATCGGACAATAGCTTT | |
| | | GTCCTTTGGGTCATGTC | |
| | | CGCTCTTCGTCCCGATC | |
| | | GCCTTTCCGTTTTGGTC | |
| | | CGCACCGGCCGCGACT | |
| | | GTCGCCGGTCCTTCTGA | |
| | | CCGAGAGACCTGCCTG | |
| | | AGTCGCCCTTCTTCCAC | |
| | | ACCACGCGGCGACCTC | |
| | | TCCTCGTCGCCACCCCT | |
| | | ATCCTCTGTGTCATCCA | |
| | | CCGTCTCCGACTGGGCT | |
| | | GGAGCTCCCCTTTGGGT | |
| | | TTTAAATGGCACGATTT | |
| | | CACTTCTCCCTCTGCGG | |
| | | TTATCTTCCTCGCCCCC | |
| | | CACCACTCCCTCCGTCG | |
| | | CCATATCCTCCATGGCT | |
| | | TCTGCCTCCAAGGTCCC | |
| | | TCCCTTCGCTACTGTTC | |
| | | GTATTTCCTCCGCCACG | |
| | | CTCTCTATTCGCGCTTT | |
| | | GTACCGCCACCCCTGCA | |
| | | GCTCACTACCAGACCA | |
| | | CGCGTCATCGTTACATT | |
| | | CGTCAGAAAGGATTTC | |
| | | CTCTGATGAGCTGAAGT | |
| | | CACGTTCCCTTTTTGGC | |
| | | TGCCACCTAGCTCCAAA | |
| | | CAACCCACTCTCCTCCG | |

TABLE 1-continued

SNP Positions within SEQ ID NOs 11, 12, or 13 that are associated with increased resistance to ASR
Table 1: SNP Positions

| Chromosome | Position | Reference allele | Rpp6907 allele |
|---|---|---|---|
| | | CTATGTGCACCGGAAA AATCTCCCCCTGTATAT GAATATTTACCGTGTGC TGAATCAGCGGTTTCCA TGGCGTTTTGACCAGTA TCCTCGCGACGTCGAAC CTCCTTTGATCTTCTAA GCTCTCCTCAGCCTCCA CCATCTCACCTATTCCC GCGACTATCTGCTTGAT ACAGTTCATGTCCCATG CAACCAAAGGTATTCC CCAACATTGGATCCAA GTTAGTCTAAAACCAG GGCGTAGACTTGGATTC CACTTCTCTATGGAGTA GAACAGGTCGCCCCAT CCTTCATCTTCTTCATT CACCATTTTCTCTGCGT TCTCTTCTGTGAGCCCC AGTAACAAAACCATGT CATCACCGATGTACTTT GGTGATATGTTTTGTCC GCTATCCCACCATATGG CTTCTTCTATGCTATCA AAGCTAGCCAAGTTTTT CAGTCTACCCACCCAG GCCTCCTTGAGCCATTG TTTACCCGTCATCGAAA TGTCCAGGTTCACTTCC GATGTGGCATTGGAAC TTATGTATTGGAGTTTG GCTGTTGTTCTCCTCTG TGCTGGTTTCGGGATAT TCGTGTTGACCACCTCC GCATACGACCGTCCTTG GATTCCCATATTCGCTT CTGGTAACCTGCTCAGG TACACTTCTGTTCTTCC CTTTTGTGTTTGTCCTG TCTCTGCTGTCCCCCTC TCGACTGTTTGTGATTC TCCCTTCTTTGGTCTCC CATATTTAGGGATATTA ACATTCATCTTCATTCC TCCGAAGAACCTATTGT CCAAATGCTGCTGAAG TTGATGCACATCTCTCA CCCCCTTATACCTCACA AAACCATATCTCCTTCC TTGGTTGTTTCTTTTCCT GGGTATGAAAACCTCT CTCACGTCTCCTTGCTG TTTAAAATGGAACCAC AAATCCTTTGCTGTTGC GTCTTCCGGGAACCTCG TAAAGTAAAAGGATAT AACGTCCTTATGGTCTC TCCAGTTCGCTCGCGTG TAGGATTGACGCTGTCC TGTGGCTAACCCTTCGA TGGTCAGATGGGAACC CTCTGACTCTCGAAATC TGACTCTAGCTCTCCTC TCTTTCCTAGTCCTAAC TCTCTCCCACCCACTGT TTCTCTCTCTACTCTCTC TCTCTCTCCATGATTGG ATTGTTCT (SEQ ID NO: 23) | |
| Gm18 | 56662924 | C | T |
| Gm18 | 56663558 | A | T |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56663630 | T | A |
| Gm18 | 56663642 | T | C |
| Gm18 | 56663911 | T | G |
| Gm18 | 56664225 | A | G |
| Gm18 | 56664232 | C | T |
| Gm18 | 56664489 | T | C |
| Gm18 | 56664670 | C | G |
| Gm18 | 56665263 | G | T |
| Gm18 | 56665270 | TTG | T |
| Gm18 | 56665533 | T | TA |
| Gm18 | 56665602 | G | A |
| Gm18 | 56666140 | CA | C |
| Gm18 | 56666204 | T | A |
| Gm18 | 56666205 | T | A |
| Gm18 | 56666616 | G | C |
| Gm18 | 56666694 | G | A |
| Gm18 | 56666897 | G | A |
| Gm18 | 56666919 | AT | A |
| Gm18 | 56667054 | GT | G |
| Gm18 | 56667061 | C | G |
| Gm18 | 56667091 | C | T |
| Gm18 | 56667228 | A | G |
| Gm18 | 56667372 | A | T |
| Gm18 | 56667399 | C | G |
| Gm18 | 56667482 | CAG | C |
| Gm18 | 56667528 | T | C |
| Gm18 | 56667541 | A | ACAGCTCGAGTTAATAT (SEQ ID NO: 24) |
| Gm18 | 56667755 | G | T |
| Gm18 | 56667840 | T | A |
| Gm18 | 56667860 | T | A |
| Gm18 | 56667861 | A | AGG |
| Gm18 | 56668194 | A | AGAAATGGAGAAAGTG (SEQ ID NO: 25) |
| Gm18 | 56668230 | CT | C |
| Gm18 | 56668264 | T | TA |
| Gm18 | 56668288 | TA | T |
| Gm18 | 56668290 | A | T |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56668400 | A | AAAT |
| Gm18 | 56668492 | A | T |
| Gm18 | 56668671 | A | C |
| Gm18 | 56668721 | A | ATAT |
| Gm18 | 56668741 | C | T |
| Gm18 | 56668770 | A | T |
| Gm18 | 56668923 | CCG | C |
| Gm18 | 56668926 | TCACC | T |
| Gm18 | 56669216 | T | G |
| Gm18 | 56676220 | C | A |
| Gm18 | 56676566 | T | G |
| Gm18 | 56676638 | C | T |
| Gm18 | 56680021 | C | G |
| Gm18 | 56680179 | C | T |
| Gm18 | 56682143 | A | C |
| Gm18 | 56682234 | C | T |
| Gm18 | 56682368 | C | CCTTCTTCAGTT (SEQ ID NO: 26) |
| Gm18 | 56682411 | A | G |
| Gm18 | 56682511 | C | T |
| Gm18 | 56682528 | C | A |
| Gm18 | 56682538 | G | C |
| Gm18 | 56682658 | T | A |
| Gm18 | 56682675 | C | A |
| Gm18 | 56682700 | C | T |
| Gm18 | 56682703 | C | T |
| Gm18 | 56682726 | T | TTTTATCATGAAA (SEQ ID NO: 27) |
| Gm18 | 56682755 | T | C |
| Gm18 | 56682839 | T | G |
| Gm18 | 56682841 | A | C |
| Gm18 | 56682852 | G | A |
| Gm18 | 56682858 | T | A |
| Gm18 | 56682870 | T | A |
| Gm18 | 56682968 | C | A |
| Gm18 | 56683053 | T | C |
| Gm18 | 56683054 | G | A |
| Gm18 | 56683110 | TTC | T |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56683296 | A | C |
| Gm18 | 56683332 | A | ATATATATATATATAT (SEQ ID NO: 28) |
| Gm18 | 56683334 | C | A |
| Gm18 | 56683428 | A | ATCC |
| Gm18 | 56683643 | A | G |
| Gm18 | 56683761 | A | G |
| Gm18 | 56683817 | T | C |
| Gm18 | 56683881 | ATGTGTGTGTG (SEQ ID NO: 82) | A |
| Gm18 | 56683894 | TGTA | T |
| Gm18 | 56684003 | A | G |
| Gm18 | 56684101 | A | T |
| Gm18 | 56684693 | T | G |
| Gm18 | 56684788 | G | A |
| Gm18 | 56684790 | C | A |
| Gm18 | 56684820 | T | A |
| Gm18 | 56684873 | T | G |
| Gm18 | 56684957 | A | G |
| Gm18 | 56684968 | C | T |
| Gm18 | 56685074 | T | G |
| Gm18 | 56685278 | TAA | T |
| Gm18 | 56685521 | C | G |
| Gm18 | 56685535 | A | AAGGGGGGAATGG (SEQ ID NO: 29) |
| Gm18 | 56685566 | C | A |
| Gm18 | 56685685 | T | C |
| Gm18 | 56685835 | T | C |
| Gm18 | 56685874 | C | A |
| Gm18 | 56685895 | C | A |
| Gm18 | 56686085 | C | T |
| Gm18 | 56686209 | T | C |
| Gm18 | 56686219 | G | A |
| Gm18 | 56686290 | TA | T |
| Gm18 | 56686387 | T | C |
| Gm18 | 56686538 | C | T |
| Gm18 | 56686683 | CA | C |
| Gm18 | 56686768 | C | A |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56686773 | G | A |
| Gm18 | 56686786 | A | ATAAAAT |
| Gm18 | 56686895 | C | T |
| Gm18 | 56686900 | T | A |
| Gm18 | 56686921 | G | A |
| Gm18 | 56686940 | AG | A |
| Gm18 | 56687096 | T | C |
| Gm18 | 56687120 | C | T |
| Gm18 | 56687358 | A | C |
| Gm18 | 56687362 | T | C |
| Gm18 | 56687459 | A | C |
| Gm18 | 56687461 | G | T |
| Gm18 | 56687462 | A | C |
| Gm18 | 56687515 | GAAAGGTGGA (SEQ ID NO: 83) | G |
| Gm18 | 56687733 | A | C |
| Gm18 | 56687735 | C | T |
| Gm18 | 56687743 | CCTATGCG | C |
| Gm18 | 56687842 | T | C |
| Gm18 | 56688141 | T | C |
| Gm18 | 56688170 | A | G |
| Gm18 | 56688353 | C | T |
| Gm18 | 56688392 | AT | A |
| Gm18 | 56688800 | T | A |
| Gm18 | 56689257 | T | G |
| Gm18 | 56689445 | T | G |
| Gm18 | 56689598 | G | GT |
| Gm18 | 56689744 | T | G |
| Gm18 | 56689862 | CA | C |
| Gm18 | 56689878 | TAA | T |
| Gm18 | 56689972 | GAA | G |
| Gm18 | 56690034 | A | AT |
| Gm18 | 56690170 | A | G |
| Gm18 | 56690474 | CA | C |
| Gm18 | 56690559 | A | ATT |
| Gm18 | 56690747 | A | T |
| Gm18 | 56690889 | T | C |
| Gm18 | 56690976 | T | G |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56691178 | C | A |
| Gm18 | 56691193 | A | C |
| Gm18 | 56691290 | G | T |
| Gm18 | 56691305 | T | A |
| Gm18 | 56691433 | G | T |
| Gm18 | 56691440 | C | T |
| Gm18 | 56692305 | T | TAATATAATTTATTTATT AA (SEQ ID NO: 84) |
| Gm18 | 56692901 | G | GA |
| Gm18 | 56692988 | G | C |
| Gm18 | 56693008 | T | C |
| Gm18 | 56693110 | T | A |
| Gm18 | 56693247 | AAATATATATATATATA TATATATATATATATAT ATATATAT (SEQ ID NO: 30) | A |
| Gm18 | 56693306 | TA | T |
| Gm18 | 56693344 | TA | T |
| Gm18 | 56693516 | T | C |
| Gm18 | 56695064 | C | G |
| Gm18 | 56697201 | T | TCA |
| Gm18 | 56697257 | G | C |
| Gm18 | 56697691 | G | T |
| Gm18 | 56697723 | G | A |
| Gm18 | 56698131 | G | T |
| Gm18 | 56698364 | G | A |
| Gm18 | 56698379 | A | G |
| Gm18 | 56698390 | T | A |
| Gm18 | 56698424 | G | A |
| Gm18 | 56698426 | G | A |
| Gm18 | 56698434 | G | A |
| Gm18 | 56698465 | C | A |
| Gm18 | 56698489 | C | A |
| Gm18 | 56698566 | GT | G |
| Gm18 | 56698734 | A | G |
| Gm18 | 56698802 | T | C |
| Gm18 | 56698808 | G | GA |
| Gm18 | 56698810 | G | A |
| Gm18 | 56698818 | T | G |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56698825 | C | T |
| Gm18 | 56699167 | CA | C |
| Gm18 | 56699334 | G | T |
| Gm18 | 56699339 | T | C |
| Gm18 | 56699344 | A | C |
| Gm18 | 56699389 | AT | A |
| Gm18 | 56699399 | C | A |
| Gm18 | 56699401 | A | ATT |
| Gm18 | 56699504 | G | A |
| Gm18 | 56699527 | C | CAAAAATAA |
| Gm18 | 56699584 | G | A |
| Gm18 | 56699588 | TA | T |
| Gm18 | 56699607 | TTCA | T |
| Gm18 | 56699622 | C | CT |
| Gm18 | 56699653 | T | A |
| Gm18 | 56699721 | G | A |
| Gm18 | 56699759 | A | ATAAATAAATAATAATA GT (SEQ ID NO: 31) |
| Gm18 | 56699770 | C | G |
| Gm18 | 56699840 | A | G |
| Gm18 | 56699965 | T | A |
| Gm18 | 56700056 | G | T |
| Gm18 | 56700068 | G | A |
| Gm18 | 56700082 | G | A |
| Gm18 | 56700086 | T | A |
| Gm18 | 56700348 | T | C |
| Gm18 | 56700360 | C | G |
| Gm18 | 56700362 | T | C |
| Gm18 | 56700612 | A | C |
| Gm18 | 56700818 | T | TG |
| Gm18 | 56700967 | G | C |
| Gm18 | 56701142 | A | G |
| Gm18 | 56701149 | T | C |
| Gm18 | 56701244 | A | C |
| Gm18 | 56701322 | A | G |
| Gm18 | 56701339 | A | G |
| Gm18 | 56701342 | T | C |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56701385 | C | T |
| Gm18 | 56701428 | C | T |
| Gm18 | 56701439 | G | T |
| Gm18 | 56701455 | T | C |
| Gm18 | 56701492 | G | A |
| Gm18 | 56701673 | C | T |
| Gm18 | 56701736 | T | C |
| Gm18 | 56701824 | A | AG |
| Gm18 | 56701832 | A | ATT |
| Gm18 | 56702001 | C | T |
| Gm18 | 56702064 | T | C |
| Gm18 | 56702101 | T | G |
| Gm18 | 56702360 | C | T |
| Gm18 | 56702698 | AT | A |
| Gm18 | 56702760 | A | C |
| Gm18 | 56702767 | G | GC |
| Gm18 | 56702770 | GATTT | G |
| Gm18 | 56702777 | T | G |
| Gm18 | 56702779 | A | G |
| Gm18 | 56702780 | C | T |
| Gm18 | 56702788 | G | A |
| Gm18 | 56702824 | A | T |
| Gm18 | 56702882 | A | G |
| Gm18 | 56702888 | C | T |
| Gm18 | 56702894 | T | C |
| Gm18 | 56702927 | A | G |
| Gm18 | 56702944 | A | G |
| Gm18 | 56703048 | T | A |
| Gm18 | 56703067 | A | G |
| Gm18 | 56703127 | T | C |
| Gm18 | 56703131 | G | A |
| Gm18 | 56703135 | T | A |
| Gm18 | 56703188 | C | T |
| Gm18 | 56703195 | A | G |
| Gm18 | 56703209 | T | C |
| Gm18 | 56703284 | A | AT |
| Gm18 | 56703290 | T | A |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56703334 | T | C |
| Gm18 | 56703375 | A | T |
| Gm18 | 56703399 | T | A |
| Gm18 | 56703404 | T | G |
| Gm18 | 56703506 | A | G |
| Gm18 | 56703564 | G | A |
| Gm18 | 56703591 | C | CTTCTTACTTGTAACTAA GTCTTTGA (SEQ ID NO: 32) |
| Gm18 | 56703608 | G | A |
| Gm18 | 56703653 | T | TA |
| Gm18 | 56703658 | G | A |
| Gm18 | 56703672 | GAA | G |
| Gm18 | 56703682 | TA | T |
| Gm18 | 56703785 | T | A |
| Gm18 | 56703798 | T | G |
| Gm18 | 56703824 | T | G |
| Gm18 | 56703833 | A | AAATT |
| Gm18 | 56703842 | C | A |
| Gm18 | 56703861 | AG | A |
| Gm18 | 56703866 | G | A |
| Gm18 | 56704030 | CT | C |
| Gm18 | 56704201 | A | G |
| Gm18 | 56704273 | T | A |
| Gm18 | 56704278 | C | A |
| Gm18 | 56704284 | G | C |
| Gm18 | 56704352 | T | TG |
| Gm18 | 56704382 | G | C |
| Gm18 | 56704398 | ATACT | A |
| Gm18 | 56704417 | T | C |
| Gm18 | 56704420 | TA | T |
| Gm18 | 56704443 | T | A |
| Gm18 | 56704456 | A | G |
| Gm18 | 56704501 | T | C |
| Gm18 | 56704508 | T | A |
| Gm18 | 56704531 | C | T |
| Gm18 | 56704539 | T | C |
| Gm18 | 56704548 | A | C |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56704611 | C | G |
| Gm18 | 56704650 | C | T |
| Gm18 | 56704669 | A | T |
| Gm18 | 56704693 | T | C |
| Gm18 | 56704697 | G | A |
| Gm18 | 56704748 | A | T |
| Gm18 | 56704760 | A | ACCATG |
| Gm18 | 56704766 | A | T |
| Gm18 | 56704771 | G | A |
| Gm18 | 56704777 | T | C |
| Gm18 | 56704845 | C | T |
| Gm18 | 56704940 | TAA | T |
| Gm18 | 56704963 | G | A |
| Gm18 | 56705061 | G | A |
| Gm18 | 56705077 | T | C |
| Gm18 | 56705088 | A | C |
| Gm18 | 56705094 | G | C |
| Gm18 | 56705113 | C | T |
| Gm18 | 56705146 | A | T |
| Gm18 | 56705200 | A | G |
| Gm18 | 56705219 | A | G |
| Gm18 | 56705251 | T | TATATTTTTTGTGTTTGG TCTTTGATAAATTTTTCT TTCGAATTTGGATTCTAA TGTTTTAAATTTTTTATCT TAAAGTCTCTATCATTAA TATGTAATCCTACATGAC TCTTAATTAGACACGTAG AAGTGTGATGTGTCATGT CAAATATAACCTTTGTGA TTTCTATTTATACATATT GGATTATTAAAAAAAAA TATTTTCTTTGTTAAAAA ATAATAAAATCCAACTT ATATAAACAATAATCCG ACATAATACATCACATTT TTACGTGTGTCCAGTTCA TAC (SEQ ID NO: 33) |
| Gm18 | 56705253 | G | A |
| Gm18 | 56705254 | G | A |
| Gm18 | 56711483 | TA | T |
| Gm18 | 56711576 | G | GA |
| Gm18 | 56711711 | A | G |
| Gm18 | 56711752 | T | TA |
| Gm18 | 56712550 | T | C |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56712561 | T | C |
| Gm18 | 56712563 | A | G |
| Gm18 | 56712847 | T | A |
| Gm18 | 56712894 | CTATATA | C |
| Gm18 | 56712934 | A | G |
| Gm18 | 56712958 | C | CCA |
| Gm18 | 56712959 | T | TGC |
| Gm18 | 56712988 | C | T |
| Gm18 | 56713017 | C | A |
| Gm18 | 56713045 | G | T |
| Gm18 | 56713064 | C | T |
| Gm18 | 56713220 | T | C |
| Gm18 | 56713259 | G | A |
| Gm18 | 56713332 | T | C |
| Gm18 | 56713478 | G | C |
| Gm18 | 56713624 | C | A |
| Gm18 | 56713748 | A | G |
| Gm18 | 56713764 | C | A |
| Gm18 | 56713852 | A | T |
| Gm18 | 56713995 | C | A |
| Gm18 | 56714029 | G | A |
| Gm18 | 56714182 | G | C |
| Gm18 | 56714236 | A | G |
| Gm18 | 56714245 | G | T |
| Gm18 | 56714295 | T | G |
| Gm18 | 56714368 | G | T |
| Gm18 | 56714611 | T | C |
| Gm18 | 56714635 | T | C |
| Gm18 | 56714850 | A | C |
| Gm18 | 56714865 | A | G |
| Gm18 | 56715062 | T | A |
| Gm18 | 56715180 | C | A |
| Gm18 | 56715529 | C | CTT |
| Gm18 | 56715568 | C | T |
| Gm18 | 56715595 | C | T |
| Gm18 | 56715695 | A | G |
| Gm18 | 56715700 | T | TGGA |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56715702 | T | G |
| Gm18 | 56715704 | AC | A |
| Gm18 | 56715707 | T | TGGA |
| Gm18 | 56715709 | T | TGG |
| Gm18 | 56715710 | A | G |
| Gm18 | 56715712 | C | T |
| Gm18 | 56715714 | G | T |
| Gm18 | 56715716 | G | GAGA |
| Gm18 | 56715717 | G | GAA |
| Gm18 | 56715720 | T | TTTTGACAAAAAC (SEQ ID NO: 34) |
| Gm18 | 56715724 | C | CTTAAA |
| Gm18 | 56715725 | C | G |
| Gm18 | 56715727 | T | TTTTAAAAG |
| Gm18 | 56715732 | A | T |
| Gm18 | 56715747 | T | C |
| Gm18 | 56715775 | C | CAACACTAACAAATTTTA (SEQ ID NO: 35) |
| Gm18 | 56715781 | A | G |
| Gm18 | 56715841 | T | C |
| Gm18 | 56715854 | T | A |
| Gm18 | 56715872 | G | A |
| Gm18 | 56715929 | C | T |
| Gm18 | 56715931 | A | G |
| Gm18 | 56715950 | G | C |
| Gm18 | 56715958 | G | A |
| Gm18 | 56715971 | C | T |
| Gm18 | 56715981 | T | C |
| Gm18 | 56715982 | A | G |
| Gm18 | 56715993 | G | A |
| Gm18 | 56716009 | A | T |
| Gm18 | 56716021 | ATT | A |
| Gm18 | 56716031 | A | T |
| Gm18 | 56716262 | C | CG |
| Gm18 | 56716273 | G | A |
| Gm18 | 56716285 | G | A |
| Gm18 | 56716310 | G | A |
| Gm18 | 56716354 | TTAA | T |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56716388 | A | T |
| Gm18 | 56716452 | T | C |
| Gm18 | 56716547 | TA | T |
| Gm18 | 56716576 | T | C |
| Gm18 | 56716720 | T | TA |
| Gm18 | 56716984 | G | A |
| Gm18 | 56717056 | T | TGC |
| Gm18 | 56717086 | A | G |
| Gm18 | 56717118 | T | C |
| Gm18 | 56717139 | T | C |
| Gm18 | 56717216 | G | A |
| Gm18 | 56717267 | T | A |
| Gm18 | 56717293 | T | C |
| Gm18 | 56717338 | C | T |
| Gm18 | 56717407 | G | C |
| Gm18 | 56717408 | G | C |
| Gm18 | 56717438 | C | T |
| Gm18 | 56717695 | G | A |
| Gm18 | 56718157 | A | T |
| Gm18 | 56718193 | G | T |
| Gm18 | 56718199 | A | AT |
| Gm18 | 56718208 | C | T |
| Gm18 | 56718334 | A | G |
| Gm18 | 56718585 | A | AT |
| Gm18 | 56718665 | A | T |
| Gm18 | 56718667 | G | A |
| Gm18 | 56718831 | A | G |
| Gm18 | 56718997 | G | A |
| Gm18 | 56719142 | C | CAAGTATGCAGGCTTTTG TACCCATAGTACCACTGG TACTATTTCAATCTATAA TATATATATTTTTGCTGA GCAAAAAAAAAA (SEQ ID NO: 36) |
| Gm18 | 56719289 | T | C |
| Gm18 | 56719463 | C | A |
| Gm18 | 56719488 | C | T |
| Gm18 | 56719491 | T | C |
| Gm18 | 56719540 | T | C |
| Gm18 | 56719572 | C | T |

TABLE 1-continued

SNP Positions within SEQ ID NQs 11, 12, or 13 that are associated with increased resistance to ASR
Table 1: SNP Positions

| Chromosome | Position | Reference allele | Rpp6907 allele |
|---|---|---|---|
| Gm18 | 56719814 | A | G |
| Gm18 | 56719828 | G | A |
| Gm18 | 56719975 | A | G |
| Gm18 | 56720147 | AAACCCATGATAACTG GTTTTAATTGTGGGCTG TCTCCATACTCTACACA AGCT (SEQ ID NO: 37) | A |
| Gm18 | 56720232 | G | T |
| Gm18 | 56720354 | G | T |
| Gm18 | 56720393 | G | A |
| Gm18 | 56720436 | A | T |
| Gm18 | 56720464 | T | C |
| Gm18 | 56720492 | T | G |
| Gm18 | 56720496 | C | CTGTCCAGCCAAGATCTT GACTGTTGTAGTTGAACT TAGTAGCTGAAGAGGAA AGAGAATGTGATGGGTG GTTGAGATTTGGGAAGG AGAGAAACCTTGCTGGG AGAGGCTGCAGAGGATC CAGATTCCTGCTATATAT TGTCATGATAACTGTCAA GTGTGAAATTGAGAGCT TGCTAATCTTGTAGAATA TATAAACCATTTTTGACT TTTTTTTTTTAAAAAAAT GATTTGATCATATGGCAT TCATGTTTGTTTGAGTTG TAGCAGTTTCTTTCTGTT CCCATAAATTGTTATCAT TCTTTTTTGAGAGTTGGA TTTACTGGTTTGAG (SEQ ID NO: 38) |
| Gm18 | 56720499 | A | G |
| Gm18 | 56720501 | T | G |
| Gm18 | 56720502 | T | C |
| Gm18 | 56720534 | T | C |
| Gm18 | 56720672 | G | C |
| Gm18 | 56720684 | T | C |
| Gm18 | 56720710 | A | C |
| Gm18 | 56720828 | C | T |
| Gm18 | 56720902 | C | T |
| Gm18 | 56720938 | T | C |
| Gm18 | 56720942 | C | T |
| Gm18 | 56721082 | C | T |
| Gm18 | 56721119 | T | C |
| Gm18 | 56721214 | G | A |
| Gm18 | 56721542 | G | A |

TABLE 1-continued

| SNP Positions within SEQ ID NQs 11, 12, or 13 that are associated with increased resistance to ASR Table 1: SNP Positions | | | |
|---|---|---|---|
| Chromosome | Position | Reference allele | Rpp6907 allele |
| Gm18 | 56721704 | C | T |
| Gm18 | 56721865 | G | A |
| Gm18 | 56722043 | G | A |
| Gm18 | 56722203 | G | T |
| Gm18 | 56722409 | G | T |
| Gm18 | 56722545 | A | C |
| Gm18 | 56722832 | C | T |
| Gm18 | 56722859 | A | C |
| Gm18 | 56723297 | G | A |

Oligonucleotide primers (herein, 'primers') can be developed and used to identify plants carrying any one of the chromosomal intervals depicted in SEQ ID NO: 11, 12, or 13 found to be highly associated with ASR resistance. Primers can also be developed and used to identify plants carrying SEQ ID NO: 2. Specifically, one having ordinary skill in the art can develop primers to detect any single nucleotide polymorphism (herein 'SNP') as identified in Table 1 in respect to identifying or producing soybean lines having any one of or a portion of the chromosome intervals depicted in SEQ ID NOs: 11, 12, or 13 that are associated with ASR resistance. A TAQMAN® assay (e.g. generally a two-step allelic discrimination assay or similar), a KASP™ assay (generally a one-step allelic discrimination assay defined below or similar), or both can be employed to identify the SNPs that associate with increased ASR resistance as disclosed herein (e.g. favorable alleles as depicted in Table 1 above). In an exemplary two-step assay, a forward primer, a reverse primer, and two assay probes (or hybridization oligos) are employed. The forward and reverse primers are employed to amplify genetic loci that comprise SNPs that are associated with ASR resistance loci (for example, any of the favorable alleles as shown in Table 1). The particular nucleotides that are present at the SNP positions are then assayed using the assay primers (which in some embodiments are differentially labeled with, for example, fluorophores to permit distinguishing between the two assay probes in a single reaction), which in each pair differ from each other with respect to the nucleotides that are present at the SNP position (although it is noted that in any given pair, the probes can differ in their 5' or 3' ends without impacting their abilities to differentiate between nucleotides present at the corresponding SNP positions). In some embodiments, the assay primers and the reaction conditions are designed such that an assay primer will only hybridize to the reverse complement of a 100% perfectly matched sequence, thereby permitting identification of which allele (s) that are present based upon detection of hybridizations.

In one embodiment of the invention, the following assay can be employed to identify the SNPs that associate with increased ASR resistance as disclosed herein:

TABLE 2

| Assays for detection of SNPs across interval | | | | | |
|---|---|---|---|---|---|
| Assay | Type of variant (SNP or InDel) | Position in BAC sequence | Physical position on chromosome | Favorable allele | Unfavorable allele |
| 1 | SNP | 282 | 56,723,297 | T | C |
| 2 | SNP | 173,304 | 56,607,175 | G | A |
| 3 | Insertion | 42631-42641 | 56,682,368 | aactgaagaag | — |
| 4 | SNP | 42,775 | 56,682,234 | A | G |
| 5 | SNP | 42,866 | 56,682,143 | G | T |
| 6 | SNP | 44,833 | 56,680,179 | A | G |
| 7 | SNP | 48,513 | 56,676,638 | A | G |
| 8 | SNP | 48,585 | 56,676,566 | C | A |
| 9 | SNP | 87,329 | 56,676,220 | T | G |

TABLE 2-continued

| Assays for detection of SNPs across interval | | | | | |
|---|---|---|---|---|---|
| 10 | SNP | 106,768 | 56,680,021 | C | G |

| | TAQ Allelic Discrimination Assay | | | |
|---|---|---|---|---|
| Assay | probe 1 sequence | probe 2 sequence | primer 1 sequence | primer 2 sequence |
| 1 | AATAGCCCCACCC TTAATT (SEQ ID NO: 39) | CAATAGCCCCATC CTTAA (SEQ ID NO: 49) | GGATGGAATGGG AAAGTCTTGATAA (SEQ ID NO: 59) | GCAAGCAAACCTC GAACCTA (SEQ ID NO: 69) |
| 2 | TCATCATGCTAAA ACTGAGTA (SEQ ID NO: 40) | CTCATCATGCTAA AATTGAGTA (SEQ ID NO: 50) | AAAACCTGCGAA GCTCCTTTACTA (SEQ ID NO: 60) | CCCACCCGTTTAT CATTTGCACTT (SEQ ID NO: 70) |
| 3 | TTGAGGAAGAACT GAAGAAGGTAGC (SEQ ID NO: 41) | ACGGATTGAGGA AGGTAGCAGAA (SEQIDNO: 51) | GTTTGTTGTCCAC GCCTGAA (SEQ ID NO: 61) | TGTCATCAAGCAT CACCAGGTA (SEQ ID NO: 71) |
| 4 | ATTGAAAATTGTT CCTGTAC (SEQ ID NO: 42) | CCTATTGAAAATT GTTCTTGTAC (SEQ ID NO: 52) | TTACGTCAATGCT CTTAAGGTCTAA (SEQ ID NO: 62) | ACTAATAACAAGG AGGTGGCATAC (SEQ ID NO: 72) |
| 5 | TGGCTTAGGAAGA AAGCTC (SEQ ID NO: 43) | TGGCTTAGGACGA AAGCT (SEQ ID NO: 53) | GCCTTGACCTCAT CCATTGATAGAG (SEQ ID NO: 63) | ACTAATAACAAGG AGGTGGCATAC (SEQ ID NO: 73) |
| 6 | ATCTCTGATCTGG CTCAC (SEQ ID NO: 44) | TCTCTGATTTGGC TCAC (SEQ ID NO: 54) | GGTGTCAACCACA TCTTCAGCTTT (SEQ ID NO: 64) | TTCTGGCGTGGAG GACAAA (SEQ ID NO: 74) |
| 7 | CAACAAATACATA TACCAAAGTC (SEQ ID NO: 45) | AGCAACAAATAC ATATATCAAAGTC (SEQ ID NO: 55) | ACTTGCTCTACTT CATAAATGGGTA (SEQ ID NO: 65) | GTCAGTGTCCTAG TTTTCCTTGA (SEQ ID NO: 75) |
| 8 | ACAAAATCATCAC CAAGTTGA (SEQ ID NO: 46) | CAAAATCATCACC CAGTTG (SEQ ID NO: 56) | ACCCATTTATGAA GTAGAGCAAGTA (SEQ ID NO: 66) | AGCGAACGGGAA CAGTCCAT (SEQ ID NO: 76) |
| 9 | ATCTGCATGCTAA TCCTG (SEQ ID NO: 47) | CTGCATGCTCATC CTG (SEQ ID NO: 57) | TCCGAGAAAGGA ATAGTTCTGTG (SEQ ID NO: 67) | GGACGACACTTTT ACATCAAACAC (SEQ ID NO: 77) |
| 10 | TTCGATCTGACTC CTGAT (SEQ ID NO: 48) | CGATCTGAGTCCT GATC (SEQ ID NO: 50) | CACCTTCTCCAAT GCCATATCTGT (SEQ ID NO: 68) | GCTTCACCAAGTC AACTCTGA (SEQ ID NO: 78) |

Genetic Mapping

Genetic loci correlating with particular phenotypes, such as rust resistance, can be mapped in an organism's genome. By identifying a marker or cluster of markers that co-segregate with a trait of interest, the breeder is able to rapidly select a desired phenotype by selecting for the proper marker (a process called marker-assisted selection, or "MAS"). Such markers may also be used by breeders to design genotypes in silico and to practice whole genome selection.

In certain embodiments, the present invention provides markers associated with enhanced resistance to rust (e.g. Asian soybean rust). Detection of these markers and/or other linked markers can be used to identify, select, and/or produce rust resistant, more specifically Asian soybean rust resistant (herein, "ASR"), plants and/or to eliminate plants that are not disease resistant from breeding programs or planting.

Genetic Loci Associated with Enhanced Disease Resistance

Markers associated with enhanced disease resistance are identified herein (see Table 1 indicating favorable markers associated with enhanced ASR resistance). A marker of the present invention may comprise a single allele or a combination of alleles at one or more genetic loci (for example, any combination of a favorable markers from Table 1. For example, the marker may comprise one or more marker alleles located within a first chromosomal interval (e.g. SEQ ID NO: 11) and one or more marker alleles located within a second chromosomal interval (e.g. SEQ ID NO: 12 or SEQ ID NO: 13).

Marker-Assisted Selection

Markers can be used in a variety of plant breeding applications. See, e.g., Staub et al., *Hortscience* 31: 729 (1996); Tanksley, *Plant Molecular Biology Reporter* 1: 3 (1983). One of the main areas of interest is to increase the efficiency of backcrossing and introgressing genes using marker-assisted selection (MAS). In general, MAS takes advantage of genetic markers that have been identified as having a significant likelihood of co-segregation with a desired trait. Such markers are presumed to be in/near the gene(s) that give rise to the desired phenotype, and their presence indicates that the plant will possess the desired trait. Plants which possess the marker are expected to transfer the desired phenotype to their progeny.

A marker that demonstrates linkage with a locus affecting a desired phenotypic trait provides a useful tool for the selection of the trait in a plant population. This is particularly true where the phenotype is hard to assay or occurs at a late stage in plant development. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing or imparting the trait. Having flanking markers decreases the chances that false positive selection will occur. The ideal situation is to have a marker within the causative gene itself, so that recombination cannot occur between the marker and the gene. Such a marker is called a "perfect marker".

When a gene is introgressed by MAS, it is not only the gene that is introduced but also the flanking regions. Gepts, *Crop Sci* 42:1780 (2002). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite soybean line. This is also sometimes referred to as "yield drag." The size of the flanking region can be decreased by additional backcrossing, although this is not always successful, as breeders do not have control over the size of the region or the recombination breakpoints. Young et al., *Genetics* 120:579 (1998). In classical breeding, it is usually only by chance that recombinations that contribute to a reduction in the size of the donor segment are selected. Tanksley et al., *Biotechnology* 7: 257 (1989). Even after 20 backcrosses, one might find a sizeable piece of the donor chromosome still linked to the gene being selected. With markers, however, it is possible to select those rare individuals that have experienced recombination near the gene of interest. In 150 backcross plants, there is a 95% chance that at least one plant will have experienced a crossover within 1 cM of the gene, based on a single meiosis map distance. Markers allow for unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers. See Tanksley et al., supra. When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the soybean genome containing increasing densities of public soybean markers has facilitated soybean genetic mapping and MAS.

Of all the molecular marker types, SNPs are the most abundant and have the potential to provide the highest genetic map resolution. Bhattramakki et al., *Plant Malec. Biol.* 48:539 (2002). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, Pharmacogenomics 1:95 (2000); Bhattramakki and Rafalski, *Discovery and application of single nucleotide polymorphism markers in plants, in* PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, MD), Invader® (Hologic, Madison, WI), SnapShot® (Applied Biosystems, Foster City, CA), Taqman® (Applied Biosystems, Foster City, CA) and Beadarrays™ (Illumina, San Diego, CA).

A number of SNP alleles together within a sequence, or across linked sequences, can be used to describe a haplotype for any particular genotype. Ching et al., *BMC Genet.* 3:19 (2002); Gupta et al., (2001), Rafalski, *Plant Sci.* 162:329 (2002b). Haplotypes can be more informative than single SNPs and can be more descriptive of any particular genotype. For example, a single SNP may be allele "T" for a specific Disease resistant line or variety, but the allele "T" might also occur in the soybean breeding population being utilized for recurrent parents. In this case, a combination of alleles at linked SNPs may be more informative. Once a unique haplotype has been assigned to a donor chromosomal region, that haplotype can be used in that population or any subset thereof to determine whether an individual has a particular gene. The use of automated high throughput marker detection platforms known to those of ordinary skill in the art makes this process highly efficient and effective.

The markers of the present invention can be used in marker-assisted selection protocols to identify and/or select progeny with enhanced Asian soybean rust resistance. Such methods can comprise, consist essentially of or consist of crossing a first soybean plant or germplasm with a second soybean plant or germplasm, wherein the first soybean plant or germplasm comprises a chromosomal interval derived from SX6907 wherein said chromosome interval comprises SEQ ID NOs 11, 12, or 13, or a portion thereof encoding ASR resistance, or wherein the chromosome interval comprises SEQ ID NO: 2 or a nucleic acid encoding SEQ ID NO: 1, and selecting a progeny plant that possesses the marker. Either of the first and second soybean plants, or both, may be of a non-naturally occurring variety of soybean. In some embodiments, the second soybean plant or germplasm is of an elite variety of soybean. In some embodiments, the genome of the second soybean plant or germplasm is at least about 50%, 55%, 60%, 65%, 70%, 75%, 80%, 85%, 90%, 95%, 97%, 99%, or 100% identical to that of an elite variety of soybean. In another embodiment, the first soybean plant comprises a chromosomal interval derived from SX6907 wherein said chromosomal interval comprises SEQ ID NOs 11, 12, or 13 and wherein the chromosome interval further comprises at least one allele as depicted in Table 1. In another embodiment, the first soybean comprises a chromosome interval comprising the nucleic acid sequence of SEQ ID NO: 2, or a portion thereof encoding ASR resistance, or the nucleic acid sequence encoding the protein of SEQ ID NO: 1, or a portion thereof encoding ASR resistance.

Producing Disease Resistant Plants

Methods for identifying and/or selecting a disease resistant soybean plant or germplasm may comprise, consist essentially of or consist of detecting the presence of a marker associated with enhanced ASR tolerance. The marker may be detected in any sample taken from the plant or germplasm, including, but not limited to, the whole plant or germplasm, a portion of said plant or germplasm (e.g., a seed chip, a leaf punch disk or a cell from said plant or germplasm) or a nucleotide sequence from said plant or germplasm. Such a sample may be taken from the plant or germplasm using any present or future method known in the art, including, but not limited to, automated methods of removing a portion of endosperm with a sharp blade, drilling a small hole in the seed and collecting the resultant powder, cutting the seed with a laser and punching a leaf disk. The soybean plant may be of a non-naturally occurring variety of soybean. In some embodiments, the genome of the soybean plant or germplasm is at least about 50%, 55%, 60%, 65%, 70%, 75%, 80%, 85%, 90%, 95%, 97%, 99% or 100% identical to that of an elite variety of soybean. In some embodiments, the marker detected in the sample may comprise, consist essentially of or consist of one or more marker alleles located within a chromosomal interval selected from:

1) a chromosomal interval comprising SEQ ID NO: 2, or a portion thereof encoding ASR resistance;
2) a chromosomal interval encoding the protein sequence of SEQ ID NO: 1, or a portion thereof encoding ASR resistance;
3) a chromosomal interval comprising SEQ ID NOs 11, 12, or 13, or a portion thereof encoding ASR resistance; or
4) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any favorable SNP marker displayed in Table 1.

Alternatively, the one or more marker alleles may be located within SEQ ID NO: 2.

Methods for producing a disease resistant soybean plant may comprise, consist essentially of or consist of detecting, in a germplasm, a marker associated with enhanced disease resistance (e.g. ASR) wherein said marker is selected from Table 1 or wherein marker is a closely linked loci of any marker described in Table 1 and producing a soybean plant from said germplasm. Alternatively, the methods may comprise, consist essentially of or consist of detecting, in a germplasm, a marker associated with SEQ ID NO: 2. The marker may be detected in any sample taken from the germplasm, including, but not limited to, a portion of said germplasm (e.g., a seed chip or a cell from said germplasm) or a nucleotide sequence from said germplasm. Such a sample may be taken from the germplasm using any present or future method known in the art, including, but not limited to, automated methods of removing a portion of endosperm with a sharp blade, drilling a small hole in the seed and collecting the resultant powder, cutting the seed with a laser and punching a leaf disk. The germplasm may be of a non-naturally occurring variety of soybean. In some embodiments, the genome of the germplasm is at least about 50%, 55%, 60%, 65%, 70%, 75%, 80%, 85%, 90%, 95%, 97%, 99%, or 100% identical to that of an elite variety of soybean. A disease resistant soybean plant is then produced from the germplasm identified as having the marker associated with enhanced disease resistance (e.g. ASR) according to methods well known in the art for breeding and producing plants from germplasm.

In some embodiments, the marker detected in the germplasm may comprise, consist essentially of or consist of one or more marker alleles located within a chromosomal interval selected from:

1) a chromosomal interval comprising SEQ ID NO: 2, or a portion thereof encoding ASR resistance;
2) a chromosomal interval encoding the protein sequence of SEQ ID NO: 1, or a portion thereof encoding ASR resistance;
3) a chromosomal interval comprising SEQ ID NOs 11, 12, or 13, or a portion thereof encoding ASR resistance; or
4) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any favorable SNP marker displayed in Table 1.

In another embodiment, the marker is located with the nucleic acid of SEQ ID NO: 2. In some embodiments, the marker detected in the germplasm may comprise, consist essentially of or consist of one or more marker alleles selected from Table 1.

Methods for producing and/or selecting an Asian soybean rust resistant/tolerant soybean plant or germplasm may comprise crossing a first soybean plant or germplasm with a second soybean plant or germplasm, wherein said first soybean plant or germplasm comprises a chromosomal interval selected from:

1) a chromosomal interval comprising SEQ ID NO: 2, or a portion thereof encoding ASR resistance;
2) a chromosomal interval encoding the protein sequence of SEQ ID NO: 1, or a portion thereof encoding ASR resistance;
3) a chromosomal interval comprising SEQ ID NOs 11, 12, or 13, or a portion thereof encoding ASR resistance;
4) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any favorable SNP marker displayed in Table 1; or
5) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any SNP marker displayed in Table 1, and crossing with a second soybean plant not comprising the chromosome interval then producing a progeny plant with increased ASR resistance. Either the first or second soybean plant or germplasm, or both, may be of a non-naturally occurring variety of soybean. In some embodiments, the second soybean plant or germplasm is of an elite variety of soybean. In some embodiments, the genome of the second soybean plant or germplasm is at least about 50%, 55%, 60%, 65%, 70%, 75%, 80%, 85%, 90%, 95%, 97%, 99% or 100% identical to that of an elite variety of soybean.

In one embodiment, the soybean plant may be used to introduce Asian soybean rust resistance/tolerance into *Glycine max* strain Williams 82.

Alternatively, methods for producing and/or selecting an Asian soybean rust resistant/tolerant soybean plant or germplasm may comprise crossing a first soybean plant or germplasm with a second soybean plant or germplasm, wherein said first soybean plant or germplasm comprises the nucleic acid sequence of SEQ ID NO: 2 or a protein encoding the amino acid sequence of SEQ ID NO: 1.

Also provided herein is a method of introgressing an allele associated with enhanced Disease (e.g. ASR, SCN, SDS, RKN, Phytopthora, etc.) resistance/tolerance into a soybean plant. Such methods for introgressing an allele associated with enhanced Disease (e.g. ASR, SCN, SDS, RKN, Phytopthora, etc.) resistance/tolerance into a soybean plant or germplasm may comprise, consist essentially of or consist of crossing a first soybean plant or germplasm comprising said allele (the donor) wherein said allele is selected from any allele listed in Table 1 or a maker in “close proximity” to a marker listed in Table 1 with a second soybean plant or germplasm that lacks said allele (the recurrent parent) and repeatedly backcrossing progeny comprising said allele with the recurrent parent. Progeny comprising said allele may be identified by detecting, in their genomes, the presence of a marker associated with enhanced Disease (e.g. ASR, SCN, SDS, RKN, Phytopthora, etc.) resistance/tolerance. The marker may be detected in any sample taken from the progeny, including, but not limited to, a portion of said progeny (e.g., a seed chip, a leaf punch disk, or a cell from said plant or germplasm) or a nucleotide sequence from said progeny. Such a sample may be taken from the progeny using any present or future method known in the art, including, but not limited to, automated methods of removing a portion of endosperm with a sharp blade, drilling a small hole in the seed and collecting the resultant powder, cutting the seed with a laser and punching a leaf disk. Either the donor or the recurrent parent, or both, may be of a non-naturally occurring variety of soybean. In some embodiments, the recurrent parent is of an elite variety of soybean. In some embodiments, the genome of the recurrent parent is at least about 50%, 55%, 60%, 65%, 70%, 75%, 80%, 85%, 90%, 95%, 97%, 99% or 100% identical to that of an elite variety of soybean.

In some embodiments, the marker used to identify progeny comprising an allele associated with enhanced resistance/tolerance to rust may comprise, consist essentially of or consist of one or more marker alleles located within a chromosomal interval selected from:

1) a chromosomal interval comprising SEQ ID NO: 2, or a portion thereof encoding ASR resistance;
2) a chromosomal interval encoding the protein sequence of SEQ ID NO: 1, or a portion thereof encoding ASR resistance;
3) a chromosomal interval comprising SEQ ID NOs 11, 12, or 13, or a portion thereof encoding ASR resistance;
4) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any favorable SNP marker displayed in Table 1; or
5) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any SNP marker displayed in Table 1 or any closely linked markers in close proximity to said intervals (SEQ ID NOs 11, 12, or 13).

In some embodiments, the marker may comprise, consist essentially of or consist of marker alleles located in at least two different chromosomal intervals. For example, the marker may comprise one or more alleles located in the chromosomal interval defined by and including any two markers in SEQ ID NOs 11, 12, or 13.

Disease Resistant Soybean Plants and Germplasms

In another embodiment, the present invention provides soybean plants and germplasms that are resistant to rust. As discussed above, the methods of the present invention may be utilized to identify, produce, and/or select a disease resistant soybean plant or germplasm (for example a soybean plant resistant or having increased tolerance to Asian Soybean Rust). In addition, to the methods described above, a soybean plant or germplasm resistant to ASR may be produced by any method whereby a marker associated with enhanced disease tolerance is introduced into the soybean plant or germplasm, including, but not limited to, transformation, protoplast transformation or fusion, a double haploid technique, embryo rescue, gene editing and/or by any other nucleic acid transfer system.

In some embodiments, the soybean plant or germplasm comprises a non-naturally occurring variety of soybean. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The disease resistant soybean plant or germplasm may be the progeny of a cross between an elite variety of soybean and a variety of soybean that comprises an allele associated with enhanced rust resistance (e.g. ASR) wherein the allele is within a chromosomal interval selected from:

1) a chromosomal interval comprising SEQ ID NO: 2, or a portion thereof encoding ASR resistance;
2) a chromosomal interval encoding the protein sequence of SEQ ID NO: 1, or a portion thereof encoding ASR resistance;
3) a chromosomal interval comprising SEQ ID NOs 11, 12, or 13, or a portion thereof encoding ASR resistance;
4) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any favorable SNP marker displayed in Table 1.

In other embodiments, the disease resistant soybean plant or germplasm may be the progeny of a cross between an elite variety of soybean and a variety of soybean that comprises an allele associated with enhanced rust resistance (e.g. ASR) wherein the allele comprises SEQ ID NO: 2 or encodes a protein of SEQ ID NO: 1.

One embodiment of the invention is a *Glycine max* plant that has Asian soybean rust resistance/tolerance and that comprise the nucleic acid sequence of SEQ ID NO: 2 or a chromosomal interval selected from:

1) a chromosomal interval comprising SEQ ID NO: 2, or a portion thereof encoding ASR resistance;
2) a chromosomal interval encoding the protein sequence of SEQ ID NO: 1, or a portion thereof encoding ASR resistance;
3) a chromosomal interval comprising SEQ ID NOs 11, 12, or 13, or a portion thereof encoding ASR resistance; or
4) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any favorable SNP marker displayed in Table 1.

In certain embodiments, the chromosomal interval confers increased Asian soybean rust (ASR) resistance as compared to a control plant not comprising said chromosomal interval. The *Glycine max* plant may be derived from strain Williams 82

The disease resistant soybean plant or germplasm may be the progeny of an introgression wherein the recurrent parent is an elite variety of soybean and the donor comprises an allele associated with enhanced disease tolerance and/or resistance wherein the donor carries a chromosomal interval or a portion thereof comprising any one of SEQ ID NOs: 11, 12, or 13, and wherein the chromosome interval comprises at least one allele selected respectively from Table 1.

The disease resistant soybean plant or germplasm may be the progeny of a cross between a first elite variety of soybean (e.g., a tester line) and the progeny of a cross between a second elite variety of soybean (e.g., a recurrent parent) and a variety of soybean that comprises an allele associated with enhanced ASR tolerance (e.g., a donor).

The disease resistant soybean plant or germplasm may be the progeny of a cross between a first elite variety of soybean and the progeny of an introgression wherein the recurrent parent is a second elite variety of soybean and the donor comprises an allele associated with enhanced ASR tolerance.

A disease resistant soybean plant and germplasm of the present invention may comprise one or more markers of the present invention (e.g. any marker described in Table 1; or any marker in close proximity to any marker as described in Table 1).

In some embodiments, the disease resistant soybean plant or germplasm may comprise within its genome, a marker associated with enhanced ASR tolerance, wherein said marker is located within a chromosomal interval selected from:

1) a chromosomal interval comprising SEQ ID NO: 2, or a portion thereof encoding ASR resistance;
2) a chromosomal interval encoding the protein sequence of SEQ ID NO: 1, or a portion thereof encoding ASR resistance;
3) a chromosomal interval comprising SEQ ID NOs 11, 12, or 13, or a portion thereof encoding ASR resistance; or
4) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any favorable SNP marker displayed in Table 1.

In other embodiments, the marker is located with the nucleic acid sequence of SEQ ID NO: 2.

In some embodiments, the disease resistant soybean plant or germplasm may comprise within its genome a marker that comprises, consists essentially of or consists of marker alleles located in at least two different chromosomal intervals. For example, the marker may comprise one or more alleles located in the chromosomal interval defined by and including any combination of two markers in Table 1 and one or more alleles located in the chromosomal interval defined by and including any combination of two markers in Table 1.

In certain embodiments, the disease resistant soybean plant is derived from *Glycine max* strain Williams 82.

Disease Resistant Soybean Seeds

The present invention also provides disease resistant soybean seeds. As discussed above, the methods of the present invention may be utilized to identify, produce, and/or select a disease resistant soybean seed. In addition to the methods described above, a disease resistant soybean seed may be produced by any method whereby a marker associated with enhanced ASR tolerance is introduced into the soybean seed, including, but not limited to, transformation, protoplast transformation or fusion, a double haploid technique, embryo rescue, genetic editing (e.g. CRISPR or TALEN or MegaNucleases) and/or by any other nucleic acid transfer system.

One embodiment of the invention is a seed from *Glycine max* strain Williams 82 that has been modified to have Asian soybean rust resistance/tolerance i In some embodiments, the disease resistant soybean seed comprises a non-naturally occurring variety of soybean. In some embodiments, the soybean seed is at least about 50%, 55%, 60%, 65%, 70%, 75%, 80%, 85%, 90%, 95%, 97%, 99% or 100% identical to that of an elite variety of soybean.

The disease resistant soybean seed may be produced by a disease resistant soybean plant identified, produced, or selected by the methods of the present invention. In some embodiments, the disease resistant soybean seed is produced by a disease resistant soybean or wild glycine plant (e.g. *Glycine tomentella*) plant comprising any one of chromosomal intervals corresponding to SEQ ID NOs: 11-13, a chromosomal interval comprising SEQ ID NO: 2, or a chromosomal interval encoding a protein of SEQ ID NO: 1, or any portion of these intervals encoding ASR resistance.

A disease resistant soybean seed of the present invention may comprise, be selected by or produced by use of one or more markers from Table 1 of the present invention.

In some embodiments, the disease resistant soybean seed may comprise within its genome, a marker associated with enhanced ASR tolerance, wherein said marker is located within a chromosomal interval selected from the group consisting of:

1) a chromosomal interval comprising SEQ ID NO: 2, or a portion thereof encoding ASR resistance;
2) a chromosomal interval encoding the protein sequence of SEQ ID NO: 1, or a portion thereof encoding ASR resistance;
3) a chromosomal interval comprising SEQ ID NOs 11, 12, or 13, or a portion thereof encoding ASR resistance; or
4) a chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any favorable SNP marker displayed in Table 1.

In other embodiments, the marker is located with the nucleic acid sequence of SEQ ID NO: 2.

Proteins Conferring Rust Resistance

In addition to providing *Glycine max* plants having increased Asian soybean rust resistance, in certain embodiments, the invention provides proteins that are related to rust resistance, in particular Asian soybean rust resistance (herein, "ASR"). In particular embodiments, these proteins confer increased Asian soybean resistance. The protein and the coding gene thereof can be used to protect plants from rust pathogens.

In certain embodiments, the proteins are encoded by the nucleic acid sequence of SEQ ID NO: 2. In other embodiments, the proteins have at least 75%, at least 85%, at least 90%, at least, at least 95%, at least 97%, at least 98%, or at least 99% identical to a protein encoded by the nucleic acid sequence of SEQ ID NO: 1.

In other embodiments, the proteins are encoded by a chromosomal interval of comprising the nucleic acid sequence of SEQ NO: 11, 12, or 13. In other embodiments, the proteins have at least 75%, at least 85%, at least 90%, at least, at least 95%, at least 97%, at least 98%, or at least 99% identical to a protein encoded by a chromosomal interval of comprising the nucleic acid sequence of SEQ NO: 11, 12, or 13.

In certain embodiment, the protein of the instant disclosures is derived from soybean and named as RppRC1. In one embodiment of the invention, the protein has the amino acid sequence of SEQ ID NO: 1. In another embodiment of the invention, the protein has an amino acid sequence at least 75%, at least 85%, at least 90%, at least, at least 95%, at least 97%, at least 98%, or at least 99% identical to the amino acid sequence of SEQ ID NO: 2. In one embodiment, the protein of the instant disclosure can be any one of the following proteins:

(A1) a protein having the amino acid sequence shown in SEQ ID NO: 1;

(A2) a protein having substitution and/or deletion and/or addition of one or several amino acid residues from and having the same function as the amino acid sequence shown in SEQ ID NO: 1;

(A3) a protein having more than 99%, more than 95%, more than 90%, more than 85%, or more than 80% homology with and having the same function as the amino acid sequence defined in either (A1) or (A2); and (A4) a fusion protein obtained by tagging at the N-terminus and/or C-terminus of the protein defined in any one of (A1) to (A3).

In another embodiment, the protein of the instant disclosure can be any one of the following proteins:

(A5) a protein having the amino acid sequence encoded by a chromosomal interval of comprising the nucleic acid sequence of SEQ NO: 11, 12, or 13;

(A6) a protein having substitution and/or deletion and/or addition of one or several amino acid residues from and having the same function as the amino acid sequence encoded by a chromosomal interval of comprising the nucleic acid sequence of SEQ NO: 11, 12, or 13;

(A7) a protein having more than 99%, more than 95%, more than 90%, more than 85%, or more than 80% homology with and having the same function as the amino acid sequence defined in either (A5) or (A6); and (A8) a fusion protein obtained by tagging at the N-terminus and/or C-terminus of the protein defined in any one of (A5) to (A7).

In these proteins, the tag refers to a polypeptide or protein which is fused and expressed together with the protein of interest by using DNA in vitro recombination technology, so as to facilitate the expression, detection, tracing and/or purification of the protein of interest. The tag may be a FLAG tag, a His tag, an MBP tag, an HA tag, a myc tag, a GST tag, and/or a SUMO tag, etc.

In these proteins, identity refers to the identity between amino acid sequences. Homology retrieval websites on the Internet can be used to determine the identity between amino acid sequences, such as the BLAST web page on the NCBI homepage website. For example, the identity value (%) can be obtained in advanced BLAST2.1 by using blastp as the program, setting the Expect value to 10, setting all Filters to OFF, using BLOSUM62 as the Matrix, setting Gap existence cost, Per residue gap cost, and Lambda ratio to 11, 1, and 0.85 (default values), respectively, and retrieving the identity of a pair of amino acid sequences for calculation.

The proteins of the present invention can be produced from the nucleic acid molecules disclosed herein or by using standard molecular biology techniques.

The present invention encompasses an isolated or substantially purified protein. The "isolated" or "purified" protein or a biologically active portion thereof is substantially or largely free of components concomitant with or interacting with the protein that are normally present in the natural environment of the protein. The protein that is substantially free of cellular materials include protein formulations having less than about 30%, about 20%, about 10%, about 5%, or about 1% (by dry weight) of contaminating proteins. When the protein or the biologically active portion thereof in the embodiments are produced by recombinant methods, most preferably, the medium has less than about 30%, about 20%, about 10%, about 5% or about 1% (by dry weight) of chemical precursors or chemicals that are not proteins of interest. Fragments and variants related proteins are within the scope of the present disclosure.

Variant proteins encompassed by the present invention are bioactive, that is, they continue to possess the required bioactivity (i.e. the ability to enhance plant resistance (i.e. plant resistance against fungal pathogens) as described in the present invention) of native proteins. Such variants can be obtained, for example, by genetic polymorphism or by human manipulation. Bioactive variants of the native protein of the present invention may have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity with the amino acid sequence of the native protein or to SEQ ID NO: 1, as determined by sequence alignment programs known in the art. The biologically active variants of the protein disclosed in the present invention may differ from the protein by as little as about 1 to 15 amino acid residues, as little as about 1 to 10 (e.g., about 6 to 10), as little as about 5, as little as 4, 3, 2 or even 1 amino acid residue.

The proteins disclosed in the instant application may be modified, for example, by including amino acid substitution, deletion, truncation, and insertion. Methods of such manipulation are known in the art. For example, amino acid sequence variants and fragments of resistant proteins can be prepared by mutating in DNA. Methods of mutagenesis and polynucleotide modification are known in the art.

In one embodiment, the protein of the invention is a biologically active fragment of SEQ ID NO: 1, which can protect plants from rust pathogens.

The proteins disclosed in the present invention also encompass naturally occurring proteins and variants, fragments, and modified forms thereof. Such variants and fragments will still have the required ability to confer or enhance plant resistance against fungal pathogens.

Nucleic Acid Molecules

Another embodiment of the invention is directed to nucleic acid molecules relating to rust resistance. These nucleic acid molecules encode a protein of the invention, i.e. a protein conferring increased resistance to rust such as e.g. Asian soybean rust. The nucleic acid molecule may be DNA, such as cDNA, genomic DNA, or recombinant DNA. The nucleic acid molecule may also be RNA, such as mRNA.

In certain embodiments, the nucleic acid molecule is the gene RppRC1 (named as RppRC1). In one embodiment of the invention, the nucleic acid molecule has the nucleic acid sequence of SEQ ID NO: 2. In another embodiment, the nucleic acid molecule has a nucleic acid sequence at least 75%, at least 85%, at least 90%, at least, at least 95%, at least 97%, at least 98%, or at least 99% identical to the nucleic acid sequence of SEQ ID NO: 2. Embodiments of the nucleic acid molecules of the instant disclosure include:

(B1) a DNA molecule having the nucleic acid sequence of SEQ ID NO: 2;

(B2) a DNA molecule hybridizing to the nucleic acid sequence of SEQ ID NO: 2 under a stringent condition and encoding the protein described above; and (B3) a DNA molecule having more than 99%, more than 95%, more than 90%, more than 85%, or more than 80% homology with the DNA sequences defined in (B1) and (B2) and encoding the protein described above.

In other embodiments, the nucleic acid molecule comprises a chromosomal interval comprising the nucleic acid sequence of SEQ ID NO: 11, 12, or 13, or a portion thereof encoding ASR resistance. In another embodiment, the nucleic acid molecule has a nucleic acid sequence at least 75%, at least 85%, at least 90%, at least, at least 95%, at least 97%, at least 98%, or at least 99% identical to a chromosomal interval comprising the nucleic acid sequence of SEQ ID NO: 11, 12, or 13. In certain embodiments, the nucleic acid molecules encode ASR resistance. Embodiments of such nucleic acid molecules include:

(B4) a DNA molecule having the nucleic acid sequence of SEQ ID NO: 11, 12, or 13 or portion thereof encoding ASR resistance;

(B5) a DNA molecule hybridizing to the nucleic acid sequence of SEQ ID SEQ ID NO: 11, 12, or 13 under a stringent condition and encoding the protein described above; and (B6) a DNA molecule having more than 99%, more than 95%, more than 90%, more than 85%, or more than 80% homology with the DNA sequences defined in (B4) and (B4) and encoding a protein conferring increased rust resistance to a plant.

As for the above genes, the stringent condition may be as follows: hybridizing at 50° C. in a mixed solution of 7% sodium dodecyl sulfate (SDS), 0.5 M $Na_3PO_4$ and 1 mM EDTA, and rinsing at 50° C. in 2×SSC, 0.1% SDS; the stringent condition may also be: hybridizing at 50° C. in a mixed solution of 7% SDS, 0.5 M $Na_3PO_4$ and 1 mM EDTA, and rinsing at 50° C. in 1×SSC, 0.1% SDS; the stringent condition may also be: hybridizing at 50° C. in a mixed solution of 7% SDS, 0.5 M $Na_3PO_4$ and 1 mM EDTA, and rinsing at 50° C. in 0.5×SSC, 0.1% SDS; the stringent condition may also be: hybridizing at 50° C. in a mixed solution of 7% SDS, 0.5 M $Na_3PO_4$ and 1 mM EDTA, and rinsing at 50° C. in 0.1×SSC, 0.1% SDS; the stringent condition may also be: hybridizing at 50° C. in a mixed solution of 7% SDS, 0.5 M $Na_3PO_4$ and 1 mM EDTA, and rinsing at 65° C. in 0.1×SSC, 0.1% SDS; the stringent condition may also be: hybridizing at 65° C. in a solution of 6×SSC and 0.5% SDS, and then washing the membrane once with 2×SSC and 0.1% SDS, and once with 1×SSC and 0.1% SDS, respectively.

In another embodiment, the nucleic acid molecule encodes the amino acid of SEQ ID NO: 1 or a protein having an amino acid sequence at least 75%, at least 85%, at least 90%, at least, at least 95%, at least 97%, at least 98%, or at least 99% identical to the amino acid sequence of SEQ ID NO: 1.

The present invention encompasses an isolated or substantially purified nucleic acid molecule. The "isolated" or "purified" nucleic acid molecule or a biologically active portion thereof is substantially or largely free of components concomitant with or interacting with the nucleic acid molecule that are normally present in the natural environment of the nucleic acid molecule. Thus, the isolated or purified nucleic acid molecule or protein is substantially free of other cellular materials or media when produced by recombinant techniques (such as PCR amplification), or chemical precursors or other chemicals when synthesized by chemical methods. Most preferably, the "isolated" nucleic acid molecule does not comprise sequences (e.g., protein coding sequences) that are naturally located flanking the nucleic acid molecule (i.e. sequences located at the 5' and 3' ends of the nucleic acid molecule) in the genomic DNA of the organism from which the nucleic acid molecule is derived. For example, in some embodiments of the present invention, the isolated nucleic acid molecule may comprise less than about 5 kb, about 4 kb, about 3 kb, about 2 kb, about 1 kb, about 0.5 kb, or about 0.1 kb of nucleotide sequences that are naturally located flanking the nucleic acid molecule in the genomic DNA of the cell from which the nucleic acid molecule is derived. Fragments and variants related to coded nucleotide sequences are within the scope of the present disclosure. "A fragment" and grammatical variations thereof refer to a portion of a nucleotide sequence or a portion of an amino acid sequence and a protein coded thereby. Fragments of the nucleotide sequence can encode protein fragments that retain the biological activity of natural proteins and have the ability to confer resistance (i.e. antifungal) in plants. Alternatively, nucleotide sequence fragments that can be used as hybridization probes do not necessarily code protein fragments that maintain biological activity. Thus, the fragment of the nucleotide sequence may be in the range of at least about 15 nucleotides, about 50 nucleotides, about 100 nucleotides and at most the full-length nucleotide sequence coding the protein disclosed herein.

The fragment of the nucleotide sequence coding the biologically active portion of the disclosed protein may code at least about 15, about 25, about 30, about 40, or 45, about 50 consecutive amino acids or at most the total number of amino acids present in the full-length protein of this embodiment (e.g., 857 amino acids for SEQ ID NO: 1). Fragments of nucleotide sequences that can be used as hybridization probes or PCR primers usually do not have to code biologically active portions of proteins.

When referring to a specified nucleic acid molecule, the term "full-length sequence" refers to the entire nucleic acid sequence of a native sequence. "A native sequence" and grammatical variations thereof are use in the present invention to refer to an endogenous sequence, i.e. an unengineered sequence present in the genome of an organism.

Therefore, the fragment of the nucleotide sequence disclosed in the present invention can code a biologically active portion of a protein, or it can be a fragment used as a hybridization probe or PCR primer. In certain embodiments, the nucleic acid molecule of the present invention comprises at least about 15, about 20, about 50, about 75, about 100, or about 150 nucleotides or at most the number of nucleotides present in the full-length nucleotide sequence disclosed herein (e.g., 2574 nucleotides for SEQ ID NO: 2).

Those skilled in the art will recognize that the nucleic acid variants of the present invention will be configured such that the open reading frame is maintained. For nucleic acid molecules, conserved variants comprise those sequences that code the amino acid sequences in the proteins of the present invention due to degeneracy of the genetic code. Native allelic variants can be identified by well-known molecular biological techniques, such as polymerase chain reaction (PCR) and hybridization techniques. Variant nucleic acid molecules also comprise synthetic nucleic acid molecules, such as those generated by using site-directed mutagenesis but still coding the proteins of the present invention. Generally, variants of a particular nucleic acid molecule disclosed herein may have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity with the particular nucleic acid molecule, as determined by sequence alignment programs well known in the art.

Variants of a particular nucleic acid molecule (i.e. a reference nucleic acid molecule) of the present invention can also be evaluated by comparing the percentage of sequence identity between the protein coded by the variant nucleic acid molecule and the protein coded by the reference nucleic acid molecule. The percentage of sequence identity between any two proteins can be calculated using sequence alignment programs known in the art. In the case where any given pair of nucleic acid molecules of the present invention is evaluated by comparing the percentage of sequence identity shared by the two proteins coded by the given pair of nucleic acid molecules, the percentage of sequence identity between the two coded proteins is at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more sequence identity.

Variant nucleic acid molecules and proteins also encompass sequences and proteins obtained by mutagenesis and recombination procedures, including but not limited to procedures such as DNA shuffling. A library of recombinant polynucleotides can be generated from a group of related sequence polynucleotides comprising sequence regions having substantial sequence identity and capable of homologous recombination in vitro or in vivo. For example, using this method, a sequence motif coding a domain of interest can be shuffled between the protein gene disclosed in the present invention and other known protein genes to obtain a new gene coding a protein having improved properties of interest, such as an increased ability to confer or enhance resistance of plants to fungal pathogens. Such DNA shuffling strategies are known in the art.

The present disclosure encompasses sequences that are isolated based on their sequence identity with the entire sequence shown herein or the variants and fragments thereof. Such sequences include sequences that are orthologues of the disclosed sequences. Genes present in different species are considered to be orthologues when their nucleotide sequences and/or protein sequences coded thereby share at least about 60%, about 70%, about 75%, about 80%, about 85%, about 90%, about 91%, about 92%, about 93%, about 94%, about 95%, about 96%, about 97%, about 98%, about 99% or more sequence identity. The function of orthologues is often highly conserved in various species. Therefore, the present disclosure encompasses isolated nucleic acid molecules that code proteins that confer or enhance fungal plant pathogen resistance and hybridize with the sequences disclosed in the present invention or variants or fragments thereof.

In PCR methods, oligonucleotide primers can be designed for PCR reactions to amplify corresponding DNA sequences from cDNA or genomic DNA extracted from any organism of interest. Methods for designing PCR primers and for cloning by PCR are known in the art and are disclosed in the following documents: Sambrook et al., (1989) Molecular Cloning: A Laboratory Manual (2nd ed., Cold Spring Harbor Laboratory Press, Plainview, N.Y.). Known PCR methods include, but are not limited to, methods using paired primers, nested primers, single-specific primers, degenerate primers, gene-specific primers, vector-specific primers, partially mismatched primers, etc.

In hybridization techniques, all or part of a known nucleic acid molecule is used as a probe that selectively hybridizes with other corresponding polynucleotides present in a set of cloned genomic DNA fragments or cDNA fragments (i.e. a genomic or cDNA library) from a selected organism. The hybridization probe may be a genomic DNA fragment, a cDNA fragment, an RNA fragment, or other oligonucleotide and may be labeled with detectable groups such as $^{32}P$ or any other detectable markers. Therefore, for example, the hybridization probe can be prepared by labeling the synthetic oligonucleotide based on the polynucleotide of this embodiment. Methods for preparing hybridization probes and constructing cDNA libraries and genomic libraries are known in the art.

Various procedures can be used to determine the presence or absence of specific sequences of DNA, RNA, or protein. These include, for example, Southern blot, Northern blot, Western blot, and ELISA analysis. These techniques are well known in the art.

The protein and the coding gene thereof and methods disclosed in the present invention can be used to regulate the content of one or more proteins in plants. The term "regulate" and grammatical variations thereof are used in the present invention to refer to an increase or decrease in the protein content in genetically modified (i.e. transformed) plants relative to the protein content from the corresponding untransformed plants (i.e. plants that have not been genetically modified according to the methods of the present disclosure).

As used herein, the term "expression" and grammatical variations thereof refer to the biosynthesis or process whereby a polynucleotide is generated, including the transcription and/or translation of a gene product. For example, the nucleic acid molecules disclosed in the present invention may be transcribed from DNA templates (such as into mRNA or other RNA transcripts) and/or the transcribed mRNA is subsequently translated into proteins. The term "gene product" and grammatical variations thereof may refer to, for example, transcripts and coded proteins. The inhibition (or increase) of the expression or function of the gene product (i.e. the gene product of interest) may be in an environment in which comparisons are made between any two plants, For example, the expression or function of a gene product in genetically modified plants is relative to the expression or function of the gene product in corresponding but susceptible wild-type plants or other susceptible plants. The expression level of a gene product in a wild-type plant may not exist. For example, a "wild type" plant may be a plant, a plant cell or a plant part that does not express an exogenous resistance gene.

Alternatively, the inhibition (or increase) of the expression or function of the target gene product may be in an environment in which comparisons are made between plant cells, organelles, organs, tissues or plant parts within the same plant or different plants and include comparisons between developmental or temporal stages of the same plant or different plants. Any method or composition that downregulates the expression of the target gene product or downregulates the functional activity of the target gene product at the transcription or translation level can be used to achieve inhibition of the expression or function of the target gene product. Similarly, any method or composition that induces or upregulates the expression of the target gene product at the transcription or translation level, or increases or activates or upregulates the functional activity of the target gene product, may be used to achieve increased expression or function of the target gene or protein. Methods for inhibiting or enhancing gene expression are well known in the art.

Genes and nucleic acid molecules disclosed in the present invention include naturally occurring sequences and mutants or modified forms thereof. The proteins disclosed in the present invention also encompass naturally occurring proteins and variants, fragments, and modified forms thereof. Such variants and fragments will still have the required ability to confer or enhance plant resistance against fungal pathogens. In one embodiment, mutations to be made in the DNA coding the variants or fragments generally do not place the sequence outside the reading frame and, preferably, will not produce complementary regions, which may produce secondary mRNA structures.

Expression Cassettes, Recombinant Vectors, Recombinant Bacteria, or Transgenic Cell Lines The instant application also provides an expression cassette, a recombinant vector, a recombinant bacterium, or a transgenic cell line containing the nucleic acid molecule described above.

The expression cassette refers to DNA capable of expressing the protein in a host cell, and the DNA not only includes a promoter that initiates transcription of the gene encoding the protein, but also includes a terminator that terminates the transcription. Furthermore, the expression cassette may further include an enhancer sequence. Promoters that may be used in the present invention include, but are not limited to: constitutive promoters, tissue-, organ- and development-specific promoters and inducible promoters. Examples of promoters include, but are not limited to: constitutive promoter 35S of cauliflower mosaic virus; a trauma inducible promoter from tomato, leucine aminopeptidase ("LAP", Chao et al., (1999) *Plant Physiol* 120: 979-992); a chemically inducible promoter from tobacco, pathogenesis related 1 (PR1) (induced by salicylic acid and BTH (benzothiadiazole-7-thiohydroxyacid S-methyl ester)); tomato protease inhibitor II promoter (PIN2) or LAP promoter (both induced by methyl jasmonate); heat shock promoter; tetracycline inducible promoter; seed-specific promoters, such as millet seed-specific promoter pF128, seed storage protein-specific promoters (e.g., phaseolin, napin, oleosin, and soybean beta conglycin promoters (Beachy et al., (1985) *EMBO J.* 4: 3047-3053)). They can be used alone or in combination with other plant promoters. Suitable transcription terminators include, but are not limited to: *Agrobacterium* nopaline synthase terminator (NOS terminator), cauliflower mosaic virus CaMV 35S terminator, tml terminator, pea rbcS E9 terminator and nopaline and octopine synthase terminator (see, for example: Odell et al., ($I^{985}$) *Nature,* 313: 810; Rosenberg et al., (1987) *Gene,* 56: 125; Guerineau et al., (1991) *Mol. Gen. Genet,* 262: 141; Proudfoot (1991) *Cell,* 64: 671; Sanfacon et al., *Genes Dev.,* 5: 141; Mogen et al., (1990) *Plant Cell,* 2: 1261; Munroe et at, (1990) Gene, 91: 151; Ballad et al., (1989) *Nucleic Acids Res.,* 17: 7891; Joshi et al., (1987) *Nucleic Acid Res.,* 15: 9627).

Constructing a recombinant expression vector containing the nucleic acid molecule. The plant expression vectors used can be Gateway system vectors or binary *Agrobacterium* vectors, such as pGWB411, pGWB412, pGWB405, pBin438, pCAMBIA1302, pCAMBIA2301, pCAMBIA1301, pCAMBIA1300, pBI121, pCAMBIA1391-Xa or pCAMBIA1391-Xb.

When using RppRC1 to construct a recombinant expression vector, any enhanced, constitutive, tissue-specific or inducible promoter can be added before the transcription initiation nucleotide, such as cauliflower mosaic virus (CAMV) 35S promoter, ubiquitin gene Ubiquitin promoter (pUbi), etc., which can be used alone or in combination with other plant promoters. In addition, when using the gene and/or chromosome intervals of the present invention to construct a plant expression vector, enhancers, including translation enhancers or transcription enhancers, can also be used, and these enhancer regions can be ATG start codons or regions adjacent to start codons, etc., but must be in the same reading frame as the coding sequence to ensure the correct translation of the entire sequence. The sources of the translation control signals and start codons are extensive and can be natural or synthetic. The translation initiation region may be from a transcription initiation region or a structural gene.

In order to facilitate identification and screening of transgenic plant cells or plants, the plant expression vector can be engineered, for example, by adding a gene (GUS gene, luciferase gene, etc.) which can be expressed in a plant and encode an enzyme which can produce a color change or a luminescent compound, an antibiotic marker having resistance (gentamicin marker, kanamycin marker, etc.), or a marker gene having resistance against a chemical reagent (such as a herbicide-resistant gene), etc.

The transgenic cell line can be either a propagating material or a non-propagating material.

In a specific embodiment, the promoter for initiating the transcription of the coding gene of the protein in the expression cassette is specifically the original endogenous promoter of the coding gene, and the nucleotide sequence of the original endogenous promoter of the coding gene is shown in SEQ ID NO: 7.

In another embodiment of the invention, the recombinant vector is specifically a recombinant plasmid obtained by cloning the nucleic acid molecule (SEQ ID NO: 2) described above between the attR1 and attR2 sites of pB2GW7 vector, and replacing the 35S promoter between the SacI and SpeI enzyme digestion sites with the endogenous promoter of RppRC1 gene shown in SEQ ID NO: 7.

The resistance gene disclosed in the present invention can be expressed as a transgene to produce a rust-resistant plant. The use of different promoters described in the present invention or known to those skilled in the art will cause gene expression to be regulated under different conditions (i.e. promoters can be selected based on desired results). For example, a higher level of expression in a particular tissue system or organ (e.g., leaves) may be required to enhance resistance. The entire gene (e.g., both the natural promoter and the coding sequence) can be inserted as a transgene, thus allowing rapid combination with other traits such as insect resistance or herbicide resistance.

In some embodiments, nucleic acid sequences can be superimposed with any combination of nucleic acid molecular sequences of interest to form plants having desired phenotypes. This superposition can be achieved by a combination of genes in a DNA construct, or by hybridizing one or more plants with transgenes with another plant strain comprising a desired combination. For example, the nucleic acid molecules or fragments thereof disclosed in the present invention can be superimposed with any other nucleic acid molecules or other genes. The resulting combination can also include multiple copies of any one of the nucleic acid molecules of interest. The nucleic acid molecules disclosed in the present invention may also be superimposed with any other gene or combination of genes to produce a plant having a desired combination of a plurality of traits. The traits include, but are not limited to, traits desired as animal feeds, such as high oil genes, balanced amino acids, increased digestibility, insect resistance, disease resistance or herbicide resistance, non-toxicity and disease resistance genes, agronomic traits (e.g., male sterility, flowering time) and/or transformation technology traits (e.g., cell cycle regulation or gene targeting).

Any method, including but not limited to cross breeding of plants by any conventional or known method or genetic transformation, can be used to gather different genes. If the traits are stacked by genetically transformed plants, the polynucleotide sequences of interest can be combined in any order at any time. For example, transgenic plants comprising one or more desired traits can be used as targets to introduce more traits through subsequent transformation. In the co-transformation scheme, traits can be introduced simultaneously with the polynucleotide of interest, which is provided by any combination of transformation cassettes. For example, if two sequences are to be introduced, the two sequences can be comprised in separate transformation cassettes (trans) or in the same transformation cassette (cis). Expression of the sequences can be driven by the same promoter or different promoters. In some cases, it is desirable to introduce a transformation cassette that can inhibit the expression of a nucleic acid molecule of interest. This can be combined with any combination of other inhibition cassettes or overexpression cassettes to generate a desired combination of traits in plants.

The constructed vector or expression cassette does not exist in the genome of the initial plant or the genome of the transgenic plant and is not located at the native locus in the genome of the initial plant.

The compositions disclosed in the present invention can be produced or maintained by a method for gene introgression. Gene introgression is sometimes referred to as "backcross" when that method is repeated two or more times. In gene introgression or backcross, "donor" parents refer to parent plants with required genes or loci to be introgressed. "Recipient" parents (used once or more) or "recurrent" parents (used twice or more) refer to parent plants in which genes or loci are introgressed. Initial hybridization produces F1 generation. The term "BC1" refers to the second use of the recurrent parents, and "BC2" refers to the third use of the recurrent parents, and so on.

The present invention may also include the described sequences which may be provided from an expression cassette or DNA construct expressed in plants of interest. The expression cassette may include 5' and 3' heterologous regulatory sequences operatively linked to the sequences disclosed in the present invention. The term "operatively linked" is used in the present invention to mean that a nucleic acid to be expressed is linked to a regulatory sequence, including a promoter, a terminator, an enhancer and/or other expression control elements (e.g., polyadenylation signals) in a manner that allows the expression of the nucleic acid (i.e. when a vector is introduced into a host plant cell, the nucleic acid is expressed in the host plant cell). Such regulatory sequences are well known in the art and include those nucleotide sequences that can be directly constitutively expressed in a variety of host cells and directly expressed in specific host cells or under specific conditions. The design of the vector may depend on, for example, the type of host cells to be transformed, or the desired expression level of nucleic acids. The expression cassette may comprise one or more additional genes to be co-transformed into the plants. Moreover, any additional gene can be provided in a plurality of expression cassettes.

The expression cassette of the present invention may comprise a plurality of restrictive enzyme digestion sites for insertion of the nucleotide sequence so as to be under the transcriptional regulation of a regulatory region. The expression cassette may also comprise selective marker genes.

The expression cassette may also comprise, in the 5'-3' transcription direction, a transcription and translation initiation region, a DNA sequence of the present disclosure, and a transcription and translation termination region that function in plants. The transcription initiation region, a promoter, may be native or similar or foreign or heterologous relative to plant hosts. In addition, the promoter may be a native sequence or alternatively a synthetic sequence. The term "heterologous" means that the initial transcription region does not exist in the native plant into which the initial transcription region is introduced. As used herein, a chimeric gene comprises a coding sequence operatively linked to a transcription initiation region which is heterologous to the coding sequence. Examples of promoters include, but are not limited to, cauliflower mosaic virus 35S and soybean ubiquitin 6.

Although heterologous promoters may preferably be used to express sequences, homologous promoters or native promoter sequences may be used. Such constructs will alter the level of expression in host cells (i.e. plants or plant cells). Therefore, the phenotypes of the host cells (i.e. the plant or plant cell) are changed.

The termination region may naturally have a transcription initiation region, naturally have an operatively linked DNA sequence of interest, or originate from another source. A readily available termination region (such as octopine synthase and nopaline synthase termination regions) can be obtained from the T1 plasmid of *Agrobacterium* tumefaciens.

Endogenous or source gene resistant orthologue can be altered by a homologous or non-homologous recombination method, such as, for example, by genome editing. When compared to an unmodified sequence, such alteration means that the nucleotide sequence has at least one modification and includes, for example: (i) replacement of at least one nucleotide, (ii) deletion of at least one nucleotide, (iii) insertion of at least one nucleotide, or (iv) any combination of (i)-(iii).

In some embodiments, genome editing techniques may be used to introduce the resistance genes disclosed in the present invention into the genome of a plant, or genome editing techniques may be used to edit resistance genes previously introduced into the genome of a plant.

Genome editing can be implemented using any available gene editing method. For example, gene editing can be achieved by introducing a polynucleotide modification template (sometimes referred to as a gene repair oligonucleotide) into a host cell, wherein the polynucleotide modification template comprises targeted modifications of genes within the genome of the host cell. The polynucleotide modification template can be single-stranded or double-stranded.

One or more genes may be optimized as desired to increase expression in transformed plants. For example, plant-preferred codons are used to synthesize genes to improve expression. Methods for synthesizing a plant-preferred gene are known in the art.

Additional sequence modifications are known to enhance the gene expression in a cell host. These sequence modifications include the elimination of the following sequences: coded pseudo-polyadenylation signals, exon-intron splicing site signals, transposon-like repeat sequences, and other such fully characterized sequences that may be harmful to gene expression. The G-C content in a sequence can be adjusted to the average level of a given cell host, which level can be calculated from known genes expressed in the host cell. The sequence can be modified if necessary, to avoid a possible hairpin secondary mRNA structure.

An expression cassette may additionally comprise a 5' leader sequence in a construct of the expression cassette. Such a leader sequence can enhance translation. Translation leader sequences are known in the art and include: small ribonucleic acid virus leader sequence, such as EMCV leader sequence (encephalomyocarditis 5' non-coding region); potato y virus group leader sequence, such as TEV leader sequence (tobacco etch virus), and human immunoglobulin heavy chain binding protein (BiP); untranslated leader sequence of coat protein mRNA (AMVRNA 4) from alfalfa mosaic virus; tobacco mosaic virus (TMV) leader sequence; as well as maize chlorotic mottle virus (MCMV) leader sequence (Lommel et al., (1991) *Virology* 81: 382-385). Other known methods for enhancing translation, such as introns, may also be utilized.

Various DNA fragments in an expression cassette can be manipulated in appropriate reading frames according to needs to ensure that DNA sequences are in the correct direction. To this end, adapters or linkers can be used to link DNA fragments. In addition, other manipulations can also be used to provide convenient restriction sites, remove excess DNA, or remove restriction sites. For this purpose, in vitro mutagenesis, primer repair, restriction, annealing, and re-replacement (e.g., conversion and transversion) may be involved.

Generally, an expression cassette may comprise selective marker genes for selecting transformed cells. The selective marker genes are used to select transformed cells or tissues. Marker genes include genes encoding antibiotic resistance, such as genes encoding neomycin phosphotransferase II (NEO) and hygromycin phosphotransferase (HPT), as well as genes conferring resistance against herbicidal compounds such as glufosinate, phosphinothricin, bromoxynil, imidazolinone and 2,4-dichlorophenoxyacetic acid (2,4-D). The above list of selective marker genes is not meant to be limiting. Any selective marker gene can be used in the present disclosure.

In order to express the target gene and/or protein of the present invention in a plant or plant cell, the method of the present invention comprises transforming the plant or plant cell with a nucleic acid molecule coding the target protein. The nucleic acid molecule of the present invention can be operatively linked to a promoter which drives expression in a plant cell. Any promoter known in the art can be used in the method of the present invention, including, but not limited to, constitutive promoters, pathogen inducible promoters, wound inducible promoters, tissue-preferred promoters, and chemically regulated promoters. The selection of the promoter may depend on the desired expression time and location in a transformed plant, as well as other factors known to those skilled in the art. Transformed cells or plants may be planted or cultivated to form a plant comprising one or more of polynucleotides introduced, for example, into cells or plants coding R proteins.

A variety of promoters can be used to put into practice the present invention. The promoters can be selected according to the desired result. That is, a nucleic acid can be combined with a constitutive promoter, a tissue-preferred promoter, or other promoters and expressed in a host cell of interest. Such constitutive promoters include, for example, the core promoter of the Rsyn7 promoter and other constitutive promoters disclosed in WO 99/43838 and U.S. Pat. No. 6,072,050, CaMV 35S promoter, rice actin, Ubiquitin, pEMU, MAS, ALS, etc. Such constitutive promoters are known in the art and are contemplated for use in the present disclosure.

Generally, using inducible promoters, especially those from pathogens, to express the gene of the present invention is beneficial to the application of the gene of the present invention. Such promoters include the promoters from pathogenesis-related proteins (PR proteins), which proteins are induced to form by pathogen infection and are, for example, PR proteins, SAR proteins, β-1,3-glucanase, chitosanases, etc.

Promoters expressed locally at or near the pathogen infection site deserve attention. In addition, because pathogens can enter plants through wounds or insect-caused lesions, wound inducible promoters can also be used for vector construction of the present invention. Such wound inducible promoters include potato protease inhibitor (pinII) gene, wun1 and wun2, win1 and win2, systemin, WIP1, MPI gene, etc.

Chemically regulated promoters can regulate gene expression in plants by applying exogenous chemical regulatory agents. According to the purpose of utilization, the promoters may be chemically inducible promoters, such as inducing gene expression by applying chemicals, or chemically repressible promoters, such as inhibiting gene expression by applying chemicals. Chemically inducible promoters are known in the art and include, but are not limited to, the maize Int-2 promoter (which is activated by benzenesulfonamide herbicide safeners), the maize GST promoter (which is activated by hydrophobic electrophilic compounds used as pre-emergence herbicides) and the tobacco PR-la promoter (which is activated by salicylic acid). Other chemically regulated promoters of interest include steroid responsive promoters (for example, glucocorticoid inducible promoters, tetracycline inducible promoters and tetracycline repressible promoters).

Tissue-preferred promoters can be used for targeted enhanced expression of target genes or proteins (e.g., polynucleotide sequences coding NB-LRR polypeptides derived from leguminous plants) in specific plant tissues. Preferred promoters for such tissues include, but are not limited to, leaf-specific promoters, root-specific promoters, seed-specific promoters, and stem-specific promoters. Tissue-specific promoters include Yamamoto et al., (1997) *Plant J.* 12 (2): 255-265; Kawamata et al., (1997) *Plant Cell Physiol.* 38 (7): 792-803; Hansen et al., (1997) *Mol. Gen Genet.* 254 (3): 337-343; Russell et al., (1997) *Transgenic Res.* 6 (2): 157-168; Rinehart et al., (1996) *Plant Physiol.* 112 (3): 1331-1341; Van Camp et al., (1996) *Plant Physiol.* 112 (2): 525-535; Canevascini et al., (1996) *Plant Physiol.* 112 (2): 513-524; Yamamoto et al., (1994) *Plant Cell Physiol.* 35 (5): 773-778; Lam, (1994) *Results Probl. Cell Differ.* 20: 181-196; Orozco et al., (1993) *Plant Mol Biol.* 23 (6): 1129-1138; Matsuoka et al., (1993) *Proc Natl. Acad. Sci. USA,* 90 (20): 9586-9590; and Guevara-Garcia et al., (1993) *Plant J.* 4 (3): 495-505. Such promoters may be used to modify the nucleotide sequences of the present disclosure.

Leaf-specific promoters are known in the art. See, for example, Yamamoto et al., (1997) *Plant J.* 12 (2): 255-265; Kwon et al., (1994) *Plant Physiol.* 105: 357-67; Yamamoto et al., (1994) *Plant Cell Physiol.* 35 (5): 773-778; Gotor et al., (1993) *Plant J.* 3: 509-18; Orozco et al, (1993) Plant Mol. Biol. 23 (6): 1129-1138; and Matsuoka et al., (1993) *Proc. Natl. Acad. Sci. USA,* 90 (20): 9586-9590.

"Seed-preferred" promoters include "seed-specific" promoters (those that are active during seed development, such as promoters of seed storage protein) and "seed germination" promoters (those that are active during seed germination). Such seed-preferred promoters include, but are not limited to, Cim1 (cytokinin induction information), mi1ps (inositol-1-phosphate synthase) and celA (cellulose synthase). Globin-1 (Glob-1) is the preferred embryo-specific promoter. For dicotyledon, seed-specific promoters include, but are not limited to, common bean β-phaseolin gene promoter, napin gene promoter, β-conglycinin gene promoter, soybean lectin gene promoter, cruciferae protein gene promoter, etc.

The expression of the nucleic acid molecules of the present invention may involve the use of complete native resistance genes, wherein the expression is driven by a homologous 5' upstream promoter sequence or other heterologous promoters. Those skilled in the art will be able to identify the resistance genes to evaluate the expression level thereof and select a preferred promoter sequence that can be used to express the resistance genes of interest. The use of homologous or heterologous resistance gene promoter sequences provides options for regulating protein expression to avoid or minimize any potentially inappropriate or undesirable results related to plant defense activation.

Specific soybean promoters include, but are not limited to, promotors from soybean ubiquitin (subi-1), elongation factor 1A, S-adenosylmethionine synthase for constitutive expression, Rpp4, and RPG1-B, and promoters comprised in gene models, such as Glyma promoters known to those skilled in the art for more closely regulating the expression provided by NB-LRR gene promoters.

In the context of the present invention, germplasm includes cells, seeds or tissues from which new plants can be generated, or plant parts such as leaves, stems, pollen, or cells that can be cultivated into whole plants.

Transforming Plants

Since the resistance gene disclosed in the present invention can be expressed as a transgene to produce a rust-resistant plant, certain embodiment of the invention are directed to methods for introducing a nucleic acid molecule into a plant. In addition to transforming soybean plants described above, the nucleic acids of the invention may be used in other plants as well.

As used herein, the term "introduction" and grammatical variations thereof refer to providing a plant with a nucleic acid molecule. In some embodiments, the nucleic acid molecule can exist in such a way that the sequence enters the interior of a plant cell, including their potential insertion into the genome of the plant. The method disclosed in the present invention does not depend on specific methods for introducing a sequence into a plant, as long as a nucleic acid molecule enters the interior of at least one cell of the plant. Methods for introducing a nucleic acid molecule into a plant are known in the art and include, but are not limited to stable transformation methods, transient transformation methods and virus-mediated methods.

Examples of methods for plant transformation include *Agrobacterium*-mediated transformation and particle bombardment, then the transformed plant can be regenerated by methods known to those skilled in the art.

A nucleic acid molecule can be transiently or stably introduced into a host cell and can remain unintegrated, for example, in plasmid form. "Stable transformation" or "stably transformed" and grammatical variations thereof mean that a nucleotide construct introduced into a plant is integrated into the genome of the plant and can be inherited by the progenies of the plant. As used herein, "transient transformation" and grammatical variations thereof mean that a nucleic acid molecule is introduced into a plant but not integrated into the genome of the plant, or a protein is introduced into a plant.

The transformation methods and the methods for introducing a nucleic acid molecular sequence into a plant may depend on the type of a plant or a plant cell to be transformed. Suitable methods for introducing a protein or a nucleic acid molecule into a plant cell include, but are not limited to, microinjection, electroporation, direct gene transfer, Lec1 transformation, and ballistic particle acceleration. As the updated methods become available, such methods can also be used in the present invention because the methods of transformation or transfection are not critical.

The transformed cells can be cultivated into plants according to conventional methods. These plants can then be grown and pollinated with the same transformation line or different lines, and then progenies with constitutive expression with required phenotypic characteristics can be identified. Two or more generations of plants can be cultivated to ensure that the expression of required phenotypic characteristics is stably maintained and inherited. The seeds are then harvested to ensure that the expression of the required phenotypic characteristics has been achieved. In some embodiments, transformed seeds or transgenic seeds have nucleotide constructs or expression cassettes stably incorporated into their genomes.

The present invention encompasses seeds comprising the nucleic acid molecular sequences disclosed in the present invention, the seeds can be developed into or used to develop one or more plants having enhanced resistance to pathogens (e.g., fungi) or infections formed by pathogens compared to, for example, the plant seeds of wild-type varieties. The present invention is characterized by seeds from transgenic leguminous plants, wherein the seeds comprise the nucleic acid molecules disclosed in the present invention.

Plants of interest include leguminous crop species, including but not limited to alfalfa (*Medicago saliva*); clover or trefoil (*Trifolium* spp.); pea, including *Pisum satinum, Gajanus cajan, Vigna unguiculata* and *Lathyrus* spp.; common bean (Fabaceae or Leguminosae); lentil (*Lens culinaris*); lupin (*Lupinus* spp.); ghaf tree (*Prosopis* spp.); long bean (*Ceratonia siliqua*), soybean (*Glycine max*), peanut (*Arachis hypogaea*) or tamarind (*Tamarindus indica*). The terms "leguminous species" and "leguminous crop species" are used herein to refer to plants and may, for example, be plants of interest. Leguminous species or leguminous crop species may be plants, plant parts or plant cells.

Regulating and Enhancing Rust Resistance

The present invention also provides for use of the proteins, nucleic acids recombinant vectors, recombinant bacterium, or transgenic cell line described herein in regulating the resistance of plants against rust. In the use, the expression level and/or activity of the protein or the coding gene thereof in the plants is increased, and the resistance of the plants against rust is enhanced.

Furthermore, the invention is directed to a method for enhancing the resistance of plants to plant diseases such as rust. The method may include conferring resistance against pathogens (e.g., rust) by introgressing resistance genes from leguminous plants into germplasm in a breeding procedure (i.e. breeding procedure for rust resistance).

Methods of introgression as disclosed herein may also be used to produce soybean plants having increased resistance to any one of the following: soy cyst nematode, bacterial pustule, root knot nematode, frog eye leaf spot, phytopthora, brown stem rot, nematode, smut, *Golovinomyces cicho-*

*racearum, Erysiphe cichoracearum, Blumeria graminis, Podosphaera xanthii, Sphaerotheca fuhginea, Pythium ultimum, Uncinula necator, Mycosphaerella pinodes, Magnaporthe grisea, Bipolaris oryzae, Magnaporthe grisea, Rhizoctonia solani, Phytophthora sojae, Schizaphis graminum, Bemisia tabaci, Rhopalosiphum maidis, Deroceras reticulatum, Diatraea saccharahs, Schizaphis graminum*, or *Myzus persicae*.

In one embodiment, the method improves the resistance against rust. The method for improving the resistance of plants against rust may include increasing the expression level and/or activity of the above-mentioned proteins in the plants, wherein improving the resistance of plants against rust can not only confer rust resistance to the plants that are not originally resistant to rust, but can also further enhance the rust resistance of the plants that are originally resistant to rust. Increasing the expression level and/or activity of the proteins in the plants can not only make the plants that do not originally express the proteins express the proteins, but can also further increase the expression level and/or activity of the proteins in the plants that originally express the proteins. Furthermore, in certain embodiments, the increasing the expression level and/or activity of the proteins in the plants can be realized either by transgenic means or by sexual hybridization.

Method for Breeding a Plant Variety

In another embodiment, the present invention provides a method for breeding a plant variety with improved resistance against rust.

The method for breeding a plant variety with improved resistance against rust may include the step of increasing the expression level and/or activity of the above-mentioned proteins in a recipient plant, wherein improving the resistance against rust can not only confer rust resistance to the plants that are not originally resistant to rust, but can also further enhance the rust resistance of the plants that are originally resistant to rust. Increasing the expression level and/or activity of the above-mentioned proteins in the recipient plant can not only make the plants that do not originally express the proteins express the proteins, but can also further increase the expression level and/or activity of the proteins in the plants that originally express the proteins.

Furthermore, increasing the expression level and/or activity of the proteins in the plant can be realized either by transgenic means or by sexual hybridization.

Methods for Breeding

In another embodiment, the invention provides for method for breeding a transgenic plant with improved resistance against rust.

The method for breeding a transgenic plant with improved resistance against rust may include introducing a nucleic acid molecule as described herein to a recipient plant to obtain a transgenic plant which has improved resistance against rust compared with the recipient plant, wherein improving the resistance against rust can not only confer rust resistance to the plants that are not originally resistant to rust, but can also further enhance the rust resistance of the plants that are originally resistant to rust.

Furthermore, introducing the nucleic acid molecule to the recipient plant can be realized by introducing the expression cassette or the recombinant vector described above into the recipient plant.

In the above method, introducing the expression cassette or the recombinant vector into the recipient plant can particularly be: transforming plant cells or tissues by using conventional biological methods such as T1 plasmid, Ri plasmid, plant virus vector, direct DNA transformation, microinjection, electroporation, *Agrobacterium*-mediated transformation, etc., and culturing the transformed plant tissues into plants.

The invention is also directed to transgenic plants obtained by the breeding methods. Accordingly, in one embodiment, the invention provides a transgenic plant with improved resistance against rust obtained by breeding using the method described in the herein, or is soybean (*Glycine max*) SX6907, or a progeny plant comprising the nucleic acid molecule described in the se above obtained after sexual hybridization using the soybean (*Glycine max*) SX6907 as a parent. In one embodiment, a derivative of the soybean (*Glycine max*) SX6907 having the accession number CGMCC No. 17575 in the China General Microbiological Culture Collection Center may be used.

The plant herein may be a whole plant, or may be a plant cell, seed, or tissue, or a plant part such as a leaf, stem, pollen, or cell that can be cultivated into a whole plant.

Assays and Kits

In certain embodiments, the nucleic acids or amino acid molecules of the invention can be used to assay plants for rust resistance. Accordingly, the invention also comprises a kit for the assay described herein. Proteins or nucleic acid molecules or expression cassettes, recombinant vectors or recombinant bacteria or transgenic cell lines comprising the nucleic acid molecules can also be packaged together with the instructions as components of the kit for completing the assay disclosed in the present invention. The kit of the present invention may include any combination of the proteins or nucleic acid molecules of the present invention or expression cassettes, recombinant vectors or recombinant bacteria or transgenic cell lines comprising the nucleic acid molecules and suitable instructions (written and/or provided as audio, visual or audio-visual materials). For example, the kit may also comprise a specific probe having a sequence corresponding to or complementary to a sequence having 80% to 100% sequence identity with a specific region of the transgenic event. The kit may comprise any reagent and material required to perform the assay or detection method.

Embodiment of the invention also include any of the following biological materials or applications:

(D1) a primer pair for amplifying the nucleic acid molecule described above. In certain embodiments, the primer pair is a primer pair 1 composed of two single-stranded DNA shown in SEQ ID NO: 3 and SEQ ID NO: 4, respectively, or a primer pair 2 composed of two single-stranded DNA shown in SEQ ID NO: 5 and SEQ ID NO: 6, respectively.

(D2) a probe for amplifying the nucleic acid molecule described above.

(D3) a kit comprising the primer pair and/or the probe.

(D4) a plant comprising the nucleic acid molecule described in the se above.

(D5) use of the primer pair or the probe or the kit in identifying whether the plant to be tested comprises the nucleic acid molecule described above.

(D6) use of the primer pair or the probe or the kit in identifying whether the plant to be tested has resistance against rust conferred by the nucleic acid molecule described above.

(D7) a DNA molecule, which is a DNA molecule shown in SEQ ID NO: 7, or a DNA molecule with promoter function obtained by the addition, deletion and/or substitution of one or more nucleotides from SEQ ID NO:7.

(D8) use of the DNA molecule in initiating the expression of a gene of interest. In certain embodiments, the gene of interest is the nucleic acid molecule described above.

Deposit information for soybean (*Glycine max*) SX6907 derivative useful in the claimed invention:

| | |
|---|---|
| Category naming: | Soybean |
| Latin name: | *Glycine max* |
| Depository: | China General Microbiological Culture Collection Center |
| Depository abbreviation: | CGMCC |
| Address: | No. 3, Yard 1, Beichen West Road, Chaoyang District, Beijing |
| Deposit date: | Friday, Jun. 28, 2019 |
| Registration number of the deposit center: | CGMCC No. 17575 |

EXAMPLES

The following examples facilitate a better understanding of the invention, but do not limit the invention. The experimental methods in the following examples are conventional methods. The test materials used in the following examples, unless otherwise specified, were purchased from general biochemical reagent stores. For the quantitative tests in the following examples, three repeated tests were set, and the results were averaged.

Example 1: Cloning of RppRC1 Gene

Soybean is an ancient tetraploid leguminous plant with self-pollination and has a genome size of about 1.1 Gbp. The response of soybean germplasm with different resistance to *Phakopsora pachyrhizi* is obviously different. Soybean (*Glycine max*) SX6907 is a rust resistance resource selected from Chinese soybean germplasm by the Oil Crops Research Institute, Chinese Academy of Agricultural Sciences. The variety is currently preserved in the China General Microbiological Culture Collection Center under the accession number CGMCC No. 17575, and the response of the variety to *Phakopsora pachyrhizi* is immunity.

The genome of soybean SX6907 (the source of RppRC1 gene) was used as a template for PCR amplification using primer F and primer R. The primer sequences are as follows:

```
F
                                  (SEQ ID NO: 3)
5'-ATGGCAGATAGTGTTGTTGCTTTTCTGC-3';
and

R
                                  (SEQ ID NO: 4)
5'-TCACAGTTCATTAGAGATTTTGAGCTTACAGC-3'.
```

The obtained amplification product is the sequence shown in SEQ ID NO: 2. SEQ ID NO: 2 is the nucleotide sequence of the RppRC1 gene, which encodes the protein shown in SEQ ID NO: 1, which protein is named as RppRC1.

Example 2: Transformation of Soybean with Soybean RppRC1 Gene

1. Construction of Recombinant Expression Vector

Taking the leaves of soybean variety SX6907 cultured under normal conditions to the growth stage of the first ternately compound leaf, extracting DNA, using the DNA as a template and amplifying by a conventional PCR method under the guidance of primer F and primer R (see Example 1 for primer sequences), performing 1% agarose gel electrophoresis detection on the PCR amplified product after the reaction completed, recovering and purifying about 2.5 kb of DNA fragment. At the same time, using the DNA as a template and amplifying by a conventional PCR method under the guidance of PF and PR to obtain 2525 bp promoter pRppRC1 fragment, and linking the fragment into the vector pB2GW7 (the vector comes from VIB-plant systems biology, website: gateway.psb.ugent.be/search) through an enzyme digestion and linking method to obtain recombinant vector pB2GW7-pRppRC1.

```
PF:
5'-GAGCTCAAAGGCTTTTTGTTAAGGGAAGGT-3'
(underlined part is SacI recognition sequence);

PR:
5'- ACTAGTTTCTGTGAAACAGGAAATCTTGGGT-3'
(underlined part is SpeI recognition sequence).
```

Then, the RppRC1 gene (SEQ ID NO: 2) was cloned into the obtained recombinant vector pB2GW7-pRppRC1 by gateway method to obtain the recombinant vector pB2GW7-RppRC1. Sequencing confirmed that the recombinant vector pB2GW7-RppRC1 is a recombinant plasmid obtained by inserting the 2574 bp DNA fragment shown in SEQ ID NO: 2 between attR1 and attR2 sites of vector pB2GW7, and replacing the 35S promoter between SacI and SpeI enzyme digestion sites with the endogenous promoter of RppRC1 gene shown in SEQ ID NO: 7.

Figure 1:
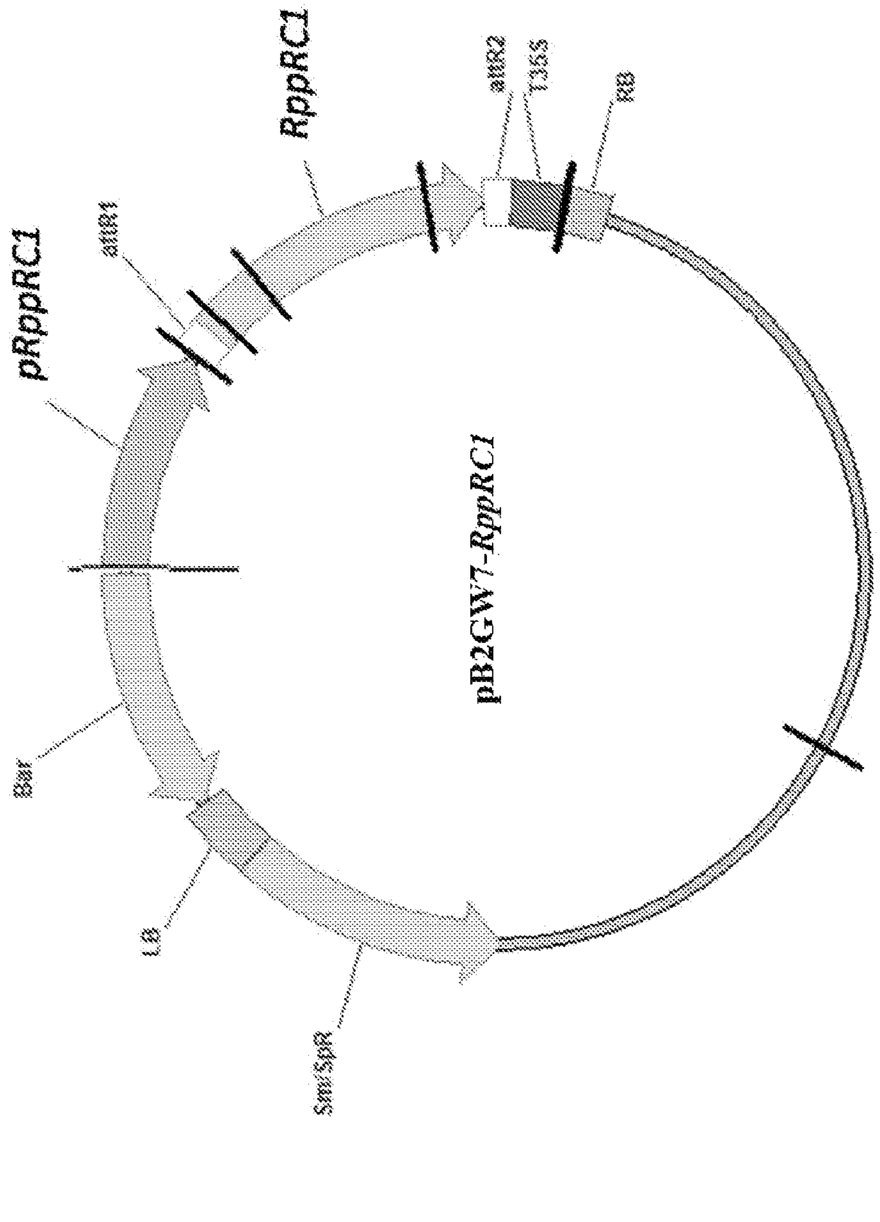
FIG. 1 is a plasmid map of a recombinant vector pB2GW7-RppRC1 with rust resistance gene RppRC1.

In the final recombinant expression vector pB2GW7-RppRC1, the promoter that initiates RppRC1 gene transcription is the original promoter pRppRC1. In addition to the above elements, the vector also comprises a spectinomycin resistance gene for bacterial selection and an herbicide resistance soybean Bar gene as a plant selective marker (FIG. 1).

2. Transformation of Soybean

The recombinant expression vector pB2GW7-RppRC1 comprising RppRC1 gene constructed in step 1 was transferred into *Agrobacterium tumefaciens* EHA105 by freeze-thaw method. Then positive transformants were selected for soybean genetic transformation.

*Agrobacterium*-mediated cotyledon node transformation (Paz, M. M., Martinez, J. C., Kalvig, A. B., et al., (2006) Plant Cell Report, 25, 206-213) was used for soybean transformation, and the transformation recipient was soybean variety Tianlong No. 1 (the variety was bred by the Oil Crops Research Institute, Chinese Academy of Agricultural Sciences (national examination number 2008023) and is available therefrom). The media used for soybean plant transformation and regeneration were as follows:

*Agrobacterium* culture medium: yeast powder 10 g/L, pancreatic protein powder 20 g/L, agar 20 g/L, and rifampicin 50 mg/L and spectinomycin 100 mg/L, as antibiotics. After sterilization, pouring the mixture of the regents into a petri dish with 9 cm diameter for use.

*Agrobacterium* liquid medium: yeast powder 10 g/L, pancreatic protein powder 20 g/L, and rifampicin, 50 mg/L and spectinomycin 100 mg/L, as antibiotics. Sterilizing for later use.

Co-cultivation medium: B5 medium 0.32 g/L, sucrose 30 g/L, ethanesulfonic acid, (2-(N-Morpholino) ethanesulfonic acid (MES)) 6.0 g/L, pH adjusted to 5.4; after sterilization, 6-Benzylaminopurine (6-BA) 1.67 mg/L, L-cysteine 400 mg/L, DL-Dithiothreitol (DTT) 150 mg/L and acetosyringone 200 μg/L were added.

Regeneration shoot induction medium: MS medium 4.4 g/L, sucrose 30 g/L, MES 0.6 g/L, agar 8 g/L, pH adjusted to 5.8; after sterilization, 6-BA 1.67 mg/L, cefotoxin (Cef) 200 mg/L, vancomycin (Van) 50 mg/L, timentim (Tim) 100 mg/L and glufosinate 8 mg/L were added. Pouring the mixture of the regents into a petri dish with 9 cm diameter for use.

Regeneration shoot elongation medium: MS medium 4.4 g/L, sucrose 30 g/L, MES 0.6 g/L, agar 8 g/L, pH adjusted to 5.8; after sterilization, gibberellin acid ($GA_3$) 0.5 mg/L, Cef 200 mg/L, Van 50 mg/L, Tim 100 mg/L and glufosinate 8 mg/L were added. Pouring the mixture of the regents into a petri dish 9 cm in diameter for use.

Rooting solution: 30 mg of indolebutyric acid (IBA), dissolved in 10 ml of clear water; stored at 4° C. and diluted 1000 times when using.

The transformation process was as follows:

Seed disinfection: taking clean seeds, spreading the seeds 1-2 layers in a 9 cm petri dish, placing the petri dish in a 300 ml dryer, placing a beaker in the dryer, adding 10 ml of 3% sodium hypochlorite solution and then 10 ml of 15% hydrochloric acid solution into the beaker, covering the dryer cover for sealing for 16-20 hours, then taking out the petri dish filled with seeds, placing the petri dish on a super clean bench for about 30 minutes and blowing off chlorine, then adding about 40 ml of sterile water into the petri dish, with transformation after 8-12 hours. This step and the following operations were performed under aseptic conditions unless otherwise emphasized.

*Agrobacterium* preparation: Monoclonal *Agrobacterium* (transferred to pB2GW7-RppRC1) was taken, streaked on a petri dish with *Agrobacterium* culture medium containing corresponding antibiotics, 3 ml of liquid *Agrobacterium* culture medium was added, the petri dish was lightly rotated to allow the liquid *Agrobacterium* culture medium to cover the petri dish, and incubated overnight at 28° C. The next day, the lawn was washed with the co-culture medium to prepare a bacterial suspension with an OD value of about 0.8-1.2 for later use.

Explant preparation: The hypocotyl of a seed was cut vertically, and two cotyledons were evenly separated along the midline of the hypocotyl. The joint of cotyledon and hypocotyl was scratched, and the true leaf at the cotyledon node was removed. Each seed can be made into two explants.

Infection and co-cultivation: The explants were placed in the bacterial suspension to ensure that all explants were immersed in the co-cultivation medium. After 20-40 min, the bacterial liquid was removed with a pipette. Two pieces of sterile round filter paper were placed in the co-culture dish (15 cm in diameter), the diameter of the filter paper (about 13-14 cm) was slightly smaller than the diameter of the dish, and 10 ml of the co-cultivation medium was added to each dish. The infected explants were spread on the filter paper with the incision upward. The dish was sealed and incubated at 22° C. under an 18 h photoperiod for 5 days.

Regeneration shoot induction: After co-culture, the explants were cut off the elongated hypocotyls and placed in the regenerated shoot induction medium. The hypocotyl region was submerged into the medium, with 6-7 explants per dish (9 cm in diameter). The dish was incubated at 24° C. under an 18 h photoperiod. Two weeks later, the calli grown from the hypocotyls were cut off and transferred to a fresh regenerated shoot induction medium for further culture for two weeks.

Regeneration shoot elongation: The cotyledons were removed from the explants, and the new calli grown from the hypocotyls were cut off. The resulting explants were transferred to a regeneration shoot elongation medium and subcultured every two weeks. The new calli grown from the hypocotyls were removed at each transfer. When the shoots elongated to more than 3 cm, the elongated shoots (>3 cm) were cut off from the explants, and the remaining explants continued to be cultured in the regeneration shoot elongation medium.

Rooting of regeneration shoot (this step can be operated under open conditions): taking an empty dish (15 cm in diameter), placing a piece of filter paper having a diameter slightly smaller than the diameter of the dish in the dish, adding water to thoroughly soak the paper, immersing the end of the elongated shoot in 3 mg/L of IBA solution for 10-20 seconds, taking the shoot out and then wrapping the end of the shoot with a piece of absorbent paper, spreading the shoot on the soaked filter paper, covering the dish, and culturing the shoot at 24° C. under an 18 h photoperiod. The lid was opened every day for ventilation, and water was supplemented appropriately to keep the filter paper moist. When the new roots grew to 2-3 cm, the culture was transferred to soil and cultivated in the greenhouse until fruiting.

At the same time, a control (empty vector control) was set up in this experiment by introducing pB2GW7 empty vector into soybean variety Tianlong No. 1.

3. Identification of Transgenic Soybean

A. PCR Identification

Partial T1 plants of 2 T0 RppRC1 transgenic soybean plants (called transformation event L1 and transformation event L2) were randomly selected (6 plants, respectively recorded as L1-1, L1-2, L1-3, L2-1, L2-2 and L2-3; L1-1, L1-2 and L1-3 were T1 individual plants of transformation event L1, and L2-1, L2-2 and L2-3 were T1 individual plants of transformation event L2), and a non-transgenic Tianlong No. 1 plant (negative) and a SX6907 plant (positive) were selected; the genomic DNA of these plants were extracted, respectively, and the target gene RppRC1 was amplified by PCR with primer F and primer R of example 1 and the size of the target product was 2574 bp; the amplified product was subjected to 1% agarose gel electrophoresis; and the plants from which a 2574 bp band was obtained were recorded as positive.

Figure 2:
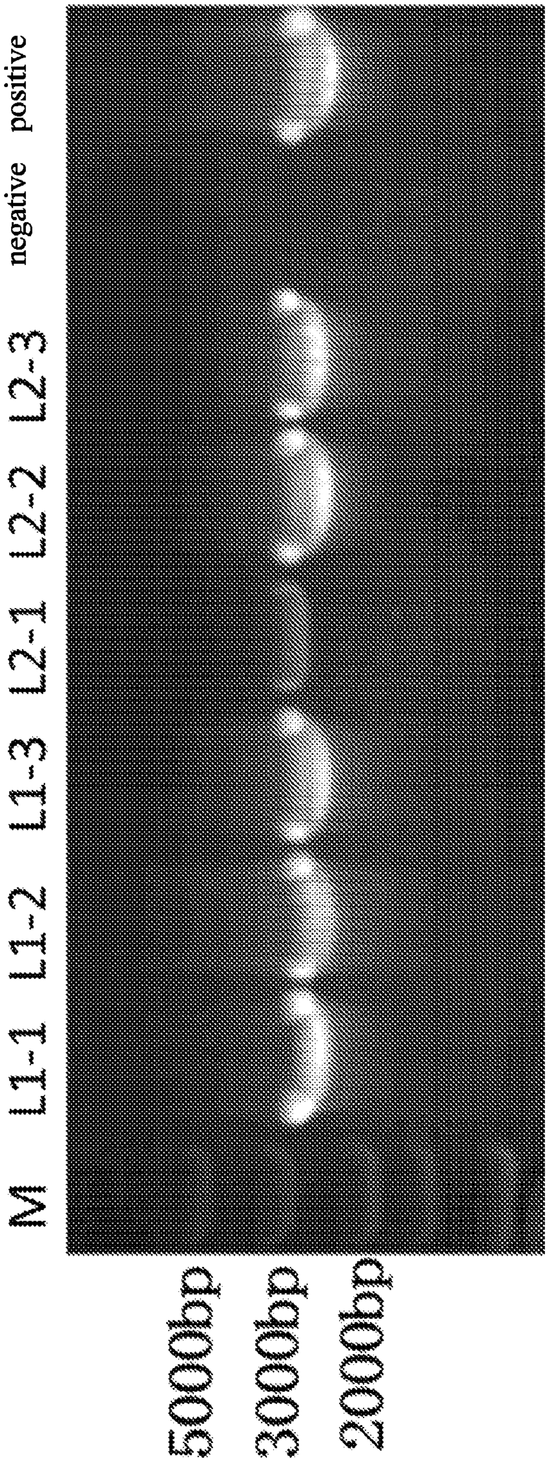
FIG. 2 is a PCR detection picture of T1 generation of RppRC1 transgenic plants. M: marker. L1-1, L1-2, and L1-3 are partial individual plants of the T1 plants of the transformation event L1, and L2-1, L2-2 and L2-3 are partial individual plants of the T1 plants of the transformation event L2, and the negative: negative control Tianlong No. 1, positive: positive control SX6907.

Results: L1-1, L1-2, L1-3, L2-1, L2-2 and L2-3 plants were all positive, non-transgenic plants were negative, and SX6907 plants were positive, as shown in FIG. 2.

B. RT-PCR Identification

The T1 RppRC1 transgenic soybean obtained in step 2 (i.e. L1-2 and L2-1 in step 1), the soybean line transformed with empty vector (CK) and the non-transgenic plant Tianlong No. 1 were taken and subjected to total RNA extraction, respectively; the resulting RNA was reverse transcribed to obtain cDNA, the resulting cDNA was used as a template to perform real-time fluorescence quantitative PCR amplification on the cDNA of the gene RppRC1 with specific primers F1 and R1, wherein soybean β-actin was used as an internal reference which was amplified with the primers FC and RC. Real-time fluorescence quantitative PCR was run on CFX Connect™ real-time fluorescence quantitative PCR instrument with 3 replicates in one parallel test. The relative expression level was calculated using the method reported by Livak KJ and Schmittgen TD (2001), i.e. $2^{-\Delta\Delta CT}$.

$$\Delta\Delta C_T = (C_{T.Target} - C_{T.Actin})_{Time\ x} - (C_{T.Target} - C_{T.Actin})_{Time\ 0}$$

Time x represents any point in time, and $Time_0$ represents a double amount of target gene expression after β-actin correction.

The sequences of the above primers are as follows:

```
F1:
                                    (SEQ ID NO: 5)
5'-TCGGCAAAGTTGGTTTTCATCT-3';

R1:
                                    (SEQ ID NO: 6)
5'-CCATTCCTGGGCTCCACATT-3';

FC
                                    (SEQ ID NO: 8)
5'-ATTGGACTCTGGTGATGGTG-3';
and

RC:
                                    (SEQ ID NO: 9)
5'-TCAGCAGAGGTGGTGAACATT-3'.
```

The results are shown in FIG. 3. The target gene RppRC1 was virtually not expressed in non-transgenic Tianlong No. 1 and plants with empty vector; however, the target gene RppRC1 was highly expressed in RppRC1 transgenic Tianlong No. 1 L1-2 and L2-1.

C. Southern Detection

The T1 RppRC1 transgenic soybean plants (L1-1, L1-2, L1-3, L1-4, L1-5, L2-1, and L2-1) obtained in step 2, the non-transgenic Tianlong No. 1 plant (negative), and the T1 plants L3-1, L3-2, L3-3, L3-4 and L3-5 transformed with empty vector were taken and subjected to genomic DNA extraction, respectively; the resulting genomic DNA was digested with endonuclease HindIII, and then the enzyme-digested products were subjected to southern detection using digoxin hybridization detection kit II (chemiluminescence method), wherein BAR gene was used as a probe, and the probe primers were as follows:

F2: 5'-AGAAACCCACGTCATGCCAGTT-3' (SEQ ID NO: 10); and

R2: 5'-ATCGTCAACCACTACATCG-3' (SEQ ID NO: 80) (421 bp).

The results are shown in FIGS. 4A and 4B. The plants L1-1, L1-2, L1-3, L1-4 and L1-5 were double copies, L2-1 and L2-1 were single copies, and the plants L3-1, L3-2, L3-3, L3-4 and L3-5 with empty vector were single copies. As for RppRC1 transgenic soybean, these may represent the copy number of RppRC1 gene.

Example 3: Detection of the Rust Resistance of Transgenic Soybean

In this example, the transgenic plants obtained in Example 2 were inoculated with the physiological race SS4 of *Phakopsora pachyrhizi* (described in "Shan Zhihui et al., Pathogenic responses of *Phakopsora pachyrhizi* in different legume hosts. *Chinese Journal of Oil Crop Sciences,* 2008, 30(4): 497-500"), which is available to the public from the applicant and can only be used to repeat the experiments of the present invention, but not for other purposes), and the disease symptoms of the plants were scored to determine the effect of RppRC1 gene against rust.

First, T0 transformation events L1 and L2 were preliminarily tested to evaluate the effect of RppRC1 transgene on rust infection. The specific operations were as follows: Fully unfolded new leaves were taken from T0 plants, and sprayed and inoculated with the suspension of the physiological race SS4 of *Phakopsora pachyrhizi* ($1\times10^5$ spores/ml) at an inoculum size of 10 μl per square centimetre. The untransformed recipient genotype Tianlong No. 1 (negative control) and the plant transformed with empty vector from the same event (empty vector control) were used as susceptible controls, and the untransformed disease resistance variety SX6907 was used as disease resistance control (positive control). After inoculation, the plants were cultured in a greenhouse at 25V with a photoperiod of 16 hours of light/8 hours of darkness and a relative humidity of 65%-85%. The disease symptoms were scored 12-15 days after inoculation. The disease resistance of the plants was determined according to the nature of the disease spots and the rupture of the sori. The plants were qualitatively rated as immunity (IM: no lesions), high resistance (R: reddish black disease spots, a small amount of spore formation) and susceptibility (S: tawny disease spots, a large amount of spore formation). Refer to "Bromfield, K R., Melching, J S., Kingsolver, C H. 1980, Virulence and Aggressiveness of *Phakopsora pachyrhizi* Isolates Causing Soybean Rust. *Phytopathology.* 70: 17-21". The results showed that both positive control and transformed plants (T0 transformation events L1 and L2) showed immunity, while plants with empty vector and negative control plants showed susceptibility, as shown in FIG. 5 and Table 3-1.

Then, the efficacy of RppRC1 gene against *Phakopsora pachyrhizi* was tested for T1 transgenic plants L1-1, L1-2, L1-3, L2-1 and L2-1, and the plant L3-1 transformed with empty vector. T1 seeds were planted under growth chamber conditions, and inoculation and identification were carried out when the plant grew to having two true leaves completely unfolded. Spore suspension of the physiological race SS4 of *Phakopsora pachyrhizi* was used for inoculation. The inoculation method was the same as above. The plant of untransformed variety Tianlong No. 1 was the susceptible control and the plant of untransformed variety SX6907 with disease resistance was the disease resistance control. Symptoms were observed 12 days later. The results showed that no disease spot formation and sorus formation were observed on the leaves of transgenic plants L1-1, L1-2, L1-3, L2-1 and L2-1 with the resistance grade of immunity. Molecular detection showed that the transgenic plants comprised the full length of and had high expression level of RppRC1 gene. The leaves of the untransformed plant and the leaves of the plant L3-1 transformed with empty vector produced tawny disease spots and produced a large amount of spores, showing a susceptible response (FIG. 6 and Table 3-2).

The results of these rust infection tests showed that RppRC1 gene can provide resistance against *Phakopsora pachyrhizi* through transgenesis.

TABLE 3-1

Resistance of T0 transgenic plants carrying RppRC1 gene against rust

| Transformation Events | Resistance |
|---|---|
| L1 | Immunity |
| L2 | Immunity |
| L3 empty vector | Susceptibility |
| Negative control Tianlong No. 1 | Susceptibility |
| Positive control SX6907 | Immunity |

TABLE 3-2

Resistance of T1 transgenic plants carrying RppRC1 gene against rust

| Transformed plants | Resistance |
|---|---|
| L1-1 | Immunity |
| L1-2 | Immunity |

TABLE 3-2-continued

| Resistance of T1 transgenic plants carrying RppRC1 gene against rust | |
|---|---|
| Transformed plants | Resistance |
| L1-3 | Immunity |
| L2-1 | Immunity |
| L2-2 | Immunity |
| L3-1 empty vector | Susceptibility |
| Negative control Tianlong No. 1 | Susceptibility |
| Positive control SX6907 | Immunity |

Examples 1-3 establish that the resistance against rust of transgenic soybean obtained by transforming RppRC1 gene into susceptible soybean variety Tianlong No. 1 is significantly higher than that of recipient parent Tianlong No. 1, indicating that RppRC1 and the coding gene thereof can regulate and control the resistance of leguminous plants against rust, and improve the rust resistance of plants after overexpression. RppRC1 and the coding gene thereof can be used to improve the disease resistance of leguminous crops and are of great significance for breeding new varieties with disease resistance.

Example 4: Use of Gene Editing for Rust Resistance Gene Allele Replacement

In this example, gene editing is used to replace a wild type gene with an interval or gene conferring increased rust resistance to *Phakopsora pachyrhizi.*

First, two gRNAs are designed to target the insertion region. In this example, gRNAs were designed to target the 736 bp region and the 1642 bp region of *Glycine max* Williams 82. A donor DNA sequence was designed including a 6057 bp portion of the interval of SEQ ID NO: 13, further modified to include 500 bp homologous arms on each side. Other examples include other portions of the interval, but typical examples will include portions containing a nucleic acid sequence that encodes the protein of claim 1.

Second, Cas12a editing machinery, gRNAs, and donor DNA are delivered to at least one plant cell using biolistic mediated transformation.

Targeted insertion events may then be screened with PCR and sequencing for example. Phenotypic evaluation may also be used.

NUMBERED EMBODIMENTS OF THE INVENTION

The following are all embodiments contemplated and encompassed within the invention. In certain aspects, numbered embodiment of the invention include:

1. A protein selected from the group consisting of:

(A1) a protein having the amino acid sequence shown in SEQ ID NO: 1;

(A2) a protein having substitution and/or deletion and/or addition of one or several amino acid residues from and having the same function as the amino acid sequence shown in SEQ ID NO: 1;

(A3) a protein having more than 99%, more than 95%, more than 90%, more than 85%, or more than 80% homology with and having the same function as the amino acid sequence defined in either (A1) or (A2); and (A4) a fusion protein obtained by tagging at the N-terminus and/or C-terminus of the protein defined in any one of (A1) to (A3).

2. A nucleic acid molecule encoding the protein of embodiment 1.

3. The nucleic acid molecule of embodiment 2, wherein the nucleic acid molecule is a gene and wherein the gene is a DNA molecule of any of:

(B1) a DNA molecule shown in SEQ ID NO: 2;

(B2) a DNA molecule hybridizing to the DNA molecule defined in (B1) under a stringent condition and encoding the protein;

(B3) a DNA molecule having more than 99%, more than 95%, more than 90%, more than 85%, or more than 80% homology with the DNA sequences defined in (B1) and (B2) and encoding the protein.

4. An expression cassette, a recombinant vector, a recombinant bacterium, or a transgenic cell line comprising the nucleic acid molecule of embodiment 2 or 3.

5. The expression cassette of embodiment 4, characterized in that the promoter for initiating the transcription of the nucleic acid molecule in the expression cassette is an original endogenous promoter, and the nucleotide sequence of the original endogenous promoter is shown in SEQ ID NO: 7.

6. The recombinant vector of embodiment 4, characterized in that the recombinant vector is a recombinant plasmid obtained by cloning the nucleic acid molecule between the attR1 and attR2 sites of pB2GW7 vector, and replacing the 35S promoter between the SacI and SpeI enzyme digestion sites with the endogenous promoter of RppRC1 gene shown in SEQ ID NO: 7.

7. Use of the protein of embodiment 1 or the nucleic acid molecule of embodiment 2 or 3, or the recombinant vector, recombinant bacterium, or transgenic cell line of any one of embodiments 4 to 6 in regulating the resistance of a plant against rust.

8. The use of embodiment 7, characterized in that in the use, the expression level and/or activity of the protein or the coding gene thereof in the plant is increased, and the resistance of the plant against rust is enhanced.

9. A method selected from:

(C1) a method for improving the resistance of a plant against rust, comprising the following steps: increasing the expression level and/or activity of the protein of embodiment 1 in the plant; or (C2) a method for breeding a plant variety with improved resistance against rust, comprising the step of increasing the expression level and/or activity of the protein of embodiment 1 in a recipient plant.

10. The method of embodiment 9, characterized in that increasing the expression level and/or activity of the protein in the plant can be realized by transgenic means or by sexual hybridization.

11. A method for breeding a transgenic plant with improved resistance against rust, comprising the following step: introducing the nucleic acid molecule of embodiment 2 or 3 to a recipient plant to obtain a transgenic plant; the transgenic plant has improved resistance against rust compared with the recipient plant.

12. The method of embodiment 11, characterized in that introducing the nucleic acid molecule to the recipient plant is realized by introducing the expression cassette or the recombinant vector of any one of embodiments 4-6 into the recipient plant.

13. A primer pair for amplifying the nucleic acid molecule of embodiment 2 or 3.

14. The primer pair of embodiment 13, characterized in that the primer pair is a primer pair 1 composed of two single-stranded DNA shown in SEQ ID NO: 3 and SEQ ID NO: 4, respectively, or a primer pair 2 composed of two single-stranded DNA shown in SEQ ID NO: 5 and SEQ ID NO: 6, respectively.

15. A probe for amplifying the nucleic acid molecule of embodiment 2 or 3.

16. A kit comprising the primer pair of embodiment 13 or 14 and/or the probe of embodiment 15.

17. A plant comprising the nucleic acid molecule of embodiment 2 or 3.

18. The plant of embodiment 17, characterized in that the plant is a transgenic plant with improved resistance against rust obtained by breeding using the method of embodiment 11 or 12, or is soybean SX6907, or a progeny plant comprising the nucleic acid molecule of embodiment 2 or 3 obtained after sexual hybridization using the soybean SX6907 as a parent; the soybean SX6907 has the accession number CGMCC No. 17575 in the China General Microbiological Culture Collection Center.

19. Use of the primer pair of embodiment 13 or 14 or the probe of embodiment 15 or the kit of embodiment 16 in identifying whether a plant to be tested comprises the nucleic acid molecule of embodiment 2 or 3.

20. Use of the primer pair of embodiment 13 or 14 or the probe of embodiment 15 or the kit of embodiment 16 in identifying whether a plant to be tested has resistance against rust conferred by the nucleic acid molecule of embodiment 2 or 3.

21. The use or method or primer pair or probe or kit or plant of any one of embodiments 7-20, characterized in that the rust is leguminous plant rust.

22. The use or method or primer pair or probe or kit or plant of embodiment 21, characterized in that the leguminous plant rust is soybean rust.

23. The use or method or primer pair or probe or kit or plant of embodiment 22, characterized in that the pathogen of soybean rust is *Phakopsora pachyrhizi* or *Phakopsora meibomiae*.

24. The use or method or primer pair or probe or kit or plant of embodiment 23, characterized in that the *Phakopsora pachyrhizi* is the physiological race SS4 of *Phakopsora pachyrhizi*.

25. The use or method or primer pair or probe or kit or plant of any one of embodiments 7-24, characterized in that the plant is a leguminous plant.

26. The use or method or primer pair or probe or kit or plant of embodiment 25, characterized in that the leguminous plant is any of: soybean, alfalfa, clover, pea, common bean, lentil, lupin, ghaf tree, carob bean, soybean, peanut or tamarind.

In another aspect, numbered embodiments of the invention include:

1. An elite *Glycine max* plant having in its genome a chromosomal interval from a second glycine plant, wherein said chromosomal interval confers increased Asian soybean rust (ASR) resistance as compared to a control plant not comprising said chromosomal interval.

2. The plant of embodiment 1, wherein the chromosome interval is derived from *Glycine max* strain SX6907.

3. The plant of embodiments 1 or 2, wherein the chromosome interval comprises SEQ ID NO: 2 or any portion thereof, wherein the portion confers increased ASR resistance in the plant.

4. The plant of embodiment 4, wherein the chromosome interval comprises a nucleic acid sequence that is at least 85%, at least 90%, or at least 95% identical to SEQ ID NO: 2.

5. The plant of anyone of embodiments 1-4, wherein the chromosome interval encodes a protein of SEQ ID NO: 1 and wherein protein confers increased ASR resistance in the plant.

6. The plant of any one of embodiments 1-5, wherein the chromosome interval from the second glycine plant is inserted into chromosome 18 of the plant.

7. The plant of anyone of embodiments 1-6, wherein the chromosome interval from the second glycine plant is inserted into the region beginning at about base pair 56,680,416 and ending at about base pair 56,677,361 on chromosome 18 of *Glycine max* strain Williams 82 or equivalent thereof in other *Glycine max* strains.

8. The plant of any one of embodiments 1-7, wherein the chromosomal interval comprises SEQ ID NOs: 11-13 or a portion of any thereof wherein said portion confers in said plant increased ASR resistance.

9. The plant of any one of embodiments 1-7, wherein the chromosomal interval comprises a SNP marker associated with increased ASR resistance wherein said SNP marker corresponds with any one of the favorable SNP markers as listed in Table 1.

10. The plant of any one of embodiments 1-9, wherein the interval is derived from chromosome 18 of the second plant.

11. The plant of any one embodiments 1-10, wherein at least one parental line of said plant was selected or identified through molecular marker selection, wherein said parental line is selected or identified based on the presence of a molecular marker located within or closely linked with said chromosome interval corresponding to any one of SEQ ID NOs: 11-13 wherein said molecular marker is associated with increased ASR resistance.

12. The plant of embodiment 11, wherein the molecular marker is a single nucleotide polymorphism (SNP), a quantitative trait locus (QTL), an amplified fragment length polymorphism (AFLP), randomly amplified polymorphic DNA (RAPD), a restriction fragment length polymorphism (RFLP) or a microsatellite.

13. The plant of embodiments 11 or 12, wherein the molecular marker is a SNP marker and the molecular marker is any favorable marker as shown in Table 1.

14. The plant of any one of embodiments 1-13, wherein the plant is an agronomically elite *Glycine max* plant having a commercially significant yield and/or commercially susceptible vigor, seed set, standability, or threshability.

15. The plant of any one of embodiments 1-13, wherein said interval is introduced into said plant genome by genome editing of sequences corresponding to and comprising any one of SEQ ID NOS: 2 or 11.

16. The plant of embodiment 15, wherein the interval is introduced by genome editing of a *Glycine max* genomic region homologous to or a ortholog to any of the intervals corresponding to SEQ ID NOs: 11-13 and further making at least one genomic edit to said *Glycine max* genomic region to include at least 1 allele change corresponding to any favorable allele as described in any of Table 1 wherein said *Glycine max* genomic region did not comprise said allele change before genome edit and further wherein said genomic edit confers in a plant increased ASR resistance.

17. The plant of embodiment 16, wherein the genomic edit is accomplished through CRISPR, TALEN, meganucleases, or through modification of genomic nucleic acids.

18. The plant of anyone one of embodiments 1-17, wherein said interval is introduced into said plant genome by transgenic expression of sequences corresponding to and comprising any one of SEQ ID NOS: 11-13.

19. The plant of any one of embodiments 1-18, wherein the chromosome interval comprises SEQ ID NO: 11, or a portion thereof conferring ASR resistance.

20. The plant of any one of embodiments 1-18, wherein the chromosome interval comprises SEQ ID NO: 12, or a portion thereof conferring ASR resistance.

21. The plant of any one of embodiments 1-18, wherein the chromosome interval comprises SEQ ID NO: 13, or a portion thereof conferring ASR resistance.

22. An agronomically elite *Glycine max* plant having commercially significant yield, comprising a chromosomal interval derived from *Glycine max* SX6907, a chromosomal interval comprising SEQ ID NO: 2, a chromosomal interval comprising SEQ ID NO: 11-13, a chromosomal interval encoding the protein of SEQ ID NO: 1, or a portion thereof wherein said chromosomal interval or portion thereof confers increased ASR resistance in said plant as compared to a control plant not comprising said chromosomal interval.

23. A plant cell, seed, or plant part derived from the plant of any one of embodiments 1-22.

24. A progeny plant from the plants of any one of embodiments 1-23.

25. A method of producing a *Glycine max* plant having increased resistance to Asian soybean rust (ASR), the method comprising the steps of:

a) providing a first *Glycine max* plant comprising in its genome a chromosomal interval corresponding to SEQ ID NOs: 11, 12 or 13, or a chromosome interval encoding the protein of SEQ ID NO: 1 or a chromosome interval comprising SEQ ID NO: 2, wherein said first *Glycine max* plant has increased resistance to ASR;

b) crossing the *Glycine max* plant of a) with a second *Glycine max* plant not comprising said chromosomal interval; and c) selecting a progeny plant from the cross of b) by isolating a nucleic acid from said progeny plant and detecting within said nucleic acid an allele that associates with increased ASR resistance and further wherein said allele is closely linked with or located within the chromosome intervals corresponding to SEQ ID NOs: 11, 12 or 13, or a chromosome interval encoding the protein of SEQ ID NO: 1 or chromosome comprising SEQ ID NO: 2, thereby producing a *Glycine max* plant having increased resistance to ASR.

26. The method of embodiment 25, wherein the allele corresponds to any of the favorable alleles as depicted in Table 1.

27. The method of embodiments 25 or 26, wherein the either first or second *Glycine max* plant is an elite *Glycine max* plant.

28. A method of producing a *Glycine max* plant with increased resistance to increased resistance to Asian soybean rust (ASR), the method comprising the steps of:

a) isolating a nucleic acid from a *Glycine max* plant;

b) detecting in the nucleic acid of a) at least one molecular marker associated with increased ASR wherein said molecular marker is located within 20 cM, 10 cM, 5 cM, 1 cM 0.5 cM, or closely linked with a chromosomal interval corresponding to a genomic region from *Glycine max* chromosome 18 comprising SEQ ID NO: 2 or SEQ ID NO: 11, or a portion thereof, wherein said portion confers to a plant increased ASR resistance;

c) selecting a plant based on the presence of the molecular marker detected in b); and d) producing a *Glycine max* progeny plant from the plant of c) identified as having said allele associated with increased ASR resistance.

29. The method of embodiment 28, wherein the molecular marker is closely linked with or consists of any one of the favorable alleles as depicted in Table 1.

30. A method of identifying or selecting a *Glycine max* plant having increased ASR resistance, the method comprising the steps of a) isolating a nucleic acid from a *Glycine max* plant;

b) detecting in the nucleic acid the presence of a molecular marker that associates with increased ASR resistance wherein the molecular marker is located within 20 cM, 10 cM, 5 cM, 1 cM, 0.5 cM of a marker as described in Table 1; and c) identifying or selecting a *Glycine max* plant having increased ASR resistance on the basis of the molecular marker detected in b).

31. The method of embodiment 30, wherein the allele detected in b) consists of any favorable marker as described in Table 1.

32. The method of any one of embodiments 28-31, wherein the molecular marker is a single nucleotide polymorphism (SNP), a quantitative trait locus (QTL), an amplified fragment length polymorphism (AFLP), randomly amplified polymorphic DNA (RAPD), a restriction fragment length polymorphism (RFLP) or a microsatellite.

33. The method of any one of embodiments 28-32, wherein the detecting comprises amplifying a marker locus or a portion of the marker locus and detecting the resulting amplified marker amplicon.

34. The method of embodiment 33, wherein the amplifying comprises: a) admixing an amplification primer or amplification primer pair with a nucleic acid isolated from the first *Glycine max* plant or germplasm, wherein the primer or primer pair is complementary or partially complementary to at least a portion of the marker locus, and is capable of initiating DNA polymerization by a DNA polymerase using the *Glycine max* nucleic acid as a template; and, b) extending the primer or primer pair in a DNA polymerization reaction comprising a DNA polymerase and a template nucleic acid to generate at least one amplicon.

35. The method of embodiments 33 or 34, wherein the amplifying comprises employing a polymerase chain reaction (PCR) or ligase chain reaction (LCR) using a nucleic acid isolated from a soybean plant or germplasm as a template in the PCR or LCR.

36. The method of any one of embodiments 28-35, wherein the nucleic acid is selected from DNA or RNA.

37. A primer diagnostic for ASR resistance, wherein said primer can be used in a PCR reaction to indicate the presence of an allele associated with ASR resistance, wherein said allele is any favorable allele as described in Table 1.

38. A method of conferring ASR resistance to *Glycine max* plants comprising:

a) providing a nucleic acid molecule from chromosome 18 of a *Glycine max* plant having ASR resistance, wherein said nucleic acid encodes ASR resistance; and b) inserting the nucleic acid molecule into chromosome 18 of a *Glycine max* strain lacking ASR resistance to thereby produce a plant having increased ASR resistance compared to a control plant not comprising the nucleic acid, wherein the nucleic acid molecule is selected from the group consisting of:

a nucleic acid encoding the protein of SEQ ID NO: 1;

a nucleic acid comprising the nucleic acid sequence of SEQ ID NO: 2 or any portion thereof, wherein the portion confers increased ASR resistance in the plant; and a chromosome interval comprising SEQ ID NO: 11.

39. The method of embodiment 38, wherein the nucleic acid molecule is derived from *Glycine max* strain SX6907.

40. The method of embodiment 38 or embodiment 39, wherein the nucleic acid molecule is inserted into chromosome 18 of a *Glycine max* plant.

41. The method of any one of embodiments 38-40, wherein the nucleic acid molecule is inserted a region beginning at about base pair 56,680,416 and ending at about base pair 56,677,361.

42. The method of any one of embodiments 39-41, wherein the method comprises Cas12a mediated gene replacement.

43. The method of any one of embodiments 38-42, wherein the method comprises 2 gRNAs.

44. The method of embodiment 43, wherein the method comprises a gRNA of SEQ ID NO: 79 and/or SEQ ID NO: 81.

45. The method of any one of embodiments 38-44, wherein the method comprises screening for the targeted insertion with PCR and/or sequencing.

46. A protein selected from:

(A1) a protein having the amino acid sequence shown in SEQ ID NO: 1;

(A2) a protein having substitution and/or deletion and/or addition of one or several amino acid residues from and having the same function as the amino acid sequence shown in SEQ ID NO: 1;

(A3) a protein having more than 99%, more than 95%, more than 90%, more than 85%, or more than 80% homology with and having the same function as the amino acid sequence defined in either (A1) or (A2); or (A4) a fusion protein obtained by tagging at the N-terminus and/or C-terminus of the protein defined in any one of (A1) to (A3).

47. A nucleic acid molecule encoding the protein of embodiment 46.

48. The nucleic acid molecule of embodiment 47, wherein the nucleic acid molecule is any of:

(B1) a DNA molecule shown in SEQ ID NO: 2;

(B2) a DNA molecule hybridizing to the DNA molecule defined in (B1) under a stringent condition and encoding the protein; or (B3) a DNA molecule having more than 99%, more than 95%, more than 90%, more than 85%, or more than 80% homology with the DNA sequences defined in (B1) and (B2) and encoding the protein.

49. An expression cassette, a recombinant vector, a recombinant bacterium, or a transgenic cell line comprising the nucleic acid molecule of embodiment 47 or 48.

50. The expression cassette of embodiment 49, characterized in that the promoter for initiating the transcription of the nucleic acid molecule in the expression cassette is an original endogenous promoter, and the nucleotide sequence of the original endogenous promoter is shown in SEQ ID NO: 7.

51. The recombinant vector of embodiment 50, characterized in that the recombinant vector is a recombinant plasmid obtained by cloning the nucleic acid molecule between the attR1 and attR2 sites of pB2GW7 vector, and replacing the 35S promoter between the SacI and SpeI enzyme digestion sites with the endogenous promoter of RppRC1 gene shown in SEQ ID NO: 7.

52. Use of the protein of embodiment 46 or the nucleic acid molecule of embodiment 47 or 48, or the recombinant vector, recombinant bacterium, or transgenic cell line of any one of embodiments 49 to 51 in regulating the resistance of a plant against rust.

53. The use of embodiment 47, wherein the expression level and/or activity of the protein or the coding gene thereof in the plant is increased, and the resistance of the plant against rust is enhanced.

54. A method for improving the resistance of a plant against rust, comprising increasing the expression level and/or activity of the protein of embodiment 46 in the plant;

55. A method for breeding a plant variety with improved resistance against rust, comprising increasing the expression level and/or activity of the protein of embodiment 46 in a recipient plant.

56. The method of embodiments 54 or 55, wherein the increasing the expression level and/or activity of the protein in the plant can be realized by transgenic means or by sexual hybridization.

57. A method for breeding a transgenic plant with improved resistance against rust, comprising the following step: introducing the nucleic acid molecule of embodiment 47 or 48 to a recipient plant to obtain a transgenic plant; the transgenic plant has improved resistance against rust compared with the recipient plant.

58. The method of embodiment 56, wherein the introducing the nucleic acid molecule to the recipient plant is realized by introducing the expression cassette or the recombinant vector of any one of embodiments 49-51 into the recipient plant.

59. A primer pair for amplifying the nucleic acid molecule of embodiment 47 or 48.

60. The primer pair of embodiment 59, wherein the primer pair is a primer pair 1 composed of two single-stranded DNA shown in SEQ ID NO: 3 and SEQ ID NO: 4, respectively, or a primer pair 2 composed of two single-stranded DNA shown in SEQ ID NO: 5 and SEQ ID NO: 6, respectively.

61. A probe for amplifying the nucleic acid molecule of embodiment 47 or 48.

62. A kit comprising the primer pair of embodiment 59 or 60 and/or the probe of embodiment 61.

63. A plant comprising the nucleic acid molecule of embodiment 47 or 48.

64. The plant of embodiment 63, wherein the plant is a transgenic plant with improved resistance against rust obtained by breeding using the method of embodiment 56 or 57, or is soybean SX6907, or a progeny plant comprising the nucleic acid molecule of embodiment 47 or 48 obtained after sexual hybridization using the soybean SX6907 as a parent; the soybean SX6907 has the accession number CGMCC No. 17575 in the China General Microbiological Culture Collection Center.

65. Use of the primer pair of embodiment 59 or 60 or the probe of embodiment 61 or the kit of embodiment 62 in identifying whether a plant to be tested comprises the nucleic acid molecule of embodiment 45 or 46.

66. Use of the primer pair of embodiment 59 or 60 or the probe of embodiment 61 or the kit of embodiment 62 in identifying whether a plant to be tested has resistance against rust conferred by the nucleic acid molecule of embodiment 47 or 48.

67. The use or method or primer pair or probe or kit or plant of any one of embodiments 52-66, wherein the rust is leguminous plant rust.

68. The use or method or primer pair or probe or kit or plant of embodiment 67, wherein the leguminous plant rust is soybean rust.

69. The use or method or primer pair or probe or kit or plant of embodiment 68, wherein the pathogen of soybean rust is *Phakopsora pachyrhizi* or *Phakopsora meibomiae.*

70. The use or method or primer pair or probe or kit or plant of embodiment 69, wherein the *Phakopsora pachyrhizi* is the physiological race SS4 of *Phakopsora pachyrhizi.*

71. The use or method or primer pair or probe or kit or plant of any one of embodiments 52-70, wherein the plant is a leguminous plant.

72. The use or method or primer pair or probe or kit or plant of embodiment 73, wherein the leguminous plant is any of: soybean, alfalfa, clover, pea, common bean, lentil, lupin, ghaf tree, carob bean, soybean, peanut, or tamarind.

What is claimed:

1. A nucleic acid molecule comprising a nucleotide sequence encoding a protein selected from:

(A1) a protein comprising an amino acid sequence that is at least 95% identical to SEQ ID NO: 1 and when expressed in a soybean plant provides increased resistance to Asian soybean rust (ASR); and (A2) a fusion protein obtained by tagging at the N-terminus and/or C-terminus of the protein defined in (A1);

wherein said nucleotide sequence is operatively linked to a heterologous regulatory sequence.

2. The nucleic acid molecule of claim 1, wherein the nucleotide sequence is at least 95% identical to SEQ ID NO: 2 and encodes the protein.

3. An expression cassette, a recombinant vector, a recombinant bacterium, or a transgenic cell line comprising the nucleic acid molecule of claim 1.

4. The expression cassette of claim 3, characterized in that the expression cassette comprises a promoter for initiating the transcription of the nucleic acid molecule in the expression cassette, wherein the promoter is an original endogenous promoter, and the nucleotide sequence of the original endogenous promoter is shown in SEQ ID NO: 7.

5. The recombinant vector of claim 3, characterized in that the recombinant vector is a recombinant plasmid obtained by cloning the nucleic acid molecule between the attR1 and attR2 sites of pB2GW7 vector, and replacing the 35S promoter between the SacI and SpeI enzyme digestion sites with the endogenous promoter of RppRC1 gene shown in SEQ ID NO: 7.

6. A method for producing a transgenic soybean plant with improved resistance against Asian soybean rust (ASR), comprising the following step: introducing a nucleic acid molecule into a recipient soybean plant to obtain a transgenic soybean plant; wherein the transgenic soybean plant has improved resistance against ASR compared with the recipient soybean plant; wherein said nucleic acid molecule comprises a nucleotide sequence encoding a protein selected from:

(A1) a protein comprising an amino acid sequence that is at least 95% identical to SEQ ID NO: 1 and when expressed in a soybean plant provides increased resistance to Asian soybean rust (ASR); and (A2) a fusion protein obtained by tagging at the N-terminus and/or C-terminus of the protein defined in (A1); and wherein said nucleotide sequence is operatively linked to a heterologous regulatory sequence.

7. The method of claim 6, wherein the introducing the nucleic acid molecule to the recipient soybean plant is realized by introducing an expression cassette or a recombinant vector comprising the nucleic acid molecule into the recipient soybean plant.

8. A soybean plant or a soybean plant cell comprising a nucleic acid molecule comprising a nucleotide sequence encoding a protein selected from:

(A1) a protein comprising an amino acid sequence that is at least 95% identical to SEQ ID NO: 1 and when expressed in a soybean plant provides increased resistance to Asian soybean rust (ASR); and (A2) a fusion protein obtained by tagging at the N-terminus and/or C-terminus of the protein defined in (A1);

wherein said nucleotide sequence is operatively linked to a heterologous regulatory sequence.

9. The nucleic acid molecule of claim 1, wherein said protein comprises an amino acid sequence that is at least 99% identical to SEQ ID NO: 1.

10. The nucleic acid molecule of claim 1, wherein said protein comprises the amino acid sequence shown in SEQ ID NO: 1.

11. The nucleic acid molecule of claim 1, wherein the nucleotide sequence is at least 99% identical to SEQ ID NO: 2 and encodes the protein.

12. The nucleic acid molecule of claim 1, wherein the nucleotide sequence is the nucleotide sequence shown in SEQ ID NO: 2.

13. The nucleic acid molecule of claim 1, wherein said heterologous regulatory sequence is a heterologous promoter.

14. The nucleic acid molecule of claim 1, wherein said heterologous regulatory sequence is a terminator, an enhancer, or a polyadenylation signal.

15. The nucleic acid molecule of claim 1, wherein said nucleotide sequence is operatively linked to a promoter sequence comprising the nucleotide sequence set forth as SEQ ID NO: 7.

16. The soybean plant or soybean plant cell of claim 8, wherein said soybean plant is an elite *Glycine max* plant or said soybean plant cell is an elite *Glycine max* plant cell.

17. The soybean plant or soybean plant cell of claim 8, wherein the protein comprises an amino acid sequence that is at least 99% identical to SEQ ID NO: 1.

18. The soybean plant or soybean plant cell of claim 8, wherein the protein has the amino acid sequence shown in SEQ ID NO: 1.

19. The soybean plant or soybean plant cell of claim 8, wherein the nucleotide sequence is at least 95% identical to SEQ ID NO: 2.

20. The soybean plant or soybean plant cell of claim 8, wherein the nucleotide sequence is at least 99% identical to SEQ ID NO: 2.

21. The soybean plant or soybean plant cell of claim 8, wherein the nucleotide sequence is the nucleotide sequence shown in SEQ ID NO: 2.

22. The soybean plant or soybean plant cell of claim 8, wherein said nucleic acid molecule is inserted into chromosome 18 of said soybean plant or soybean plant cell.

23. The soybean plant or soybean plant cell of claim 8, wherein said nucleotide sequence is operatively linked to a promoter having the sequence set forth as SEQ ID NO: 7.

24. The method of claim 6, wherein the protein comprises an amino acid sequence that is at least 99% identical to SEQ ID NO: 1.

25. The method of claim 6, wherein the protein has the amino acid sequence shown in SEQ ID NO: 1.

26. The method of claim 6, wherein the nucleotide sequence is at least 95% identical to SEQ ID NO: 2.

27. The method of claim 6, wherein the nucleotide sequence is at least 99% identical to SEQ ID NO: 2.

28. The method of claim 6, wherein the nucleotide sequence has the nucleic acid sequence shown in SEQ ID NO: 2.

29. The method of claim 6, wherein said recipient soybean plant is an elite *Glycine max* plant.

30. The method of claim 6, wherein the method comprises Cas12a mediated gene replacement.

31. The method of claim 6, wherein said nucleic acid molecule is inserted into chromosome 18 of a *Glycine max* plant.

32. The method of claim 6, wherein said nucleotide sequence is operatively linked to a promoter having the sequence set forth as SEQ ID NO: 7.

33. The soybean plant or soybean plant cell of claim 8, wherein said nucleotide sequence is operatively linked to a promoter which drives expression in said soybean plant or said soybean plant cell.

34. The soybean plant or soybean plant cell of claim 8, wherein said heterologous regulatory sequence is a heterologous promoter.

35. The soybean plant or soybean plant cell of claim 8, wherein said heterologous regulatory sequence is a terminator, an enhancer, or a polyadenylation signal.

36. The method of claim 6, wherein said nucleotide sequence is operatively linked to a promoter which drives expression in said soybean plant.

37. The method of claim 6, wherein said heterologous regulatory sequence is a heterologous promoter.

38. The method of claim 6, wherein said heterologous regulatory sequence is a terminator, an enhancer, or a polyadenylation signal.

* * * * *

SEQUENCE LISTING

```
<160> NUMBER OF SEQ ID NOS: 84

<210> SEQ ID NO 1
<211> LENGTH: 857
<212> TYPE: PRT
<213> ORGANISM: Glycine max

<400> SEQUENCE: 1

Met Ala Asp Ser Val Val Ala Phe Leu Leu Asp Asn Leu Ser Arg Leu
1               5                   10                  15

Leu Glu Asp Glu His Lys Leu Leu Ser Gly Val Glu Asp Lys Val Asn
            20                  25                  30

Ser Leu Cys Asn Glu Leu Lys Phe Ile His Ile Phe Leu Lys Asn Ser
        35                  40                  45

Glu Gly Lys Arg Ser His Asp Thr Val Lys Glu Val Val Ser Gln Ile
    50                  55                  60

Arg Asp Val Ala His Lys Ala Glu Asp Val Val Asp Thr Tyr Val Thr
65                  70                  75                  80

Asn Ile Thr Arg His Lys Gln Arg Ser Lys Leu Ser Lys Leu Phe His
                85                  90                  95

Leu Lys Glu Gln Val Met Val Leu His Gln Val Asn Ser Asp Ile Glu
            100                 105                 110

Lys Ile Arg Ser Gln Ile Asp Asp Ile Tyr Lys Asn Arg Asp Arg Tyr
        115                 120                 125

Gly Ile Gly Glu Gly Glu Phe Arg Ser Glu Glu Ala Ala Ala Glu Ala
    130                 135                 140

Glu Ser Leu Leu Lys Arg Arg Arg Glu Val Glu Glu Glu Asp Val Val
145                 150                 155                 160

Gly Leu Val His Asp Ser Ser His Val Ile Gln Glu Leu Met Glu Ser
                165                 170                 175

Glu Ser Arg Leu Lys Val Val Ser Ile Ile Gly Met Gly Gly Leu Gly
            180                 185                 190

Lys Thr Thr Leu Ala Arg Lys Ile His Asn Asn Asn Gln Val Gln Leu
        195                 200                 205

Arg Phe Pro Cys Leu Ala Trp Val Ser Val Ser Asn Asp Tyr Arg Pro
    210                 215                 220

Lys Glu Cys Leu Leu Ser Leu Leu Lys Cys Ser Met Ser Ser Thr Ser
225                 230                 235                 240

Glu Phe Glu Lys Leu Ser Glu Glu Glu Leu Lys Lys Lys Val Ala Glu
                245                 250                 255

Trp Leu Lys Glu Lys Arg Tyr Leu Val Val Leu Asp Asp Ile Trp Glu
            260                 265                 270

Thr Gln Val Trp Asp Glu Val Lys Gly Ala Phe Pro Asp Asp Gln Thr
        275                 280                 285

Gly Ser Arg Ile Leu Ile Thr Ser Arg Asn Lys Asp Val Ala His Tyr
    290                 295                 300
```

```
Ala Gly Thr Ala Ser Pro Tyr Asp Leu Pro Ile Leu Asn Glu Asp Glu
305                 310                 315                 320

Ser Trp Glu Leu Phe Thr Lys Lys Ile Phe Arg Gly Glu Glu Cys Pro
                325                 330                 335

Ser Asp Leu Glu Pro Leu Gly Arg Ser Ile Val Lys Thr Cys Gly Gly
            340                 345                 350

Leu Pro Leu Ala Ile Val Val Leu Ala Gly Leu Val Ala Lys Lys Glu
        355                 360                 365

Lys Ser Gln Arg Glu Trp Ser Arg Ile Lys Asp Val Ser Trp His Leu
    370                 375                 380

Thr Glu Asp Lys Thr Gly Val Met Asp Ile Leu Lys Leu Ser Tyr Asn
385                 390                 395                 400

Asn Leu Pro Gly Arg Leu Lys Pro Cys Phe Leu Tyr Phe Gly Ile Tyr
                405                 410                 415

Pro Glu Asp Tyr Glu Ile Ser Ala Arg Gln Leu Ile Gln Tyr Trp Ile
            420                 425                 430

Ala Glu Gly Phe Ile Gln Pro Gln Lys Thr Gly Ile Ala Asp Thr Thr
        435                 440                 445

Glu Leu Glu Asp Val Ala Asp Phe Tyr Leu Asp Glu Leu Val Asp Arg
    450                 455                 460

Ser Leu Val Gln Val Ala Glu Arg Arg Ser Asp Gly Gly Val Lys Thr
465                 470                 475                 480

Cys Arg Ile His Asp Leu Leu Arg Asp Leu Cys Leu Ser Glu Ser Lys
                485                 490                 495

Ser Asp Lys Phe Leu Glu Val Cys Thr Asn Ser Asn Ile Asp Thr Val
            500                 505                 510

Ser Asn Thr Asn Pro Arg Arg Met Ser Ile His Leu Lys Gly Asp Ser
        515                 520                 525

Gly Val Ser Ala Asn Thr Phe Asn Lys Ser Cys Thr Arg Ser Met Phe
    530                 535                 540

Ile Phe Gly Ser Asp Asp Arg Met Asp Leu Val Pro Val Leu Lys Asn
545                 550                 555                 560

Phe Glu Leu Ala Arg Val Leu Asp Cys Asp Ser Phe Ile Gly Phe Ser
                565                 570                 575

Ser Tyr Pro Val Pro Arg Asp Leu Lys Arg Met Ile His Leu Arg Tyr
            580                 585                 590

Leu Arg Ile Cys Val Lys His Leu Pro Asp Cys Val Cys Ser Leu Trp
        595                 600                 605

Asn Leu Glu Thr Leu Asp Val Thr Tyr Glu Thr Thr Val Ser Ser Lys
    610                 615                 620

Ile Trp Thr Leu Lys Arg Leu Arg His Leu Tyr Leu Ser Gly Gly Gly
625                 630                 635                 640

Lys Leu Pro Val Val Leu Pro Lys Ala Asn Arg Met Glu Asn Leu Gln
                645                 650                 655

Thr Leu Leu Leu Asp Gly Ser Tyr Gly Ile Asp Thr Tyr Pro Gln Gln
            660                 665                 670

Val Ile Ser Leu Leu Lys Ile Asp Ile Phe Pro Arg Leu Arg Lys Leu
        675                 680                 685

Ala Leu Arg Tyr Pro Asp Gly Pro Asp Met Leu Ser Ser Leu His His
    690                 695                 700

Leu Ser Asn Leu Arg Ser Leu Lys Val Ile Arg Gly Phe Glu Leu Pro
705                 710                 715                 720
```

```
Ser Asp Thr Asn Ala Phe Pro Ser Asn Leu Thr Lys Ile Thr Leu Ala
                725                 730                 735

Ala Val Arg Asp Leu His Phe Met Lys Thr Leu Gly Gln Leu Thr Asn
            740                 745                 750

Leu Gln Ile Leu Lys Leu Arg Phe Gly Lys Val Gly Phe His Leu Asp
        755                 760                 765

Ile Gly Arg Gly Glu Phe Pro Gln Leu Gln Val Leu His Met Thr Gln
    770                 775                 780

Ile Asn Val Arg Gln Trp Arg Leu Glu Lys Asp Ala Met Pro Arg Leu
785                 790                 795                 800

Arg His Leu Val Ile Asn Asp Cys Glu Glu Leu Ser Glu Leu Pro Glu
                805                 810                 815

Glu Leu Trp Ser Met Thr Ala Leu Arg Val Val His Val Ser Arg Pro
            820                 825                 830

Ser Glu Glu Leu Ala Asn Ser Leu Lys Asn Val Glu Pro Arg Asn Gly
        835                 840                 845

Cys Lys Leu Lys Ile Ser Asn Glu Leu
    850                 855


<210> SEQ ID NO 2
<211> LENGTH: 2574
<212> TYPE: DNA
<213> ORGANISM: Glycine max

<400> SEQUENCE: 2

atggcagata gtgttgttgc ttttctgcta gataacttgt ctcggctgct tgaagatgag      60

cacaagttgc tttctggcgt ggaggacaaa gtcaactctc tttgcaatga gctcaagttt     120

atacacatct tcctcaagaa ttccgagggc aagcgcagtc atgacacagt gaaagaagtg     180

gtgagccaaa tcagagatgt cgcccacaaa gctgaagatg tggttgacac ctacgttacc     240

aacatcacca ggcataaaca gagaagcaaa ctgagcaagt tattccacct caaagaacaa     300

gtcatggtgc ttcaccaagt caactctgac atagagaaga tcaggagtca gatcgatgac     360

atctataaga acagggacag atatggcatt ggagaaggtg aattccgaag cgaagaagct     420

gctgcagagg cagaatcact cctcaaaaga aggagggagg tggaggaaga agatgtggtg     480

ggcttagtgc atgactcaag ccatgtaatt caggaactca tggagagtga gtcacgtctt     540

aaagttgttt ccataattgg aatgggaggg ttgggtaaga ccactcttgc ccgtaagatc     600

cataacaaca atcaagtgca gctgcggttt ccttgccttg catgggtttc tgtgtccaat     660

gattacagac ccaaggaatg tcttctcagc cttctcaaat gctcaatgtc atccacatct     720

gaatttgaaa aattaagtga ggaagaactg aagaagaagg tagcggaatg gttgaaagag     780

aagaggtatc tggtagtgct tgatgacatc tgggaaaccc aagtatggga tgaggttaaa     840

ggagcctttc cagatgacca aacaggtagt agaattctca taacaagtcg caacaaagac     900

gtggcacact atgctggaac tgcgtctccc tacgaccttc ccatcctcaa tgaagatgaa     960

agctgggaac tcttcacaaa gaagattttt cgaggtgaag aatgcccgtc tgatttagag    1020

cctctgggta gatccattgt gaaaacttgt gggggtttac cacttgccat tgtggtttta    1080

gcaggactcg ttgccaagaa ggagaagtca caaagagagt ggtcaagaat caaggatgtg    1140

agttggcatc ttacagagga taagactgga gtgatggata tactgaagct tagctacaac    1200

aacttgcctg gaagattaaa gccttgcttt ctgtattttg gaatctatcc agaagactat    1260

gagatcagtg caagacaatt gatccaatat tggatcgcag aagggttcat acaaccacaa    1320
```

```
aaaactggaa ttgcagatac aacagaactg gaagatgtag ctgactttta cttggatgag   1380
ctggtggatc gcagcttggt gcaagtggca gaaagaagga gtgatggggg tgtcaagaca   1440
tgtcggattc atgatcttct acgtgatctt tgcttgtcag aaagcaagtc tgataagttt   1500
ctggaggttt gcacaaactc caacattgat accgtcagta ataccaatcc ccgtagaatg   1560
tccatccact tgaaaggaga ctcgggtgtc tctgcaaaca catttaacaa atcatgcact   1620
cgttctatgt tcatctttgg tagtgatgat agaatggacc tagttcctgt tttgaaaaac   1680
ttcgagttgg cccgtgtgct tgattgtgat tcgtttattg ggttttcgtc ttatccagtc   1740
cccagagatt tgaagaggat gatccatcta agatacttga gaatatgcgt caagcacctt   1800
ccagattgtg tatgcagcct ttggaatcta gaaacactgg atgtaacata tgaaaccaca   1860
gtatccagta aaatttggac gttgaagcgg ctgagacatc tttatttgag tgggggaggg   1920
aagttaccag tcgtcctgcc aaaagcaaat agaatggaga atctccaaac ccttttgtta   1980
gatggtagct atggtataga cacgtatcca caacaagtga tttccctgtt gaaaattgac   2040
atatttccta ggttgcgaaa attagctttg cgctatcctg atggaccaga tatgttatca   2100
agtctacacc acctcagcaa tcttcgtagc ctaaaagtaa ttcgcggttt tgaacttcca   2160
tcagacacca atgcgtttcc atcaaatctt accaagataa ccttagcagc agtccgggat   2220
ttacatttca tgaagacact ggggcaactt accaaccttc aaatcttgaa actaagattc   2280
ggcaaagttg gttttcatct tgatattggc aggggagagt tcccgcaact tcaagtgctt   2340
catatgacgc aaataaatgt aagacaatgg agattagaga aagatgcaat gcctcgactt   2400
cgccatctgg tcattaatga ctgtgaagaa ttgtcagagc ttccagaaga actttggtca   2460
atgactgcct taagagtggt gcatgtttca cggccctccg aagaattggc taacagtctc   2520
aaaaatgtgg agcccaggaa tggctgtaag ctcaaaatct ctaatgaact gtga         2574
```

<210> SEQ ID NO 3
<211> LENGTH: 28
<212> TYPE: DNA
<213> ORGANISM: Artificial Sequence
<220> FEATURE:
<223> OTHER INFORMATION: Artificially Synthesized

<400> SEQUENCE: 3

```
atggcagata gtgttgttgc ttttctgc                                        28
```

<210> SEQ ID NO 4
<211> LENGTH: 32
<212> TYPE: DNA
<213> ORGANISM: Artificial Sequence
<220> FEATURE:
<223> OTHER INFORMATION: Artificially Synthesized

<400> SEQUENCE: 4

```
tcacagttca ttagagattt tgagcttaca gc                                   32
```

<210> SEQ ID NO 5
<211> LENGTH: 22
<212> TYPE: DNA
<213> ORGANISM: Artificial Sequence
<220> FEATURE:
<223> OTHER INFORMATION: Artificially Synthesized

<400> SEQUENCE: 5

```
tcggcaaagt tggttttcat ct                                              22
```

<210> SEQ ID NO 6
<211> LENGTH: 20
<212> TYPE: DNA
<213> ORGANISM: Artificial Sequence
<220> FEATURE:
<223> OTHER INFORMATION: Artificially Synthesized

<400> SEQUENCE: 6
ccattcctgg gctccacatt 20

<210> SEQ ID NO 7
<211> LENGTH: 2525
<212> TYPE: DNA
<213> ORGANISM: Artificial Sequence
<220> FEATURE:
<223> OTHER INFORMATION: Artificially Synthesized

<400> SEQUENCE: 7
aaaggctttt ttgttaaggg aaggtgtcct aagtactaac ccacgaagga atgagggaag 60
tgaggatggt aacatgtcaa ataaatttgg aatttagttc ccgaaatttt tgagtgttaa 120
ttattgtagg aatttactca tttcatgata aaacttgaca tggagtaccg gacttaaaaa 180
agaaaaacat gacatgaagt ggatttggag tcaagttttc tctcaaggca aactggattt 240
attctccgta ctcacttatt aaacaaggtt aaaacaatta ggtttgattg acattttggc 300
cttcagggtt gtctttataa ttttttcata tacgaaaaaa gttataagtt ttaatttctg 360
tacacacata taagttaagt tttgatctcc gtgatcaacg cagctagtat gtatgtggca 420
cctattcatt tgctttactg agccttctca agtgtttgtt gtccacgcct gaatataatg 480
atttattcaa gaaaacaacg gattgaggaa gaactgaaga aggtagcaga atggttgaag 540
gggaaaaatt acctggtgat gcttgatgac atatgggatg aggttaaagg tgcatttcca 600
gatgaccaaa atggtagcag aatactaata acaaggaggt ggcatactat gtacaagaac 660
aattttcaat aggatcatct tagaccttaa gagcattgac gtaaagatag atgacgaaga 720
tcaagccatc attctgttga gctttcgtcc taagccattt gatcattttg ctgatacaat 780
gttgtataga aaggctactc tatcaatgga tgaggtcaag gctgctttga actcaaaaga 840
aaatcaaggg gagaatgact ctggcagtaa aagactcttt tctactttct tgtgctgatg 900
tcagtttttt gtctcctttt ttctttcatg gtcattattg tgctgatgtt ttaacatcat 960
ttacatgttt attgtaaaag gctctttgct ctggcagagt ttgatgagat gatttgcaat 1020
tcctctgctt ctttctattc acttttctgc tttcttgtgt tccacaacca cttgaccaga 1080
tttttcagtt agcttagcat ttaagcctga gaaattatgc atcatttcat ttgtttgttg 1140
tacaaccata tttaatgtta acctctctcc cttgttttc cattctaaac atggatcatg 1200
tttttgttta ttggtctaaa gtgttgtttc atgttatttt tctttctctt ttcccaatgg 1260
aaggtccttt catgatttag ttagaataga taactgataa cacaattagt tggaaaggaa 1320
gatgttagag tgtatgttga taatgggaga caaatcatag tgatcagttt tagaattgga 1380
gtgaaagcat acagacattg cttttgtgcc ttgtctctgc tactctaccc aaacctttgc 1440
tggttttatc atggatataa ttcattattt tatgatcttt ttggtagatt ttctaccaaa 1500
attcatttct tcttttcggt gatgctatat agtacgaatt agttttgcac caagaagtac 1560
gaatccactt ggcaaaatat gatcgtacaa atattaattt gaaagaataa aatctagaca 1620
tgcaagttct aactaccctc tttcaaactg gaatttgtgg aattgttgga attttggaaa 1680
agcttgttct ttacatcaat gtatatattc tcccaaattg tcttacaaca caaaaaaact 1740
tgagtatttt cttacatatt atctgcctac atttttgcgc ttaactggat tatggaaaaa 1800
taatttgcta atgagatata ctaggacaga tggatgaaaa ttacaccaac ttttaacaaa 1860
ggtttaaata cagttttttt ttatttataa tttatcatat ttttgccttt agtctttata 1920
tttttttttg tttttaagct ttgtaaatta tatttatttt atttttaatt tttaaagcac 1980
cttaaataat attttgacaa gtgaaaaaaa gtgttatcta aaatgttaga acgaaaaata 2040
aaaaaatata atttataagg actaaacttt ttttacaaaa aaaataaaaa aaatactaaa 2100
gaataaaaaa atatttaaga caataacaat ttgctgaata caacagaaaa gttagttaga 2160
acacaataac aatttttaaa gattattgtt aaagactctg cattttaaaa ttctaactaa 2220
tttttgtttc taaaccatgg aagactttta tttcataaac acaataacaa ttaaacaaaa 2280
ctcacaattt aaaaaaaaat cagagtcatc aaatatatta atatttaaag acagaaaaaa 2340
aaataaacaa ataaagttga gaaagccaac ctataattaa aaaggttgac agaaacgcgg 2400
gtccacgcgt atgcgcgttc tttcccttta ttggcgtcca cttgttatct ttcgttctct 2460
actctgtaaa ttatctgtcc acaaactctc tagagtttcc acccaagatt tcctgtttca 2520
cagaa 2525

<210> SEQ ID NO 8
<211> LENGTH: 20
<212> TYPE: DNA
<213> ORGANISM: Artificial Sequence
<220> FEATURE:
<223> OTHER INFORMATION: Artificially Synthesized

<400> SEQUENCE: 8
attggactct ggtgatggtg 20

<210> SEQ ID NO 9
<211> LENGTH: 21
<212> TYPE: DNA
<213> ORGANISM: Artificial Sequence
<220> FEATURE:
<223> OTHER INFORMATION: Artificially Synthesized

<400> SEQUENCE: 9
tcagcagagg tggtgaacat t 21

<210> SEQ ID NO 10
<211> LENGTH: 22
<212> TYPE: DNA
<213> ORGANISM: Artificial Sequence
<220> FEATURE:
<223> OTHER INFORMATION: Artificially Synthesized

<400> SEQUENCE: 10
agaaacccac gtcatgccag tt 22

<210> SEQ ID NO 11
<211> LENGTH: 32767
<212> TYPE: DNA
<213> ORGANISM: Artificial Sequence
<220> FEATURE:
<223> OTHER INFORMATION: Artificially Synthesized

<400> SEQUENCE: 11
ggatccgtag acaatgtcgg tggcaaggat gcagtctgtt agcaaaacaa atggtaggaa 60
gaactaatga tcaacacaaa tagtgaagca gcagtaaaag ctttcaatta aaagcaaatt 120
tacaaaggct gcataacatt tatgatgggt ttggatgagt ggtaaggaga agagaaaaat 180

```
gacacaaacc cttgtgtaga agatatttaa tgagatggga tggaatggga aagtcttgat    240
aagtacagga ttgtgaatga acaaatgcac caatagcccc atccttaatt tggatatatg    300
attttctgat tcttgatgta gaacaactgc tagagccttt caattgcatt actaggttcg    360
aggtttgctt gcttgtgtaa gtgagaaggg aagattgaaa ataagatgga atgaagaaaa    420
aataaattaa agtcatggct caaagtgaaa ataagtatat tttattttcc tatttctcat    480
gtttctgcta aaggcaagtg tacattcatc tcaattcacc taccaaacta tgcagatact    540
aagaccatgc atgtccagga aatataatca taaattcgct aactatccac ctaccgaacc    600
aagcagatac caagaccatg catgtccagg aaatataatc ataattcata acagactagc    660
acaagtttaa gtctttattt gtatatttat atagaagtta cccttgatga tggcgtaacg    720
gatggtggct caagagatag cctagcagaa cctgactgtg aaccctgtat aattcagatt    780
acagagtaaa cataggaaca agtttcaaag gaaagtaaac aagggaaaac cttgaggggt    840
gggggaaggg ggaactacaa tataaaacca aacttgactg cattcattct ttggcttata    900
gttaaataaa tttactaagc taatgaacaa aatatatact attaaactaa caagacatcc    960
tataaaatag cctattatgc ctaattgata ataacagttc tcccaaaagg cataattgca   1020
ttgataaatg ggagttgagg aaaatgcttt accctggaag agggtgaaac tggtggaagc   1080
tcaagggctg gcctggaaga actggaagaa gatgcctata taatataaaa atgtcttagt   1140
atattatatt atatactata tacagcaaaa aaatagaaag aagataattg aaagcagatc   1200
tgaaattaag actgcaaagc caaagccaga aaaaaaatat ccatcgtaac taatggaagt   1260
ctggttcatg cctgaatata ctctgtggat ctgctattct ccaaagtctt ggtaaattga   1320
cacaacatgt tcactccttc aattgtggcc acctaagcag attaaagccg gtaaaaagta   1380
aatcacagat ataaacaata ttcataacct aaaaaaggtc tataattaaa ttatgcagtg   1440
actgaagtca aattgaccat acctgcttct cttctatttc tttaatttta gattcctgag   1500
aagccaagta atcaggttta agttaaaaca cccaataata aattaaagaa ataactgaat   1560
tgttgcaatt gatttaccag aacatggact gcaacatgaa aagacttcga atcttcactt   1620
attgtatctg ctttccgttg aattacatat atctgcaaca ggagatattc tattgttaaa   1680
caaggaagaa gacaaaatta gacataaaaa atctttactc acatcctccc tggtactttc   1740
agtaatggca gcacattctt ctaaattttt atccagaccg ttgattcttg cagataattt   1800
cttcttggta tcctgaaacc attgcagata agtaattttt cattctcaat aacttcatgg   1860
taaaacaact gtcaatgtaa ttcttaatgt ccagataaag aaagaaaagt aaactgagct   1920
gaatgcaaaa tttaaaagca tcatcattta tagaacacac aaagttcctt ttcaaaattt   1980
tgtttgaaat ataagatttg ttcgattcaa taatggaacc ataccaattt tcacaatgaa   2040
agtgataaat gtaagttatg cacttaacga ggtcacaaaa tatttacatg aataatatta   2100
ccacaaaggc ttgacagtaa aatcaagctc aaagattatt tgaatgcagt cataataaag   2160
agaatgagct caattaagta gtattttttg tctctctgtt gatctaaatg acacatttat   2220
cctaacgtgc acttccagtg tttcagggga accacacatg agctcgatgt ataaaacatg   2280
aacaaactaa gatcatcatc aagttcatat gttacgtatt ttctagttca aaagcatcag   2340
aataaataat acataattat gttattaaaa atatttaatg atttgctcct tgacattttg   2400
ttatatagct gtactctagt taacagatag ttatcaactt atcattcatt gtcatctttg   2460
ataaagaatg tctggttttg acacagtcta agaagaacaa actatgcaat aaaagggaaa   2520
```

-continued aattacccca attgattcat aaagctttcc catctgatta ccaattgatg tgcaagcatc 2580
agacaaacca cgccttgttg caaacatcag atcaggaagc ttccatccct gcaaacacac 2640
gagagccata aaactcattc ataagagagt ggggtaattg aagatttgga gatagtatgg 2700
tgagataaaa gaaaattcat ttttaaaaaa attagagaat aagtgaacta acagccagct 2760
gctcaggcat aaagtttagt atagctaaat tcatgtacta tgacagatct aagtgtaaga 2820
gagaagggac aagccttcaa gaatttgtgg gaataataca tgtagattgt tgtaatataa 2880
caagcaacaa aattgttgat tttcttgcat agttttaaga gttctctttt tgggtgcata 2940
aattttattc ccagaaacta aaattcctgg atttgccact ccatgcaaac ctgccaacta 3000
ataatcatct aacagcaagt aatggatagt tgattctgct ctaagttatg tggaaaatat 3060
tagtaacatg agttgagctc aactcaaacc agtaaatcca actctcaaaa aagaatgata 3120
acaatttatg ggaacagaaa gaaactgcta caactcaaac aaacatgaat gccatatgat 3180
caaatcattt ttttaaaaaa aaaaagtcaa aaatggttta tatattctac aagattagca 3240
agctctcaat ttcacacttg acagttatca tgacaatata tagcaggaat ctggatcctc 3300
tgcagcctct cccagcaagg tttctctcct tcccaaatct caaccaccca tcacattctc 3360
tttcctcttc agctactaag ttcaactaca acagtcaaga tcttggctgg acagtggcgg 3420
gagagaaatt aagtggagag tatccgtgtg caaagagcag atggcactcg ttaaaagcac 3480
caatatttaa attcaaatta gccataaagc ttccaataag aatgtatcac tacagcatcc 3540
tgttacttaa atcaaaaatt gagagagaaa agacattacc ttccaccaaa cgtatccata 3600
tcctaccaca acaataacaa tcactgttgc atattttctc ccacctgtgc atttcccaaa 3660
caagtcagaa aataaaaaag gagtaaaaaa taataaggaa acattgtttt gcaaattaac 3720
acgtcaacat ttattaaatt gctgaagaaa taacaaaagg cccctataat gtgtataaga 3780
aagtagctaa ccagtacctg ttccacttgc atttacaata gtgattgatc tatctctagc 3840
aagaagttgt agttcctgcc gaagactgtt aacctgtaga tcaacagtta atcagaattt 3900
tcaattaccc ctgtattgct atattggtat atatttacaa atatagcatt tgttttagta 3960
gccaattcaa caggggggaa ataaaaatcc cacttcaact gctaagtgct aaaagatata 4020
actttaatta tataaatgtt ttcattcaat tcatagaatg tcagaactca gcattattag 4080
cactctatat tgggaatcta tgataaaaat gaatgcacag tgtaacttca taaattccca 4140
aagcagcaga cccagcatgc actttaactt taaataattt atgatcagat cacaacctac 4200
ttcagaatga atgttgtaac agaatcaatg ctatgaatta tagtacttgt gacccagttg 4260
tttgtttcaa ttttgaaaca tgcaacagaa gctattttta gttctcagac aagtacgagg 4320
ttaattgtta agattagcat taacattata tacatttact tgtacgtaac atatgttcaa 4380
aatacaactt cagttgttat gaataagaca tatatatgag taaaaaaaat atgcatatgc 4440
tcagaactca agtcatgtat atgattcact aaatgatgtt cagcatgatg catgagacta 4500
aacttaacta gacaaagaac tattcctaat taaaataaaa ttaaatataa tcaataatga 4560
aaaggcagca acaacaacaa cgacatgcat acctgagcca acaaagcatc attatgcggc 4620
tgctttttaa cagttggagc aggatcatcg cttttaagtt gcctcaaaac aacctggcaa 4680
aaaagtctac aatcagtaaa aagcctgcat actttttttt ttttgctcag caaaaatata 4740
tatattatag attgaaatag taccagtggt actatgggta caaaagcctg catacttgat 4800
taccaagaat aaatgacagt taccatatac tcactatatt aatagaaatt ggacccaatc 4860
acagatataa aataatagca accaaaatat tgccaaactt gggattttag gatacaagac 4920

```
aagttgaaag aatttgccta aatttctcaa gtacatacaa caacaaccag tgtatcccaa   4980
caggtggaat cagccacata gatcaagcag ggttctatta aaaaaccaaa gttttagtaa   5040
aactatttag aacatggtct ttttactatt ttttaatagt gtctcctaat atttccttgg   5100
ccttcatcca atcaaactat cttccatatg tttcctttga tccatttgtc tcactactag   5160
actagagcct ctattggcct tcttacatga ctaaactacc ttaggaaagt ttccatcatc   5220
ttctccttat aatcacatat tatacccaaa atagtcccct taacaggaat cctaaatgta   5280
tgccattctc atctatattg ctttgtagtg tacattgtag taaaataaat caaatcctat   5340
atgttgccat tctcattttt gcttgcatga gttagagcat tatgatagtc ttcaacacta   5400
tttttttttg ttttataaat tcgatttctg aaatacaatt ccccccatac ccttacctta   5460
ggtctagaaa ttgcaccccc cataccataa accctctcct acacattcac acaacgtagc   5520
tacagtacag actagctctc cttgaacttc tgttgtttta aatatcatct caatcatacc   5580
actttggaca ccgaaaagag gataatcgca tcttaaaaca tgggaggggt agcaaaatca   5640
taagcatcat ttaccgagag ggaaaaaaaa ttgcatttat caatttgtac ccgtcagcat   5700
agttcattaa atgtatacat ccttcactag tgaaaaaaaa aatgcataaa aaaaataaca   5760
aaaacagcag cacccagaga aacaagttga gctttcaaaa cccaacctta aaagcaccag   5820
aggcgagacc agagacatct ggcagacgcc cttcttttgc aattactgaa ccagctatac   5880
ctaaaacaca aacaagcaaa cgaacgcatt tcagtgaggc attcaaaatt cgagtttcgt   5940
cgaaaaacct agattaacgt gccaccacga gcaaacgaac ctaaattgag atggcatcaa   6000
ttttggggga aaaaaagatt tggagaaaat aattaaaatt aaataaagag aatgacagtg   6060
tgtgtgaacc tgcgccgacg agaatgaaga gcttgccgag tgaaagagcc atggcgccag   6120
tgagtctgag caaacaagct agcgcactct gttgcgaagc atttagcgcg aaacgatgcg   6180
tttaggatta ggctatgtgc gattgtgcgt tgagattgtt tatgtttggg cactggtgag   6240
aattgatcag cgagacaaag aagacaatga aatcgaacaa acccttgcga ttgcggtgct   6300
ccctgctcct ttgtttcctc agtggacgac cctagttttg aagctgtgaa aataaataaa   6360
aatactagta tattaatagt atattccctt tctagttgtg caacaaacaa caattacaaa   6420
tatgagttta gagtgtgttt tgaatgaaag atggaaatat tattaaagat aaacttttgt   6480
acttttttta ttgggaccta ttgattatac tctatctttt atttttcaca aatggattat   6540
attctatctc aattcaaatt tatctttatt tttatatttt ttattttttta tcatgtaaat   6600
caaacatacc attaatactt ataaaatata gactcatata cagtataaga cagttttata   6660
taattaatta ataataaaat attattcata atatttttaa aataaaagaa aataagtgga   6720
tatattaata atgtattata ttatcattaa attataaatg attatgtaag ataagtttgt   6780
tatttttat aataattata atgttatatt cttaaataaa taagtttata ttattatcta   6840
aaggaagaga gataacgtag aatacaaaaa ttgacataaa atattgcaat gataacacct   6900
ctccctcatt aaacaaattg acaaatttta aaaatcatac caataataat aaaatatttt   6960
atatgattta tacatacatg attactaaat tcttaaaata attattattt atgtttataa   7020
acttatctct tttaatttga gattggatta cattgtaaaa ttaatttatt ctgcaagtat   7080
atatgaacta attttctata tttatcacta tgaacatgag tataaaaaaa tggaggagaa   7140
aaatctttgt catcaaattt gtaaatacaa ttagcagatc tcatttgcct aattatctgt   7200
ctggtttcat gtcagatttt ttttacctta tttattagaa gtttggataa ccaggccatt   7260
```

```
cttcctttaa gtggtttcca aattcttcaa cattgtgtcg cccaagccat gaagatccct   7320
attttattgt tattattatt actattatta ttaagtgtta atttaattgt tatctttcat   7380
tattgtggct ttttttaata ctaatgtgcc caataatcta tttaaaagaa taatctgtat   7440
tcaatttttg atatgtgaaa aaaattaaat caaccacaat catcacattc cgtggtttaa   7500
agatataact taatcaaatt aagatagtta atatttatga tttcaacatt cattcatttt   7560
taaatattta attattatta ttattaaaaa taatttattg agtgaatatc aaaattgaac   7620
tgtgtcatga tgtaacaagt tatgaatcgt gattatcatt tgccacataa tcaggtaacg   7680
tgacattaaa actgttaata gagaaaaaaa tgtaggggac gaaaaacgct aaaaaaaata   7740
tttagaaatt aaaaataaat ttgacaaaaa gtttagagat aaaaaaaaca aatttaatcc   7800
taaaataatc tgtaatattc ctttttaaaa agtaacgaaa tatgtgcaat attatgtgat   7860
tttccggcta gtatcttatt atttctttct ttttgtcttt taattattgg acaaacaatc   7920
gaatatggcc agaagctagc cttggataga ggctttacgc acatcatcat ttgaatctga   7980
ttctacagag gacggtatcc tactatccct agtctcccaa ctctgcaggg atgaccatgt   8040
ggcataaatc tcaaaaacat ctaagtgtaa ttaaatcaaa tattatctca ctcacaccga   8100
agtggttggt cattaattat tcagttttat tcatctaata cattgtaaat gtcatggact   8160
tggttaaaat ttgttagtgt tgaccaaagt aaagataagt agtaggaaag ttgacttaca   8220
ctcaagaatc ttttaaaatc tttaagattg tttttgtcaa aatattctct caaaatccca   8280
atccaataca tccattagct tgttattaca tcaaaatagg atatagttgg acatgggagt   8340
gtcttttcta tatattaaac tatcttacat agtatttcct caatcacaag gaaacaccag   8400
tccaccttgg aagaactcct atcttagcct tctaggcatc aggcatgcca gagtcaatac   8460
tctcaagaga aatgtgagtt tgtaactttt aatggaaaag attaaactca acactgaaaa   8520
ctgtattttg atcatacata tatataaacc taacgaataa aaaaaaatac atgtatgtac   8580
ctaggacatc accactttag aattgagatt gaaccttcgc cttaaaactg aataacaacg   8640
caatattgtt ggggcaaaat acataagata tgtctattct gaaaaaaata acaacaataa   8700
acccttatcc cactaggtca aaatcaaaat gaaataaaaa tgcaactaac taacaacatc   8760
atctgcctgc aaaagagtgc ctttaaaatc catcttgaaa agggttatat ttttttaatt   8820
ttatttattt aatttgtaat ttcacctgag ttgataatcg aacctgaggc aaaaagaaac   8880
atgagcatcc ttctctcctg cacgctagga aatggtataa ttgacatttg tgatgttcct   8940
tcttgctgct tctattctcc caagaattcc cttaactgct atatcaaatg catcttcaat   9000
ggtctctaat ctagaacttg gataacgata tattatcctt ggaataagtc ttacaatctc   9060
ctttctcatt gccaacactt cactttttgg aactctagac aatttctcat tgatcattac   9120
tctcttctct ctgacatctc tttctggtat gtacacagag tagctagaac catttctggg   9180
caaatgccac aaatattggt tatatgctga ttctggatga aagaaaacag gaatgcaacc   9240
tgccaaaatt gagtcaaaag ttgatctcct agtgaatgaa tcccctggag gctgtaaaca   9300
gaaaactgag ctctgaaaca cctttgtaac atgcacagga tcattgcaat aattatgacc   9360
gtcattgcaa cttagaagtt tgcagctcct agaggattgg cattgtttga ttatctcatt   9420
tctgatggag gatgatgaat tagaattagg ccttggagca cctgcaaatg aaaacaagta   9480
aggccttttc acttttatca tttttttctg ccactgaaaa acctccttat ccttggaggg   9540
gtgaaagtaa gttggatatg ggattggaaa ctcattgacc tttgagccag attcaattag   9600
cataattgac atgtttcttg cttctggaaa aagcattagc ttggtgcccc agtcatcatt   9660
```

```
attttctgtt cttctcctga agtcccaacc aactctccct ccaaccatga aatgatctct   9720
accccacatt cttttccatt cgggttgttg agccagccac ttcactagtt cttttggtga   9780
agcatctctg attgaaacat tgaagcctcc ccagaggtac tgacccacat caaggccagc   9840
atagtagggt acatatatag cagaagccag tgaggaatca ttggttaagc acttgtagtt   9900
cttcattgtg ttatggaaaa taacctcaag tgaaaattgg ttagttgcat accagctttc   9960
cttcaataga gccttctcct ttgatttctc aataaccttc tgtccaaggc ctaagttaga  10020
catgtaaggg cacatatcat cccacttcat gagagagtga caccccttca gcaaatcctc  10080
attgaacctg ctagcaagat cataaacata gacatattga cctgaacaag aatccaaatt  10140
tctagtggac aaatttgaaa caagtccaac attgtctcta ttcaaaggag gggaactcat  10200
gtggactctc ttatccactt caccatgtgc ttcaggaact atggtctctg tgtgattctc  10260
tacaatgtac cttggtatat tggaggcccc acttgataca ctattttgat tggtatgatt  10320
aaattttcta ggacaatcgg cattttcatt ataattgaaa gaagaatttg atggtaaaaa  10380
tgtaatgcca cgatcactca cagccatata atagtcccag agaagtaatg acatacaaaa  10440
aatgaaggag gtgaaaaaca caaaccggat tttatcaaag tacttgctca acggagggtt  10500
gtccatgttt tctttttggc cttttgagat tcagtaaaag tgaatgtgtt tttctctgat  10560
gatatgggga gagggtgaca tagagagatt tgtgtaatgc aaagtttgtg tgtgatttgg  10620
ggactttatc aaaggaatga tctgatatgg aaaagaaaag tgggaaagat attattgaca  10680
ttgaaaattt cctttttac ttgaaaagac tgaataacaa tggaaagtaa tcaaagtatt  10740
actgtttaat tgaagaaagc attaaaaata aaatcgtgca aaggatcaaa aaccaaaatt  10800
aatagtactg taattccgta catgaatatt tctcaagaga tgtgcttcac aacatacatt  10860
caatgcatta agattgagat tcttttatta taatattgat aatcatacat atatgtttat  10920
gatattatac gattgggtcc agatcttggg aaatgcttcc ccattatcat ttagtatcta  10980
aatggtcttc attgattttc tatagttatt ccagagacac cagatagcaa caccatgcat  11040
ggagaagcag cacaatgtag accttcaggc ttcagccacc ttatttataa ctatatatag  11100
ccacccacta tatgaaattc caaaatccac cttttatatt ataaaattcg aaatctactt  11160
aattattaat taaaagttat agtttttatt ttacttatta ctaacaatta attattaaag  11220
taatatttca ttaaataaaa ttatttttat ttttagatta aaattttcaa gatctatttt  11280
taaattttaa tttatatttt ttattatcca taagttttat tcttttatta aaaatttacg  11340
ttttaggtat attttgaatt tttacaaatt actggtgtaa tggactggat aatttttagt  11400
tataggtgat atgaatattg caaatatata cagctgctga agtgattaat gatataatat  11460
catgtaaatt ataaaagcct gtttacaaat tattcattga tttttgcatc ttaagttcag  11520
tagagtgtgt aaattatgat aaatccttga taccagataa aaaaataaaa agagaacagt  11580
attattgcta acttcgttat ttttggggaa cagatccaag aagcatgcaa aaagggtagt  11640
acacgatact atcattatcc tctatcatta tggcctgaac aattagacat tcaactcgta  11700
gttgcaaaga ttaaattgca agagccgagt tctatcaact gatctatatt cccctgagcc  11760
aaatgaagta tgcacgaagg agttaagtca gttttctatt cgttttcttg acgcagtgga  11820
gcagttcact ggcgccatgg acaagccctg gtttggagga tttgctgatt gggaagtgat  11880
ggaaacgggg ttgatagtta cataattact gggttactgt gaagaggttg aaagatgcta  11940
gttggaactt ggaagagtgc gttcagggat cacattttcc taatggcagc agcccttctc  12000
```

ccttattcac ggtatgtatg tatgtattct tattttttaa agcttcttta atcacactgc 12060
aagtgattgc tcattcatta tttttcagtt ttaattcgta taatatataa ttctcctaaa 12120
ctcaaatatt gggaaaatta aataattaat gttggcctac actcatgagt catgatcatg 12180
aataatgggt gaatataaat gggttcaagg ggagtggttt gcttgggaaa tccaagtgtt 12240
ttaagaggtt tttaatggag atcgaagtgg ctgtgttgga ttactcatgg aggtggcgga 12300
aagatcaatc aggaaactac atacatagct ttgtgagatc ttcaattcgg ttcttgtatt 12360
gatgacactt tggcaaatac ttggaatctg aaagtccctc caaagatcat tttttttttc 12420
ctttggagac ttgtcagaaa caggctccgt agtggtgata atctgctaag gaggaacgtc 12480
gtggtaagtg gtggctgctt tttttttttt tatctgagaa taaaaaacag tgttaaggaa 12540
attataacaa atcacgcgtt atattcaacc aaatgagtta gactacctta actagtggtg 12600
acatttatag ttgtcatttt gctatggttg gttgggtgga tctgaatagt tacttacccg 12660
catctgtaaa atcacacaac tcacagcacg agtttttgtt gcttggaaca aagattatgc 12720
aagcaagtga agagtagttt ggtgggggtg ttatatgtgt actcttggaa cacattagat 12780
aatattgatt taaacgaaaa gatctttcat aggcagaaca tcatacagga tattatttta 12840
atttccattc gtggacctga ctcaagaatt tcgatgcatc cttttcatac tcatatgttc 12900
agtggtgctt gaatccaggt gtgtgtttga aggagtagca tgatcctctt atcaaatttt 12960
gttattgaac tgctatatga tttagtgatc ctcaggtttg ttgtttcctg actgatgagt 13020
tctgtagtac tggattagtt taaaagagat ttcaatggat gtgtcccttt aaaggaaaaa 13080
aaaaattata taatgagtaa ttaaaatata ataaagggga tggggggagt acttagcaaa 13140
aatagcaagt agaaatttgg cccaactctc aggcaggggc tgagctaggc catttctttt 13200
gaggggggca aatttaaaaa ctaaaattaa ttatacttac aatattaata tgttaaattt 13260
aactaataat taaaatatct ataataatta ttatatttga acatcataat taatcataaa 13320
ttatttttaa aatcaaattt atttattttc ctaatgataa aaaaaccaag ttttattttt 13380
taatttgaga ataataagaa tttaaatttt atgcatgatc tgttgttcat gattgttgta 13440
tggtgatgaa tcagcaagca tagatcagtg tattgagacg tgtgtttgac acacctcttt 13500
aaggatttat tcacgtgtgt aaatttccca caatttaatt ggtcctttct aagagcttaa 13560
attttataat tataaatcaa ttaaaaatta ttctagatat aatttttaaa ataattacta 13620
taaaatttag taattttagc atacataatg catagcaata attgaatgat aatatatata 13680
taacatttat agtgctagtg tatttacatt aaattatagg attactatat ctctacttta 13740
aaaaaaacta caatgaaata aatatttttt atctttttat taaaaaaatt agtgaaaagg 13800
aagatgtctt aaaaattatg aaaattgatg gtcttataat tttttagaag tgtatctatt 13860
ttgaatgatg agaaagatag aaagatagca aaaaatacgt gagatgcaat aggtcaagtg 13920
aagagaaaga aaaggaaaga taaaaaaaaa aatgatggaa aaagggttat aaaaaataac 13980
aaaaaaaagt atataaaatc attattgaaa aagtatatgc ccatatttat gtatttcttt 14040
cttctttaga aatgaatttc tacagcatat acacacacat cagtcgtcta actcagaaac 14100
atcaacggtc tactacttca aacacactat acatgtccaa ttggacacat cactaaagac 14160
attcggatac atattaattc ttccttgatt agagattgat tactattatc gtattggata 14220
ttaacaaaac atattcagat ttttgtcttt gattttattc ctaaacaccc cgtctcatta 14280
gcttcagaat tcttcatttc caacctcaat tctttgattt gagaaataac cctgttatag 14340
gttcaaagat tttcttctac aaataaatga accccataca aggtagacga ataaaaaaat 14400
acatgtatgt acctagggca tcaccacatt agaattgaga tcgaaccttt gccttaaaaa 14460
tgaataacaa cgcaatattt actgggggaa atacatagga tatgtctatt ctgaaaaaat 14520
aacaacaaca aagtcttgtc cgggtgaaaa tcaaactgaa atgaacatgc agctaagtga 14580
caacatcttc tgcctgcaag accattccaa gttcttataa gagtgcttta aaatccatct 14640
cgaaaaggga tatattttct gaattttttt atttaatttg taatttcacc tgactggata 14700
attgaacctg aggcaaagag aaacatagaa tccttgtctc ctgcacatta ggaaatggta 14760
taattgacat ttgtaatgtt ccttcttact gcttctattc tcccaagaat tcccttaact 14820
gctataccaa atgcatcttc aacggtcact gatctagaac ttggataacg atatattatt 14880
cttggaataa gtcttattat ctcctttctc atttccaaca cttcactttt tggaacctta 14940
gacaacttct cattgatcat tactctcttc tctctgacat ctctttctgg tatgtacaca 15000
gagtagctag aaccatttct gggcaaatgc cacaaatatt ggttatatgc tgattctgga 15060
tgaaagaaaa caggaatgca acctgccaaa attgagtcaa aagttgatct cctagtgaat 15120
gaatcccctg gaggctgtaa acagaaaact gagctctgaa acacctttgt aacatgcaca 15180
ggatcattgc aataattatg accatcattg caacttagaa gtttgcagct cctagaggat 15240
tgacattgtt tgattatttc atttctgatg gaggatgatg aatgccttga agcacctgca 15300
aatgaaaaca agtaaggcct tgaaactttt atcatttttt tctgccactg aaaaaactct 15360
ttatccttgg aggggtgaaa gtaagttgga tatgggattg gaaactcatt gtcctttgaa 15420
ccagattcaa ttagcaaaat tgacatgttt cttgcttctg gcaaaagcat tagcttggtg 15480
ccccagtcat tattattttc tgttcttctc ctgaagtccc aaccaattct ccctacaacc 15540
atgaaatgat ccctacccca cattcttttc cactcgggtt gtcgtgccag ccatttcact 15600
agttcttttg gtgaagcatc tctgattgaa acattgaagc ctccccagag gtactgaccc 15660
acatcaaggc cagcatagta gggtacatat atagcagaag cctgtgagga atcattggtt 15720
aagcacttgt agttcttcag tgtgttatgg aaaataactt caagtgaaaa ttggttggtt 15780
gcataccagc tttccttcaa caaaaccttc tcctttgatt tctcaataac cttaggtcca 15840
aggcctaagt tagacatgta aagacacata tctatcgact tcctgagaga gtgacaccct 15900
ttcagcaaat cttcattgaa cctgctagca agatcataaa catagatata ttgaccagaa 15960
caagaatcca aatttcttgt gggaacattt gtaacaactc caacattgtc tctatccaaa 16020
ggaggggaat tcatgtggac tctcttatcc acttcaccat gtgctgcagg aactatggtc 16080
tctgtgtgat tctctacaat gcgccttggt atattggagg caccacttgt tacaccattt 16140
tgattggtat gattagattt tctaggacaa tcggcagtgt cattaagatt gaaagaagaa 16200
tttgagggtt taggcatgtg tgcttgtttt gcatcattca tgttgaaaaa taaaaaggta 16260
atgccatgac cactcacagc catgtaatag tccaagagaa gcaatgacaa acataagata 16320
aaggaggtga aaaacacaaa ccggatttta tcaaagtact tcctcaacgg aggcttgccc 16380
atgttttctg tttggccaga tgtttacatt aacccacaca ccatgcttaa ctaattgagc 16440
tgaaaccctt cattttgttt ggccttttaa aattcagtta aagagaatgt gttttctctt 16500
atgatatggg gagacataga gagatttgtg taaagcttta gtgttatttg gggcctgtat 16560
caaagttatg atctcatatg gaaaagaaaa gaagaaaaga tattattgac tttaaaatat 16620
agtaatgagt attcctttaa gttgagagga acaactaaat atttggtgat ttgaactaat 16680
gttttttaaa cactaatttt ttgttttttt tatattttct tttttctca tctttaatat 16740 atttatcaaa ttttctaatt atttttttaa ataaatcata attttattat tattttacat 16800
aattacttca cttcagtgtt aatcatatca aaatcttata atttaacaag tcaaaatttt 16860
taagtttcaa ttaaattttt aagttcaagc tagtttttca actaatttga tcatttatct 16920
ttattatatc tttattaata tacaccatgt ctaaattttc ctcaaaaaaa cttttaagga 16980
taattattta atttcatatt ctaaaaataa cgttgcaaca actatgaaat ataatttcat 17040
attaatacaa aaggtcacgt aattatttat aaatactttt gtattaatat taaaatacga 17100
aggtattaat tacgcaattt catatttaaa aaaagtcatc tttattttat ctttattata 17160
taaattataa agtaatgtac accaagtcta aatttttccc tcaaagattt tgaggataat 17220
tatgtaattt catactctac ataaaaagtc acaataatta tgaaacagaa ttaatttcac 17280
attaatacaa agtattaatt atgcaatttc gtattttaaa aaagtcatct ttattaaata 17340
taaaaaaatg tatatatata tatataataa agatatatta atttattatc cataagtatt 17400
tattaaataa ataaatacag attttaagaa aaaaaaaatt ttgttggcat aataaaaaat 17460
catgagatta aactatgtaa aaattatcaa aataaatttt atctcttcca acatatctac 17520
agttatagta aaaaaaaaaa attaaactaa tgtcaacatt tgtttgtaaa gaagtcaatc 17580
atctatcaat tctgtttgac tttgtttgta ttttaaggaa gtatttatta gtagtttaaa 17640
aatatttgat ttatgaagca tattttaaga gaatatttat taatcataag tatttatatt 17700
tataattact aatttaaatt tattattcta ggtttcaaaa tagtttttat atgtaataag 17760
aatagtaaat atgaatttaa ttatttagtt ccaactaaaa aatttaaaat tttaagatga 17820
taaagtttgg taattattat atctttatct ttatctccaa agataggttg ttgggaccct 17880 tttttttaa aaaaaaaag ggtaaatagt ataatttttt attacattta atagatttat 17940
gtttttcatt attattatta ttattattat tattgttaca attttcaatt gttaaaatac 18000
catatgcttt gaattaattt tttttgttat taaatgagtt cctaaaattt ggcatcattt 18060
tcacattttc aaatagtagt ttttgattac ttactgtaaa ttgtgcaatt tcaataatta 18120
ttattgaatg ccctttataa cccattggcc aaccatacaa caggttaatt ttcaaataaa 18180
tttcaaaatt aaaagattca ctatttttaa aaatttaaaa ggttgaccat catttgcttc 18240
ttctcaattc tcaagcattt aaaaggatcg ttcctttctc tttgctggag gggaccacgg 18300
tggatagagt aactaacttt gcgagctatt cgagaaggtt agtctggtct atatgaatca 18360
tattttaaga aaatgtttgt taatcataag tatttatatt tataattact aatttagaaa 18420
aaaaagtatt tatatataat aagattaata aatatgaact taattattta attatagcta 18480
aaaattaatt ttttaagaat acattaataa taaattttaa caattatgat gtctttatct 18540
ttatctctat ataaagatat aaagataggg ttggtgggag ctagtttttt cttcaaataa 18600
gggtaaataa gacatttttt tctattacat ctaatagatt tgtctttttc aacaataata 18660
ataatatatt attattacaa ttttcaatct ttaaaatact atatgctttg aatttatttt 18720
ttttgttttt ttaatgtgat ttttttatta agtgagttcc taaaatttgc catcattttc 18780
acattttcaa atagtaattt tttattactt acagtaaatt gtgcaatttc aacacttgaa 18840
tgccccttta taacccattg accaacgata caacaggtta attttcaaat aaatttgaaa 18900
attaaaaaaa atcaccattt tcaacaatct aattctcaag cattcaaaat gaattgttcc 18960
ttgacttcct tcatctttgc tagaggggac cctgctaggc acgtagagta attaattttc 19020
cgagctttct gagaatgtta gagaggttta tatgaaccat atttttaata aaatgtttgt 19080
taataataag tatttatatt tataatcatt aatttaactt gtgcaatttt aacgattatt 19140
attgaatgcc ctttataacc cattgaccaa ccctacaaca ggttagcttt atcttaattc 19200
tcaggcattt aaaaagaatt gttccttcat atttgctgga ggggatcaat aagacatttt 19260
ttcttttaca tttaatagat ttgtcttttc aatattatta ttattagact taaatatatt 19320
ttttctatga taaatacata ttttttatat ttgatcctaa taaatttcgg attgagtccc 19380
taatatttta aaaaatttat cttagatact tactgttagt tcgtatgaac tggacacacg 19440
taaaaatgtg atgtattatg tcggattatt gtttatataa gttggatttt attatttttt 19500
aacaaagaaa atattttttt ttaataatcc aatatgtata aatagaaatc acaaaggtta 19560
tatttgacat gacacatcac acttctacgt gtctaattaa gagtcatgta ggattacata 19620
ttaatgatag agactttaag ataaaaaatt taaaacatta gaatccaaat tcgaaagaaa 19680
aatttatcaa agaccaaaca caaaaaatat atatttatca agaaccaaac atatatttaa 19740
cccttattat tacaccattt tcaattttaa aaatatcata ttctttgaaa ttattatttt 19800
tattaaatga gttccaaaaa tttgacatca ttttcacatc ttcaaataat ggtttttatt 19860
acttagggta aacggtgcaa tttcgacaat tattattgaa tgccctttat aacccattga 19920
ccaaccctac aacaggttaa ttttcaaata aatttcaaaa ttaaaaaatt caccattttt 19980
aacaatttaa aaggtttatc ctctcattca tgttttttta ttataacttt taacaataaa 20040
aaattataat ttttagagta aaatatgttt aaagtctttg taaaatttga aaagtattaa 20100
tttaattttc ataaaacttt tggtattaat ttgatcatgt aaaaataaac acatattttt 20160
catgatcctc agtagtaact ctgatagata ataatctgac atggttaata tatttaaatg 20220
tgtaatttaa ttataaatga attaaataat ttgtggcggt taaaatttcc tgaatgaatt 20280
gaacaatgtt tttgcagcta aaaccttaaa aattacaatt tttgtcactt attgtatgat 20340
tttctcgcat tttctgatgt gatgagaaaa ataaaataac aatgagttct aatgtcttct 20400
aagtgtgctt gaaaaagaag gtaaagagag aaaatgatta agttagttag ttaatttctt 20460
aaagaaacca tctaatagag ttattaataa aggaccatta aaaatatact ttatttttat 20520
gtggaccaaa ttcatgtttt tttattggat caaagatcat gttcttaatg gccaaccgaa 20580
agtcattgat ggtggacaat tacaccccat cacattcatg atattaaaat tttacctttt 20640
gcaccctcta aatttatata tggaacccat taccaagtaa catacccta tattgacata 20700
tggatgtgca aaaatagtct ctcactatga taaaattaca aataatttat tatttttatc 20760
tactaaataa atttccccta ctagtctagg gtctttccgt gggtgttttt aacctattgg 20820
attaaaaact aattaaactc atgattttgt tatgataaca aaaacaaaac aaaaatacat 20880
tcaaaagcat gacggcaaag agtgatgaga ggggagagag ggaaaaaaag aaaagaaatg 20940
aatgaaagaa gaaaaggata agaggaaaga agaaaggaaa agaggaaaga gtggtggctg 21000
gagaagggtg aggtgaaatc attcaaaagg tatcttggtc tatgttcttg atttatagtg 21060
tcaagagtaa ttttatagga atcaatagta tcatcccttt aaataagatt gagcaattca 21120
aaattaattt tcagagccca taaattattg atttaaccgt ttaacctatt ttatttttaa 21180
aacaatgatt taacctactt ttacacaagt tacaaatcaa cgatgataat ctttttttatt 21240
ctgaattaat gatgataatc tgttaacttg agtaatataa tttttttcaa ttttctctag 21300
tttttttatg caaaatatgg ttacggtatt tcattcataa tcaatgatta aatccaatgg 21360
ggagctgaat caaagactta gttacaagta agaagtccta aagtccttac taaagaataa 21420
atcacatgat taacttgtct cccgctaaaa ctcatcctag aatgatgacc cagtattgcc 21480
atgagtggga tagtcaacaa tcatcttaca accaattttc tctagttttg ttgcttgaaa 21540
actttttat gatttatcac tcttattttt ttatatagtt tcaatcttag taaatactat 21600
caaataaata atttttgtaa cacaattaat aattttacgt tggagaaagt ggaaaaaaaa 21660
cctttacata tcatatgatt tgttcataat atttttataa aataattaat tagacatgta 21720
ccaagtcata tgggacagac tcaagtcaaa ataaaatata tttaaaactt atattctgtt 21780
aatccaactc tcttttttat caagttattc ctccatttat tggacttaac acatttaaca 21840
ttcctacttt cttgttgtgg tacatgactc aatttgtcat tgccacttgg aatagttggg 21900
ttccttggag agtggctctc ccctcaagct atgcacttta aaaatatttc gaatactttc 21960
tgccttgtga tgatggtaat tttttccaaa gtaatttatc ttacctttga atgcacccat 22020
cggtgaaaat tttgtttttt agccaagatt cccaaaaaac tgctttgctt tacgaaaata 22080
tattaaaatt ctgaagttat cttacggtga tattttcaca taaaaatgtt tttaaaaaaa 22140
tattcattaa aacatataca aaatttttga aacctgcatt cattcacaat aaaaccagta 22200
gtcgaaactc aactggcaaa attgactttg actaataaaa gtatatgtat atcacaccac 22260
ccaactaatt gaagttaaaa aaaatgaaat gtattttacc caatcatgaa ataaggataa 22320
aatgaataaa aaacaaatag atggccacgc gcaaaaaata ttactagaag agctcccttg 22380
tgattcactc tatgatgttg atatacacaa gttaagtaag actcaataat aggctcagac 22440
taagttaact aattacttct aaatgacata cttataaagg aaataaagtg gatggaacaa 22500
aaactctata atgcaaagat gtgaaaaaat ctgcaaaaga atgccttagt acacaagtga 22560
tgctagttag gaggagccca ctttggaata tgattattat ttgggagctt gtagaggaac 22620
agaagttagt tatagaaccc agtactaatc caacttattg gcctagcaat cttaaaagca 22680
tttttatttt tcatacaaat tcctaaagca ggttgagttg cacagtttaa ccaactaacc 22740
actctattac tctaacacac ccactccatt atcatttata tatacacata ccaaacttgg 22800
attgaaaata gtttcctttc cgcacgtaaa tcattctaac ttgctcataa agacaaacag 22860
gaacctaaat ataaccccat tctaggtacc ctttttgat agatagatag ctatataggc 22920
taataagctc ttgaatatta gaacttgcta tagctataca cacataaaat ttggggttag 22980
gaagagatga gaaaccgtat tgaaagatta gtagttccat ggtctttcag ctgtgcttcc 23040
cattcaagtg tgaaattagg tgcacccaaa ggaccaaaag aagattcaaa aggaactatt 23100
gtttcaagta gtttctgctt tctttcttat cagcatccat ttctctattc aattttttt 23160
ctttgttaag tgattggagt gctatcttgt aatttgagat attcgttatg caaggaagac 23220
aagaaggaca agatagatca ttcatcaggg cccaaatgaa gagaggcaag ccttctgggt 23280
ttctggttct accaaagcct aatgtagcta ctagcataca gagaataatc aagggcatca 23340
agaatttatc tcaattattt ggtgagtaca acaatctcta tttttattaa ttaattttgt 23400
ttgttatgaa tcatggctgg tcttaattac atgaaatttc aatttccatt acccgataaa 23460
aattaaagaa acatataaat cattttatca atatattcta attagcagac aatcatacta 23520
ctccttgagt gatcaaatat ttgattatta agtttgtatg tatgtgtgaa aaaaaattca 23580
ataaaagata taagcttctt aaatatatct tcatatctca aaaaattagt ttccaaagtc 23640
tttgtcctga acagcccata aatcatttct taaatgtata taatttatgg taggtggtgc 23700
attattcttt atcctttctg atatataatt ctctttttct tgtggatctt tctcttcttc 23760
ttttttatg tgttatatga ttacttttgg actatgtatg acctgggcta ctcaacttgt 23820
ccaattgaat atactggaca caacttttat gggcccataa cattagaaaa atgaaacata 23880

```
tatatgtagc tgaaatttag aggcatcgaa ggagttagtt agatcagagg agtagtttga  23940
agttttgaag gccgattatg attttaggtg attatattaa ctcgtctccc ttatttgaaa  24000
tgattttatc cagctgtgga gtatggggac actaaattct aataatatgc atacaacata  24060
attgtatttg attttagtgt ctgaatccta cctactaaag aaacggacac aacattaaat  24120
aaatgagacc ttagcaaaat atatgaaatc atgtataatt aaaaaaacaa tactcgttag  24180
ttaagttaaa aagtagataa tgataaaact aacgaaaata gttatgaaat catctgtaca  24240
accaataatg aaattagtaa cctgagttct gtggcaaaaa atggaaaaca aggaatgcaa  24300
taactaaaca caaatttaaa agactcttgc aagaactctc aaccctacgt tgatctaaaa  24360
ctgtctctgt gtgtgattaa gttttttaa catctacaca ttaagttatt aaaatttgat  24420
ctatcattca agaaaatttg tcattggtgc cttttcaaaa atagaataaa tgtcgttgga  24480
ctgggctttg cttacagcat atggactggg ctagagccac atttaaggtt aattttaata  24540
taattctttg cttaagttat tataatattc taacttattt aaactctaca tgtttatatt  24600
cgctctgttg catctttgta atgtgtcgat tgttgaatgt tttcttcact tgaatttagt  24660
ttacaaaaaa gaggatgtcg aaaaaatgga acctgagatg gaaattgggt atccaacaga  24720
tgtgaagcat gtgacacata ttggaattga tgggtcaaca accattacaa ataatgtcaa  24780
gggttgggac aatctgaagg cacctgaatt attgtctctg tctccaattt cattcaagca  24840
atttgaattg gccatggcta gccaagctca atatcctctc attaacgatc ttaattcctc  24900
taaatgtggt tagaacactt tatgggaatg atggcacttc caagtccctt cttctaattg  24960
tagattaatg atgattgatg acgatgtatt taggagttca tatacaagtg cataaattga  25020
atattcgtga atgtttgtaa tctctttcac tctttgtttt gctcggttct tgagattgcc  25080
taagcttcat tacttcaagt cttccatttt aaaattgagt ttttctgtct ataatatttt  25140
atcaatcaaa agaaagaaaa aagcttagta ggactcactt tttatcaact aaaaatttgt  25200
tttaagttat ccatcgctat tcatttaact attattattt atttattaca gattttacct  25260
ataaatattc actggtgtgg atgttgtagt catctctaca catgtaaatt ttgatttgac  25320
aataaatcta ccttaaaact aaataaattg attgatatat ccttctattt ccaggaaaaa  25380
aaagaagcaa acataatgat aatacacttt tttattattc ttaataattt tctattattc  25440
tcttattact ttgatcatat atgtttttat ttttttattt ttgtctcagt ttatttcgtt  25500
tgaagtccaa aaatgaaaaa aaaaacattt ttagctatgt cttatttttt atttaatttt  25560
tggagatcat tccacaacat agccaataca attaattttt tttaaaaaaa tatacacaaa  25620
attagtaaaa tgattttttt tgggttcatt aattaattaa tacggtgcct tggaggattg  25680
taatatacgc cgacaacaaa tgtggctctt tagtcatttc ataaactaaa ttggcatgtt  25740
cattcaacaa atatatttct aagattaaag catcattttt aaaacatatt ccttagcttt  25800
ttaaacatat aaaacaattc ataattaaat aatatatatt ttgtacagta aaagttatac  25860
aaaaatttat ataatcatga cagagattga ataagacaga gaagtgttaa atacaacaag  25920
caacgtgatg aaaagaacta gagaaaaaaa actactaatg ttatagaaaa tggtgtaaat  25980
atttgttata taatataaat ctataatttg atataaagag taaaagagtg attaagtttt  26040
agattaaatt gcatactgat ataataaaaa tatatatttt agattaattt acaaaatatt  26100
gcttcaattt taacctattg gtactttttt tcccccaaaa ttataagttt acattattct  26160
cactcaaact ttaaacatat agtaattatt tcattttttt ttctagaagt ataactaagt  26220
```

tccatacaac tttatatgta tattctaaaa aattattaga aagaataaaa gatattcaac 26280
tgttaatgat gaaaaaattg tgaattatta aacatttaaa atccaaacag ataattgaaa 26340
atttaagaaa taatttatca aaattataaa attatgccaa gcttttgtca ttaaagttaa 26400
gtttatgttc tagaaaagac catttgttta tggtttagtg tgtctattga gttgacaaac 26460
aaagaagtgt gtactattga gtacaattaa ttatagaaga taattcgttg ataagtttct 26520
ttccgttgcc gttacttatg tcattctcca gttctttctt tattccttaa ccatttcccc 26580
ccctcttctt cactctattc tttccatagt taaaaacttt taatttcaaa ctagggagaa 26640
taattttaat aaaattaatt ttaaattagt aatgtcatta caataaataa ataatatata 26700
taaactaatt ttaagttaaa aagtgtgtta ataaaagatt ttaaattgtg atcacaattt 26760
cttaatccct gattacaatt ttcttatttt ttgagtatta aaataattat tttaaaataa 26820
tttgaattat attttgtgat tgaaagtgta taaaaattat tattttaatt ttaataataa 26880
tttttcatat tttaataaaa gatgtacatt ttaacataag cttatgtcaa caattaattt 26940
cagtccattt cttttgcaat aataatcacg ttagaagaga atagacccgc gaatctgaat 27000
cagaaaaaat ataggaataa atagacttgc caactaaacc gagtgaaggg gcaataaggt 27060
cattcgaggt gtcctcctta ttatttgtcg gtgccgtagc gtggttcttt gcctcaaagc 27120
cagtctgttc ttacttaaac atcgaacact tcgtgtccca cctagacctt acccaccgtc 27180
gattccccta aacgtgttcg acatttaatc acacacacta agcacacata acaccatcgg 27240
agaaggacct tccatcaacc cataactagt cgtagtatta tttcattgat tctctccctt 27300
ctctttctct ctgcgacaac agatgatgga gacgacggcg aagcgaaacg ctgtcgttgc 27360
gccaatcgcg gcgttgttgt tggtggtgct actcgcggcg agtgtggtgg tggaggctca 27420
ggagaactcg gacgtgaaga cgctggtgaa gcacatgcac gggaagaagt actgcgacaa 27480
aggatgggaa tgtaagggct ggtcaattta ctgttgtaac ctcactatta ctgattattt 27540
ccagacctac cagttcgaga atctcttctc caagcggaac tcgccggtgg cgcacgccgt 27600
cggattttgg gactaccact cgttcatcgc cgctgccgcg cttttcgagc cgcaagggtt 27660
cggcaccacc gggaacaaga cgatgcagat gatggagatt gcggcgttcc tcggacacgt 27720
cggcagcaag acctcttgtg agtactactc tcgtatcgat aatttgttga tttagttttg 27780
tcaacttcgt tgagattgcg cgcgcgtgtg agagagagtt tgtttaggtt gagctagcgg 27840
tttttgaggt tgtgagatct gtgtgtgttg tagtgtttga gacttcgaat gatttggatt 27900
ttgttgttgt gttgcataat ttgatttctg tgctgtaaac cttgttttgt ttggaactgg 27960
agtcggtgca gtcgattttt catgcattta catagtcatt gaatgatttg gatttgttat 28020
tgtgttgtct gatttgattg ctattttgta agccttgatt tgtttggaac tgtattctgt 28080
gcattcaatt tttttcatgc attcaggcag ttgttgcatt tgtaactgac tattggatga 28140
agattggacg actcggattt tgaatgtgta ttttatggtc tggtttatca aaataaagca 28200
tgagtcatcc gatcttcatt caacggatct gagtagatga atgtgtgaat gcgtggaaaa 28260
ttgtcttaga tgtctttatt tgtgatttac atggtgtctg atgtgtttaa gcacattttg 28320
tgaggtagaa tgttgttttg tgagagttga tttatcggag acatgtgaat aggatttatt 28380
gtttgtgttg tgggagttgc gtgtggtgca gcggttgatt tagttttgct ttaaatttgg 28440
acaactgtgt ggtgttattg ttcttataat gctggtgtca ggtggttatg gagtggctac 28500
cggaggacct ttggcctggg gtctttgtta caaccatgaa atgagtccta tgcagtcata 28560
ctgtgatgac tacttcaaac tcacataccc ctgtacacct ggtgctgagt actatggtcg 28620

```
tggagctatt cccattttct ggtatgtgta tgtttgtttg gctgtatgta taatagaagc  28680
atattttcct ggttttggaa ttgcctgttt attgtcattg tttgaataaa ttgcgctgta  28740
atacatagag atgcctaaag gtagctagtc ttagaaagtt tctttatcat tcctgaaaat  28800
tgccattctt ctcaaatttt tcttgtattg tttaacttaa gtattctgca atatccctga  28860
ccagtctgta ccaaatcaat tagacttgtt gaaaggttaa ccaaacatcc caaggttatt  28920
tgttcttaat ttatagcttc ccctattgtc tgaaaaaatg agttaataga tagcagttag  28980
gtactagtgc tctcaacaat taattcatcc gaagcacctc aatggctatg atcataaaca  29040
ctttagcaaa gaagtatatg gcctgagcag tctatgaaat gtaaatgaca catttcatag  29100
aaagataact attatatggt taaaaccttt aaaatatcat ttagcttccc attgtgcgat  29160
tataggtcct tcaaatcaca ataaagaaaa tataagagtt aagtgggcat tgcaaagttt  29220
tgaaagatta tagtaatgaa aaagaaactg ttgcaacaag agataaagta ggataagggt  29280
gggggaaata gaacaaaagc agtaattgat tagttactgc agagatacag agctggattt  29340
ctgggtttgt gtaaatgatt tatgaaatta tcagtgatac caatgaaaat taaaaataat  29400
gtatgcatgt gcagattttc agttaagacc agtcaagtct taaacctgtt cccttacttt  29460
ctattgttct gatatactag tttctgtttg gtctgaatgg taggatattt gaccatatca  29520
gtatattggc agtgtgatca acttaagtag catctcagac tgtcaactga cattttgtca  29580
aagaagaaat tgtttgaaga tttaaactag tattttatgc atatttttag gcaagtctag  29640
ttatatttca ttggagccat tttttacttg aaacgtatag ataggctgta agaaaactat  29700
ttattaggtt ttatcaacat cattgtgctt gttgaatgtg gaggttatac ttaatggtat  29760
catcaatata ggaactacaa ctatggtgct gttggagaag ctttgaagat cgacctactc  29820
agccatccag aatacataga gcagaatgcc acccttgctt tccaggctgc tatttggaga  29880
tggatgacac caatgaaaaa gtcacagccc tctgcgcatg atgcctttgt cggcaactgg  29940
aagcctacca agaatgatac tatggagaat cgtcttcctg gatttggcac tacaatgaac  30000
attctctatg gggatggtgt ttgtggacaa ggtgatgtgg actcgatgaa caatatcgtt  30060
tcccattacc agtattatct tgaccttcta ggtgttggtc gagaacaggc tgggccccat  30120
gaaatcctta catgcgctga gcaggttcct ttcaacccat cttccaaacc tgcttcttca  30180
tcttaagatt atatttatta gcatatgata ttgttgtacc aatccctttg aaagtgaaag  30240
ttaataaggg ttcttgaaat tattggtatg caataatttt gaactgcgtg gtagtgtggg  30300
aattcattat atagcttttg ttcgttgtta tctagaagtt ttagtcattt gtaatatcat  30360
atgtcgtgaa aaatttgtat ctggtatata tgtacgttat gggcgatttt gttattttta  30420
tatatacatt ccttggttgc aatgtaaatt tgaatatggt catgtcaaac aaaatccatt  30480
tcgagtcatc taggtcttca ttagtggcta acaatataag ttatttatgc cacgtattta  30540
aaatttcaat taaatagcat tattgtacat ctgccacgca gagaaaatag aggaaaatga  30600
tttgcgtgtt aatttttaag atgacagggt tatgttctaa ttttgcattt gacataaagt  30660
ctgctttatg ttttaacaag agtaataaat gtcttttttt agaattatcc tcctttcggg  30720
gtgattgcct catgttaata tcaaatctac cagaagcaac acgagatagt agtattttga  30780
tgatttttgt gaagcctata atgaaagcat aaggtatgaa aatattttca ggggaaatgt  30840
gttccattct aattcaaata agggcatctt gtaggtttca atacaaaaat ttgcaaagta  30900
atccctataa atcgtctgta aaataagtaa tgtaaatctg caacctaata aaattatctt  30960
```

cttggccgaa atatgatcag ttgccacatt tgtccataaa tctgaatcta ataatatgaa 31020
aagttgagat aaaaatttat tgtcgtttat agaaataaat aaatggaccg gtctttactc 31080
atacagcaga ataaataaag ggacttatat ccttcacctc tctaaagact aaagtggctt 31140
ttcttatttt ggaataccta tttcgggtag gttatagagt cctcttttat tttagaatat 31200
aatcatactc taagatagtt attttaaaag agtcttattc tgaaatgata ctctagaata 31260
taattttttg cattccagaa tagctatttc aatatatgta agttttcgta ttgtgtggaa 31320
acatatctta ttctaaaata atagttttgg agtactcctt tggcaatggt gttttcaaag 31380
atgaactcct gcgcaaacat aagcttctcc agggacaaat ccatggtggt ggaactccca 31440
acagaggcct tcatggaggt gtggcggcaa ttgtcaacgg tgttccgatc atatggcaaa 31500
catactgtcg tgagcgacaa atcagagtgg cgttccactg tgggccaatg tggcttgcac 31560
gactataggc ccaaaggctg tatctgttca taattaatcg atcgagcgca attttacttg 31620
gattacagtg atgttttctc gtttttatga ttcacaacat ccctgtatat atatatatat 31680
atatatatat atatatatat ataatatata tatatatata tttacaatgt attagttaac 31740
ttattgaatt caaatgttaa tttaaataca caatgataaa aaaaaggata acgtagtttg 31800
atcaagtcta atatttggaa agtacaaggc taagaaaaca agtacatcta aaataagctt 31860
ttagaagaaa aaaattaaga cggtaacgaa taatcttata actcatttaa ccttctccat 31920
gaaagcgttc gtgcacaaga aaataatcgt attagataat gttttctgaa aatgtaaaaa 31980
ggatttctct agttatttat ttttattata gattagatat ctaaatttag tagttatggg 32040
cacaaatgat tatggttgac atatttttcg agtgtcctcc ggcgtggatt cggattgcta 32100
ttttaacgga ttttttaagt tttcttttac tgtggtttct agtttgagct taactctctt 32160
ttagcaccaa aaataaaaat gatattaaac ttattttagt tttattgata tgtattgatg 32220
atttaatggt atagttatca tgttttgtta aaaaaaaaga atcattttta cgatgttgac 32280
atttttttca cagatagata ctgtcatttt agatagtttt gtattttaat acacttgtct 32340
acattattta gttgctcata agtttacaat cattaagtaa aataaataat attaattaag 32400
tattttaatt agaaatattt aatcaataat gttgcattgc tgcttaaatt tactataaag 32460
agtgtgtgtg tgagttatgt gatgaagtag tgtttctaca tttcttgttg cacaaatgtt 32520
acctaaacaa tttcatgtta actttagaga atgaaaggtt aggcatgcaa ttttactctt 32580
atgactaatt agtattttag actgtgcaat gacaagataa ttgtctaatt tatataacta 32640
aaatttgtaa tatattaata tattttaata aataaattat attataatta aatttaaaat 32700
aaataatatt tttaacttat aaaatatatt ttagacttat gataaacaaa ttatatagtg 32760
ataacag 32767

<210> SEQ ID NO 12
<211> LENGTH: 32767
<212> TYPE: DNA
<213> ORGANISM: Artificial Sequence
<220> FEATURE:
<223> OTHER INFORMATION: Artificially Synthesized

<400> SEQUENCE: 12
ttattaggtt ttatcaacat cattgtgctt gttgaatgtg gaggttatac ttaatggtat 60
catcaatata ggaactacaa ctatggtgct gttggagaag ctttgaagat cgacctactc 120
agccatccag aatacataga gcagaatgcc acccttgctt tccaggctgc tatttggaga 180
tggatgacac caatgaaaaa gtcacagccc tctgcgcatg atgcctttgt cggcaactgg 240

```
aagcctacca agaatgatac tatggagaat cgtcttcctg gatttggcac tacaatgaac    300
attctctatg gggatggtgt ttgtggacaa ggtgatgtgg actcgatgaa caatatcgtt    360
tcccattacc agtattatct tgaccttcta ggtgttggtc gagaacaggc tgggccccat    420
gaaatcctta catgcgctga gcaggttcct ttcaacccat cttccaaacc tgcttcttca    480
tcttaagatt atatttatta gcatatgata ttgttgtacc aatccctttg aaagtgaaag    540
ttaataaggg ttcttgaaat tattggtatg caataatttt gaactgcgtg gtagtgtggg    600
aattcattat atagcttttg ttcgttgtta tctagaagtt ttagtcattt gtaatatcat    660
atgtcgtgaa aaatttgtat ctggtatata tgtacgttat gggcgatttt gttattttta    720
tatatacatt ccttggttgc aatgtaaatt tgaatatggt catgtcaaac aaaatccatt    780
tcgagtcatc taggtcttca ttagtggcta acaatataag ttatttatgc cacgtattta    840
aaatttcaat taaatagcat tattgtacat ctgccacgca gagaaaatag aggaaaatga    900
tttgcgtgtt aatttttaag atgacagggt tatgttctaa ttttgcattt gacataaagt    960
ctgctttatg ttttaacaag agtaataaat gtcttttttt agaattatcc tcctttcggg   1020
gtgattgcct catgttaata tcaaatctac cagaagcaac acgagatagt agtattttga   1080
tgatttttgt gaagcctata atgaaagcat aaggtatgaa aatattttca ggggaaatgt   1140
gttccattct aattcaaata agggcatctt gtaggtttca atacaaaaat ttgcaaagta   1200
atccctataa atcgtctgta aaataagtaa tgtaaatctg caacctaata aaattatctt   1260
cttggccgaa atatgatcag ttgccacatt tgtccataaa tctgaatcta ataatatgaa   1320
aagttgagat aaaaatttat tgtcgtttat agaaataaat aaatggaccg gtctttactc   1380
atacagcaga ataaataaag ggacttatat ccttcacctc tctaaagact aaagtggctt   1440
ttcttatttt ggaataccta tttcgggtag gttatagagt cctcttttat tttagaatat   1500
aatcatactc taagatagtt attttaaaag agtcttattc tgaaatgata ctctagaata   1560
taattttttg cattccagaa tagctatttc aatatatgta agttttcgta ttgtgtggaa   1620
acatatctta ttctaaaata atagttttgg agtactcctt tggcaatggt gttttcaaag   1680
atgaactcct gcgcaaacat aagcttctcc agggacaaat ccatggtggt ggaactccca   1740
acagaggcct tcatggaggt gtggcggcaa ttgtcaacgg tgttccgatc atatggcaaa   1800
catactgtcg tgagcgacaa atcagagtgg cgttccactg tgggccaatg tggcttgcac   1860
gactataggc ccaaaggctg tatctgttca taattaatcg atcgagcgca attttacttg   1920
gattacagtg atgttttctc gtttttatga ttcacaacat ccctgtatat atatatatat   1980
atatatatat atatatatat ataatatata tatatatata tttacaatgt attagttaac   2040
ttattgaatt caaatgttaa tttaaataca caatgataaa aaaaaggata acgtagtttg   2100
atcaagtcta atatttggaa agtacaaggc taagaaaaca agtacatcta aaataagctt   2160
ttagaagaaa aaaattaaga cggtaacgaa taatcttata actcatttaa ccttctccat   2220
gaaagcgttc gtgcacaaga aaataatcgt attagataat gttttctgaa aatgtaaaaa   2280
ggatttctct agttatttat ttttattata gattagatat ctaaatttag tagttatggg   2340
cacaaatgat tatggttgac atatttttcg agtgtcctcc ggcgtggatt cggattgcta   2400
ttttaacgga ttttttaagt tttcttttac tgtggtttct agtttgagct taactctctt   2460
ttagcaccaa aaataaaaat gatattaaac ttattttagt tttattgata tgtattgatg   2520
atttaatggt atagttatca tgttttgtta aaaaaaaaga atcattttta cgatgttgac   2580
```

```
atttttttca cagatagata ctgtcatttt agatagtttt gtattttaat acacttgtct   2640
acattattta gttgctcata agtttacaat cattaagtaa aataaataat attaattaag   2700
tattttaatt agaaatattt aatcaataat gttgcattgc tgcttaaatt tactataaag   2760
agtgtgtgtg tgagttatgt gatgaagtag tgtttctaca tttcttgttg cacaaatgtt   2820
acctaaacaa tttcatgtta actttagaga atgaaaggtt aggcatgcaa ttttactctt   2880
atgactaatt agtattttag actgtgcaat gacaagataa ttgtctaatt tatataacta   2940
aaatttgtaa tatattaata tattttaata aataaattat attataatta aatttaaaat   3000
aaataatatt tttaacttat aaaatatatt ttagacttat gataaacaaa ttatatagtg   3060
ataacagatt tctattttga gcacatgtga ctaattattg aatcatctta aaatgcatat   3120
tctagttcaa tttaatttga atcagattga tattcgagat aactttttca attttcagtt   3180
tatgtagtta taactttgca gttcaattat cacaatgtgc ttctgattga atatgttgat   3240
gaacacactt caattatagg aaacatggaa aacacaagtc ttttctctca tttgtttctc   3300
ccatgaaatc tctgtagact ttttccaagt cccactcctt aaaaaatgtt gtcgggacaa   3360
acttgttccc cagatttaca gtcaaataaa tacgatcgag tttggacaaa caaggatgaa   3420
gaccagataa actacctcaa cctcatgcca tgcatgattt ttttcttctt aatagaaatt   3480
ttaataatca aattgatgca cagactattt tttcttcttt tttttttac cactttagtt   3540
gggatctttg atttttttta aagagattct aaaatatttt tactagtttt aatcgtttga   3600
tcagttatga gatttgttct cataaattta atatgtattg tgaattgaat tagacttgtt   3660
gcataaacag tattctttta aaataataga agttgggtga ttgaaataat cgactttgtt   3720
gactgagtca ccaacatgtt cacgttaagt tttttaatcg tgaaactgac gcgcatggaa   3780
gccaaacacg tgcatgtaca tttacgagta aaaaatggat gaatctagaa tgtcgttaat   3840
ttagacaaag aggaaatttg gtagtgtttt ctgctattac acaatctttc caaagaaaaa   3900
ccttcaacaa tctattttgt cttcatcata tatataacat gagatattga ttatccttat   3960
ttttaatcaa ttaaatcact taattttttt taaaaagtat ttttacaatg ttgataaaat   4020
cggcctgccc aattcctcat atttgttttt tactcgatta attcattcat tactggttca   4080
agtttattta tttaagtaaa taaataaatt taaacttaaa attaaactta tttaaatgaa   4140
tggaacccaa gctttgaaaa ttcaacatta tataaagatt gatgaatagc tcgtttatgt   4200
atatataaat catgtttttt atgaaaataa ttttatctct taaaaataag ttaaatagat   4260
tattaagtat gttttctatt aatttttaac ttcacttatc acatgctaga ctcatttttc   4320
tattagtaga taattattaa aaattatatt gataaagttt aaaatttatt taagaaaatt   4380
ttcataaaaa aataattaag ctataaatga gctaaataag tcaatctaaa gttttaatat   4440
ttcataacaa accaaatcca aactttctac aaggctagat taaataaata aatcaagctt   4500
gagtcattaa tttttttcc cacaaacata gtccaagttt caagagctca actggattta   4560
cccttattta catccctagt gttaaatatt tgaaagaaga gtttatagtc tataataatc   4620
ctataaagtt tgaacaaaag gtggtctaaa taataatttt tccaatccct tataattaat   4680
taacgagtcg tttgttatga gactatttta gtgattttga taaaaaaaaa atagcttatt   4740
tactttttga cgcaacttat ttactaagaa agataactta tgacaactac accaattcca   4800
tttataattt tttttggtct gtaaatcaat caacaatgaa tgccaattag taaaatttga   4860
cgactatgac aattccattt gattctgtca accaacagtg tacatcaatt gttttaattg   4920
accattaatt atagtagatg gaaaaagact aatattttaa atgaaaaaaa atttaaaaat   4980
```

```
ggtataattt tttgaataaa gtctctgtcg tatacacttt tttttggaag aaatgtctta   5040
tacatgcatg gttaataatt gagtcccaat taacgtattt aagagactct ctattttaag   5100
gtaaagagat cataattatc ataacttttt ttaatgttat ttttacacaa actaattaat   5160
atatttaagg gactagtatt attttggact aaatttatta tgatttaaaa gtaactttaa   5220
atctaaaact taacataaaa tcttaaaaaa ataaaataaa agttatttgt ttttttaact   5280
aaaaaatatt tttataacta aaaaaaagtt ttttttccgg tcacaccaat ttattcaata   5340
tgaaagtaga aagaaacaaa aaatataact tgtttttaaa atttattttc cttatttaaa   5400
aaataagtat ttttattttt tttgctacaa ttttaattaa cctagctttt tttaaatgaa   5460
aaaaataaaa atgtgaataa ctatttttttg gtaggcgaaa aattaggaat aagttgaatc   5520
aagcattact ttaatatttc acaaaaaaaa aactttaatc tcttcttgaa atgcaccaat   5580
ctctccctta cagtgaaaaa aatatgctta aaataaatat aacatgtctt aactcttcaa   5640
ataaatatgc ttaatgtgaa agtttttttt tccgtaaaaa aaaaaaaact cttaataaac   5700
ttttcttcgt acaggcaatt ggaaattaaa ctcaaatcaa tctacttaac ttaaaaacat   5760
gatttattgt ctttaataga tttgactgtt tttcgaacca ccgacatcta acagagaaga   5820
atagatcaag taatgataaa ccattaataa cattgaatta agtcattaaa agtaagtgtt   5880
acgtactttt gataatttac gaaatttaaa accgtatttg aaccgaaatt atgataatgg   5940
catgaagttc atccgtcata ttaggtatat ccttttacat attttttgac ataattttaa   6000
ttatttaacg attgtgtaaa attttctgac aaaaatatat ttaaattatt cagtaaaata   6060
ttttatatga gacttattta acattaaata ttaggtataa aaaaactgtc actgtggatc   6120
tattaattaa ttagtgattt taaatttgaa aattttaaat caataaatat tgataagttt   6180
ggatggattg tttattctaa aaatctatga aaatataatg tttttgtgta tacattttta   6240
catctatttt atttttataa ttgcattcat aagttattat tttatcttta taattatttt   6300
cacaaatcat tcactatatt atatttattt ttaattaaaa aatatgaaaa tgcagtgaga   6360
catgaagtgc ctattttttc cttataaaaa taaaaattat aacttgaacc gaattaatct   6420
aataagattt gagttactta ggcagagtta taaagccact taaataaaat aaattaataa   6480
ataaatttaa cattgaatta agtcattaaa agtaggtgtt acgtaaaatt ctatgacaaa   6540
aatacattta aattatttag tataatattt tatatgagac ttatttaacg ttgaaaaaaa   6600
tgtcagtgtg gatctattaa ttcattagtg attttaaatt tgaaaatttt aatttattga   6660
taagattgaa tgaattgttt attctaaaat tctataatgt gaacatgacg ttttagtgta   6720
tacatatttt tatatttatt ttatctttac aactatatta gtaagttatt attttatttt   6780
tataattatt tttacaaatt attcactagt attgtctttt attttaatta aaaaaaaagc   6840
atgaaaatac agtaagatag gagatactta ttttctcttc ataaaaacaa aaattataac   6900
ctaaactgag tcaatctaat tacatttgag gtagtttgat tggattataa agccacccat   6960
attaaataaa ttaataaaca cataaaaaat agaaaaataa atattgatgt aaaattataa   7020
taaaagaaaa ttttctgaaa aaaagttgaa atgaatataa tttattagta ctttgttttc   7080
tgattccata atcctatcca tccactcccg agaaacccaa tcatccgcac cgtccaatcc   7140
gcgcgtcatt gtttatttat gacgttgtcg ttctgatcca tactctcaat caatatttaa   7200
ttcccttatt ttttgcgtgg cggagaaaca aaatctgttt gcttcaaagc caccacctgc   7260
cggtgacgca cccgctcgtg acggtagcgc tgcccttaac gttttccgac acaagacgac   7320
```

```
gaacgcctcg ttcaattctt cttcaaccga catttttgtt tgattcgaag attcgcttct   7380
cagttttcgc gggcgattct caaggaaccc aaggagatag cgctggatcg agaatctcga   7440
ttcggttatt tgcgatttca cgctttgatt tttgcgctat tcagcatacg cgtttttca    7500
gttccgattc tcgcgctttc cgacaagttt actgtgctga tacacggctg gaatttccga   7560
tttcattgca atcatgactc aggttccatt tttaattgct tttttctttt atgcgtttga   7620
ttgtgttagt ttctgaatct gaatgtctag ggccatggtt tgtggtttct gaaatgatta   7680
taattttttt tttttatcaa atgttaattg ttttgttagc aataggaatc gaacctgcca   7740
ccttttccac ctttccttct ttcttaacca cccaaccaaa cttatatctt catgaaatga   7800
ttataatgat ggtgtttgat catgattatg atgatgacga tgaatatgaa tatgattatg   7860
atgatgacga tgaatatgaa tatgaacatg attacgatga tgacgatgat tgtgattatg   7920
atgatgtttg attattgttg taatgatgat gatgattgtg gcaggcggtg gaggtgctga   7980
atcggtatgg gacggatctg gtgggggagc cgagaggttc tgattctgag tgtttggcgg   8040
gttttgagtg ttttctgaac attgtgaggg cattgggaat gggatcgtgc atctcggagg   8100
ttggagctgg tggaagttcc cctcctcttc ttcctttttc gcctgaatca aacatggatg   8160
gtgggaagag gaggaggtta aggggttcct cttcctttga tttcaaagtg cctgggagga   8220
tgttcttgaa tgggtcaagc gaggttgcat ccatgtattg caagcaagga agaaaaggga   8280
tcaaccaaga tgctatgctt gtttgggagg ttagcctgcc ctccccccctc tcagcatcta   8340
ttaatgttgt ttcgggatat tgtctttttc attacatttg tatgattgta tgcacattat   8400
gtggtttgca gtaatagaaa tgaaggaagt ttaaaaggaa tcaaagttga gtaggtattc   8460
tgcttttgtc ataagttttt ttattttatt ttttaaatca ttgaattggt tagttatgtc   8520
ttattgttta gcatatcttt cagcttagaa caagtttaca tgatttagtg cttaaatttt   8580
tattttttttt gtgtgtattt ggaataaata tgagctgata tgtggagcct tgaagtaatg   8640
agtatgctat tacctttgtc tgacctttac ctctgttcat ttcttttcca aatactcttc   8700
tcaatcttct taggttgtta gtagtgcctt gtcatactgc caatgcagta taaaatataa   8760
ataacatcct ccctccattc ttttctaata gatcattgtg ttctccatct cttcccactt   8820
cagcatagtt tgaatgagat acatcaattt tacaaaacaa tagtttttgt tataatgtcc   8880
tacatcggcc aagaacatgg ccaaaatact ccttataaca gttgaaaaaa tcttctttcc   8940
ttgagttaac ttttggggtt gagttaaacc taacccattg ctatagtttc tttattctct   9000
ttctcttaca atttgagtct tcagatgtgt actcacagtt ttgttgtttc agtttgcact   9060
aacgttaatg atctagatat taataatgtg tacaaaactt tgtctatttt ccttgtgcag   9120
aacttttgtt caaaggaaga caccattttt tgtggtgttt ttgatggtca tggaccttat   9180
ggccacaagg ttgcaaagaa agttagggat tcttttcctt taaagcttaa tgcccaatgg   9240
gatttgcatc ataagaatag agatggactc agtgatcata gcagcgccac aggaagttat   9300
aaatctgaag ggaatggatt tagactggtg gatgagaaaa ctagtcccac tgatcatgaa   9360
cttgatgaaa cagatactat tttgacatta cgagaatctt ttttgaaggc ttgtaagatt   9420
atggataaag aactgaagca tcatcctgat attgactgct tttgtagtgg gactacagca   9480
gttactttgg tcaagcaggt aagaaatata aattacaatg taatgttctc ttgattattt   9540
cttatttgct ttttacatgt ggtttactga tgttctttca ggggctggac cttgttattg   9600
gaaatgttgg tgactcgaga gctgtattgg gtacccgaga tcatgaggat tcccttattg   9660
ctgttcagtt gaccgttgac cttaagccaa atcttccaag tacctctctt tctctcttct   9720
```

```
cccctccatt ccccccctcca ttccccccctt gtgtgtatct tctcaatgaa cttgataagt   9780
tggagaactc catctcctta ttttatttcc cttgaaatat tgaatcaata ttgccagctt   9840
cataattatg atgtgagtga cagtgcttgt ctgatttaga taaatgaact tgataagttg   9900
aagaactcca tctctttctc ttttctgttt tgattttacc ctgtgtcttt gggagattta   9960
aataggtttc cctctgcttt atggagataa tctctatttt ttttatcaaa caatacaaat  10020
tccctgtagc tgaaacctta ctttttttctt tgtttctctg atttattata tctaacttca  10080
atgccttttt ctcttttgtt ttagggcctg tttggataag cttctttaga agcacttcca  10140
agagaagaaa ataagaagaa aataatgatg agtttcttca taagataaaa tgagttatct  10200
attagctacc cattaactaa tttgtagaag ctctctcata tagcttctct aaaagatgag  10260
aggacgtcta caaattagct aatggttagc taatggacaa ctcattttta tggaaaagct  10320
catttcattt ttttcttcat atcttctcct aaaagtgctt ccagagaagc ttacccaaac  10380
ggacccttat ccaatatatt tcattggttc cctttttagaa caacttgact tttgtgagac  10440
aaatgttttc aggattggtg aatctatatt ttcattgtat gatttaataa actctgtgac  10500
ttggaaattg gaatttattt tgatttttga tacatcagtc agtgtggcat atctatatgg  10560
gtatgaatgt gtgatgtaaa gttgttttcc cttaggggaa gaagagagga tcaagcttcg  10620
tagaggaagg gttttttccc ttcagaatga acctgatgtg gctcgagttt ggctgcctaa  10680
ctctgatttc cctggtcttg ctatggctcg ggcatttgga gatttttgcc ttaaggactt  10740
tggattgatt gctgttccag atatctcata tcaccgcctt accgagaagg atgaatttgt  10800
tgtgttagca acagatgggg taaggcctta tgaggctctt ttcttatgat atactgtctt  10860
ctatgatctg catgtgttga aattgattca tttcaatatc atatttgtag ttagccaatt  10920
ctaaaatgaa aatatgaaat tgactttaaa tagtatttga atgccacttg caacagttaa  10980
aaaaaccaaa tttggttcta atttcactgt atttaaattg acatcttact gtttaagcta  11040
actacttatc atgtaaaact tattattatg agttaactac taatgtaaat gatgaacaca  11100
aacctaatat caaaagctgt atcaatatat atttttttgat ccagttgtat ctcaaaccca  11160
tgttcatata cacagataca catgttattt ctattctctt tcaaactgga atttgtaaat  11220
tgttgagctt ttggaaaagc ttgttcttta catcaatata gcgatttacc cttttctttc  11280
gcctctcctt tgaagttgta actctaattt ttctcttatg gtccatatta tgttgtaact  11340
tgaaaattta tattctctga attgtcttat atatatatat atataatata tatacaaata  11400
catacttgat tagatggaat attgaattat tttaaactgt tggattcttg gggggcagatt  11460
tgggatgttc tgtcaaatga agaagttgtg gacattgtgg catctgctcc acagtctact  11520
gctgctagag cactggttga gtcagctgtt cgggcatgga agacaaaatt tcctttttgt  11580
aaggttgatg attgtgccgc agtttgcctc ttctttgatt ctgattcaga tttcaagtca  11640
acagatacaa aagacaagtt aataccggag gcatctattg accaatctga gcagttagct  11700
ttacttggtg aaaagggagt tggaaatgaa gctgaaaaaa agcagcaata gcgcaagttt  11760
tgtaccatgt ctctcccaag ccttgttggt tttatcgaaa aggttgggta aattgtgccg  11820
caacagtcaa aagagaaagg aggatcatta ttttgatgat ttttcggtag ttttctgcca  11880
atattctttt cattatttat ctttcatttc cttcgacagc atttgaggga agagggggtt  11940
atatatatat atatatatat atatatatat atttcttatc tggaggaaaa ggggtaccgg  12000
gcttttttttt ttgttgctgg aggtcatttt ccttctctgt atatttggta gatttggagt  12060
```

```
ttttgtaaat ccaactctct agattcatat tatatagtct gttctgaagt ctgccgtttt  12120
tcatttgcat cattcttagg ttatagtttc caatttagtc tgtgaaaaca tgagaactgg  12180
aaagaattgg atttatttct tatggacttt cgagtcaggt tttgtacct ctgtgttgtg  12240
ttgccgtcag ggattaatga tattgtctgt gtgatcctat tatgggtttt gtgtggaaaa  12300
tttactctga cggaaatttg tctttaagct atacgagtaa aactgtattt accttttgat  12360
ttaaatttta ttatttcatg attttaactt aattttgaga aggataaatt atttttaaaa  12420
aaggcttttt tgttaaggga aggtgtccta agtactaacc cacgaaggaa tgagggaagt  12480
gaggatggta acatgtcaaa taaatttgga atttagttcc cgaaattttt gagtgttaat  12540
tattgtagga atttactcat ttcatgataa aacttgacat ggagtaccgg acttaaaaaa  12600
gaaaaacatg acatgaagtg gatttggagt caagttttct ctcaaggcaa actggattta  12660
ttctccgtac tcacttatta aacaaggtta aaacaattag gtttgattga cattttggcc  12720
ttcagggttg tctttataat tttttcatat acgaaaaaag ttataagttt taatttctgt  12780
acacacatat aagttaagtt ttgatctccg tgatcaacgc agctagtatg tatgtggcac  12840
ctattcattt gctttactga gccttctcaa gtgtttgttg tccacgcctg aatataatga  12900
tttattcaag aaaacaacgg attgaggaag aactgaagaa ggtagcagaa tggttgaagg  12960
ggaaaaatta cctggtgatg cttgatgaca tatgggatga ggttaaaggt gcatttccag  13020
atgaccaaaa tggtagcaga atactaataa caaggaggtg gcatactatg tacaagaaca  13080
attttcaata ggatcatctt agaccttaag agcattgacg taaagataga tgacgaagat  13140
caagccatca ttctgttgag ctttcgtcct aagccatttg atcattttgc tgatacaatg  13200
ttgtatagaa aggctactct atcaatggat gaggtcaagg ctgctttgaa ctcaaaagaa  13260
aatcaagggg agaatgactc tggcagtaaa agactctttt ctactttctt gtgctgatgt  13320
cagttttttg tctccttttt tctttcatgg tcattattgt gctgatgttt taacatcatt  13380
tacatgttta ttgtaaaagg ctctttgctc tggcagagtt tgatgagatg atttgcaatt  13440
cctctgcttc tttctattca cttttctgct ttcttgtgtt ccacaaccac ttgaccagat  13500
ttttcagtta gcttagcatt taagcctgag aaattatgca tcatttcatt tgtttgttgt  13560
acaaccatat ttaatgttaa cctctctccc ttgtttttcc attctaaaca tggatcatgt  13620
ttttgtttat tggtctaaag tgttgtttca tgttattttt ctttctcttt tcccaatgga  13680
aggtcctttc atgatttagt tagaatagat aactgataac acaattagtt ggaaaggaag  13740
atgttagagt gtatgttgat aatgggagac aaatcatagt gatcagtttt agaattggag  13800
tgaaagcata cagacattgc ttttgtgcct tgtctctgct actctaccca aacctttgct  13860
ggttttatca tggatataat tcattatttt atgatctttt tggtagattt tctaccaaaa  13920
ttcatttctt cttttcggtg atgctatata gtacgaatta gttttgcacc aagaagtacg  13980
aatccacttg gcaaaatatg atcgtacaaa tattaatttg aaagaataaa atctagacat  14040
gcaagttcta actaccctct ttcaaactgg aatttgtgga attgttggaa ttttggaaaa  14100
gcttgttctt tacatcaatg tatatattct cccaaattgt cttacaacac aaaaaaactt  14160
gagtattttc ttacatatta tctgcctaca tttttgcgct taactggatt atggaaaaat  14220
aatttgctaa tgagatatac taggacagat ggatgaaaat tacaccaact tttaacaaag  14280
gtttaaatac agtttttttt tatttataat ttatcatatt tttgccttta gtctttatat  14340
tttttttgt ttttaagctt tgtaaattat atttatttta tttttaattt ttaaagcacc  14400
ttaaataata ttttgacaag tgaaaaaaag tgttatctaa aatgttagaa cgaaaaataa  14460
```

```
aaaaatataa tttataagga ctaaactttt tttacaaaaa aaataaaaaa aatactaaag  14520
aataaaaaaa tatttaagac aataacaatt tgctgaatac aacagaaaag ttagttagaa  14580
cacaataaca atttttaaag attattgtta aagactctgc attttaaaat tctaactaat  14640
ttttgtttct aaaccatgga agacttttat ttcataaaca caataacaat taaacaaaac  14700
tcacaattta aaaaaaaatc agagtcatca aatatattaa tatttaaaga cagaaaaaaa  14760
aataaacaaa taaagttgag aaagccaacc tataattaaa aaggttgaca gaaacgcggg  14820
tccacgcgta tgcgcgttct ttccctttat tggcgtccac ttgttatctt tcgttctcta  14880
ctctgtaaat tatctgtcca caaactctct agagtttcca cccaagattt cctgtttcac  14940
agaaatggca gatagtgttg ttgcttttct gctagataac ttgtctcggc tgcttgaaga  15000
tgagcacaag ttgctttctg gcgtggagga caaagtcaac tctctttgca atgagctcaa  15060
gtttatacac atcttcctca agaattccga gggcaagcgc agtcatgaca cagtgaaaga  15120
agtggtgagc caaatcagag atgtcgccca caaagctgaa gatgtggttg acacctacgt  15180
taccaacatc accaggcata aacagagaag caaactgagc aagttattcc acctcaaaga  15240
acaagtcatg gtgcttcacc aagtcaactc tgacatagag aagatcagga gtcagatcga  15300
tgacatctat aagaacaggg acagatatgg cattggagaa ggtgaattcc gaagcgaaga  15360
agctgctgca gaagcagaat cactcctcaa aagaaggagg gaggtggagg aagaagatgt  15420
ggtgggctta gtgcatgact caagccatgt aattcaggaa ctcatggaga gtgagtcacg  15480
tcttaaagtt gtttccataa ttggaatggg agggttgggt aagaccactc ttgcccgtaa  15540
gatccataac aacaatcaag tgcagctgcg gtttccttgc cttgcatggg tttctgtgtc  15600
caatgattac agacccaagg aatgtcttct cagccttctc aaatgctcaa tgtcatccac  15660
atctgaattt gaaaaattaa gtgaggaaga actgaagaag aaggtagcgg aatggttgaa  15720
agagaagagg tatctggtag tgcttgatga catctgggaa acccaagtat gggatgaggt  15780
taaaggagcc tttccagatg accaaacagg tagtagaatt ctcataacaa gtcgcaacaa  15840
agacgtggca cactatgctg gaactgcgtc tccctacgac cttcccatcc tcaatgaaga  15900
tgaaagctgg gaactcttca caaagaagat tttcgaggt gaagaatgcc cttctgattt  15960
agagcctctg ggtagatcca ttgtgaaaac ttgtgggggt ttaccacttg ccattgtggt  16020
tttagcagga ctcgttgcca agaaggagaa gtcacaaaga gagtggtcaa gaatcaagga  16080
tgtgagttgg catcttacag aggataagac tggagtgatg gatatactga agcttagcta  16140
caacaacttg cctggaagat taaagccttg ctttctgtat tttggaatct atccagaaga  16200
ctatgagatc agtccaagac aattgatcca atattggatc gcagaagggt tcatacaacc  16260
acaaaaaact ggaattgcag atacaacaga actggaagat gtagctgact tttacttgga  16320
tgagctggtg gatcgcagct tggtgcaagt ggcagaaaga aggagtgatg gggtgtcaa  16380
gacatgtcgg attcatgatc ttctacgtga tctttgcttg tcagaaagca agtctgataa  16440
gtttctggag gtttgcacaa actccaacat tgataccgtc agtaatacca atccccgtag  16500
aatgtccatc cacttgaaag gagactcggg tgtctctgca aacacattta acaaatcatg  16560
cactcgttct atgttcatct ttggtagtga tgatagaatg gacctagttc ctgttttgaa  16620
aaacttcgag ttggcccgtg tgcttgattg tgattcgttt attgggtttt cgtcttatcc  16680
agtccccaga gatttgaaga ggatgatcca tctaagatac ttgagaatat gcgtcaagca  16740
ccttccagat tgtgtatgca gcctttggaa tctagaaaca ctggatgtaa catatgaaac  16800
```

cacagtatcc agtaaaattt ggacgttgaa gcggctgaga catctttatt tgagtggggg 16860
agggaagtta ccagtcgtcc tgccaaaagc aaatagaatg gagaatctcc aaacccttt 16920 gttagatggt agctatggta tagacacgta tccacaacaa gtgatttccc tgttgaaaat 16980
tgacatattt cctaggttgc gaaaattagc tttgcgctat cctgatggac cagatatgtt 17040
atcaagtcta caccacctca gcaatcttcg tagcctaaaa gtaattcgcg gttttgaact 17100
tccatcagac accaatgcgt ttccatcaaa tcttaccaag ataaccttag cagcagtccg 17160
ggatttacat ttcatgaaga cactggggca acttaccaac cttcaaatct tgaaactaag 17220
attcggcaaa gttggttttc atcttgatat tggcagggga gagttcccgc aacttcaagt 17280
gcttcatatg acgcaaataa atgtaagaca atggagatta gagaaagatg caatgcctcg 17340
acttcgccat ctggtcatta atgactgtga agaattgtca gagcttccag aagaactttg 17400
gtcaatgact gccttaagag tggtgcatgt ttcacggccc tccgaagaat tggctaacag 17460
tctcaaaaat gtggagccca ggaatggctg taagctcaaa atctctaatg aactgtgaaa 17520
ggcaagtggg accgccttct tacattgcag acataagttg tagtctttca atatccttca 17580
taatatttgt tttttaatcc cgaccccatt tccattttct ttgtccaaat aaatttccaa 17640
tttaaaatag cggatattca aattgagaat ggatgttgct tccttgccgt gtatggagtt 17700
gtgtctcatg attattgatt acatatttat aatacctaga gtttcttttc tatttgtgaa 17760
taatatatta aattaagggg gtgtcatgta aaagagaagt tttttttcc ctaaaaatta 17820 tatattaaaa aatttatttt ctcatatttg atatacattt ttaaaaataa atactaatgt 17880
aaaatgatat tttttgaaaa tatttttaat caatttctca tgaaaacttg aatatttatg 17940
tatatgtata tatatagttt aactatattt aatcttgaat tactaatcat tcctcacagt 18000
tattatacac tacaaaagta atcctacgat taattaactt tatcatagta atcatagcca 18060
ttgaaaatta accatattcc tttacatcca atcaaaagaa ggagaaaaaa aaacaaattc 18120
ttttagcacg tttaaatgtt aaagctaatt attcaaatga ctaagaagaa aaattataag 18180
ctccaaagta aaacattgat tatcaaatta tcctatctaa aactctaaag aagttatgtt 18240
aatgttaaat gaaatattca ttcggcccaa ttgttaaaaa aaatcatagc tgtacaaatt 18300
agagaaataa gatgaaaagg gagagaaata tgaaataaaa tagttaatgc aatacaaaga 18360
gataaagaaa aaaaaatgaa ttgtaaaaaa tgtaataagt atttgttgta acaatattat 18420
aactcttgct aaaaataggt caaacaaatg gagtcaacca gcacagaaat gctctacaat 18480
aactaatgtt aaatatttgc aactataact tcaattccgt gcgtgacttg tatatgttaa 18540
ttatacattt ggcattgaga tccaagctaa gtcaaaaatc aaagtctaat aacatataca 18600
attggtggta agattttgca atttacatat tcaccatggg aattgagaag aaaaatttga 18660
cccaaagcga aggttcccaa tggtcagtgt cctagttttc cttgaagatt acatttataa 18720
atcatggaag ttcctgaaaa gtcaatttct cacatagcat ttttttcatg ttctttctat 18780
tttcaaatcc tttgaccata attttgactt tgatatatgt atttgttgct tcatttcaat 18840
atacccattt atgaagtaga gcaagtagag acaaaatcat cacccagttg atgtttaaac 18900
cacaagcaaa agaaatgtag tggaaaccaa ctaaatggac tgttcccgtt cgctcatccc 18960
tcactttaat gcttgaagaa cctgtgagat acagcataga aaatattact aatgagccat 19020
tatgcaaaat taaaggaaat aatgcaagtc atttgaattt gatttcttat aattttttg 19080 acaattctac ccaaaccttt atataacacg tcaatcctat attatcttta attcatcaat 19140
taaacataag taagaaatct gatgtgaaac aaaaagtaag tggataaaaa gaaataagga 19200

```
cgacactttt acatcaaaca cctccaggat cagcatgcag atactttaaa gttttaaaat  19260
ggatcgttaa actacacaga actattcctt tctcagaatt aagaactaag ggtcaactcc  19320
gtttgagaaa aatgttttat tatttttcat tttcaatttt cacaaaaatg ggagagttga  19380
gacaaatgtg aaaaaaatac taaatttaca tgttctatta tagatgtttt cacaaaaatc  19440
tacaaatgtt ttatattatt catttatatt atttaaaata cagaagatta taaagaacta  19500
ataatgatac ttacagttgt actcagtcca tccaataacc tgattttcaa ggtcatagat  19560
gtattacatg ttctattata gatgttttca caaaaatcta caaatgtttt atatcattca  19620
tttatattat ttaaaataca gaagattata aagaactaat aatgatactt acagttgtac  19680
tcagtccatc caataacctg attttcaagg tcatagaaga caagtttatt tgtaagcact  19740
aaatctgcaa caaataaaaa tacaggtgag gctgcatagt aaggtcatgg aaagcaagct  19800
ttctagtgat ccaaagttgt gataactcca ttataattta catctagaaa aaatataagg  19860
aaatttcttc caccagtaaa aataatacat ttattataat atttagcttg taagtttctt  19920
ccaaaacaag catggggcca cttctctcca taaaaaatct caagaccaat aatatgctac  19980
aaaactttca ccagcaaatt gcaaaaggtt gtcagaacct acattcacac ctttaagccc  20040
cctatcaatt aatcatcata tctttgacca gattaaataa aaagtaaaaa agaaaaaaca  20100
gaaaaaggcc cttctcagct aaatcctcgt cttttgcttt agaaggaaga tttaggatgt  20160
agtaatcgaa agcaaacttc tactacctct tgatttagga acttgtatca aaaaatacag  20220
aacacagccc aatttctttc aaatctccag ttaagatact cacaagatcc tatacaaatg  20280
tattccagga tatgcattta taatgtattt gtcttgttta tttaagaact cagaagtaat  20340
caggttcaaa aatatctttt atctcaaaat gccattaaaa aagtaaccct ttctttcctc  20400
ttataatggc tacggcagtc tcattctaaa tctggaagca gtattcagca aattggtggc  20460
aaatatatct atcggtacag aaaaggattt gaagagaata cctcccaata aggtcatatt  20520
tttgctatct cttgattgtg tcccactatt ttgccaacca atacaccaga aatctccctg  20580
cagatgcaca ttagtatttt atttatagta tggtatataa agattatgat catagaaatc  20640
attgacataa aaaagaccag ctcagtagta gtgcacatta ataaatgagt cttttgaaaa  20700
atcattttaa aactattgcg agtatctaaa attacaaaaa gaataacagt tttataaggtt  20760
gaaaatacga aaagataata tttggtgcat ttgcaaattg caactccaga atccattctg  20820
gaactcaaaa ctaatttgaa gcagatggga tacaaaaggt ttttaaaatg cattgtgggc  20880
actttgggca gaagcaactt tttattactt tagcccagaa tacagttagg ccaagatgca  20940
gttggtctaa tatatataga gagagaggag ggatcaagtt actttaagag gaactctttt  21000
aaagttactc tccatcctca cactgttcat tctcttgaaa cctaatagtt gtaatgagta  21060
attaatctta atcattagat tttaaggaaa tgaatggtga agatgaggag taactctctt  21120
agagttactc ttgaaactct tgaagtaact tgattcctct tcatatatat atatatgaca  21180
tagaaggccg acaacaggtc ccaaaacaag ccaaataaaa ctcggctaat cataacaaaa  21240
cacacaaaga tataatgaga tttgcaatat acttacagac ggaaataaat aatcttgtgg  21300
ataaaccttc aacgagagcc cattttcaaa ataaaatgtg acagctggaa atccatcatc  21360
aacactgcaa cataaaataa aataaccatt acacccctac atgaagctga taatacagac  21420
ataaatgcat aggatatgca aagggagcag tccagttatc aaagcactcc aacaatacat  21480
actcaataag aaagttcata gaacaaaacc tacaaaatat tataacttaa tttcaaaaag  21540
```

agtttttccg attatcaaat taagatttca aatggcaaat attttttgtc cacttatcaa 21600
acccatagtc aaaatggcaa gatttcctag acaattcctt taacatataa tgtagattac 21660
aatttacatg caaatgtcgt tattactatt atcaagaaaa gaatttatta agacagaaaa 21720
aaaagatata gagacaggat aagaaatcct catggattac agatgacacc actaaaataa 21780
aaggaaaaaa gaaacaaaaa tcaagacatt tgcaacacgg caaaccaaca aagagcataa 21840
aaccataaac cagccactac agattaagta acaacattaa catgatcaaa taaaaatcat 21900
aaaacaatat gtgaaccgat actgtaaaac aagcaacaga attaaaagga aaaaatttca 21960
aagcatacat tcattactgc atactacagt gaaaatagaa aaaatatata acaggaagat 22020
aagacatcta ccaaaataaa aaacaaagtg agagagtgaa tagtcctatc ctggaaaact 22080
tgctatgcca tgaaaaagtt acttgaagat ccaggaatat aacctcaaac accaaccact 22140
acagatgtca ttgctcatga cagcaagctt aaacaatgcc aacatggcat tcaattgcca 22200
tattgaagga tggtgactaa tttaaacaaa taataacaac aaaacaatga aatcagtgag 22260
tgaagaactg agttgatact agaggagctg gtctggtaaa cttaatggta atttcaccct 22320
gttcaaaaaa gatttctcac catacaattt tcaaaggaga tcaaagtaaa acagaatttg 22380
ccaaaagtca aaaccacttc tgatgtgttt ttgtgcagtc ttctggtttc ctttaccaca 22440
cattgctgaa ggacaattct acctagaaca gaggagacaa acactcacca ccttgccatt 22500
tttaatgtga catatgccat gcatcatgga caacacagct atgggagtgc aactgtgcca 22560
tgttcaatag catgcaaaag aagttttaga gaaagtgacc ctcaacacac ccagtatgga 22620
agcacatact tttaacaaca ttgtcaaccc tgaaccacca ttatcaaaac cacacacttt 22680
aggtccttcc ttccaaaaca aactggacta caaagaattc ttctaaaacc tgtatgccga 22740
agtaagctag caaaacactt gcgcttgttc caaccaacag caagacacta tatgcataca 22800
atatgcacgc atgcaatatg catatttctt ttcagatgtg ttcaagaaag aaaagattat 22860
gttagcagtt aaacccccag ttatagtagc aatacagtat atggattagt taatatgaat 22920
gttatgcatc ctacctctca gaatattgaa aacatgtata ctcgtcatgg agagtctgaa 22980
cttttagatc gggttgctga gaaattatct aacaagagaa agcaattcag acaactgcaa 23040
tgtaaattta gaaatttagt aatttgcaaa atttaagatt tttatgtacc ttatatacta 23100
gcggctcata aattccttca ggcagatagg ccaaggttgt accactgtca attattgtcc 23160
cttttctgtc tccttgtgtt gatgtatctg ttgatagact aaggaaagca tggccaactt 23220
gaactgcagt catattaaca ctgtagtgtg gcctaaaaaa ccaaattttc aaatgtcata 23280
ttctctcaaa atatggattt ttgtaaacca atatctgaat agaagagaga ttctatcatt 23340
aagatctcat agctaaggct atgtttgacc cagcttattt tttgcttaaa agctacatta 23400
aagttaaagc taaaataaaa actttaaaat taaagtagaa gttgtttggt agtcttagct 23460
taaaaactcc ttttaagata aaagatttgt ttcaactagt tacggaagaa aagaaggagg 23520
gaagatatgt ggctaatttt aaaaagctac tttagttagg gttttttaa atgctaattt 23580
tctccctttt catttattta atggtcctca aatattaaga gtttttctct aaatgtgttt 23640
ggctcagttt ctccttttaa ggagaagaaa aaggaaaaaa gagccgggcc aaacacctac 23700
atatgtggcc tagatactac ttataatgac ttgggcaagc ttccaaggtt gattcagccc 23760
cagtctgata tcaattctag taaaagtaaa caaaactatg agtgcataaa caaaattgac 23820
caacatccag catatagaag catccagcat ggacatgaaa atttaacaaa gatatattgt 23880
tttttcattt agaatatagg ggaagaaagt gctgactttt atggttgaaa accactgaaa 23940

```
tcctaccgcc agcttcaact aacatgagtt cactttacat tccaattaca gtttacacat  24000
gacaccttca gcttcaaaga atcttttaaa ccaaaatttt aataccactg aaatgatgac  24060
ctcgttagcc agttgaggcc tacattccat ttagagtgta gatgtgttga gacatgtcac  24120
tgatgacttg agaagaaacc attaatcaat actccccctg gactcatata taagcaaaaa  24180
agtgatcttg taagttggac ttaaatataa gcaaatctaa ctaattttgt cttatttaat  24240
gctatcattc ctaaaacatc cctcatttaa ttgtaattct attttcaatg actctttttt  24300
attcatgata gcaagttcca acgaaagata ttttagaaat aaccttattt tttcgcttga  24360
gattagtaaa attaaatgat gtcaactaat tttctaaatt agtgtgaaat tagttatttt  24420
tgcttatata tgagtccaaa gggagtatct agcaaggaca ggctagagta gagcttataa  24480
aggcttggga aatcctcacc tcatgggcta gttcttgggt taatttagcc caaattcaat  24540
agaagctaca tgttttatta tatcgtaaaa cattaaaata tttgcacaaa aaataatgta  24600
gtcactaaca aaaacatgat taaaaaaaaa ctagaacaaa cttatcttca aaagagtaat  24660
taataacact ataagaaaaa ctaatctcat tctaaagtgt attaagtgaa tggcatactg  24720
gtctggtaat aatggagtca tgttcacttt aggttgcaca acatgcccaa tagcaaatat  24780
accacctcca tttactccat ttaagcaatg agcaaacatc tttttcactt tgccagaaga  24840
agcaagttgt gaaatcattg atgaattagc ttttccaaat ccaagtattc caccaagtgc  24900
ctcttcattc gaagaactta gatctccaga ttgtctagca ccacaactac aaaacagcaa  24960
aaaactcatt ttaaatataa aaagagggag aaatatgaac caaaagatgc atgcaataga  25020
caacattaaa ttatcataca caataagaat caccgagaaa ccattataac ctgaatgcct  25080
ccaaaatcac atcaagctgt ttgagtatta gaaaaaggta tttctaggag tgttccatat  25140
gataaggtgt tctattcact gcctcaatat ttactaaacc atgttattta cagcatgttt  25200
ggtaaaactg aaaactttag cattggaaga ttataaattc aagcgctgat attgtgctaa  25260
aggaagctat tagcatttaa catacctaac aaagataaaa caaacgaaat tattgtccag  25320
gaaatagttc ctgttgatac atcactgact gcacaaatgc tgaattattc aatatttttt  25380
ttacataaat ttatttttca gattgagtag ggttcaagct tggaacacaa caaaaggagg  25440
actgcaagaa gtacaagcct atatcaatat caacgtcagc agtctcactc tcaatcttac  25500
tcaaattggt agctgaccca aaccaatatc aaaatcaagt attttttcag gctccaatat  25560
tagttttggt gaggagttgg acgcaattta tatacttcat aatgaaataa aaagcatact  25620
cgacagtttt tgaaaagcaa tgcctgcaca ccagtgcacc cactttatgt taatatcata  25680
tgcagatatg agaaattatg ctattgcaag tttgcaacta aagcaacagg ttaaattact  25740
atgaacaaac atgcatggta ttggtatctg agttcatgac ttatgagaaa ttaatgtcca  25800
ctaacagcaa cagatcaaaa gtaatagaca tacacaatac ataatagcac acattactgc  25860
caaaagaaaa ctcacccaaa tacaatactt ccatttgctg aatcagtttt aaggtcccca  25920
gacacttgat cataaagtac gatatccttt acaaagtaac cagcagtcga gctcccatca  25980
ccatatatct ccagatatgg acaggaaata ttagcagtgc atccggtcag cagaccccca  26040
ttgatctctt tgcaaaactc ttgatcacag ggaacaaatt taccagagga ggattccttt  26100
atgtcgtaga gtgtaaggtc catcttcgat acacagaaaa agaaattcaa atgaataaaa  26160
acatcaaatg ttgaaatgag aaggctgtac atgattcagc catgtgagaa ttgtcttgca  26220
agggatggtc taccatggta cacgccctga tagtgtaaag gattttatac actctcaacc  26280
```

```
aatcagaaac tcccatgtaa ggtaattatg ttgaatttta tcataactca tttaaaagtc  26340
acccctagca tgatttccga ttagttgaca gtgcaaaaga tcgctacaca atgcataaat  26400
tttaaactca ggttgtaatc catcctaatt ttaaaatgca tacacaaagc acaaaaaaaa  26460
aaaaaaaaaa ctaagcaagc acgtttggca agtaatgaag ataataaggg tagcttaaac  26520
taaaaagatg agaagcattc accaaggttg cttctggtgg ggcattcttt gcactgaatg  26580
caattcaccc acataatgtc actaccttac taattatcag gcaccgatgg tattcttctt  26640
gatattggca ggggagagtt cccgcaactt caagtgcttc atatgagggg aatatatgta  26700
agaaaatgga gattaaagaa agatacaatg cctcgtcttc gacgtctggt cattgacagt  26760
tgtgagttgc ctgagcttcc agaagagctt tggtcattga ctgccttact aatggtgcat  26820
gtttcgtcgc cctcccaaga attggctaac agtctaaaaa atgtggtgct gaggaatggc  26880
tgtaagctca taatctctaa aagttgtgtt gatgaatggt tttaagctca caatcatcta  26940
gtgcttcata actgttggaa taatggcaat gcaagtgggc attgctgggt tttgttatgg  27000
tctttctata tccatcatga taacgtgcag tggttcttat cattctgtat ctttctaact  27060
ttctaatctc attgccacac gtgttgtgat tgctagattt ccattttaat ctcagttttt  27120
gtctaatttc tttttctttc ttggaccttt gttctgaagt tgtaacttta tttacatgtt  27180
gattgtaaaa ggatatttat tctggcagtg tttgattaaa tgatttgtaa ttcctctgct  27240
tctgtctatt cacttttcta ctttcttttc ttagatgacc cgatatttct gttagcttag  27300
cattgaggca tgagttacat atatgcatta tttcattcat ttgttgttca gtgtgctcaa  27360
ctatatttga ttgtgcgtta attttccctc ttttcccctt cttttcccat ccaaagtaag  27420
tgtttcgtct ggtccctaat ataaagtatt taacttttt ccattattta tcctattaaa  27480
tactctaact atatgtactt ttaggtaatt atgcataata ttgttattta tgacaagtta  27540
actatcatta ataagagtaa aattgataca ttaatttatt tatttttatt ggtatgtgta  27600
attttgttat ttttatttat tggttttggt gttgtctcac gagatgtctt tttcctggtt  27660
gaggtgtgtt tctcttctca tttcttagat ggaatagtta cttgataaca taattaattg  27720
tataatggga gataaatggt tttcatcttc tcttctcatt tcttttttc ccattcattt  27780
ttctggccga gtgatacaga ggagtaaagg aatgaggact tgtttcaagt aagagtaact  27840
ccaaaatagc aaagagactg aaaagggaat ttctgagtaa taatttctct gccttctttc  27900
attccgtgct tggatacata taggatagat ttttccccta ataacctgag gatacgagta  27960
ataaattcaa acagaattca gattctaata acaatatgaa aatgatcaat tttaggtgat  28020
aaaagtaatt actcttaaaa ctaaatggca gagctagtgt ccaacctagt ccttcgtaga  28080
catggcaatg gggcggatcg ggtacagata ttgtctcccc aatctcttac cccgactcct  28140
caacatatcc ccatacccga tacccgacag gtttgagttt attgtctcat ccccgtaccc  28200
gtcgggtatc gggtatcccc aaccccaatc cacacaccat ttagaaaaat atttttttt  28260
ttgtaaaaaa atattaaaaa tttgatttta gaaaaaaata aattgattgt taaacattta  28320
tttttaacta cttatatatc aataaattta ttataacgcg tgtgtctaca taaatagtta  28380
aaaaaataat attaaattat gtaaaaattt taaaataaaa ttaactagta ataaaaatta  28440
tgtcttttga ttaaattatg caaaaattct aaagatttta agtggcaggg cgggtttggg  28500
ttcggggtcg gaacgggtct agtaatccca tacccgtacc cgtacccgac ttttggttat  28560
tgaaaaaaac ccgaattcat actcataccc ggtcaactcg gatattaccc gtcaaagttg  28620
ggacggacac tcatttcttg tgtccttgtg tcactcttct caagcttggg tctcttttta  28680
```

```
ttgggcccaa cacttatttc ttgtgtcctt gtgtcacttg ggccaactgg cctatagtga  28740
taagacatat ttgttatgtt cgtaacacta acacccagtt tctattagaa tgctgttact  28800
tggaatttga gaaggaattg gagtgaaaaa atcttacaga aagcagcaat gacattgctt  28860
ttgatgatat tttggtagtt tctatgtcaa aattcttttt ttttctcttt ccttaccatt  28920
tgtatccttt tatagtattt ttttttcact ccatttaaca tttgttacat aaaagacatg  28980
acaggaccaa tatattacat catcagatgt ttgatagtgg ataatcaact aaagaaagaa  29040
ctaaaataat tgattttgaa aaaaaaaaac taattatttt aatttaagaa ttaaaaaaaa  29100
tcaaaatttg cattatacga aactaaaact aaattttaag cctaataata taatgttcac  29160
aaggtgacta aacgaccagg gtaagtggta actcctcctt tttggtcctc tactatcata  29220
aattaatgag cttataacta gttctcatat ggtaacaaaa agacgtaaaa aatgtttacc  29280
tttaaagctg catacatcag acggtattca acaagaaata gaaatattag cagcaacaga  29340
tttgaagtgg aatgttttga tttcttatat attcagaaga gttgaaatta aacaacttaa  29400
agcagagttc aagctcactg aatactgata ctttgtcctc tgagaagtta atctccggat  29460
gctacgcact ccttattttt ctttcacttt atgcaattta aatacctctc catttcaatg  29520
gcataattct aaaatgttca tcagataagt cctaaaagat ttcccaaatt attcttgatt  29580
cgttttcccc ggcaactagt ttattacaaa aaaaatcaca gaaggaaaag gaagacacgt  29640
gtgaatgcta ggactaaaga gtgtttgacc gttgacgtca aggtgaagtt tctcttgact  29700
tgcctcgcag cttctcaata atatcacagc tcgaaaaaga agacacaatc ggtaaggtga  29760
agtttctctt gccttgcctg gcagcttccc aactactacc aatatgtgct tatgtacttt  29820
ggtctcagta taggatatat gtgctcagtg cctcctccaa agcattaata tactttcact  29880
taccaaatca aatggatact gaaattgatg agagcattga cgaggccgat atcagatttg  29940
atgcaaggag ttatagttcc agactgaaca gtatgataag gagtgagact gagtcaattt  30000
tgggagcatc ccctgtccat gagggagcag ctgcagaaga ggtgcgccaa atcagagatg  30060
tcgcccacaa agctgaagat gtggttgaca cttacgttgc caacatcgcc aaatcagaca  30120
tggtgcttca ccaagtcaac tctgacatag agaagatcag gagtgtgctc aatgagatct  30180
atgagaacag cattggagaa ggtgaattcc gaagcgaaga agctgctgca gaagcagaat  30240
cactcctcaa gagaaggagg gaggtggagg aagaagatgt agtgggctta gtgcatgact  30300
caagccatgt aattcaggaa ctcatggaaa gtgagtcacg tcttaaagtt gtgtccataa  30360
ttggaatggg agggttgggt aagaccactc ttgcccgtaa gatctataac aacaatcaag  30420
tgcagctgtg gtttccttgc cttgcatggg tttctgtgtc caacgattac agacccatgg  30480
tatttcttct cagccttctc aaatgttcaa tgtcatccat atctgaattt gaagaattaa  30540
gtgaggcaga actgaagaag gtagcagaat ggttgaaagg gaagaagtat ctggtagtgc  30600
ttgatgacat ctgggaaacc caagtatggg atgaggttaa aggagccttt ccagatgacc  30660
aaacaggtag tagaattctc ataacaagtc gcaacaaaga ggtggcacac tatgctggaa  30720
ctgcgtctcc ctactacctt cccatcctca atgaagatga aagctgggaa ctcttcacaa  30780
agaagatttt tcgaggtgaa gaatgcccat ctgatttaga tcctctgggt agatccattg  30840
tgaaaacttg tgggggttta ccacttgcta tcgtgatttt agcaggactc gttgtcaaga  30900
aggagaagtc acaaagagag tggtcaagaa tcaaggaagt gagtaggcat cttatagagg  30960
ataagactgg agtgatggat atactgaagc ttagctataa caacttgcct ggaagattaa  31020
```

```
agccttgctt tctgtatttt ggaatctatc cagaagacta tgacatcagt gcaaagcaat  31080
tgatccaata ttggatcgca gaaggtttca tacaaccaca aaaaactgga attgcagata  31140
caacagaact ggaagatgta gctgactttt acttggatga gctagtggat cgcagcttgg  31200
tgcaagtggc aaaaaggagg agtgatgggg tgtcaagaca tgtcggattc atgatcttct  31260
acgtgttctt tgcatgtcag aaagcaagtc tgataagttt ctggaggttt gcacaaactc  31320
caacattgat accgtcacta ataccaatcc ccgtagaatt tccatccact ggaaacgaga  31380
cttggatgtc tctgcaaaca tatttcacaa atcatgcact cgttctatgt tcatctttgg  31440
tgaaaatcgt agcatgaatc tagttcctgt tttgaaaaac ttcaagttgg ctcgtgtgct  31500
tggttgtgat atgatgcaag ggtttggtc tgattcagtc tccagagatt tgaagaggat  31560
gatccatcta agatacttga gaatagaagt ggagcacctt ccagattgtg taagcagcct  31620
ttggaatcta gaaacactgc atgtaagata tcgtgggaca gtatccagta aaatttggac  31680
gttgaagcgg ctgagacatc tttatttgat aggggaaag ataccagtcg tcctgccaaa  31740
agcaaataga atggagaatc tccaaaccct tttgttatcg ggtaattatt cacaacaaac  31800
tctttcccgg ttgaacagtg gcatatttcc caggttgcga aaattagctt tacgctttgg  31860
atttcaattc gccatgttac caagtctaca ccacctcaac aatcttcata gcctaaatgt  31920
aatgtaccct tttgaacttc catcagacac caatgcgttt ccatcaaatc ttaccaagat  31980
aaccttgaag ctagatgcag actgtgaccg tgatctccaa cctttaatga agacactagg  32040
gcgacttacc aaccttcaaa tcttgaaact tattaatttt ggtttattgt cctatggggt  32100
agagcttctt gatattggca ggggagagtt cccgcaactt caattgcttc atatgggtaa  32160
aataaatgta agacaatgga gattagagaa agatgcaatg cctcgacttc gacgtctggt  32220
cattgacagt tgtgagttgc ctgagcttcg agaagagctt tggtcattga ctgccttaat  32280
aatggtgcat gttgttagaa aaataaaata aaaaaatgaa ggaaaataaa tatgaagaag  32340
atgcacagtc ttgaattaaa taacaaaata gcagtaacaa attaaattta attgacaaca  32400
cataaataat gcattatatc ataatgagca caaggaaaaa ttaaataaag ggaaagaatt  32460
aaatagcctg ggttgaagcg tgtaaacgct attcttagag agaaaacgcc cccactgcac  32520
gggtaagaaa ttctgattgc gctcttctcc caagttacga caacccgttg gttccgatcg  32580
tgtgcagcga aaggatcccc gaaccttatg aacaccaatg ctcttgctct cacaaaaatt  32640
aaggaaaaga aagagataaa tttttggcag aaagaaacca gagctctcag tctgtcattt  32700
ctaggaaaga ggaaagagat atatataggc attttgcaac aacaaaatat taccgttaga  32760
aatataa                                                           32767
```

```
<210> SEQ ID NO 13
<211> LENGTH: 32767
<212> TYPE: DNA
<213> ORGANISM: Artificial Sequence
<220> FEATURE:
<223> OTHER INFORMATION: Artificially Synthesized

<400> SEQUENCE: 13
```

```
ttttatttcc cttgaaatat tgaatcaata ttgccagctt cataattatg atgtgagtga    60
cagtgcttgt ctgatttaga taaatgaact tgataagttg aagaactcca tctctttctc   120
ttttctgttt tgattttacc ctgtgtcttt gggagattta aataggtttc cctctgcttt   180
atggagataa tctctatttt ttttatcaaa caatacaaat tccctgtagc tgaaacctta   240
ctttttttctt tgtttctctg atttattata tctaacttca atgccttttt ctcttttgtt   300
```

```
ttagggcctg tttggataag cttctttaga agcacttcca agagaagaaa ataagaagaa    360
aataatgatg agtttcttca taagataaaa tgagttatct attagctacc cattaactaa    420
tttgtagaag ctctctcata tagcttctct aaaagatgag aggacgtcta caaattagct    480
aatggttagc taatggacaa ctcattttta tggaaaagct catttcattt ttttcttcat    540
atcttctcct aaaagtgctt ccagagaagc ttacccaaac ggacccttat ccaatatatt    600
tcattggttc ccttttagaa caacttgact tttgtgagac aaatgttttc aggattggtg    660
aatctatatt ttcattgtat gatttaataa actctgtgac ttggaaattg gaatttattt    720
tgatttttga tacatcagtc agtgtggcat atctatatgg gtatgaatgt gtgatgtaaa    780
gttgttttcc cttaggggaa gaagagagga tcaagcttcg tagaggaagg gtttttttccc    840
ttcagaatga acctgatgtg gctcgagttt ggctgcctaa ctctgatttc cctggtcttg    900
ctatggctcg ggcatttgga gatttttgcc ttaaggactt tggattgatt gctgttccag    960
atatctcata tcaccgcctt accgagaagg atgaatttgt tgtgttagca acagatgggg   1020
taaggcctta tgaggctctt ttcttatgat atactgtctt ctatgatctg catgtgttga   1080
aattgattca tttcaatatc atatttgtag ttagccaatt ctaaaatgaa aatatgaaat   1140
tgactttaaa tagtatttga atgccacttg caacagttaa aaaaaccaaa tttggttcta   1200
atttcactgt atttaaattg acatcttact gtttaagcta actacttatc atgtaaaact   1260
tattattatg agttaactac taatgtaaat gatgaacaca aacctaatat caaaagctgt   1320
atcaatatat attttttgat ccagttgtat ctcaaaccca tgttcatata cacagataca   1380
catgttattt ctattctctt tcaaactgga atttgtaaat tgttgagctt ttggaaaagc   1440
ttgttcttta catcaatata gcgatttacc cttttctttc gcctctcctt tgaagttgta   1500
actctaattt ttctcttatg gtccatatta tgttgtaact tgaaaattta tattctctga   1560
attgtcttat atatatatat atataaatata tatacaaata catacttgat tagatggaat   1620
attgaattat tttaaactgt tggattcttg ggggcagatt tgggatgttc tgtcaaatga   1680
agaagttgtg gacattgtgg catctgctcc acagtctact gctgctagag cactggttga   1740
gtcagctgtt cgggcatgga agacaaaatt tcctttttgt aaggttgatg attgtgccgc   1800
agtttgcctc ttctttgatt ctgattcaga tttcaagtca acagatacaa aagacaagtt   1860
aataccggag gcatctattg accaatctga gcagttagct ttacttggtg aaaagggagt   1920
tggaaatgaa gctgaaaaaa agcagcaata gcgcaagttt tgtaccatgt ctctcccaag   1980
ccttgttggt tttatcgaaa aggttgggta aattgtgccg caacagtcaa aagagaaagg   2040
aggatcatta ttttgatgat ttttcggtag ttttctgcca atattctttt cattatttat   2100
ctttcatttc cttcgacagc atttgaggga agagggggtt atatatatat atatatatat   2160
atatatatat atttcttatc tggaggaaaa ggggtaccgg gctttttttt ttgttgctgg   2220
aggtcatttt ccttctctgt atatttggta gatttggagt ttttgtaaat ccaactctct   2280
agattcatat tatatagtct gttctgaagt ctgccgtttt tcatttgcat cattcttagg   2340
ttatagtttc caatttagtc tgtgaaaaca tgagaactgg aaagaattgg atttatttct   2400
tatggacttt cgagtcaggt ttttgtacct ctgtgttgtg ttgccgtcag ggattaatga   2460
tattgtctgt gtgatcctat tatgggtttt gtgtggaaaa tttactctga cggaaatttg   2520
tctttaagct atacgagtaa aactgtattt accttttgat ttaaatttta ttatttcatg   2580
attttaactt aattttgaga aggataaatt atttttaaaa aaggcttttt tgttaaggga   2640
```

```
aggtgtccta agtactaacc cacgaaggaa tgagggaagt gaggatggta acatgtcaaa   2700
taaatttgga atttagttcc cgaaattttt gagtgttaat tattgtagga atttactcat   2760
ttcatgataa aacttgacat ggagtaccgg acttaaaaaa gaaaaacatg acatgaagtg   2820
gatttggagt caagttttct ctcaaggcaa actggattta ttctccgtac tcacttatta   2880
aacaaggtta aaacaattag gtttgattga cattttggcc ttcagggttg tctttataat   2940
tttttcatat acgaaaaaag ttataagttt taatttctgt acacacatat aagttaagtt   3000
ttgatctccg tgatcaacgc agctagtatg tatgtggcac ctattcattt gctttactga   3060
gccttctcaa gtgtttgttg tccacgcctg aatataatga tttattcaag aaaacaacgg   3120
attgaggaag aactgaagaa ggtagcagaa tggttgaagg ggaaaaatta cctggtgatg   3180
cttgatgaca tatgggatga ggttaaaggt gcatttccag atgaccaaaa tggtagcaga   3240
atactaataa caaggaggtg gcatactatg tacaagaaca attttcaata ggatcatctt   3300
agaccttaag agcattgacg taaagataga tgacgaagat caagccatca ttctgttgag   3360
ctttcgtcct aagccatttg atcattttgc tgatacaatg ttgtatagaa aggctactct   3420
atcaatggat gaggtcaagg ctgctttgaa ctcaaaagaa aatcaagggg agaatgactc   3480
tggcagtaaa agactctttt ctactttctt gtgctgatgt cagtttttttg tctccttttt   3540
tctttcatgg tcattattgt gctgatgttt taacatcatt tacatgttta ttgtaaaagg   3600
ctctttgctc tggcagagtt tgatgagatg atttgcaatt cctctgcttc tttctattca   3660
cttttctgct ttcttgtgtt ccacaaccac ttgaccagat tttcagttta gcttagcatt   3720
taagcctgag aaattatgca tcatttcatt tgtttgttgt acaaccatat ttaatgttaa   3780
cctctctccc ttgtttttcc attctaaaca tggatcatgt tttgtttat tggtctaaag   3840
tgttgtttca tgttattttt ctttctcttt tcccaatgga aggtcctttc atgatttagt   3900
tagaatagat aactgataac acaattagtt ggaaaggaag atgttagagt gtatgttgat   3960
aatgggagac aaatcatagt gatcagtttt agaattggag tgaaagcata cagacattgc   4020
ttttgtgcct tgtctctgct actctaccca aacctttgct ggttttatca tggatataat   4080
tcattatttt atgatctttt tggtagattt tctaccaaaa ttcatttctt cttttcggtg   4140
atgctatata gtacgaatta gttttgcacc aagaagtacg aatccacttg gcaaaatatg   4200
atcgtacaaa tattaatttg aaagaataaa atctagacat gcaagttcta actaccctct   4260
ttcaaactgg aatttgtgga attgttggaa ttttggaaaa gcttgttctt tacatcaatg   4320
tatatattct cccaaattgt cttacaacac aaaaaaactt gagtattttc ttacatatta   4380
tctgcctaca tttttgcgct taactggatt atggaaaaat aatttgctaa tgagatatac   4440
taggacagat ggatgaaaat tacaccaact tttaacaaag gtttaaatac agttttttttt   4500
tatttataat ttatcatatt tttgccttta gtctttatat tttttttgt ttttaagctt   4560
tgtaaattat atttatttta tttttaattt ttaaagcacc ttaaataata ttttgacaag   4620
tgaaaaaaag tgttatctaa aatgttagaa cgaaaaataa aaaaatataa tttataagga   4680
ctaaactttt tttacaaaaa aaataaaaaa aatactaaag aataaaaaaa tatttaagac   4740
aataacaatt tgctgaatac aacagaaaag ttagttagaa cacaataaca atttttaaag   4800
attattgtta aagactctgc attttaaaat tctaactaat ttttgtttct aaaccatgga   4860
agacttttat ttcataaaca caataacaat taaacaaaac tcacaattta aaaaaaaatc   4920
agagtcatca aatatattaa tatttaaaga cagaaaaaaa aataaacaaa taaagttgag   4980
aaagccaacc tataattaaa aaggttgaca gaaacgcggg tccacgcgta tgcgcgttct   5040
```

ttccctttat tggcgtccac ttgttatctt tcgttctcta ctctgtaaat tatctgtcca 5100
caaactctct agagtttcca cccaagattt cctgtttcac agaaatggca gatagtgttg 5160
ttgcttttct gctagataac ttgtctcggc tgcttgaaga tgagcacaag ttgctttctg 5220
gcgtggagga caaagtcaac tctctttgca atgagctcaa gtttatacac atcttcctca 5280
agaattccga gggcaagcgc agtcatgaca cagtgaaaga agtggtgagc caaatcagag 5340
atgtcgccca caaagctgaa gatgtggttg acacctacgt taccaacatc accaggcata 5400
aacagagaag caaactgagc aagttattcc acctcaaaga acaagtcatg gtgcttcacc 5460
aagtcaactc tgacatagag aagatcagga gtcagatcga tgacatctat aagaacaggg 5520
acagatatgg cattggagaa ggtgaattcc gaagcgaaga agctgctgca gaagcagaat 5580
cactcctcaa aagaaggagg gaggtggagg aagaagatgt ggtgggctta gtgcatgact 5640
caagccatgt aattcaggaa ctcatggaga gtgagtcacg tcttaaagtt gtttccataa 5700
ttggaatggg agggttgggt aagaccactc ttgcccgtaa gatccataac aacaatcaag 5760
tgcagctgcg gtttccttgc cttgcatggg tttctgtgtc caatgattac agacccaagg 5820
aatgtcttct cagccttctc aaatgctcaa tgtcatccac atctgaattt gaaaaattaa 5880
gtgaggaaga actgaagaag aaggtagcgg aatggttgaa agagaagagg tatctggtag 5940
tgcttgatga catctgggaa acccaagtat gggatgaggt taaaggagcc tttccagatg 6000
accaaacagg tagtagaatt ctcataacaa gtcgcaacaa agacgtggca cactatgctg 6060
gaactgcgtc tccctacgac cttcccatcc tcaatgaaga tgaaagctgg gaactcttca 6120
caaagaagat ttttcgaggt gaagaatgcc cttctgattt agagcctctg ggtagatcca 6180
ttgtgaaaac ttgtgggggt ttaccacttg ccattgtggt tttagcagga ctcgttgcca 6240
agaaggagaa gtcacaaaga gagtggtcaa gaatcaagga tgtgagttgg catcttacag 6300
aggataagac tggagtgatg gatatactga agcttagcta caacaacttg cctggaagat 6360
taaagccttg ctttctgtat tttggaatct atccagaaga ctatgagatc agtccaagac 6420
aattgatcca atattggatc gcagaagggt tcatacaacc acaaaaaaact ggaattgcag 6480
atacaacaga actggaagat gtagctgact tttacttgga tgagctggtg gatcgcagct 6540
tggtgcaagt ggcagaaaga aggagtgatg gggtgtcaa gacatgtcgg attcatgatc 6600
ttctacgtga tctttgcttg tcagaaagca agtctgataa gtttctggag gtttgcacaa 6660
actccaacat tgataccgtc agtaatacca atccccgtag aatgtccatc cacttgaaag 6720
gagactcggg tgtctctgca aacacattta acaaatcatg cactcgttct atgttcatct 6780
ttggtagtga tgatagaatg gacctagttc ctgttttgaa aaacttcgag ttggcccgtg 6840
tgcttgattg tgattcgttt attgggtttt cgtcttatcc agtccccaga gatttgaaga 6900
ggatgatcca tctaagatac ttgagaatat gcgtcaagca ccttccagat tgtgtatgca 6960
gcctttggaa tctagaaaca ctggatgtaa catatgaaac cacagtatcc agtaaaattt 7020
ggacgttgaa gcggctgaga catctttatt tgagtggggg agggaagtta ccagtcgtcc 7080
tgccaaaagc aaatagaatg gagaatctcc aaaccctttt gttagatggt agctatggta 7140
tagacacgta tccacaacaa gtgatttccc tgttgaaaat tgacatattt cctaggttgc 7200
gaaaattagc tttgcgctat cctgatggac cagatatgtt atcaagtcta caccacctca 7260
gcaatcttcg tagcctaaaa gtaattcgcg gttttgaact tccatcagac accaatgcgt 7320
ttccatcaaa tcttaccaag ataaccttag cagcagtccg ggatttacat ttcatgaaga 7380

-continued

```
cactggggca acttaccaac cttcaaatct tgaaactaag attcggcaaa gttggttttc   7440
atcttgatat tggcagggga gagttcccgc aacttcaagt gcttcatatg acgcaaataa   7500
atgtaagaca atggagatta gagaaagatg caatgcctcg acttcgccat ctggtcatta   7560
atgactgtga agaattgtca gagcttccag aagaactttg gtcaatgact gccttaagag   7620
tggtgcatgt ttcacggccc tccgaagaat tggctaacag tctcaaaaat gtggagccca   7680
ggaatggctg taagctcaaa atctctaatg aactgtgaaa ggcaagtggg accgccttct   7740
tacattgcag acataagttg tagtctttca atatccttca taatatttgt tttttaatcc   7800
cgaccccatt tccatttcct ttgtccaaat aaatttccaa tttaaaatag cggatattca   7860
aattgagaat ggatgttgct tccttgccgt gtatggagtt gtgtctcatg attattgatt   7920
acatatttat aatacctaga gtttcttttc tatttgtgaa taatatatta aattaagggg   7980
gtgtcatgta aaagagaagt tttttttcc ctaaaaatta tatattaaaa aatttatttt   8040
ctcatatttg atatacattt ttaaaaataa atactaatgt aaaatgatat tttttgaaaa   8100
tatttttaat caatttctca tgaaaacttg aatatttatg tatatgtata tatatagttt   8160
aactatattt aatcttgaat tactaatcat tcctcacagt tattatacac tacaaaagta   8220
atcctacgat taattaactt tatcatagta atcatagcca ttgaaaatta accatattcc   8280
tttacatcca atcaaaagaa ggagaaaaaa aaacaaattc ttttagcacg tttaaatgtt   8340
aaagctaatt attcaaatga ctaagaagaa aaattataag ctccaaagta aaacattgat   8400
tatcaaatta tcctatctaa aactctaaag aagttatgtt aatgttaaat gaaatattca   8460
ttcggcccaa ttgttaaaaa aaatcatagc tgtacaaatt agagaaataa gatgaaaagg   8520
gagagaaata tgaaataaaa tagttaatgc aatacaaaga gataaagaaa aaaaaatgaa   8580
ttgtaaaaaa tgtaataagt atttgttgta acaatattat aactcttgct aaaaataggt   8640
caaacaaatg gagtcaacca gcacagaaat gctctacaat aactaatgtt aaatatttgc   8700
aactataact tcaattccgt gcgtgacttg tatatgttaa ttatacattt ggcattgaga   8760
tccaagctaa gtcaaaaatc aaagtctaat aacatataca attggtggta agattttgca   8820
atttacatat tcaccatggg aattgagaag aaaaatttga cccaaagcga aggttcccaa   8880
tggtcagtgt cctagttttc cttgaagatt acatttataa atcatggaag ttcctgaaaa   8940
gtcaatttct cacatagcat ttttttcatg ttctttctat tttcaaatcc tttgaccata   9000
attttgactt tgatatatgt atttgttgct tcatttcaat atacccattt atgaagtaga   9060
gcaagtagag acaaaatcat cacccagttg atgtttaaac cacaagcaaa agaaatgtag   9120
tggaaaccaa ctaaatggac tgttcccgtt cgctcatccc tcactttaat gcttgaagaa   9180
cctgtgagat acagcataga aaatattact aatgagccat tatgcaaaat taaaggaaat   9240
aatgcaagtc atttgaattt gatttcttat aattttttttg acaattctac ccaaaccttt   9300
atataacacg tcaatcctat attatcttta attcatcaat taaacataag taagaaatct   9360
gatgtgaaac aaaaagtaag tggataaaaa gaaataagga cgacactttt acatcaaaca   9420
cctccaggat cagcatgcag atactttaaa gttttaaaat ggatcgttaa actacacaga   9480
actattcctt tctcagaatt aagaactaag ggtcaactcc gtttgagaaa aatgttttat   9540
tatttttcat tttcaatttt cacaaaaatg ggagagttga gacaaatgtg aaaaaaatac   9600
taaatttaca tgttctatta tagatgtttt cacaaaaatc tacaaatgtt ttatattatt   9660
catttatatt atttaaaata cagaagatta taaagaacta ataatgatac ttacagttgt   9720
actcagtcca tccaataacc tgattttcaa ggtcatagat gtattacatg ttctattata   9780
```

```
gatgttttca caaaaatcta caaatgtttt atatcattca tttatattat ttaaaataca   9840
gaagattata aagaactaat aatgatactt acagttgtac tcagtccatc caataacctg   9900
attttcaagg tcatagaaga caagtttatt tgtaagcact aaatctgcaa caaataaaaa   9960
tacaggtgag gctgcatagt aaggtcatgg aaagcaagct ttctagtgat ccaaagttgt  10020
gataactcca ttataattta catctagaaa aaatataagg aaatttcttc caccagtaaa  10080
aataatacat ttattataat atttagcttg taagtttctt ccaaaacaag catggggcca  10140
cttctctcca taaaaaatct caagaccaat aatatgctac aaaactttca ccagcaaatt  10200
gcaaaaggtt gtcagaacct acattcacac ctttaagccc cctatcaatt aatcatcata  10260
tctttgacca gattaaataa aaagtaaaaa agaaaaaaca gaaaaaggcc cttctcagct  10320
aaatcctcgt cttttgcttt agaaggaaga tttaggatgt agtaatcgaa agcaaacttc  10380
tactacctct tgatttagga acttgtatca aaaaatacag aacacagccc aatttctttc  10440
aaatctccag ttaagatact cacaagatcc tatacaaatg tattccagga tatgcattta  10500
taatgtattt gtcttgttta tttaagaact cagaagtaat caggttcaaa aatatctttt  10560
atctcaaaat gccattaaaa aagtaaccct ttctttcctc ttataatggc tacggcagtc  10620
tcattctaaa tctggaagca gtattcagca aattggtggc aaatatatct atcggtacag  10680
aaaaggattt gaagagaata cctcccaata aggtcatatt tttgctatct cttgattgtg  10740
tcccactatt ttgccaacca atacaccaga aatctccctg cagatgcaca ttagtatttt  10800
atttatagta tggtatataa agattatgat catagaaatc attgacataa aaaagaccag  10860
ctcagtagta gtgcacatta ataaatgagt cttttgaaaa atcattttaa aactattgcg  10920
agtatctaaa attacaaaaa gaataacagt tttataaggtt gaaaatacga aaagataata  10980
tttggtgcat ttgcaaattg caactccaga atccattctg gaactcaaaa ctaatttgaa  11040
gcagatggga tacaaaaggt ttttaaaatg cattgtgggc actttgggca gaagcaactt  11100
tttattactt tagcccagaa tacagttagg ccaagatgca gttggtctaa tatatataga  11160
gagagaggag ggatcaagtt actttaagag gaactctttt aaagttactc tccatcctca  11220
cactgttcat tctcttgaaa cctaatagtt gtaatgagta attaatctta atcattagat  11280
tttaaggaaa tgaatggtga agatgaggag taactctctt agagttactc ttgaaactct  11340
tgaagtaact tgattcctct tcatatatat atatatgaca tagaaggccg acaacaggtc  11400
ccaaaacaag ccaaataaaa ctcggctaat cataacaaaa cacacaaaga tataatgaga  11460
tttgcaatat acttacagac ggaaataaat aatcttgtgg ataaaccttc aacgagagcc  11520
cattttcaaa ataaaatgtg acagctggaa atccatcatc aacactgcaa cataaaataa  11580
aataaccatt acacccctac atgaagctga taatacagac ataaatgcat aggatatgca  11640
aagggagcag tccagttatc aaagcactcc aacaatacat actcaataag aaagttcata  11700
gaacaaaacc tacaaaatat tataacttaa tttcaaaaag agtttttccg attatcaaat  11760
taagatttca aatggcaaat attttttgtc cacttatcaa acccatagtc aaaatggcaa  11820
gatttcctag acaattcctt taacatataa tgtagattac aatttacatg caaatgtcgt  11880
tattactatt atcaagaaaa gaatttatta agacagaaaa aaaagatata gagacaggat  11940
aagaaatcct catggattac agatgacacc actaaaataa aaggaaaaaa gaaacaaaaa  12000
tcaagacatt tgcaacacgg caaaccaaca aagagcataa aaccataaac cagccactac  12060
agattaagta acaacattaa catgatcaaa taaaaatcat aaaacaatat gtgaaccgat  12120
```

actgtaaaac aagcaacaga attaaaagga aaaaatttca aagcatacat tcattactgc 12180
atactacagt gaaaatagaa aaaatatata acaggaagat aagacatcta ccaaaataaa 12240
aaacaaagtg agagagtgaa tagtcctatc ctggaaaact tgctatgcca tgaaaaagtt 12300
acttgaagat ccaggaatat aacctcaaac accaaccact acagatgtca ttgctcatga 12360
cagcaagctt aaacaatgcc aacatggcat tcaattgcca tattgaagga tggtgactaa 12420
tttaaacaaa taataacaac aaaacaatga aatcagtgag tgaagaactg agttgatact 12480
agaggagctg gtctggtaaa cttaatggta atttcaccct gttcaaaaaa gatttctcac 12540
catacaattt tcaaaggaga tcaaagtaaa acagaatttg ccaaaagtca aaaccacttc 12600
tgatgtgttt ttgtgcagtc ttctggtttc ctttaccaca cattgctgaa ggacaattct 12660
acctagaaca gaggagacaa acactcacca ccttgccatt tttaatgtga catatgccat 12720
gcatcatgga caacacagct atgggagtgc aactgtgcca tgttcaatag catgcaaaag 12780
aagttttaga gaaagtgacc ctcaacacac ccagtatgga agcacatact tttaacaaca 12840
ttgtcaaccc tgaaccacca ttatcaaaac cacacacttt aggtccttcc ttccaaaaca 12900
aactggacta caaagaattc ttctaaaacc tgtatgccga agtaagctag caaaacactt 12960
gcgcttgttc caaccaacag caagacacta tatgcataca atatgcacgc atgcaatatg 13020
catatttctt ttcagatgtg ttcaagaaag aaaagattat gttagcagtt aaaccccccag 13080
ttatagtagc aatacagtat atggattagt taatatgaat gttatgcatc ctacctctca 13140
gaatattgaa aacatgtata ctcgtcatgg agagtctgaa cttttagatc gggttgctga 13200
gaaattatct aacaagagaa agcaattcag acaactgcaa tgtaaattta gaaatttagt 13260
aatttgcaaa atttaagatt tttatgtacc ttatatacta gcggctcata aattccttca 13320
ggcagatagg ccaaggttgt accactgtca attattgtcc cttttctgtc tccttgtgtt 13380
gatgtatctg ttgatagact aaggaaagca tggccaactt gaactgcagt catattaaca 13440
ctgtagtgtg gcctaaaaaa ccaaattttc aaatgtcata ttctctcaaa atatggattt 13500
ttgtaaacca atatctgaat agaagagaga ttctatcatt aagatctcat agctaaggct 13560
atgtttgacc cagcttattt tttgcttaaa agctacatta aagttaaagc taaaataaaa 13620
actttaaaat taaagtagaa gttgtttggt agtcttagct taaaaactcc ttttaagata 13680
aaagatttgt ttcaactagt tacggaagaa aagaaggagg gaagatatgt ggctaatttt 13740
aaaaagctac tttagttagg gttttttaa atgctaattt tctccctttt catttattta 13800
atggtcctca aatattaaga gtttttctct aaatgtgttt ggctcagttt ctccttttaa 13860
ggagaagaaa aaggaaaaaa gagccgggcc aaacacctac atatgtggcc tagatactac 13920
ttataatgac ttgggcaagc ttccaaggtt gattcagccc cagtctgata tcaattctag 13980
taaaagtaaa caaaactatg agtgcataaa caaaattgac caacatccag catatagaag 14040
catccagcat ggacatgaaa atttaacaaa gatatattgt tttttcattt agaatatagg 14100
ggaagaaagt gctgactttt atggttgaaa accactgaaa tcctaccgcc agcttcaact 14160
aacatgagtt cactttacat tccaattaca gtttacacat gacaccttca gcttcaaaga 14220
atcttttaaa ccaaaatttt aataccactg aaatgatgac ctcgttagcc agttgaggcc 14280
tacattccat ttagagtgta gatgtgttga gacatgtcac tgatgacttg agaagaaacc 14340
attaatcaat actccccctg gactcatata taagcaaaaa agtgatcttg taagttggac 14400
ttaaatataa gcaaatctaa ctaattttgt cttatttaat gctatcattc ctaaaacatc 14460
cctcatttaa ttgtaattct attttcaatg actctttttt attcatgata gcaagttcca 14520

```
acgaaagata ttttagaaat aaccttattt tttcgcttga gattagtaaa attaaatgat  14580
gtcaactaat tttctaaatt agtgtgaaat tagttatttt tgcttatata tgagtccaaa  14640
gggagtatct agcaaggaca ggctagagta gagcttataa aggcttggga aatcctcacc  14700
tcatgggcta gttcttgggt taatttagcc caaattcaat agaagctaca tgttttatta  14760
tatcgtaaaa cattaaaata tttgcacaaa aaataatgta gtcactaaca aaaacatgat  14820
taaaaaaaaa ctagaacaaa cttatcttca aaagagtaat taataacact ataagaaaaa  14880
ctaatctcat tctaaagtgt attaagtgaa tggcatactg gtctggtaat aatggagtca  14940
tgttcacttt aggttgcaca acatgcccaa tagcaaatat accacctcca tttactccat  15000
ttaagcaatg agcaaacatc tttttcactt tgccagaaga agcaagttgt gaaatcattg  15060
atgaattagc ttttccaaat ccaagtattc caccaagtgc ctcttcattc gaagaactta  15120
gatctccaga ttgtctagca ccacaactac aaaacagcaa aaaactcatt ttaaatataa  15180
aaagagggag aaatatgaac caaaagatgc atgcaataga caacattaaa ttatcataca  15240
caataagaat caccgagaaa ccattataac ctgaatgcct ccaaaatcac atcaagctgt  15300
ttgagtatta gaaaaaggta tttctaggag tgttccatat gataaggtgt tctattcact  15360
gcctcaatat ttactaaacc atgttattta cagcatgttt ggtaaaactg aaaactttag  15420
cattggaaga ttataaattc aagcgctgat attgtgctaa aggaagctat tagcatttaa  15480
catacctaac aaagataaaa caaacgaaat tattgtccag gaaatagttc ctgttgatac  15540
atcactgact gcacaaatgc tgaattattc aatatttttt ttacataaat ttatttttca  15600
gattgagtag ggttcaagct tggaacacaa caaaaggagg actgcaagaa gtacaagcct  15660
atatcaatat caacgtcagc agtctcactc tcaatcttac tcaaattggt agctgaccca  15720
aaccaatatc aaaatcaagt attttttcag gctccaatat tagttttggt gaggagttgg  15780
acgcaattta tatacttcat aatgaaataa aaagcatact cgacagtttt tgaaaagcaa  15840
tgcctgcaca ccagtgcacc cactttatgt taatatcata tgcagatatg agaaattatg  15900
ctattgcaag tttgcaacta aagcaacagg ttaaattact atgaacaaac atgcatggta  15960
ttggtatctg agttcatgac ttatgagaaa ttaatgtcca ctaacagcaa cagatcaaaa  16020
gtaatagaca tacacaatac ataatagcac acattactgc caaaagaaaa ctcacccaaa  16080
tacaatactt ccatttgctg aatcagtttt aaggtcccca gacacttgat cataaagtac  16140
gatatccttt acaaagtaac cagcagtcga gctcccatca ccatatatct ccagatatgg  16200
acaggaaata ttagcagtgc atccggtcag cagaccccca ttgatctctt tgcaaaactc  16260
ttgatcacag ggaacaaatt taccagagga ggattccttt atgtcgtaga gtgtaaggtc  16320
catcttcgat acacagaaaa agaaattcaa atgaataaaa acatcaaatg ttgaaatgag  16380
aaggctgtac atgattcagc catgtgagaa ttgtcttgca agggatggtc taccatggta  16440
cacgccctga tagtgtaaag gattttatac actctcaacc aatcagaaac tcccatgtaa  16500
ggtaattatg ttgaatttta tcataactca tttaaaagtc acccctagca tgatttccga  16560
ttagttgaca gtgcaaaaga tcgctacaca atgcataaat tttaaactca ggttgtaatc  16620
catcctaatt ttaaaatgca tacacaaagc acaaaaaaaa aaaaaaaaaa ctaagcaagc  16680
acgtttggca agtaatgaag ataataaggg tagcttaaac taaaaagatg agaagcattc  16740
accaaggttg cttctggtgg ggcattcttt gcactgaatg caattcaccc acataatgtc  16800
actaccttac taattatcag gcaccgatgg tattcttctt gatattggca ggggagagtt  16860
```

```
cccgcaactt caagtgcttc atatgagggg aatatatgta agaaaatgga gattaaagaa  16920
agatacaatg cctcgtcttc gacgtctggt cattgacagt tgtgagttgc ctgagcttcc  16980
agaagagctt tggtcattga ctgccttact aatggtgcat gtttcgtcgc cctcccaaga  17040
attggctaac agtctaaaaa atgtggtgct gaggaatggc tgtaagctca taatctctaa  17100
aagttgtgtt gatgaatggt tttaagctca caatcatcta gtgcttcata actgttggaa  17160
taatggcaat gcaagtgggc attgctgggt tttgttatgg tctttctata tccatcatga  17220
taacgtgcag tggttcttat cattctgtat ctttctaact ttctaatctc attgccacac  17280
gtgttgtgat tgctagattt ccattttaat ctcagttttt gtctaatttc tttttcttc  17340
ttggaccttt gttctgaagt tgtaacttta tttacatgtt gattgtaaaa ggatatttat  17400
tctggcagtg tttgattaaa tgatttgtaa ttcctctgct tctgtctatt cacttttcta  17460
ctttcttttc ttagatgacc cgatatttct gttagcttag cattgaggca tgagttacat  17520
atatgcatta tttcattcat ttgttgttca gtgtgctcaa ctatatttga ttgtgcgtta  17580
atttccctc ttttcccctt cttttcccat ccaaagtaag tgtttcgtct ggtccctaat  17640
ataaagtatt taactttttt ccattattta tcctattaaa tactctaact atatgtactt  17700
ttaggtaatt atgcataata ttgttattta tgacaagtta actatcatta ataagagtaa  17760
aattgataca ttaatttatt tatttttatt ggtatgtgta attttgttat ttttatttat  17820
tggttttggt gttgtctcac gagatgtctt tttcctggtt gaggtgtgtt tctcttctca  17880
tttcttagat ggaatagtta cttgataaca taattaattg tataatggga gataaatggt  17940
tttcatcttc tcttctcatt tctttttttc ccattcattt ttctggccga gtgatacaga  18000
ggagtaaagg aatgaggact tgtttcaagt aagagtaact ccaaaatagc aaagagactg  18060
aaaagggaat ttctgagtaa taatttctct gccttctttc attccgtgct tggatacata  18120
taggatagat tttccccta ataacctgag gatacgagta ataaattcaa acagaattca  18180
gattctaata acaatatgaa aatgatcaat tttaggtgat aaaagtaatt actcttaaaa  18240
ctaaatggca gagctagtgt ccaacctagt ccttcgtaga catggcaatg gggcggatcg  18300
ggtacagata ttgtctcccc aatctcttac cccgactcct caacatatcc ccatacccga  18360
tacccgacag gtttgagttt attgtctcat ccccgtaccc gtcgggtatc gggtatcccc  18420
aaccccaatc cacacaccat ttagaaaaat attttttttt ttgtaaaaaa atattaaaaa  18480
tttgatttta gaaaaaaata aattgattgt taaacattta tttttaacta cttatatatc  18540
aataaattta ttataacgcg tgtgtctaca taaatagtta aaaaaataat attaaattat  18600
gtaaaaattt taaaataaaa ttaactagta ataaaaatta tgtcttttga ttaaattatg  18660
caaaaattct aaagatttta agtggcaggg cgggtttggg ttcggggtcg gaacgggtct  18720
agtaatccca tacccgtacc cgtacccgac ttttggttat tgaaaaaaac ccgaattcat  18780
actcataccc ggtcaactcg gatattaccc gtcaaagttg ggacggacac tcatttcttg  18840
tgtccttgtg tcactcttct caagcttggg tctcttttta ttgggcccaa cacttatttc  18900
ttgtgtcctt gtgtcacttg ggccaactgg cctatagtga taagacatat ttgttatgtt  18960
cgtaacacta acacccagtt tctattagaa tgctgttact tggaatttga gaaggaattg  19020
gagtgaaaaa atcttacaga aagcagcaat gacattgctt ttgatgatat tttggtagtt  19080
tctatgtcaa aattcttttt ttttctcttt ccttaccatt tgtatccttt tatagtattt  19140
ttttttcact ccatttaaca tttgttacat aaaagacatg acaggaccaa tatattacat  19200
catcagatgt ttgatagtgg ataatcaact aaagaaagaa ctaaaataat tgattttgaa  19260
```

```
aaaaaaaaac taattatttt aatttaagaa ttaaaaaaaa tcaaaatttg cattatacga  19320
aactaaaact aaattttaag cctaataata taatgttcac aaggtgacta aacgaccagg  19380
gtaagtggta actcctcctt tttggtcctc tactatcata aattaatgag cttataacta  19440
gttctcatat ggtaacaaaa agacgtaaaa aatgtttacc tttaaagctg catacatcag  19500
acggtattca acaagaaata gaaatattag cagcaacaga tttgaagtgg aatgttttga  19560
tttcttatat attcagaaga gttgaaatta aacaacttaa agcagagttc aagctcactg  19620
aatactgata ctttgtcctc tgagaagtta atctccggat gctacgcact ccttattttt  19680
ctttcacttt atgcaattta aatacctctc catttcaatg gcataattct aaaatgttca  19740
tcagataagt cctaaaagat ttcccaaatt attcttgatt cgttttcccc ggcaactagt  19800
ttattacaaa aaaaatcaca gaaggaaaag gaagacacgt gtgaatgcta ggactaaaga  19860
gtgtttgacc gttgacgtca aggtgaagtt tctcttgact tgcctcgcag cttctcaata  19920
atatcacagc tcgaaaaaga agacacaatc ggtaaggtga agtttctctt gccttgcctg  19980
gcagcttccc aactactacc aatatgtgct tatgtacttt ggtctcagta taggatatat  20040
gtgctcagtg cctcctccaa agcattaata tactttcact taccaaatca aatggatact  20100
gaaattgatg agagcattga cgaggccgat atcagatttg atgcaaggag ttatagttcc  20160
agactgaaca gtatgataag gagtgagact gagtcaattt tgggagcatc ccctgtccat  20220
gagggagcag ctgcagaaga ggtgcgccaa atcagagatg tcgcccacaa agctgaagat  20280
gtggttgaca cttacgttgc caacatcgcc aaatcagaca tggtgcttca ccaagtcaac  20340
tctgacatag agaagatcag gagtgtgctc aatgagatct atgagaacag cattggagaa  20400
ggtgaattcc gaagcgaaga agctgctgca gaagcagaat cactcctcaa gagaaggagg  20460
gaggtggagg aagaagatgt agtgggctta gtgcatgact caagccatgt aattcaggaa  20520
ctcatggaaa gtgagtcacg tcttaaagtt gtgtccataa ttggaatggg agggttgggt  20580
aagaccactc ttgcccgtaa gatctataac aacaatcaag tgcagctgtg gtttccttgc  20640
cttgcatggg tttctgtgtc caacgattac agacccatgg tatttcttct cagccttctc  20700
aaatgttcaa tgtcatccat atctgaattt gaagaattaa gtgaggcaga actgaagaag  20760
gtagcagaat ggttgaaagg gaagaagtat ctggtagtgc ttgatgacat ctgggaaacc  20820
caagtatggg atgaggttaa aggagccttt ccagatgacc aaacaggtag tagaattctc  20880
ataacaagtc gcaacaaaga ggtggcacac tatgctggaa ctgcgtctcc ctactacctt  20940
cccatcctca atgaagatga aagctgggaa ctcttcacaa agaagatttt tcgaggtgaa  21000
gaatgcccat ctgatttaga tcctctgggt agatccattg tgaaaacttg tgggggttta  21060
ccacttgcta tcgtgatttt agcaggactc gttgtcaaga aggagaagtc acaaagagag  21120
tggtcaagaa tcaaggaagt gagtaggcat cttatagagg ataagactgg agtgatggat  21180
atactgaagc ttagctataa caacttgcct ggaagattaa agccttgctt tctgtatttt  21240
ggaatctatc cagaagacta tgacatcagt gcaaagcaat tgatccaata ttggatcgca  21300
gaaggtttca tacaaccaca aaaaactgga attgcagata caacagaact ggaagatgta  21360
gctgactttt acttggatga gctagtggat cgcagcttgg tgcaagtggc aaaaaggagg  21420
agtgatgggg tgtcaagaca tgtcggattc atgatcttct acgtgttctt tgcatgtcag  21480
aaagcaagtc tgataagttt ctggaggttt gcacaaactc caacattgat accgtcacta  21540
ataccaatcc ccgtagaatt tccatccact ggaaacgaga cttggatgtc tctgcaaaca  21600
```

-continued

```
tatttcacaa atcatgcact cgttctatgt tcatctttgg tgaaaatcgt agcatgaatc  21660
tagttcctgt tttgaaaaac ttcaagttgg ctcgtgtgct tggttgtgat atgatgcaag  21720
gggtttggtc tgattcagtc tccagagatt tgaagaggat gatccatcta agatacttga  21780
gaatagaagt ggagcacctt ccagattgtg taagcagcct ttggaatcta gaaacactgc  21840
atgtaagata tcgtgggaca gtatccagta aaatttggac gttgaagcgg ctgagacatc  21900
tttatttgat agggggaaag ataccagtcg tcctgccaaa agcaaataga atggagaatc  21960
tccaaaccct tttgttatcg ggtaattatt cacaacaaac tctttcccgg ttgaacagtg  22020
gcatatttcc caggttgcga aaattagctt tacgctttgg atttcaattc gccatgttac  22080
caagtctaca ccacctcaac aatcttcata gcctaaatgt aatgtaccct tttgaacttc  22140
catcagacac caatgcgttt ccatcaaatc ttaccaagat aaccttgaag ctagatgcag  22200
actgtgaccg tgatctccaa cctttaatga agacactagg gcgacttacc aaccttcaaa  22260
tcttgaaact tattaatttt ggtttattgt cctatggggt agagcttctt gatattggca  22320
ggggagagtt cccgcaactt caattgcttc atatgggtaa aataaatgta agacaatgga  22380
gattagagaa agatgcaatg cctcgacttc gacgtctggt cattgacagt tgtgagttgc  22440
ctgagcttcg agaagagctt tggtcattga ctgccttaat aatggtgcat gttgttagaa  22500
aaataaaata aaaaaatgaa ggaaaataaa tatgaagaag atgcacagtc ttgaattaaa  22560
taacaaaata gcagtaacaa attaaattta attgacaaca cataaataat gcattatatc  22620
ataatgagca caaggaaaaa ttaaataaag ggaaagaatt aaatagcctg ggttgaagcg  22680
tgtaaacgct attcttagag agaaaacgcc cccactgcac gggtaagaaa ttctgattgc  22740
gctcttctcc caagttacga caacccgttg gttccgatcg tgtgcagcga aaggatcccc  22800
gaaccttatg aacaccaatg ctcttgctct cacaaaaatt aaggaaaaga aagagataaa  22860
tttttggcag aaagaaacca gagctctcag tctgtcattt ctaggaaaga ggaaagagat  22920
atatataggc attttgcaac aacaaaatat taccgttaga aatataaccg ttggaaaacc  22980
aacctacagt tgttgttaag actttggcaa gtgcaccaaa tcgtgacaag tagtaaagct  23040
cggaagtccg agtatcgtgt ccacatggat tttattgcac ttattcaata cctctcaatt  23100
tgtaagtggg agtaaaatag taaaaataag aatgaaagta ggaatagagt gctattacta  23160
aaacaaataa ggaaaaaggg aaacaattaa tagaaatgcc aagaccagac aaacccaatt  23220
ggcctacgat gcatgtaaat aggatattca ttatcaatga aatggtatta gttctaccca  23280
catctgttaa ctacttgccc ctgatgcctc acgttggcaa gcctatttta actaactatc  23340
tcccaaatgc ctttgtgaag attcaataat taaaatgcat taagattaag ttctagatgt  23400
tgcttaaatg catgggcagt gagttatcat tttatgccta gcaatgctaa cccaatgatt  23460
cttttcttta gatgttctat taggtgttac cctttcccaa gcgtataacc cctaaaactg  23520
atgcatgcat tgaatcttaa atattattga gaattaccct ctctcgagcg aataaaaccc  23580
aaaaagagat ctaagaatga atgcaagaat aaaaaaaaaa gaaatggaac agaaaaatct  23640
ggaataaatt ccccttgtatt gataactctt gaagctcatt gtacatcgtt ggctttttag  23700
gcctgccagg ccctagctag gggtttagcc actcatggcc attgagggct tacaactggg  23760
gatgaaagaa agaataggct aataaaacaa agaatatata gagagaaaag aaactcaggc  23820
ttgaggaact gagagtagtg ctctgagacg ggatgatgtt tccttgggac tacctctcta  23880
tttatagctg ctgaagtggg cttatgggcc ttcgtaatag cgctcagcgc cacacctcgc  23940
gcttagcgcg ttcagatcac gcgctgggcg ccccacgcac gctggacctg tgcttctgtt  24000
```

ggatcgggcg ctgggcgcct agctgggctt agcgcgcgta acggtttcca ccttcgtgct 24060
taacgccacg ctcagcgtct gcagttagtt gatcgcttag cgccagatgc gcgctcagcg 24120
cccctattgg attgggcctg cttcagaatt tcttcttttt ttcttccttt ctgtgccact 24180
tttgctaaat gcaaccttat tttttgtatc tgcaaccaga aattcaatta aattaatttt 24240
ctcactttta attacaaata actgctaaat aattaatttt aagccaaaat ttgactattt 24300
aactcctata aattcacaat tatttagcag ttatcagttg tcacaacaaa tataacaaac 24360
tagtttgact cattaaaaca aaatcttaag agaatctaaa ataaatatta ttttataaaa 24420
tagaattaat atatatttat aaattttaaa ttaaaacaca aatatttacc aacattcccc 24480
cacataattt aaaattttaa aatatatttt ctaaaagata atttgtataa aaacataaga 24540
gaaagagcat gtgatattgt atttcggtat aaggaacctt ctgggtttga gccttatacc 24600
tagggtttat gaattttcat ccgagaaaaa tgtagtgatt tgattgtctt gaactacata 24660
ttctttaacc ggactttagt acacaacccc tacaatattg gtgttcaatt aggttctaat 24720
cagtggtagc gcgttacacg gccttgcgct tgtatcttgt ttcgtaagtg tcccttagag 24780
attagcccat atctcacagt ggcggcccca ccaccacact cactaggtga atcctcaaag 24840
agtgggttgt gaccccaccc ctacaaaaat tgtcatcgga ttcattaaga ggtatttttt 24900
tttccaccaa aaatacacat atataaatac ctcaacctta atattgtcac aatttataat 24960
acacctcgtc ataggaatga gaaacggaac agctccgtca aatttcattt tggtgtactt 25020
tagtcaacaa acaatttcgt tgttacccgt tgaactccat tcatgggatc accaatcaca 25080
cggagacggg tgtccattgt tgtaactaaa taatgggctt tagtctcatt cccctcgacg 25140
actcaagtac ttgttgacgc gccaaccctt ttgtaagcgg atccgcaata ttattttctg 25200
acctgacaaa gtcaagagaa atgacaccat gagaaatcaa atttctgata gacttattca 25260
acaatgtttt agatactgct actagtgaga ctgagtttct taaaaatttg ttatgtgctc 25320
taccattgtt gaataagcct atacctccaa ttccaatggg ttgtgatagt ccaatgggtt 25380
gtgatagtta agagaatcta aaataaatat tattttataa aaaaattaat atatatttat 25440
aaattttaaa ttaaaacaca aatatttaga gaaagatgca atgcctcgac ttcgacgtct 25500
ggtcattgac agttgtgagt tgcctgagct tccagaagag ctttggtcat tgactgcctt 25560
actaatggtg catgtttcgt cgccctccca agaattggcc aacagtctca aaaatgtgga 25620
gccgaggaat ggctgtaagc tcataatctc taattaatgc ttcacaactg ttggagtaag 25680
gcaaatgcaa gtgggtctgt catcttaaat tgcagacata agttgtagtc attcaatatc 25740
cttcatcata acttaacttg gctggcagac aatctgtaat gttcggtgct tcttgtcatc 25800 tctattttc taatattaac gtcactcttc acggttatat tttcatttta atctcagttt 25860
ttgtgtaatt tcttttatca ctgtaattgc aattgcttta ccccacacca caactaacct 25920
tgctctcata acgcaccctc ttcctagacc gaaagaatct gagagaaata aacatttttt 25980
atataatatt tgttttttaa tcccgacccc atttcgattt tctttgccaa ataaatttcc 26040
aatttaaaat agcggaaatt caaattgaga atggatgttg cttccttgcc gtgtatggag 26100
ttgtgtctca tgattacata tctataatac ctagagtttc ttatccattt atgaataata 26160
tattaaatgt ctatttttct aatattaatg tcacccttca ctgttatatt ttcatttttc 26220
gaaaatattt ttaatcaatt tatcatgaaa acttgaatat ttaagtatat gtatatatat 26280
agtttaacta tatttaattt tgaattacta atcattcctc agaattatta tacactacaa 26340
aagtaatcct acgattaatt aactttccca tagccattgg aaattaacca tattccttta 26400
catccaatca aaagaagaag aaaaaaaaaa caaattcatt tagcacgttt aattgttaaa 26460
gctaattatt caaatgacta agaagaaaaa ttataagctc caaagtaaaa cattgattat 26520
caaattatcc tatctaaaac tctaaaaagg ttatgttaat gttaaatgaa atattcattc 26580
ggcccatttg ttaaaaaaaa ttatagctgt acaaattaga gaaataagat ggaaagggag 26640
agaaatatga aataaaatag ttaatgcaat acaaagataa agaaaaaata tgaatcgtaa 26700
aaaatgtaat aagtatttgt tgtaacaata ttataactct tgctaaaaat aggtcaaaca 26760
aatggagtca accagcacag aaatgctcta caataactaa tgttaaatat ttgcaactat 26820
aacttcaatt ccgtgcatga gttgtatatg ttaattatac atttggcgtt gaaatccaag 26880
ctaagtcaaa aataaaagtc taataacata tacaattggt ggtaagattt tgcaatttac 26940
atattcacca cgggaattca gaagaaaaat tttacccacg gcgaaggttc ccaatggtca 27000
gtgtcctagt tttccttgaa gattacattt ataaatcatg gaagttcctg aaaagtcaat 27060
ttctcactta gcattttttt catgttcttt ctattttcaa atcctttgac cataattttg 27120
actttggtat atgtatttgt tgcttcattt caatataccc atttatgaag tagagcaagt 27180
agagacaaaa tcatcaccca gttgatgttt aaaccacaag caaaagaaat gtagtgaaaa 27240
ccaactaaat ggactgttcc cgttcgctca tccctcactt taatgcttga agaacctgtg 27300
agatacagca tagaaaatat tattaaatga gcaattatgc aaaattaaag gaaataatgc 27360
aagtcatttg aaaaatcatt ttaaaactac tgcgagtatc taaaattaca aaaagaataa 27420
cggttaataa ggtttgaaaa taccaaaaga taatatttgg tgcatttgca aattcaaact 27480
ccagaatcca ttctggaact caaaactaat ttgaagcaga tgggatacaa aaggttttta 27540
atatgcattg tgggcacttt gggcagaagc aactttttgt tactttagcc cagaatacag 27600
ttaggccatg atgcagttgg gtctaatata tatatatata gagcggaggg atcaagttac 27660
tttactgtct atcctcacac attcttgaaa tctaatagtt gtaatgaata tttaatctta 27720
atcattagat tgtaagagaa tgaatgatga agatgaggag taactctata tatatatata 27780
tatatatata tgacatagaa ggcaaccaac aggtcccaaa caagccaaat aaaactctgc 27840
taatcataac aaaacacaaa gatataatga gatttgcaat atacttacag agggaaataa 27900
ataatcatgt ggataaacaa tcatctagtg cttcataact tcttgataat ggcaatgcaa 27960
gtgggcattg ttgggttttg ttatggtctt ttatatccat cacgataacg ggcagtggtt 28020
cttatcattc tgtatctttc taatctcatt gccacacgtg ttgtgactgc tagatttcca 28080
ttttaatctc agtttttgtc taatttcttt ttctttcttg gtcctttgtt ctgagtttgt 28140
aactttattt acatgttgat tgtaaaagga tctttgttct ggcagtgttt gattaaatga 28200
tttgtaagaa tggcagtgtt tgattaaatg atttgtaaga atgtttatca cttactatga 28260
agtaggaaca aacgacttgc atattagacc tactacattc accttatctt ttataaaatg 28320
cctgataatt tctacatatt tcgcgggtca tgttgaatgt tacggaaaat actactatat 28380
attgtcttgt tttctcgtac aatatataca atttcttgga gagagtttta ggaagttgca 28440
actctttaga attctcttaa gccataaaat ttcacaaatt ttttgggtgt ttgccgtata 28500
tttacttctc taagtaacca aaatttcccc atcaaaagtg ccagatgtta actgatccct 28560
gctcttatgc atgtatatag ataatcatct ggttcccaaa ctctaattgg cgcacaacca 28620
cagaacagaa ctctactttc ctgtgttcca cgaccacttt accagatttt tctgataggt 28680
tagcattgaa gcctgagaga aattatgcat catttcattt gcttgttgta caaccatctt 28740
taattttgca ttaattaatt taaacctttc tcccttgttt ttcgattcta aacatggatc 28800
acgtttttgt ttattggttt aaagtgttgt ttcatgttat ttttctttcc cttttcccga 28860
ttgatggtcc tttcatgatt tagttaggat agatacctga taacacaatt agttcgaaag 28920
gaagatgtta gagtgtatat agatagtggg agacaaatca taatgatcag ttttataatt 28980
ggagtgaaag cagacagata ttgcttttgt gccatgtctc tataactcaa cccaaacctt 29040
tgctggtttt accatggata agaaaattgt gctgcaacag tccaagagat atagttcatt 29100
attttatgat ctttttggta gatttctgcc aaattcattt cttcttttca gcgatgctat 29160
atagtacgaa ttagttttgc accaagaaat acgaatccac ttggcaaaat attgttggac 29220
aaatattaat ttgaaagaat aaaatctaga catgcaagtt ctaactaccc tctctcaaac 29280
tggtgttaga gtacaggtgt aaagtgaaag taaaaaggtt gaacacgtga acaaataact 29340
tataaacctg agtttaaggt gttgggttag agtgtggtgt cagaccataa cggtaaaatt 29400
gttggaaatt taattagatc aactattcat aaaaatttaa atatattttt tatccttata 29460
atttaatatt tttttgttt ctaattaatg taaagttttt tttttagttt tggtaaatta 29520
tgtttgatac tttagataat attttgacaa gtgtaaaaat tattatctaa aacatcacaa 29580
gaacaaaaaa gaaaattaaa aaaatataat ttgtaagaaa aaaataattt aataaacact 29640
aaaaaatcac taaattataa gcagtaaaaa atatttaaac ctttgataaa aaagaaaaaa 29700
agaagagtac atttaataaa atttgctgaa ccctgcagaa agattggtta gaacacaata 29760
acgatgttta aagattactg ttaaagactc tgcattttat aattctaact aattgttgtt 29820
tctaaactat ggacgacttt gatttcagaa acacgataac aattcaacaa aactaacaat 29880
ctaaaaagaa aatcagagtc ataacatata ttaatattta aaagaaagaa aaaaaggcta 29940
cgcagttaaa gttgaaaagt caaattataa ataaaaaagg ttgataaaaa cgtgggtcca 30000
agaatattcg cgccctttc ctgtattggc gtccacttgt tatcgttcgt tgtctactcg 30060
gcatactatc tgtccacaaa ctctctagag tttccacgca agatttcctg tattacaaaa 30120
atggctgata gtgttgttgc ttttgtgcta gataacttgt ctcggctgct tgaagatgag 30180
cacaagttgc tttctggcgt ggaggacaaa atcaactctc tttgcaatga gctcaagttt 30240
atacacatct tcctcaagaa ttctgagggc aagcgcagtc atgagatcgt gaaagaagtg 30300
gtgagccaaa tcagagatgt cgcccacaaa gctgaagatg tggttgacac ctacgttacc 30360
aacatcacca ggcataaaca gagaagcaaa ctgagcaagt tattccacct caaagaacaa 30420
gtcatggtgc ttcaccaagt caactctgac atagagaaga tcaggagtca gatcgatgac 30480
atctataaga acagggacag atatggcatt ggagaaggtg aattccgaag cgaagaagct 30540
gctgcagaag cagaatcact cctcaaaaga aggagggagg tggaggaaga agatgtagtg 30600
ggcttagtgc atgactcaag ccatgtaatt caagaactca tggaaagtga gtcacgtctt 30660
aaagttgttt ccataattgg aatgggaggg ttgggtaaga ccactcttgc ccgtaagatc 30720
tataacaaca atcaagtgca gctgtggttt ccttgccttg catgggtttc tgtgtccaac 30780
gattacagac tcaaggaatt tcttctcagc cttctcaaat gtttaatgtc atccacctct 30840
aaatttaaaa aattaagtga ggaagaactg aagaagaagg tagcagaatg gttgaaatta 30900
agtgaggaag aactgaagaa gaaggtagca aaactgttca aagggaagaa gtatctggta 30960
gtgcttgatg acatctggac aacccaagta tggtatgagg ttaaaggagc ctttccagat 31020
gaccaaacag gtagtagaat tctcataaca agtcgcatca aagaggtggc acactatgct 31080

```
ggagctgtgt ctccctacga ccttcccatc ctcgatgaag ataaaagctg ggaactcttc  31140
acaaagaaga tttttcgagg tgaagaatgc ccgtctgatt tagagcctct gggtagatcc  31200
attgtgaaaa cttgtggggg tttaccactt gccattgtgg ttttagcagg actcgttgcc  31260
aagaaggaga agtcacaaag agagtggtca agaatcaagg aagtgagttg gcatctttct  31320
gaggataaga ctgaagtgat ggatatactg aaacttagct ataacaactt gcctggaaga  31380
ttaaagcctt gctttctgta ttttggaatc tatccagaag actatgagat caaagcaagg  31440
caattgatca aatattggat cgcagaaggg ttcatacaag cacaaaaaac tggaattgca  31500
gatacaacag aactggaaga tgtagctgac ttttacttgg atgagctggt ggatcgcagc  31560
ttggtgcaag tggcaaaaag gaggagtgat gggggtgtca agacatgtcg gattcatgat  31620
cttctacgcg atctttgctt gtcagaaagc aagtttgata agtttctgga ggtttgcaca  31680
aattccaaca ttcataccgt cagtaatacc aatccccgta gaatgtccat ccactggaaa  31740
cgagactcaa atgtgtctgc aaacacattt aataaatcat gcactcgttc tatgttcatc  31800
tttggtagta atactacggt cctagttcct gttttgaaaa acttcaagtt ggcccgtgtg  31860
cttggttgtg gtgtgtatca agggttttgg tcttattcag tccccagata tttgaagagg  31920
atgatccatc taagatactt gagaatagaa gtcaagcacc ttccagatag tgtatgcagc  31980
ctttggaatc tagaaacact ggatgtaaca tatgaaacca cagtatccag taaaatttgg  32040
acgttgaagc gactgagaca tctttatttg agtgggggag ggaagctacc agtcgtcctg  32100
ccaaaagcaa atagaatgga gaatctccaa accctttttgt tatcgggtaa ttattcacaa  32160
caaactcttt cccggttgaa cagtggcata tttccgaggt tgcgaaaatt agctttgcgc  32220
tatgctgttg aatcagacat gttaccaatt ctacaccacc tcaacaatct tcatagccta  32280
aaagtaatgt acgcaattga acttctatca gacagcaatg cgtttccatc aatcttcata  32340
gtcttaagag tggtgcatgt ttcacggccc tccgaagaat tggctaacag tcttaaaaat  32400
gtggagccca ggaatggctg taagctcata gtctctaatt aatgcttcac aactgttgga  32460
gtaaggcaaa tgcaagtggg tctgtactct tacattacag acataagttg tagcttttct  32520
atatccttca tcataactta atttggcttt taggcaatgg taatgttcgg tgcttcttgt  32580
cattctgtat ttttctaata ttaatgtcac ccttcactgt tatattttca ttttactctg  32640
tttttgtcta atttctttta tcattgtaat tacaatcgct ttaccccaca ccccaactaa  32700
ccttgctatc gtaacctttc ttttatcatt gtctaatatt tgttttttaa tcccgacccc  32760
atttcca                                                            32767
```

<210> SEQ ID NO 14
<211> LENGTH: 25
<212> TYPE: DNA
<213> ORGANISM: Artificial Sequence
<220> FEATURE:
<223> OTHER INFORMATION: Artificially Synthesized

<400> SEQUENCE: 14

```
gtatatttat atatatatat atata                                            25
```

<210> SEQ ID NO 15
<211> LENGTH: 10
<212> TYPE: DNA
<213> ORGANISM: Artificial Sequence
<220> FEATURE:
<223> OTHER INFORMATION: Artificially Synthesized

<400> SEQUENCE: 15
aatatgcttt 10

<210> SEQ ID NO 16
<211> LENGTH: 34
<212> TYPE: DNA
<213> ORGANISM: Artificial Sequence
<220> FEATURE:
<223> OTHER INFORMATION: Artificially Synthesized

<400> SEQUENCE: 16
tgggtcaacc tgaatgagtc agggttgacc caaa 34

<210> SEQ ID NO 17
<211> LENGTH: 12
<212> TYPE: DNA
<213> ORGANISM: Artificial Sequence
<220> FEATURE:
<223> OTHER INFORMATION: Artificially Synthesized

<400> SEQUENCE: 17
ctttctttaa tt 12

<210> SEQ ID NO 18
<211> LENGTH: 25
<212> TYPE: DNA
<213> ORGANISM: Artificial Sequence
<220> FEATURE:
<223> OTHER INFORMATION: Artificially Synthesized

<400> SEQUENCE: 18
attcaaaaat attttttaa taatt 25

<210> SEQ ID NO 19
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 19
attaaattta aattgattgt taat 24

<210> SEQ ID NO 20
<211> LENGTH: 14
<212> TYPE: DNA
<213> ORGANISM: Artificial Sequence
<220> FEATURE:
<223> OTHER INFORMATION: Artificially Synthesized

<400> SEQUENCE: 20
ctattataca ccga 14

<210> SEQ ID NO 21
<211> LENGTH: 11
<212> TYPE: DNA
<213> ORGANISM: Artificial Sequence
<220> FEATURE:
<223> OTHER INFORMATION: Artificially Synthesized

<400> SEQUENCE: 21
cattaaggcc t 11

<210> SEQ ID NO 22
<211> LENGTH: 11
<212> TYPE: DNA

<213> ORGANISM: Artificial Sequence
<220> FEATURE:
<223> OTHER INFORMATION: Artificially Synthesized

<400> SEQUENCE: 22
ttaagtatat g 11

<210> SEQ ID NO 23
<211> LENGTH: 6262
<212> TYPE: DNA
<213> ORGANISM: Artificial Sequence
<220> FEATURE:
<223> OTHER INFORMATION: Artificially Synthesized

<400> SEQUENCE: 23
atttcttctt taattgtttt tttttttttt ttgctcagca aaattaaata tattatagat 60
gagtaccaga ggtactaaaa tatacagatt tagagccata ttacaagtag ttttggacag 120
acaatgatac agtagctgaa atatcccaaa aactactcaa ataagacttg gagctatact 180
ctaaacctat gatgctgtcc taagaaaagc atctttgaga tttgaagacc attgattgaa 240
atgtagagag aaatcttttt caaaacatct gagccatgtc cataaaataa acactgcatc 300
atccattaat ttatgagtgt caaaattagc attggagaaa atgatgctgt tcctatgctt 360
ccaaatcgag taagtgagag cgaaccacca ccactgccat ctttttccc tgcaacccta 420 cggaagctcc aaagatatgc tgactaaaat gctgatccgg ctgataaggg aaaacaccca 480
tcatatttac ccaagactgt gactcccacc atagaggact aactttactg cagtggaaaa 540
ataagtgact tgcagtctct tccacagatc tgcataaggg gcacaagtac tcttgtaact 600
caacccgctt ctttctcaaa ttggctttag ttggcagttt gtcttgaatc aacctccacg 660
cgaagatagc cactttcaat gggaccctaa gcttccataa ttccttgaac tttccatcct 720
gctcttctcc cactgtgaca tgatgtattg ccttatatgc actcttagtc gaataacagc 780
cactaggctc tgctgcccac ttccattggt cacttaattc cggcctgatt gtgaaccctt 840
ccagctgttg gaggaaagct accgccatat ctatctcgct atcaaacaaa ggtctcctcc 900
acttaagact ccattcccac ccaccttctt tcgcagcacc tatttgatga atgaaatgat 960
gtttttgagc tgatatggta tacaatctag gatatttatc agctaagcag ttgtctccgc 1020
ctatccacct atcctcccaa aacttaaact tgtccccaca tccgaccctc cacaatatca 1080
acctattcag ctgttgacct tgattcatgc tttgatttac tatctttaga tccctccacc 1140
atgatgattc agtactagcc ctcgaagctc catcaagact cctccatcct ccatactttg 1200
attcaaggac tctagcccaa gtctcctcct gattctgaaa catctcccat ttccattttc 1260
ctaataatga tgtgttgaac gagatgatat ccttgactcc caacccacct tgttcctttg 1320
gcaaacacac cttttcccac ttgatccaag ggatcttatt ttgatcagct gcaccacccc 1380
ataagaagtt cctttgtaat ctggttatct tgctaatcac ctgcctaggg accctgaaaa 1440
aagatagaaa ataaattgga atagatgtta gcactgaatt tatgagaatc actctccccc 1500
caaaagacaa gtgtctctgt ttccatcctg ccagttttct ctcacactta ttgattaaag 1560
gttcccacgt ctgacatctt ctaggattag caccaatagg tatgccaaga tatgtgaaag 1620
gaaaagacat caatccacag ttgagataac tggatgcacc ataagtccac tgctcaggca 1680
ccccaaaggc cccacaacta ctcttggcga aatttatctt taaccccgat gacatctcaa 1740
aagcacgaag tattgcattg attgttctta cattcgctaa tgttgcctct cccaaaaata 1800
gtgtcatctg catactgaag caggctaatc tccaccttct ttgagcccac taaaaatccc 1860

```
ttatagaatc ctccctcaat tgctttggtc attagaccgc tcaaaccttc tgcaacaata   1920
ttaaacaaaa ggggtgataa tggatccccc tgtctaagac ctttctgtgg atagaactcc   1980
ttcgtagggc ttccatttac caagactgag atggaagctg attttaaaca tctctgtatc   2040
cactgaatcc acttcggtcc aaaacccaat ctcctcatca tgtatatcaa aaaatcccaa   2100
gacactaagt catacgcctt ctcatagtcc accttgaaaa ccatgcatgg tttttgacat   2160
cttttggcct cttcaactac ctcatttgca atcaccacac tatgaagcat gtgcctacct   2220
tgtatgaatg ctgactgacg atcactaatt atgaggggca taactctctt cagtctatta   2280
ggcaacactt tagcgaggat tttataggta catccgatga gtgaaatagg tctatattca   2340
ttcaaccctt gagggtccgc caccttcggg attaaagcta tgaatgatgc gttcaagccc   2400
ctcgggaaga ctccgttgac atagaactcg tcaaagaatc taagaaaatc tggtttgatg   2460
acctcccaaa attgcttgat gaatttgaaa ttgaacccgt ctgggcccgg acttttatca   2520
cttccacaac tccaaacagc cctccttatc tcctcttcct gaaagtgctc gactaacatg   2580
gcattctgat gggaatcaat ggtattgaag ctgatcccat tcagagttgg cctatcaaaa   2640
tctgtttcct ggaacctctg tgaaaaaaat ctcctaactt cctctttgac ttcagccggc   2700
tcctccttcc acatcccatc aaccatcagt ccatttaggc tattggatcg cctcctggaa   2760
tttatcagca aatgttaata cctcgaatta caatcaccct ccttaatcca cctggatctt   2820
gccttctgac gtaacagcga ctcatgagtt tgggctgcct cccaaacctt ctgctgcaac   2880
ttctttttga gtatccgctc attatcatcc agtggtctgt ctgctgattc ctcttctagt   2940
ttgttcaact cttcctctat cctcttgaaa cggcttaaag tgtctccaaa gtgatcttta   3000
ttccacgcct ttatcttctg tttgagggcc ttgaatttgt tttttaaaac atgacccccc   3060
catccactct gagtattgga tgaccaggtt tcggacacca acttcttaaa agatacatca   3120
gataaccaac aatccaatag tctgaaaggt tttgggcccc aatcaatggt tttagatcta   3180
agcaatatgg gacaatggtc cgaaaaattc ctggctagcg gtgtttggac cgatccgggc   3240
catttggaaa gccactctgg ggaaacgaag gctctatcca acttgctttt agctgtaccg   3300
ttcggtctaa accatgtaaa tctctttccc acccaaggcg cttcttctaa ttccaactcc   3360
tcaatccagc tattaaaatc ccgtatgctt ccatccacca tccccctctg cgaagacccc   3420
actctttctc cacttatcct gatgttgtta aagtccccta taatacacca ataaccattt   3480
ggattctgga ttttcagctg agtgacttta tcccataaca cccttttgtc ctgcaggtta   3540
catggggagt atatatttac aacatgcact gctatggatt cttgacccca ctttcctgac   3600
agtagtatga agcccgatcc agctgatttg ctctccacct tcagagactt ttgattccaa   3660
atacagagaa taccaccagc tgtatttacg gctggaacct cctcccagca gaaatcagaa   3720
ttcccccata gagccctgca catactctta ttgaccgttt ccttctttgt ttcttgtaag   3780
cataaaaggt caatatgata ctctttgacc atacgtctaa ttgctggcca tttaaccccc   3840
ctccccaacc cccttacatt ataagagatg atattcatga gtcccttccc cttcctccca   3900
agctatctgc ctcttttcca tctctatctt ccatttctgt caactgttga acataatctc   3960
tttgagtttt tcctgttgtc agtcccaact ccttgatcat tctccataga ctttcttcgt   4020
gcgagtcaaa agtttcctcc tggagctgat tttcctgcct attgtgagtt gatgatgttt   4080
ctgtttgtat ttgggggttg gctgatccac gtccctcgtt atctcgctgg aatagtccat   4140
tttgaacatg ctctgggctt gaaagcactt ggttcgaaac aacctcacct atttgggctt   4200
```

```
taactctctt cattttccct ttacgggaat acgttaacaa aggggttagg agaggtgttg   4260
tttttaaaac tgggccattt ttgggagaag gacataattt aggtggggtg ttaatagctt   4320
ggcccaaatc cagcagcccc atcatctcct tgtcacgtga cttgggtgag gggattcaa    4380
aattatgttt gtcttcctcg tacaccatgc ctccaacgtt tcttgtctgc ctcctcatac   4440
tattttcata caaattgccc aaaccgtcag ggccgacatc ccccccgagg ttatcttctt   4500
cccctaaatc ggtcttccct tcttcctgcg acactggtag ctcacggtcc ctggtctgca   4560
cgcatttatc acctgtcagt gcattatctg cttgcttcac gacccatcgg acaatagctt   4620
tgtcctttgg gtcatgtccg ctcttcgtcc cgatcgcctt tccgttttgg tccgcaccgg   4680
ccgcgactgt cgccggtcct tctgaccgag agacctgcct gagtcgccct tcttccacac   4740
cacgcggcga cctctcctcg tcgccacccc tatcctctgt gtcatccacc gtctccgact   4800
gggctggagc tccccttttgg gttttaaatg gcacgatttc acttctccct ctgcggttat  4860
cttcctcgcc ccccaccact ccctccgtcg ccatatcctc catggcttct gcctccaagg   4920
tccctccctt cgctactgtt cgtatttcct ccgccacgct ctctattcgc gctttgtacc   4980
gccacccctg cagctcacta ccagaccacg cgtcatcgtt acattcgtca gaaaggattt   5040
cctctgatga gctgaagtca cgttcccttt ttggctgcca cctagctcca aacaacccac   5100
tctcctccgc tatgtgcacc ggaaaaatct ccccctgtat atgaatattt accgtgtgct   5160
gaatcagcgg tttccatggc gttttgacca gtatcctcgc gacgtcgaac ctcctttgat   5220
cttctaagct ctcctcagcc tccaccatct cacctattcc cgcgactatc tgcttgatac   5280
agttcatgtc ccatgcaacc aaaggtattc cccaacattg gatccaagtt agtctaaaac   5340
cagggcgtag acttggattc cacttctcta tggagtagaa caggtcgccc catccttcat   5400
cttcttcatt caccattttc tctgcgttct cttctgtgag ccccagtaac aaaaccatgt   5460
catcaccgat gtactttggt gatatgtttt gtccgctatc ccaccatatg gcttcttcta   5520
tgctatcaaa gctagccaag tttttcagtc tacccaccca ggcctccttg agccattgtt   5580
tacccgtcat cgaaatgtcc aggttcactt ccgatgtggc attggaactt atgtattgga   5640
gtttggctgt tgttctcctc tgtgctggtt tcgggatatt cgtgttgacc acctccgcat   5700
acgaccgtcc ttggattccc atattcgctt ctggtaacct gctcaggtac acttctgttc   5760
ttccctttttg tgtttgtcct gtctctgctg tccccctctc gactgtttgt gattctccct  5820
tctttggtct cccatattta gggatattaa cattcatctt cattcctccg aagaacctat   5880
tgtccaaatg ctgctgaagt tgatgcacat ctctcacccc cttatacctc acaaaaccat   5940
atctccttcc ttggttgttt cttttcctgg gtatgaaaac ctctctcacg tctccttgct   6000
gtttaaaatg gaaccacaaa tcctttgctg ttgcgtcttc cgggaacctc gtaaagtaaa   6060
aggatataac gtccttatgg tctctccagt tcgctcgcgt gtaggattga cgctgtcctg   6120
tggctaaccc ttcgatggtc agatgggaac cctctgactc tcgaaatctg actctagctc   6180
tcctctcttt cctagtccta actctctccc acccactgtt tctctctcta ctctctctct   6240
ctctccatga ttggattgtt ct                                             6262
```

<210> SEQ ID NO 24
<211> LENGTH: 17
<212> TYPE: DNA
<213> ORGANISM: Artificial Sequence
<220> FEATURE:
<223> OTHER INFORMATION: Artificially Synthesized

<400> SEQUENCE: 24
acagctcgag ttaatat 17

<210> SEQ ID NO 25
<211> LENGTH: 16
<212> TYPE: DNA
<213> ORGANISM: Artificial Sequence
<220> FEATURE:
<223> OTHER INFORMATION: Artificially Synthesized

<400> SEQUENCE: 25
agaaatggag aaagtg 16

<210> SEQ ID NO 26
<211> LENGTH: 12
<212> TYPE: DNA
<213> ORGANISM: Artificial Sequence
<220> FEATURE:
<223> OTHER INFORMATION: Artificially Synthesized

<400> SEQUENCE: 26
ccttcttcag tt 12

<210> SEQ ID NO 27
<211> LENGTH: 13
<212> TYPE: DNA
<213> ORGANISM: Artificial Sequence
<220> FEATURE:
<223> OTHER INFORMATION: Artificially Synthesized

<400> SEQUENCE: 27
ttttatcatg aaa 13

<210> SEQ ID NO 28
<211> LENGTH: 16
<212> TYPE: DNA
<213> ORGANISM: Artificial Sequence
<220> FEATURE:
<223> OTHER INFORMATION: Artificially Synthesized

<400> SEQUENCE: 28
atatatatat atatat 16

<210> SEQ ID NO 29
<211> LENGTH: 13
<212> TYPE: DNA
<213> ORGANISM: Artificial Sequence
<220> FEATURE:
<223> OTHER INFORMATION: Artificially Synthesized

<400> SEQUENCE: 29 aagggggaa tgg 13

<210> SEQ ID NO 30
<211> LENGTH: 42
<212> TYPE: DNA
<213> ORGANISM: Artificial Sequence
<220> FEATURE:
<223> OTHER INFORMATION: Artificially Synthesized

<400> SEQUENCE: 30
aaatatatat atatatatat atatatatat atatatatat at 42

<210> SEQ ID NO 31
<211> LENGTH: 19
<212> TYPE: DNA

<213> ORGANISM: Artificial Sequence
<220> FEATURE:
<223> OTHER INFORMATION: Artificially Synthesized

<400> SEQUENCE: 31
ataaataaat aataatagt 19

<210> SEQ ID NO 32
<211> LENGTH: 26
<212> TYPE: DNA
<213> ORGANISM: Artificial Sequence
<220> FEATURE:
<223> OTHER INFORMATION: Artificially Synthesized

<400> SEQUENCE: 32
cttcttactt gtaactaagt ctttga 26

<210> SEQ ID NO 33
<211> LENGTH: 289
<212> TYPE: DNA
<213> ORGANISM: Artificial Sequence
<220> FEATURE:
<223> OTHER INFORMATION: Artificially Synthesized

<400> SEQUENCE: 33
tatatttttt gtgtttggtc tttgataaat ttttctttcg aatttggatt ctaatgtttt 60
aaatttttta tcttaaagtc tctatcatta atatgtaatc ctacatgact cttaattaga 120
cacgtagaag tgtgatgtgt catgtcaaat ataacctttg tgatttctat ttatacatat 180
tggattatta aaaaaaaata ttttctttgt taaaaaataa taaaatccaa cttatataaa 240
caataatccg acataataca tcacattttt acgtgtgtcc agttcatac 289

<210> SEQ ID NO 34
<211> LENGTH: 13
<212> TYPE: DNA
<213> ORGANISM: Artificial Sequence
<220> FEATURE:
<223> OTHER INFORMATION: Artificially Synthesized

<400> SEQUENCE: 34
ttttgacaaa aac 13

<210> SEQ ID NO 35
<211> LENGTH: 18
<212> TYPE: DNA
<213> ORGANISM: Artificial Sequence
<220> FEATURE:
<223> OTHER INFORMATION: Artificially Synthesized

<400> SEQUENCE: 35
caacactaac aaatttta 18

<210> SEQ ID NO 36
<211> LENGTH: 84
<212> TYPE: DNA
<213> ORGANISM: Artificial Sequence
<220> FEATURE:
<223> OTHER INFORMATION: Artificially Synthesized

<400> SEQUENCE: 36
caagtatgca ggcttttgta cccatagtac cactggtact atttcaatct ataatatata 60
tatttttgct gagcaaaaaa aaaa 84

<210> SEQ ID NO 37
<211> LENGTH: 54
<212> TYPE: DNA
<213> ORGANISM: Artificial Sequence
<220> FEATURE:
<223> OTHER INFORMATION: Artificially Synthesized

<400> SEQUENCE: 37
aaacccatga taactggttt taattgtggg ctgtctccat actctacaca agct 54

<210> SEQ ID NO 38
<211> LENGTH: 332
<212> TYPE: DNA
<213> ORGANISM: Artificial Sequence
<220> FEATURE:
<223> OTHER INFORMATION: Artificially Synthesized

<400> SEQUENCE: 38
ctgtccagcc aagatcttga ctgttgtagt tgaacttagt agctgaagag gaaagagaat 60
gtgatgggtg gttgagattt gggaaggaga gaaaccttgc tgggagaggc tgcagaggat 120
ccagattcct gctatatatt gtcatgataa ctgtcaagtg tgaaattgag agcttgctaa 180
tcttgtagaa tatataaacc atttttgact tttttttttt aaaaaaatga tttgatcata 240
tggcattcat gtttgtttga gttgtagcag tttctttctg ttcccataaa ttgttatcat 300 tctttttga gagttggatt tactggtttg ag 332

<210> SEQ ID NO 39
<211> LENGTH: 19
<212> TYPE: DNA
<213> ORGANISM: Artificial Sequence
<220> FEATURE:
<223> OTHER INFORMATION: Artificially Synthesized

<400> SEQUENCE: 39
aatagcccca cccttaatt 19

<210> SEQ ID NO 40
<211> LENGTH: 21
<212> TYPE: DNA
<213> ORGANISM: Artificial Sequence
<220> FEATURE:
<223> OTHER INFORMATION: Artificially Synthesized

<400> SEQUENCE: 40
tcatcatgct aaaactgagt a 21

<210> SEQ ID NO 41
<211> LENGTH: 25
<212> TYPE: DNA
<213> ORGANISM: Artificial Sequence
<220> FEATURE:
<223> OTHER INFORMATION: Artificially Synthesized

<400> SEQUENCE: 41
ttgaggaaga actgaagaag gtagc 25

<210> SEQ ID NO 42
<211> LENGTH: 20
<212> TYPE: DNA
<213> ORGANISM: Artificial Sequence
<220> FEATURE:
<223> OTHER INFORMATION: Artificially Synthesized

<400> SEQUENCE: 42

```
attgaaaatt gttcctgtac                                                   20


<210> SEQ ID NO 43
<211> LENGTH: 19
<212> TYPE: DNA
<213> ORGANISM: Artificial Sequence
<220> FEATURE:
<223> OTHER INFORMATION: Artificially Synthesized

<400> SEQUENCE: 43

tggcttagga agaaagctc                                                    19


<210> SEQ ID NO 44
<211> LENGTH: 18
<212> TYPE: DNA
<213> ORGANISM: Artificial Sequence
<220> FEATURE:
<223> OTHER INFORMATION: Artificially Synthesized

<400> SEQUENCE: 44

atctctgatc tggctcac                                                     18


<210> SEQ ID NO 45
<211> LENGTH: 23
<212> TYPE: DNA
<213> ORGANISM: Artificial Sequence
<220> FEATURE:
<223> OTHER INFORMATION: Artificially Synthesized

<400> SEQUENCE: 45

caacaaatac atataccaaa gtc                                               23


<210> SEQ ID NO 46
<211> LENGTH: 21
<212> TYPE: DNA
<213> ORGANISM: Artificial Sequence
<220> FEATURE:
<223> OTHER INFORMATION: Artificially Synthesized

<400> SEQUENCE: 46

acaaaatcat caccaagttg a                                                 21


<210> SEQ ID NO 47
<211> LENGTH: 18
<212> TYPE: DNA
<213> ORGANISM: Artificial Sequence
<220> FEATURE:
<223> OTHER INFORMATION: Artificially Synthesized

<400> SEQUENCE: 47

atctgcatgc taatcctg                                                     18


<210> SEQ ID NO 48
<211> LENGTH: 18
<212> TYPE: DNA
<213> ORGANISM: Artificial Sequence
<220> FEATURE:
<223> OTHER INFORMATION: Artificially Synthesized

<400> SEQUENCE: 48

ttcgatctga ctcctgat                                                     18


<210> SEQ ID NO 49
<211> LENGTH: 18
<212> TYPE: DNA
<213> ORGANISM: Artificial Sequence
```

<220> FEATURE:
<223> OTHER INFORMATION: Artificially Synthesized

<400> SEQUENCE: 49
caatagcccc atccttaa 18

<210> SEQ ID NO 50
<211> LENGTH: 22
<212> TYPE: DNA
<213> ORGANISM: Artificial Sequence
<220> FEATURE:
<223> OTHER INFORMATION: Artificially Synthesized

<400> SEQUENCE: 50
ctcatcatgc taaaattgag ta 22

<210> SEQ ID NO 51
<211> LENGTH: 23
<212> TYPE: DNA
<213> ORGANISM: Artificial Sequence
<220> FEATURE:
<223> OTHER INFORMATION: Artificially Synthesized

<400> SEQUENCE: 51
acggattgag gaaggtagca gaa 23

<210> SEQ ID NO 52
<211> LENGTH: 23
<212> TYPE: DNA
<213> ORGANISM: Artificial Sequence
<220> FEATURE:
<223> OTHER INFORMATION: Artificially Synthesized

<400> SEQUENCE: 52
cctattgaaa attgttcttg tac 23

<210> SEQ ID NO 53
<211> LENGTH: 18
<212> TYPE: DNA
<213> ORGANISM: Artificial Sequence
<220> FEATURE:
<223> OTHER INFORMATION: Artificially Synthesized

<400> SEQUENCE: 53
tggcttagga cgaaagct 18

<210> SEQ ID NO 54
<211> LENGTH: 17
<212> TYPE: DNA
<213> ORGANISM: Artificial Sequence
<220> FEATURE:
<223> OTHER INFORMATION: Artificially Synthesized

<400> SEQUENCE: 54
tctctgattt ggctcac 17

<210> SEQ ID NO 55
<211> LENGTH: 25
<212> TYPE: DNA
<213> ORGANISM: Artificial Sequence
<220> FEATURE:
<223> OTHER INFORMATION: Artificially Synthesized

<400> SEQUENCE: 55
agcaacaaat acatatatca aagtc 25

<210> SEQ ID NO 56
<211> LENGTH: 19
<212> TYPE: DNA
<213> ORGANISM: Artificial Sequence
<220> FEATURE:
<223> OTHER INFORMATION: Artificially Synthesized

<400> SEQUENCE: 56
caaaatcatc acccagttg 19

<210> SEQ ID NO 57
<211> LENGTH: 16
<212> TYPE: DNA
<213> ORGANISM: Artificial Sequence
<220> FEATURE:
<223> OTHER INFORMATION: Artificially Synthesized

<400> SEQUENCE: 57
ctgcatgctc atcctg 16

<210> SEQ ID NO 58
<211> LENGTH: 17
<212> TYPE: DNA
<213> ORGANISM: Artificial Sequence
<220> FEATURE:
<223> OTHER INFORMATION: Artificially Synthesized

<400> SEQUENCE: 58
cgatctgagt cctgatc 17

<210> SEQ ID NO 59
<211> LENGTH: 25
<212> TYPE: DNA
<213> ORGANISM: Artificial Sequence
<220> FEATURE:
<223> OTHER INFORMATION: Artificially Synthesized

<400> SEQUENCE: 59
ggatggaatg ggaaagtctt gataa 25

<210> SEQ ID NO 60
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 60
aaaacctgcg aagctccttt acta 24

<210> SEQ ID NO 61
<211> LENGTH: 20
<212> TYPE: DNA
<213> ORGANISM: Artificial Sequence
<220> FEATURE:
<223> OTHER INFORMATION: Artificially Synthesized

<400> SEQUENCE: 61
gtttgttgtc cacgcctgaa 20

<210> SEQ ID NO 62
<211> LENGTH: 25
<212> TYPE: DNA
<213> ORGANISM: Artificial Sequence
<220> FEATURE:
<223> OTHER INFORMATION: Artificially Synthesized

<400> SEQUENCE: 62
ttacgtcaat gctcttaagg tctaa 25

<210> SEQ ID NO 63
<211> LENGTH: 25
<212> TYPE: DNA
<213> ORGANISM: Artificial Sequence
<220> FEATURE:
<223> OTHER INFORMATION: Artificially Synthesized

<400> SEQUENCE: 63
gccttgacct catccattga tagag 25

<210> SEQ ID NO 64
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 64
ggtgtcaacc acatcttcag cttt 24

<210> SEQ ID NO 65
<211> LENGTH: 25
<212> TYPE: DNA
<213> ORGANISM: Artificial Sequence
<220> FEATURE:
<223> OTHER INFORMATION: Artificially Synthesized

<400> SEQUENCE: 65
acttgctcta cttcataaat gggta 25

<210> SEQ ID NO 66
<211> LENGTH: 25
<212> TYPE: DNA
<213> ORGANISM: Artificial Sequence
<220> FEATURE:
<223> OTHER INFORMATION: Artificially Synthesized

<400> SEQUENCE: 66
acccatttat gaagtagagc aagta 25

<210> SEQ ID NO 67
<211> LENGTH: 23
<212> TYPE: DNA
<213> ORGANISM: Artificial Sequence
<220> FEATURE:
<223> OTHER INFORMATION: Artificially Synthesized

<400> SEQUENCE: 67
tccgagaaag gaatagttct gtg 23

<210> SEQ ID NO 68
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 68
caccttctcc aatgccatat ctgt 24

<210> SEQ ID NO 69

<211> LENGTH: 20
<212> TYPE: DNA
<213> ORGANISM: Artificial Sequence
<220> FEATURE:
<223> OTHER INFORMATION: Artificially Synthesized

<400> SEQUENCE: 69
gcaagcaaac ctcgaaccta 20

<210> SEQ ID NO 70
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 70
cccacccgtt tatcatttgc actt 24

<210> SEQ ID NO 71
<211> LENGTH: 22
<212> TYPE: DNA
<213> ORGANISM: Artificial Sequence
<220> FEATURE:
<223> OTHER INFORMATION: Artificially Synthesized

<400> SEQUENCE: 71
tgtcatcaag catcaccagg ta 22

<210> SEQ ID NO 72
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 72
actaataaca aggaggtggc atac 24

<210> SEQ ID NO 73
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 73
actaataaca aggaggtggc atac 24

<210> SEQ ID NO 74
<211> LENGTH: 19
<212> TYPE: DNA
<213> ORGANISM: Artificial Sequence
<220> FEATURE:
<223> OTHER INFORMATION: Artificially Synthesized

<400> SEQUENCE: 74
ttctggcgtg gaggacaaa 19

<210> SEQ ID NO 75
<211> LENGTH: 23
<212> TYPE: DNA
<213> ORGANISM: Artificial Sequence
<220> FEATURE:
<223> OTHER INFORMATION: Artificially Synthesized

<400> SEQUENCE: 75
gtcagtgtcc tagttttcct tga 23

<210> SEQ ID NO 76
<211> LENGTH: 20
<212> TYPE: DNA
<213> ORGANISM: Artificial Sequence
<220> FEATURE:
<223> OTHER INFORMATION: Artificially Synthesized

<400> SEQUENCE: 76
agcgaacggg aacagtccat 20

<210> SEQ ID NO 77
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 77
ggacgacact tttacatcaa acac 24

<210> SEQ ID NO 78
<211> LENGTH: 21
<212> TYPE: DNA
<213> ORGANISM: Artificial Sequence
<220> FEATURE:
<223> OTHER INFORMATION: Artificially Synthesized

<400> SEQUENCE: 78
gcttcaccaa gtcaactctg a 21

<210> SEQ ID NO 79
<211> LENGTH: 27
<212> TYPE: DNA
<213> ORGANISM: Artificial Sequence
<220> FEATURE:
<223> OTHER INFORMATION: Artificially Synthesized

<400> SEQUENCE: 79
tttccctgta ttggcgtcca cttgtta 27

<210> SEQ ID NO 80
<211> LENGTH: 19
<212> TYPE: DNA
<213> ORGANISM: Artificial Sequence
<220> FEATURE:
<223> OTHER INFORMATION: Artificially Synthesized

<400> SEQUENCE: 80
atcgtcaacc actacatcg 19

<210> SEQ ID NO 81
<211> LENGTH: 27
<212> TYPE: DNA
<213> ORGANISM: Artificial Sequence
<220> FEATURE:
<223> OTHER INFORMATION: Artificially Synthesized

<400> SEQUENCE: 81
tttaacaaat gggacgaatg aatattt 27

<210> SEQ ID NO 82
<211> LENGTH: 11
<212> TYPE: DNA

```
<213> ORGANISM: Artificial Sequence
<220> FEATURE:
<223> OTHER INFORMATION: Artificially Synthesized

<400> SEQUENCE: 82

atgtgtgtgt g                                                            11


<210> SEQ ID NO 83
<211> LENGTH: 10
<212> TYPE: DNA
<213> ORGANISM: Artificial Sequence
<220> FEATURE:
<223> OTHER INFORMATION: Artificially Synthesized

<400> SEQUENCE: 83

gaaaggtgga                                                              10


<210> SEQ ID NO 84
<211> LENGTH: 20
<212> TYPE: DNA
<213> ORGANISM: Artificial Sequence
<220> FEATURE:
<223> OTHER INFORMATION: Artificially Synthesized

<400> SEQUENCE: 84

taatataatt tatttattaa                                                   20
```